US011578118B2

(12) United States Patent
Taylor et al.

(10) Patent No.: US 11,578,118 B2
(45) Date of Patent: Feb. 14, 2023

(54) SYSTEMS AND METHODS TO PRODUCE B CELLS GENETICALLY MODIFIED TO EXPRESS SELECTED ANTIBODIES

(71) Applicant: Fred Hutchinson Cancer Center, Seattle, WA (US)

(72) Inventors: Justin J. Taylor, Seattle, WA (US); Howell F. Moffett, Seattle, WA (US)

(73) Assignee: Fred Hutchinson Cancer Center, Seattle, WA (US)

( * ) Notice: Subject to any disclaimer, the term of this patent is extended or adjusted under 35 U.S.C. 154(b) by 293 days.

(21) Appl. No.: 16/757,707

(22) PCT Filed: Oct. 19, 2018

(86) PCT No.: PCT/US2018/056789
§ 371 (c)(1),
(2) Date: Apr. 20, 2020

(87) PCT Pub. No.: WO2019/079772
PCT Pub. Date: Apr. 25, 2019

(65) Prior Publication Data
US 2021/0198344 A1    Jul. 1, 2021

Related U.S. Application Data

(60) Provisional application No. 62/623,371, filed on Jan. 29, 2018, provisional application No. 62/580,303, filed on Nov. 1, 2017, provisional application No. 62/575,275, filed on Oct. 20, 2017.

(51) Int. Cl.
| | |
|---|---|
| *A61K 35/17* | (2015.01) |
| *C07K 16/10* | (2006.01) |
| *C07K 16/08* | (2006.01) |
| *C07K 16/12* | (2006.01) |
| *C07K 16/24* | (2006.01) |
| *C12N 15/86* | (2006.01) |
| *C12N 15/90* | (2006.01) |

(52) U.S. Cl.
CPC .......... *C07K 16/1027* (2013.01); *A61K 35/17* (2013.01); *C07K 16/082* (2013.01); *C07K 16/085* (2013.01); *C07K 16/087* (2013.01); *C07K 16/088* (2013.01); *C07K 16/1018* (2013.01); *C07K 16/1045* (2013.01); *C07K 16/1282* (2013.01); *C07K 16/241* (2013.01); *C12N 15/86* (2013.01); *C12N 15/907* (2013.01); *C12N 2310/20* (2017.05); *C12N 2510/00* (2013.01); *C12N 2750/14143* (2013.01); *C12N 2800/80* (2013.01)

(58) Field of Classification Search
None
See application file for complete search history.

(56) References Cited

U.S. PATENT DOCUMENTS

| | | |
|---|---|---|
| 5,604,090 A | 2/1997 | Alexander et al. |
| 7,981,632 B2 | 7/2011 | Schmidt |
| 8,637,035 B2 | 1/2014 | Wu et al. |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,932,814 B2 | 1/2015 | Cong et al. |
| 8,945,839 B2 | 2/2015 | Zhang |
| 8,993,233 B2 | 3/2015 | Zhang et al. |
| 8,999,641 B2 | 4/2015 | Zhang et al. |
| 9,403,900 B2 | 8/2016 | Williamson et al. |
| 9,469,685 B2 | 10/2016 | Ahmed et al. |
| 9,512,204 B2 | 12/2016 | Maynard et al. |
| 2001/0034062 A1 | 10/2001 | Koenig |
| 2002/0106729 A1 | 8/2002 | Bleck |
| 2002/0146422 A1 | 10/2002 | Bachmann et al. |
| 2003/0083474 A1 | 5/2003 | Schmidt |
| 2007/0020279 A1 | 1/2007 | Johnson |
| 2012/0102582 A1 | 4/2012 | Haynes et al. |
| 2012/0167237 A1 | 6/2012 | Bradley et al. |
| 2012/0207673 A1 | 8/2012 | Christ et al. |
| 2013/0078249 A1 | 3/2013 | Ast et al. |

(Continued)

FOREIGN PATENT DOCUMENTS

| | | |
|---|---|---|
| JP | 2017505780 A | 2/2017 |
| WO | WO2011085247 | 7/2011 |

(Continued)

OTHER PUBLICATIONS

Stewart-Jones, et al., "A Cysteine Zipper Stabilizes a Pre-Fusion F Glycoprotein Vaccine for Respiratory Syncytial Virus," PLoS One, vol. 10, No. 6, 2015, 16 pages.

Swanson, et al., "A monomeric uncleaved respiratory syncytial virus F antigen retains prefusion-specific neutralizing epitopes," J Virol., vol. 88, No. 20, 2014, pp. 11802-11810.

Symington & Gautier, "Double-strand break end resection and repair pathway choice," Annu. Rev. Genet., vol. 45, 2011, pp. 247-271.

Taylor, et al., "A germinal center-independent pathway generates unswitched memory B cells early in the primary response," Journal of Experimental Medicine, vol. 209, No. 3, 2012, pp. 597-606.

(Continued)

*Primary Examiner* — Nicole Kinsey White
(74) *Attorney, Agent, or Firm* — C. Rachal Winger; Chrystal Quisenberry; Lee & Hayes PC

(57) ABSTRACT

Systems and methods to genetically modify B cells to express selected antibodies are described. The systems and methods can be used to: obviate the need for classical vaccinations; provide protection against infectious agents for which no vaccinations are currently available; provide protection against infectious agents when patients are otherwise immune-suppressed; and/or provide a benefit provided by a therapeutic antibody, such as in the treatment of autoimmune disorders.

23 Claims, 110 Drawing Sheets

Specification includes a Sequence Listing.

(56) References Cited

U.S. PATENT DOCUMENTS

| | | | |
|---|---|---|---|
| 2014/0356908 | A1 | 12/2014 | Grosvelt et al. |
| 2015/0056171 | A1 | 2/2015 | Burack et al. |
| 2016/0159866 | A1 | 6/2016 | Ichtchenko et al. |
| 2016/0159874 | A1 | 6/2016 | Tavernier et al. |

FOREIGN PATENT DOCUMENTS

| | | |
|---|---|---|
| WO | WO2013148256 | 10/2013 |
| WO | WO2014018423 A2 | 1/2014 |
| WO | WO2014093595 A1 | 6/2014 |
| WO | WO2014093622 A2 | 6/2014 |
| WO | WO2014093635 A1 | 6/2014 |
| WO | WO2014093655 A2 | 6/2014 |
| WO | WO2014093661 A2 | 6/2014 |
| WO | WO2014093694 A1 | 6/2014 |
| WO | WO2014093701 A1 | 6/2014 |
| WO | WO2014093709 A1 | 6/2014 |
| WO | WO2014093712 A1 | 6/2014 |
| WO | WO2014093718 A1 | 6/2014 |
| WO | WO2014145599 A2 | 9/2014 |
| WO | WO2014204723 A1 | 12/2014 |
| WO | WO2014204724 A1 | 12/2014 |
| WO | WO2014204725 A1 | 12/2014 |
| WO | WO2014204726 A1 | 12/2014 |
| WO | WO2014204727 A1 | 12/2014 |
| WO | WO2014204728 A1 | 12/2014 |
| WO | WO2014204729 A1 | 12/2014 |
| WO | WO2015065964 A1 | 5/2015 |
| WO | WO2015089351 A1 | 6/2015 |
| WO | WO2015089354 A1 | 6/2015 |
| WO | WO2015089364 A1 | 6/2015 |
| WO | WO2015089419 A2 | 6/2015 |
| WO | WO2015089427 A1 | 6/2015 |
| WO | WO2015089462 A1 | 6/2015 |
| WO | WO2015089465 A1 | 6/2015 |
| WO | WO2015089473 A1 | 6/2015 |
| WO | WO2015089486 A2 | 6/2015 |
| WO | WO2016205711 A1 | 12/2016 |
| WO | WO2017106657 A1 | 6/2017 |
| WO | WO2017127807 A1 | 7/2017 |
| WO | WO2017176806 | 10/2017 |

OTHER PUBLICATIONS

Taylor, et al., "Apoptosis and antigen affinity limit effector cell differentiation of a single naive B cell," Science, vol. 347, No. 6223, 2015, pp. 784-787.
Taylor, et al., "Hapten-specific naive B cells are biomarkers of vaccine efficacy against drugs of abuse," J. Immunol. Methods, vol. 405, 2014, pp. 74-86.
Taylor, et al., "Heterogeneity in the differentiation and function of memory B cells," Trends Immunol., vol. 33, No. 12, 2012, pp. 590-597.
The IMpact-RSV Study Group, "Palivizumab, a humanized respiratory syncytial virus monoclonal antibody, reduces hospitalization from respiratory syncytial virus infection in high-risk infants. The IMpact-RSV Study Group," Pediatrics, vol. 102, No. 3 Pt. 1, 1998, pp. 531-537.
The PREVENT Study Group, "Reduction of respiratory syncytial virus hospitalization among premature infants and infants with bronchopulmonary dysplasia using respiratory syncytial virus immune globulin prophylaxis." Pediatrics, vol. 99, No. 1, 1997, pp. 93-99.
Watson, et al., "The Individual and Population Genetics of Antibody Immunity," Cell Press, vol. 38, No. 7, 2017, pp. 459-470.
Widjaja, et al., "Recombinant Soluble Respiratory Syncytial Virus F Protein That Lacks Heptad Repeat B, Contains a GCN4 Trimerization Motif and Is Not Cleaved Displays Prefusion-Like Characteristics," PLoS One, vol. 10, No. 6, 2015, 19 pages.
Wilcox, et al., "Bezlotoxumab for Prevention of Recurrent Clostridium difficile Infection," New England Journal of Medicine, vol. 376, No. 4, 2017, pp. 305-317.
Williams, et al., "Evaluation of the response to a booster dose of hepatitis B vaccine in previously immunized healthcare workers," Vaccine, No. 19, No. 28-29, 2001, pp. 4081-4085.
Wolfe, et al., "DNA Recognition by Cys2His2 Zinc Finger Proteins," Annual Review of Biophysics and Biomolecular Structure, vol. 29, 2000, pp. 183-212.
Yassine, et al., "Hemagglutinin-stem nanoparticles generate heterosubtypic influenza protection," Nature Medicine, vol. 21, No. 9, 2015, pp. 1065-1070.
Zetsche, et al., "Cpf1 Is a Single RNA-Guided Endonuclease of a Class 2 CRISPR-Cas System," Cell, vol. 163, No. 3, 2015, pp. 759-771.
Office Action dated Oct. 18, 2022 for Japanese Patent Application No. 2020-522004, 15 pages.
Invitation to Pay Additional Fees dated Dec. 10, 2018 for International Application No. PCT/US2018/056789, 2 pages.
Search Report and Written Opinion dated Feb. 15, 2019 for International Application No. PCT/US2018/056789, 17 pages.
Extended European Search Report dated Nov. 9, 2021 for European Patent Application No. 18869188.5, 12 pages.
Li, et al., "A role for the IgH intronic enhancer Eu in enforcing allelic exclusion," Journal of Experimental Medicine, vol. 206, No. 1, 2009, pp. 153-167.
Aurnhammer, et al., "Universal Real-Time PCR for the Detection and Quantification of Adeno-Associated Virus Serotype 2-Derived Inverted Terminal Repeat Sequences," Human Gene Therapy Methods, vol. 23, No. 1, 2012, pp. 18-28.
Bauer & Jilg, "Hepatitis B surface antigen-specific T and B cell memory in individuals who had lost protective antibodies after hepatitis B vaccination," Vaccine, vol. 24, No. 5, 2006, pp. 572-577.
Bibikova, et al., "Enhancing Gene Targeting with Designed Zinc Finger Nucleases," Science, vol. 300, No. 5620, 2003, 1 page.
Bibikova, et al., "Targeted Chromosomal Cleavage and Mutagenesis in Drosophila Using Zinc-Finger Nucleases," Genetics, vol. 161, No. 3, 2002, pp. 1169-1175.
Bird, et al., "Single-chain antigen-binding proteins," Science, vol. 242, No. 4877, 1988, pp. 423-426.
Blanco, et al., "New insights for development of a safe and protective RSV vaccine," Hum. Vaccin., vol. 6, No. 6, 2010, pp. 482-492.
Boch, et al., "Breaking the Code of DNA Binding Specificity of TAL-Type III Effectors," Science, vol. 326, No. 5959, 2009, pp. 1509-1512.
Broadbent, et al., "Respiratory syncytial virus, an ongoing medical dilemma: an expert commentary on respiratory syncytial virus prophylactic and therapeutic pharmaceuticals currently in clinical trials," Influenza Other Respir. Viruses, vol. 9, No. 4, 2015, pp. 169-178.
Choi, et al., "Production of Recombinant Adeno-Associated Viral Vectors for In Vitro and In Vivo Use," Molecular Biology, vol. 78, No. 1, 2007, 24 pages.
Christian, et al., "Targeting DNA Double-Strand Breaks with TAL Effector Nucleases," Genetics, vol. 186, No. 2, 2010, pp. 757-761.
Correia, et al., "Proof of principle for epitope-focused vaccine design," Nature, vol. 507, No. 7491, 2014, pp. 201-206.
Delpy, et al., "B Cell Development Arrest Upon Insertion of a neo Gene Between JH and EMu: Promoter Competition Results in Transcriptional Silencing of Germline JH and Complete V(D)J Rearrangements," Journal of Immunology, vol. 169, No. 12, 2002, pp. 6875-6882.
Deng, et al., "Pharmacokinetics and Exposure-Response Analysis of RG7667, a Combination of Two Anticytomegalovirus Monoclonal Antibodies, in a Phase 2a Randomized Trial To Prevent Cytomegalovirus Infection in High-Risk Kidney Transplant Recipients," Antimicrobial Agents and Chemotherapy, vol. 62, No. 2, 12 pages.
Dole, et al., "A First-in-Human Study To Assess the Safety and Pharmacokinetics of Monoclonal Antibodies against Human Cytomegalovirus in Healthy Volunteers," Antimicrobial Agents and Chemotherapy, vol. 60, No. 5, 2016, pp. 2881-2887.
Donnelly, et al., "Analysis of the aphthovirus 2A/2B polyprotein 'cleavage' mechanism indicates not a proteolytic reaction, but a novel translational effect: a putative ribosomal 'skip'," Journal of General Virology, vol. 82, No. 2, 2001, pp. 1013-1025.

(56) References Cited

OTHER PUBLICATIONS

Elliott, et al., "Gene conversion tracts from double-strand break repair in mammalian cells," Molecular and Cellular Biology, vol. 18, No. 1, 1998, pp. 93-101.
Garg, et al., "Vaccination with the RSV fusion protein formulated with a combination adjuvant induces long-lasting protective immunity," J Gen. Virol., vol. 95, Part 5, 2014, pp. 1043-1054.
Haasken, et al., "Macrophage Scavenger Receptor 1 (Msr1, SR-A) Influences B Cell Autoimmunity by Regulating Soluble Autoantigen Concentration," Journal of Immunology, vol. 191, No. 3, 2013, pp. 1055-1062.
Hamilton, et al., "General Approach for Tetramer-Based Identification of Autoantigen-Reactive B Cells: Characterization of La- and snRNP-Reactive B Cells in Autoimmune BXD2 Mice," Journal of Immunology, vol. 194, No. 10, 2015, pp. 5022-5034.
Haryadi, et al., "Optimization of heavy chain and light chain signal peptides for high level expression of therapeutic antibodies in CHO cells," PLOS One, vol. 10, No. 2, 2015, 16 pages.
Helmreich, et al., "The secretion of antibody by isolated lymph node cells," J. Biol. Chem., vol. 236, No. 2, 1961, pp. 464-473.
Hibi and Dosch, "Limiting dilution analysis of the B cell compartment in human bone marrow," Eur. J. Immunol., vol. 16, No. 2, 1986, pp. 139-145.
Hsiau, et al., "Inference of CRISPR Edits from Sanger Trace Data," bioRxiv, 2018, 17 pages.
Hsu, et al., "DNA targeting specificity of RNA-guided Cas9 nucleases," Nat. Biotechnol., vol. 31, No. 9, 2013, pp. 827-832.
Kay, et al., "Evidence for gene transfer and expression of factor IX in haemophilia B patients treated with an AAV vector," Nature Genetics, vol. 24, No. 257, 2000, pp. 257-261.
Kim, et al., "Establishment and characterization of BALB/c lymphoma lines with B cell properties," J. Immunol., vol. 122, No. 2, 1979, pp. 549-554.
Kim, et al., "Hybrid restriction enzymes: zinc finger fusions to Fok I cleavage domain," PNAS USA, vol. 93, No. 3, 1996, pp. 1156-1160.
Koerber, et al., "An improved single-chain Fab platform for efficient display and recombinant expression," J. Mol. Biol., vol. 427, No. 2, 2015, pp. 576-586.
Love, et al., "Individual VH promoters vary in strength, but the frequency of rearrangement of those VH genes does not correlate with promoter strength nor enhancer-independence," Mol. Immun., vol. 37, No. 1-2, 2000, pp. 29-39.
Luo, et al., "Engineering human hematopoietic stem/progenitor cells to produce a broadly neutralizing anti-HIV antibody after in vitro maturation to human B lymphocytes," Blood, vol. 113, No. 7, 2009, pp. 1422-1431.
Malkin, et al., "Safety and immunogenicity of a live attenuated RSV vaccine in healthy RSV-seronegative children 5 to 24 months of age," PLoS One, vol. 8, No. 10, 2013, 10 pages.
McGuire, et al., "Specifically modified Env immunogens activate B-cell precursors of broadly neutralizing HIV-1 antibodies in transgenic mice," Nature Communications, vol. 7, No. 10618, 2016, 10 pages.
McHeyzer-Williams, et al., "Molecular programming of B cell memory," Nat. Rev. Immunol., vol. 12, No. 1, 2011, pp. 24-34.
McLellan, et al., "Structure-Based Design of a Fusion Glycoprotein Vaccine for Respiratory Syncytial Virus," Science, vol. 342, No. 6158, 2013, pp. 592-598.
Meissner & Kimberlin, "RSV immunoprophylaxis: does the benefit justify the cost?," Pediatrics, vol. 132, No. 5, 2013, pp. 915-918.
Miller, et al., "A Tale nuclease architecture for efficient genome editing," Nature Biotechnology, vol. 29, No. 2, 2011, pp. 143-148.
Miller, et al., "An improved zinc-finger nuclease architecture for highly specific genome editing," Nature Biotechnology, vol. 25, No. 7, 2007, pp. 778-785.
Miller, et al., "Repetitive zinc-binding domains in the protein transcription factor IHA from Xenopus oocytes," EMBO J., vol. 4, No. 6, 1985, pp. 1609-1614.
Moscou & Bogdanove, "A Simple Cipher Governs DNA Recognition by TAL Effectors," Science, vol. 326, No. 5959, 2009, 1 page.
Munir, et al., "Nonstructural Proteins 1 and 2 of Respiratory Syncytial Virus Suppress Maturation of Human Dendritic Cells," Journal of Virology, vol. 82, No. 17, 2008, pp. 8780-8796.
Murphy, et al., "Enhanced pulmonary histopathology is observed in cotton rats immunized with formalin-inactivated respiratory syncytial virus (RSV) or purified F glycoprotein and challenged with RSV 3-6 months after immunization," Vaccine, vol. 8, No. 5, 1990, pp. 497-502.
Nakai, et al., "Adeno-associated viral vector-mediated gene transfer of human blood coagulation factor IX into mouse liver," Blood, vol. 91, No. 12, 1998, pp. 4600-4607.
Nanton, et al., "Direct visualization of endogenous *Salmonella*-specific B cells reveals a marked delay in clonal expansion and germinal center development," Eur. J. Immunol., vol. 45, No. 2, 2015, pp. 428-441.
Pape, et al., "Different B cell populations mediate early and late memory during an endogenous immune response," Science, vol. 331, No. 6021, 2011, pp. 1203-1207.
Schmidt & Skerra, "The Strep-tag system for one-step purification and high-affinity detection or capturing of proteins," Nature Protocols, vol. 2, No. 6, 2007, pp. 1528-1535.
Schnepp & Johnson, "Adeno-associated virus delivery of broadly neutralizing antibodies," Curr. Opin. HIV AIDS, vol. 9, No. 3, 2014, pp. 250-256.
Schumann, et al., "Generation of knock-in primary human T cells using Cas9 ribonucleoproteins," PNAS, vol. 112, No. 33, 2015, pp. 10437-10442.
Skaricic, et al., "Genetic delivery of an anti-RSV antibody to protect against pulmonary infection with RSV," Virology, vol. 378, No. 1, 2008, pp. 79-85.
Snijder, et al., "An Antibody Targeting the Fusion Machinery Neutralizes Dual-Tropic Infection and Defines a Site of Vulnerability on Epstein-Barr Virus," Immunity, vol. 48, No. 4, 2018, pp. 799-811.
Sternberg & Doudna, "Expanding the Biologist's Toolkit with CRISPR-Cas9," Mol. Cell, vol. 58, No. 4, 2015, pp. 568-574.

VDJ recombination (2000kb)      Class switch recombination (100kb)

FIG. 11A

Human Eμ intronic enhancer sequence:

GTAGTTGAAAAGTGGTCTTGAAAAATACTAAAATGAAGGCCACTCTATCAGAATATCAAAGT
GTTTCTCCTTAATCACAAAGAGAAAACGAGTTAACCTAAAAAGATTGTGAACACAGTCATTA
TGAAAATAATGCTCTGAGGTATCGAAAAAGTATTTGAGATTAATTATCACATGAAGGGATAA
CAAGCTAATTTAAAAAACTTTTTGAATACAGTCATAAACTCTCCCTAAGACTGTTTAATTTCT
TAAACATCTTACTTTAAAAATGAATGCAGTTTAGAAGTTGATATGCTGTTTGCACAAACTAGC
AGTTGATAAGCTAAGATTGGAAATGAAATTCAGATAGTTAAAAAAAGCCTTTTCAGTTTCGG
TCAGCCTCGCCTTATTTTAGAAACGCAAATTGTCCAGGTGTTGTTTTGCTCAGTAGAGCACT
TTCAGATCTGGGCCTGGGCAAAACCACCTCTTCACAACCAGAAGTGATAAATTTACCAATT
GTGTTTTTTGCTTCCTAAAATAGACTCTCGCGGTGACCTGCTTCCTGCCACCTGCTGTGG
GTGCCGGAGACCCCCATGCAGCCATCTTGACTCTAATTCATCATCTGCTTCCAGCTTCGCT
CAATTAATTAAAAAAATAAACTTGATTTATGATGGTCAAAACGCAGTCCCGCATCGGGGCCG
ACAGCACTGTGCTAGTATTTCTTAGCTGAGCTTGCTTTGGCCTCAATTCCAGACACATATCA
CTCATGGGTGTTAATCAAATGATAAGAATTTCAAATACTTGGACAGTTAAAAAAATTAATATA
CTTGAAAATCTCTCACATTTTTAAGTCA (SEQ ID NO: 85)

Human Intronic Region 1 to Target for Genetic Construct Insertion:

CTACATGGACGTCTGGGGCAAAGGGACCACGGTCACCGTCTCCTCAGGTAAGAATGGCCA
CTCTAGGGCCTTTGTTTTCTGCTACTGCCTGTGGGGTTTCCTGAGCATTGCAGGTTGGTCC
TCGGGGCATGTTCCGAGGGGACCTGGGCGGACTGGCCAGGAGGGGATGGGCACTGGGG
TGCCTTGAGGATCTGGGAGCCTCTGTGGATTTTCCGATGCCTTTGGAAAATGGGACTCAG
GTTGGGTGCGTCTGATGGAGTAACTGAGCCTGGGGGCTTGGGGAGCCACATTTGGACGA
GATGCCTGAACAAACCAGGGGTCTTAGTGATGGCTGAGGAATGTGTCTCAGGAGCGGTGT
CTGTAGGACTGCAAGATCGCTGCACAGCAGCGAATCGTGAAATATTTTCTTTAGAATTATGA
GGTGCGCTGTGTGTCAACCTGCATCTTAAATTCTTTATTGGCTGGAAAGAGAACTGTCGGA
GTGGGTGAATCCAGCCAGGAGGGACGCGTAGCCCCGGTCTTGATGAGAGCAGGGTTGGG
GGCAGGGGTAGCCCAGAAACGGTGGCTGCCGTCCTGACAGGGGCTTAGGGAGGCTCCAG
GACCTCAGTGCCTTGAAGCTGGTTTCCATGAGAAAAGGATTGTTTATCTTAGGAGGCATGC
TTACTGTTAAAAGACAGGATATGTTTGAAGTGGCTTCTGA GAAAAATGGTTAAGAAAATTAT
(SEQ ID NO: 1)

FIG. 11B

| | |
|---|---|
| Human_Region_1_gRNA_1 | GGTCCTCGGGGCATGTTCCGAGG (SEQ ID NO: 5) |
| Human_Region_1_gRNA_2 | GGGCATGTTCCGAGGGGACCTGG (SEQ ID NO: 6) |
| Human_Region_1_gRNA_3 | GCATTGCAGGTTGGTCCTCGGGG (SEQ ID NO: 7) |
| Human_Region_1_gRNA_4 | TCCTCGGGGCATGTTCCGAGGGG (SEQ ID NO: 8) |
| Human_Region_1_gRNA_5 | GGCATGTTCCGAGGGGACCTGGG (SEQ ID NO: 9) |
| Human_Region_1_gRNA_6 | GTCTCAGGAGCGGTGTCTGTAGG (SEQ ID NO: 10) |
| Human_Region_1_gRNA_7 | AGCATTGCAGGTTGGTCCTCGGG (SEQ ID NO: 11) |
| Human_Region_1_gRNA_8 | CCTGGGCGGACTGGCCAGGAGGG (SEQ ID NO: 12) |
| Human_Region_1_gRNA_9 | ACTGGGGTGCCTTGAGGATCTGG (SEQ ID NO: 13) |
| Human_Region_1_gRNA_10 | CCCCAGTGCCCATCCCCTCCTGG (SEQ ID NO: 14) |
| Human_Region_1_gRNA_11 | CTAAGACCCTGGTTTGTTCAGG (SEQ ID NO: 15) |
| Human_Region_1_gRNA_12 | TGTGGATTTTCCGATGCCTTTGG (SEQ ID NO: 16) |
| Human_Region_1_gRNA_13 | AGGACCAACCTGCAATGCTCAGG (SEQ ID NO: 17) |
| Human_Region_1_gRNA_14 | CTCAGGTTGGGTGCGTCTGATGG (SEQ ID NO: 18) |
| Human_Region_1_gRNA_15 | CCCTCCTGGCCAGTCCGCCCAGG (SEQ ID NO: 19) |
| Human_Region_1_gRNA_16 | GGCCAGGAGGGGATGGGCACTGG (SEQ ID NO: 20) |
| Human_Region_1_gRNA_17 | GAGATGCCTGAACAAACCAGGGG (SEQ ID NO: 21) |
| Human_Region_1_gRNA_18 | AGGGGTCTTAGTGATGGCTGAGG (SEQ ID NO: 22) |
| Human_Region_1_gRNA_19 | ATGGGCACTGGGGTGCCTTGAGG (SEQ ID NO: 23) |
| Human_Region_1_gRNA_20 | TTCCGATGCCTTTGGAAAATGGG (SEQ ID NO: 24) |

FIG. 11B (cont'd)

| | |
|---|---|
| Human_1_gRNA_1 | GGUCCUCGGGGCAUGUUCCG (SEQ ID NO: 290) |
| Human_1_gRNA_2 | GGGCAUGUUCCGAGGGGACC (SEQ ID NO: 291) |
| Human_1_gRNA_3 | GCAUUGCAGGUUGGUCCUCG (SEQ ID NO: 88) |
| Human_1_gRNA_4 | UCCUCGGGGCAUGUUCCGAG (SEQ ID NO: 292) |
| Human_1_gRNA_5 | GGCAUGUUCCGAGGGGACCU (SEQ ID NO: 293) |
| Human_1_gRNA_6 | GUCUCAGGAGCGGUGUCUGU (SEQ ID NO: 89) |
| Human_1_gRNA_7 | AGCAUUGCAGGUUGGUCCUC (SEQ ID NO: 294) |
| Human_1_gRNA_8 | CCUGGGCGGACUGGCCAGGA (SEQ ID NO: 295) |
| Human_1_gRNA_9 | ACUGGGGUGCCUUGAGGAUC (SEQ ID NO: 296) |
| Human_1_gRNA_10 | CCCCAGUGCCCAUCCCCUCC (SEQ ID NO: 297) |
| Human_1_gRNA_11 | CUAAGACCCCUGGUUUGUUC (SEQ ID NO: 298) |
| Human_1_gRNA_12 | UGUGGAUUUUCCGAUGCCUU (SEQ ID NO: 299) |
| Human_1_gRNA_13 | AGGACCAACCUGCAAUGCUC (SEQ ID NO: 300) |
| Human_1_gRNA_14 | CUCAGGUUGGGUGCGUCUGA (SEQ ID NO: 301) |
| Human_1_gRNA_15 | CCCUCCUGGCCAGUCCGCCC (SEQ ID NO: 302) |
| Human_1_gRNA_16 | GGCCAGGAGGGGAUGGGCAC (SEQ ID NO: 303) |
| Human_1_gRNA_17 | GAGAUGCCUGAACAAACCAG (SEQ ID NO: 304) |
| Human_1_gRNA_18 | AGGGGUCUUAGUGAUGGCUG (SEQ ID NO: 305) |
| Human_1_gRNA_19 | AUGGGCACUGGGGUGCCUUG (SEQ ID NO: 306) |
| Human_1_gRNA_20 | UUCCGAUGCCUUUGGAAAAU (SEQ ID NO: 307) |

FIG. 12A

Human Intronic Region 2 to Target for Genetic Construct Insertion

CTCACTTTAGGATAAGTTTTAGGTAAAATGTGCATCATTATCCTGAATTATTTCAGTTAAGCA
TGTTAGTTGGTGGCATAAGAGAAAACTCAATCAGATAGTGCTGAAGACAGGACTGTGGAGA
CACCTTAGAAGGACAGATTCTGTTCCGAATCACCGATGCGGCGTCAGCAGGACTGGCCTA
GCGGAGGCTCTGGGAGGGTGGCTGCCAGGCCCGGCCTGGGCTTTGGGTCTCCCCGGAC
TACCCAGA GCTGGGATGCGTGGCTTCTGCTGCCGGGCCGACTGGCTGCTCAGGCCCCA
GCCCTTGTTAATGGACTTGGAGGAATGATTCCATGCCAAAGCTTTGCAAGGCTCGCAGTGA
CCAGGCGCCCGACATGGTAAGAGACAGGCAGCCGCCGCTGCTGCATTTGCTTCTCTTAAA
ACTTTGTATTTGACGTCTTATTTCCACTAGAAGGGGAACTGGTCTTAATTGCTTGATGAAGA
GCAGGAGACTCATTTATGTGAGTCTTTTGAGTGACCATTGTCTGGGTCACTCCCATTTAACT
TTCCCTAAAGCCCATTTGAAGGAGAGGTCGCACGAGCTGCTCCACAACCTCTGAATGGGG
ATGGCATGGGTAATGATGCTTGAGAACATACCAAGCCCCACTGGCATCGCCCTTGTCTAAG
TCATTGACTGTAGGTCATCATCGCACCCTTGAAAGTAGCCCATGCCTTCCAAAGCGATTTAT
GGTAAATGGCAGAATTTTAAGTGGCAAATTCAGATAAAATGCATTTCTTGGTTGTTTCCAAT
GATGACTGTT ATCTAGAGGGAATTTAAAGGCAGGGGTTTACTGCAGACTCAGAAGGGAGG
GGATGCTCCGGGAAGGTGGAGGCTCTGAGCATCTCAATACCCTCCTCTTGGTGCAGAAGA
TATGCTGCCACTTCTAGAGCAAGGGGACCTGCTCATTTTTATCACAGCACAGGCTCCTAAA
TTCTTGGTCTCATTCTCAAGATGTTTTAATGACTTTAAAGCAGCAAAGAAATATTCCACCCA
GGTAGTGGAGGGTGGTAATGATTGGTAATGCTTTGGAACCAAAACCCAGGTGGCGCTGGG
GCAGGAC TGCAGGGAACTGGGGTATCAAGTAGAGGGAGACAAAAGATGGAAGCCAGC
CTGGCTGTGCAGGAACCCGGCAATGAGATGGCTTTAGCTGAGACAAGCAGGTCTGGTGG
GCTGACCATTTCTGGCCATGACAACTCCATCCAGCTTTCAGAAATGGACTCAGATGGGCAA
AACTGACCTAAGCTGACCTAGACTAAACAAGGCTGAAC (SEQ ID NO: 2)

FIG. 12B

| | |
|---|---|
| Human_region2_gRNA_1 | CTGACGCCGCATCGGTGATT<u>CGG</u> (SEQ ID NO: 25) |
| Human_region2_gRNA_2 | TTAGACAAGGGCGATGCCAGT<u>GG</u> (SEQ ID NO: 26) |
| Human_region2_gRNA_3 | CGTGCGACCTCTCCTTCAAA<u>TGG</u> (SEQ ID NO: 27) |
| Human_region2_gRNA_4 | AGCATATCTTCTGCACCAAG<u>AGG</u> (SEQ ID NO: 28) |
| Human_region2_gRNA_5 | ATATTCCACCCAGGTAGTGG<u>AGG</u> (SEQ ID NO: 29) |
| Human_region2_gRNA_6 | GTGCGACCTCTCCTTCAAAT<u>GGG</u> (SEQ ID NO: 30) |
| Human_region2_gRNA_7 | AGGTCCCCTTGCTCTAGAAG<u>TGG</u> (SEQ ID NO: 31) |
| Human_region2_gRNA_8 | CTCTAGATAACAGTCATCAT<u>TGG</u> (SEQ ID NO: 32) |
| Human_region2_gRNA_9 | TTGTCTAAGTCATTGACTGT<u>AGG</u> (SEQ ID NO: 33) |
| Human_region2_gRNA_10 | CCAAAGCGATTTATGGTAAA<u>TGG</u> (SEQ ID NO: 34) |
| Human_region2_gRNA_11 | TCTTTTGAGTGACCATTGTC<u>TGG</u> (SEQ ID NO: 35) |
| Human_region2_gRNA_12 | CCATTTACCATAAATCGCTT<u>TGG</u> (SEQ ID NO: 36) |
| Human_region2_gRNA_13 | AGGGCGATGCCAGTGGGGCT<u>TGG</u> (SEQ ID NO: 37) |
| Human_region2_gRNA_14 | AGCTAAAGCCATCTCATTGC<u>CGG</u> (SEQ ID NO: 38) |
| Human_region2_gRNA_15 | CCACAACCTCTGAATGGGGA<u>TGG</u> (SEQ ID NO: 39) |
| Human_region2_gRNA_16 | TTAATTGCTTGATGAAGAGC<u>AGG</u> (SEQ ID NO: 40) |
| Human_region2_gRNA_17 | TAGACAAGGGCGATGCCAGT<u>GGG</u> (SEQ ID NO: 41) |
| Human_region2_gRNA_18 | AAGCTGACCTAGACTAAACA<u>AGG</u> (SEQ ID NO: 42) |
| Human_region2_gRNA_19 | GCAGGAACCCGGCAATGAGA<u>TGG</u> (SEQ ID NO: 43) |
| Human_region2_gRNA_20 | TCTGTTCCGAATCACCGATG<u>CGG</u> (SEQ ID NO: 44) |

FIG. 12B (cont'd)

| | |
|---|---|
| Human_2_gRNA_1 | CUGACGCCGCAUCGGUGAUU (SEQ ID NO: 308) |
| Human_2_gRNA_2 | UUAGACAAGGGCGAUGCCAG (SEQ ID NO: 309) |
| Human_2_gRNA_3 | CGUGCGACCUCUCCUUCAAA (SEQ ID NO: 310) |
| Human_2_gRNA_4 | AGCAUAUCUUCUGCACCAAG (SEQ ID NO: 311) |
| Human_2_gRNA_5 | AUAUUCCACCCAGGUAGUGG (SEQ ID NO: 312) |
| Human_2_gRNA_6 | GUGCGACCUCUCCUUCAAAU (SEQ ID NO: 313) |
| Human_2_gRNA_7 | AGGUCCCUUGCUCUAGAAG (SEQ ID NO: 314) |
| Human_2_gRNA_8 | CUCUAGAUAACAGUCAUCAU (SEQ ID NO: 315) |
| Human_2_gRNA_9 | UUGUCUAAGCAUUGACUGU (SEQ ID NO: 316) |
| Human_2_gRNA_10 | CCAAAGCGAUUUAUGGUAAA (SEQ ID NO: 317) |
| Human_2_gRNA_11 | UCUUUUGAGUGACCAUUGUC (SEQ ID NO: 318) |
| Human_2_gRNA_12 | CCAUUUACCAUAAAUCGCUU (SEQ ID NO: 319) |
| Human_2_gRNA_13 | AGGGCGAUGCCAGUGGGGCU (SEQ ID NO: 320) |
| Human_2_gRNA_14 | AGCUAAAGCCAUCUCAUUGC (SEQ ID NO: 321) |
| Human_2_gRNA_15 | CCACAACCUCUGAAUGGGGA (SEQ ID NO: 322) |
| Human_2_gRNA_16 | UUAAUUGCUUGAUGAAGAGC (SEQ ID NO: 323) |
| Human_2_gRNA_17 | UAGACAAGGGCGAUGCCAGU (SEQ ID NO: 324) |
| Human_2_gRNA_18 | AAGCUGACCUAGACUAAACA (SEQ ID NO: 325) |
| Human_2_gRNA_19 | GCAGGAACCCGGCAAUGAGA (SEQ ID NO: 326) |
| Human_2_gRNA_20 | UCUGUUCCGAAUCACCGAUG (SEQ ID NO: 327) |

FIG. 13A

Mouse Eμ intronic enhancer sequence:

AGTCTAGATAATTGCATTCATTTAAAAAAAAAGTCTTTCTCCTAAAATGAATACTCAGAAAGT
GGTCTTGAAAAAGATTTGTGAAGCCGTTTTGACCAGAATGTCAAAGTCTTAATAGTAAGGCA
AAACAAACAACTAAAAAAGATCATGAACAAAGTCACTGTAAATGCTTCGGGTATTGGAAAAG
AATTGAATGGAGACCAATAATCAGAGGGAAGAATAATAGAGTAATTTTAAGAAGTTTTCTAA
ATATATTAGAAATTAAAGACACTAAAGTCCTTCAATTTCTTACATAACCTAATTTTGAAAATGA
ATTCTAAATACATTTTAGAAGTCGATAAACTTAAGTTTGGGGAAACTAGAACTACTCAAGCT
AAAATTAAAAGGTTGAACTCAATAAGTTAAAAGAGGACCTCTCCAGTTTCGGCTGAATCCTC
AACTTATTTTAGAAATGCAAATTACCCAGGTGGTGTTTTGCTCAGCCTGGACTTTCGGTTTG
GTGGGGCTGGACAGAGTGTTTCAAAACCACTTCTTCAAACCACAGCTACAAGTTTACCTAG
TGGTTTTATTTTCCCTTCCCCAAATAGCCTTGCCACATGACCTGCTTCCTGCCAGCTGCTGC
AGGTGTTCTGGTTCTGATCGGCCATCTTGACTCCAACTCAACATTGCTCAATTCATTTAAAA
ATATTTGAAACTTAATTTATTATTGTTAAAAGTCAGTTCTGAATAGGTTATGAGAGAGCCTCA
CTCCCATTCCTCGGTTAAACTTTAAGTAATATCAGTTCTACACAAACAAGACCTCAAACTGA
TTGACAAGAATTTTGGACATTTAAAAAAATGAGTACTTGAAAACCCTCTCACATTTTAAAGTC
ACAGTATTTAACTATTTTTCCTAGGAACCAACTTAAGAGTAAAAGCAACATCTTCTAATATTC
CATACACATACTTCTGTGTTCCTTTGAAAGCTGGACTTTTGCAGGCTCCACCAGACCTCTCT
AGACA (SEQ ID NO: 86)

Mouse Intronic Region 1 to Target for Genetic Construct Insertion:

GGACTACTGGGGTCAAGGAACCTCAGTCACCGTCTCCTCAGGTAAGAATGGCCTCTCCAG
GTCTTTATTTTTAACCTTTGTTATGGAGTTTTCTGAGCATTGCAGACTAATCTTGGATATTTG
TCCCTGAGGGAGCCGGCTGAGAGAAGTTGGGAAATAAACTGTCTAGGGATCTCAGAGCCT
TTAGGACAGATTATCTCCACATCTTTGAAAAACTAAGAATCTGTGTGATGGTGTTGGTGGAG
TCCCTGGATGATGGGATAGGGACTTTGGAGGCTCATTTGAAGAAGATGCTAAAACAATCCT
ATGGCTGGAGGGATAGTTGGGGCTGTAGTTGGAGATTTTCAGTTTTTAGAATAAAAGTATTA
GTTGTGGAATATACTTCAGGACCACCTCTGTGACAGCATTTATACAGTATCCGATGCATAG
GGACAAAGAGTGGAGTGGGGCACTTTCTTTAGATTTGTGAGGAATGTTCCGCACTAGATTG
TTTAAAACTT CATTTGTTGGAAGGAGAGCTGTCTTAGTGATTGAGTCAAGGGAGAAAGGC
ATCTAGCCTCGGTCTCAAAAGGGTAGTTGCTG (SEQ ID NO: 3)

FIG. 13B

| | |
|---|---|
| Mouse_Region_1_gRNA_1 | CAACTACCCTTTTGAGACCGAGG (SEQ ID NO: 45) |
| Mouse_Region_1_gRNA_2 | TTATACAGTATCCGATGCATAGG (SEQ ID NO: 46) |
| Mouse_Region_1_gRNA_3 | TATACAGTATCCGATGCATAGGG (SEQ ID NO: 47) |
| Mouse_Region_1_gRNA_4 | CATCTAGCCTCGGTCTCAAAAGG (SEQ ID NO: 48) |
| Mouse_Region_1_gRNA_5 | CACTCTTTGTCCCTATGCATCGG (SEQ ID NO: 49) |
| Mouse_Region_1_gRNA_6 | ATCTAGCCTCGGTCTCAAAAGGG (SEQ ID NO: 50) |
| Mouse_Region_1_gRNA_7 | AAGTTTTAAACAATCTAGTGCGG (SEQ ID NO: 51) |
| Mouse_Region_1_gRNA_8 | AAGATGCTAAAACAATCCTATGG (SEQ ID NO: 52) |
| Mouse_Region_1_gRNA_9 | TGCTAAAACAATCCTATGGCTGG (SEQ ID NO: 53) |
| Mouse_Region_1_gRNA_10 | AAGTCCCTATCCCATCATCCAGG (SEQ ID NO: 54) |
| Mouse_Region_1_gRNA_11 | GGGAGAAAGGCATCTAGCCTCGG (SEQ ID NO: 55) |
| Mouse_Region_1_gRNA_12 | TGAGCATTGCAGACTAATCTTGG (SEQ ID NO: 56) |
| Mouse_Region_1_gRNA_13 | TTAGTTGTGGAATATACTTCAGG (SEQ ID NO: 57) |
| Mouse_Region_1_gRNA_14 | TGGTGGAGTCCCTGGATGATGGG (SEQ ID NO: 58) |
| Mouse_Region_1_gRNA_15 | GTGGAGATAATCTGTCCTAAAGG (SEQ ID NO: 59) |
| Mouse_Region_1_gRNA_16 | AGTCCCTATCCCATCATCCAGGG (SEQ ID NO: 60) |
| Mouse_Region_1_gRNA_17 | ATCTTGGATATTTGTCCCTGAGG (SEQ ID NO: 61) |
| Mouse_Region_1_gRNA_18 | GGGATAGTTGGGGCTGTAGTTGG (SEQ ID NO: 62) |
| Mouse_Region_1_gRNA_19 | CAGGTAAGAATGGCCTCTCCAGG (SEQ ID NO: 63) |
| Mouse_Region_1_gRNA_20 | TCTCTCAGCCGGCTCCCTCAGGG (SEQ ID NO: 64) |

FIG. 13B (cont'd)

| | |
|---|---|
| Mouse_1_gRNA_1 | CAACUACCCUUUUGAGACCG (SEQ ID NO: 328) |
| Mouse_1_gRNA_2 | UUAUACAGUAUCCGAUGCAU (SEQ ID NO: 87) |
| Mouse_1_gRNA_3 | UAUACAGUAUCCGAUGCAUA (SEQ ID NO: 329) |
| Mouse_1_gRNA_4 | CAUCUAGCCUCGGUCUCAAA (SEQ ID NO: 330) |
| Mouse_1_gRNA_5 | CACUCUUUGUCCCUAUGCAU (SEQ ID NO: 331) |
| Mouse_1_gRNA_6 | AUCUAGCCUCGGUCUCAAAA (SEQ ID NO: 332) |
| Mouse_1_gRNA_7 | AAGUUUUAAACAAUCUAGUG (SEQ ID NO: 333) |
| Mouse_1_gRNA_8 | AAGAUGCUAAAACAAUCCUA (SEQ ID NO: 334) |
| Mouse_1_gRNA_9 | UGCUAAAACAAUCCUAUGGC (SEQ ID NO: 335) |
| Mouse_1_gRNA_10 | AAGUCCUAUCCCAUCAUCC (SEQ ID NO: 336) |
| Mouse_1_gRNA_11 | GGGAGAAAGGCAUCUAGCCU (SEQ ID NO: 337) |
| Mouse_1_gRNA_12 | UGAGCAUUGCAGACUAAUCU (SEQ ID NO: 338) |
| Mouse_1_gRNA_13 | UUAGUUGUGGAAUAUACUUC (SEQ ID NO: 339) |
| Mouse_1_gRNA_14 | UGGUGGAGUCCCUGGAUGAU (SEQ ID NO: 340) |
| Mouse_1_gRNA_15 | GUGGAGAUAAUCUGUCCUAA (SEQ ID NO: 341) |
| Mouse_1_gRNA_16 | AGUCCUAUCCCAUCAUCCA (SEQ ID NO: 342) |
| Mouse_1_gRNA_17 | AUCUUGGAUAUUUGUCCCUG (SEQ ID NO: 343) |
| Mouse_1_gRNA_18 | GGGAUAGUUGGGGCUGUAGU (SEQ ID NO: 344) |
| Mouse_1_gRNA_19 | CAGGUAAGAAUGGCCUCUCC (SEQ ID NO: 345) |
| Mouse_1_gRNA_20 | UCUCUCAGCCGGCUCCCUCA (SEQ ID NO: 346) |

FIG. 14A

Mouse Intronic Region 2 to Target for Genetic Construct Insertion

TTATTTCAGTTGAACATGCTGGTTGGTGGTTGAGAGGACACTCAGTCAGTCAGTGACGTGA
AGGGCTTCTAAGCCAGTCCACATGCTCTGTGTGAACTCCCTCTGGCCCTGCTTATTGTTGA
ATGGGCCAAAGGTCTGAGACCAGGCTGCTGCTGGGTAGGCCTGGACTTTGGGTCTCCCAC
CCAGACCTGGGAATGTATGGTTGTGGCTTCTGCCACCCATCCACCTGGCTGCTCATGGAC
CAGCCAGCCTCGGTGGCTTTGAAGGAACAATTCCACACAAAGACTCTGGACCTCTCCGAA
ACCAGGCACCGCAAATGGTAAGCCAGAGGCAGCCACAGCTGTGGCTGCTGCTCTTAAAGC
TTGTAAACTGTTTCTGCTTAAGAGGGACTGAGTCTTCAGTCATTGCTTAGGGGGAGAAAG
AGACATTTGTGTGTCTTTTGAGTACCGTTGTCTGGGTCACTCACATTTAACTTTCCTTGAAA
AACTAGTAAAAGAAAAATGTTGCCTGTTAACCAATAATCATAGAGCTCATGGTACTTTGAGG
AAATCTTAGAAAGCGTGTATACAATTGTCTGGAATTATTTCAGTTAAGTGTATTAGTTGAGGT
ACTGATGCTGTCTCTACTTCAGTTATACATGTGGGTTTGAATTTTGAATCTATTCTGGCTCTT
CTTAAGCAGAAAATTTAGATAAAATGGATACCTCAGTGGTTTTTAATGGTGGGTTTAATATA
GAAGGAATTTAAATTGGAAGCTAATTTAGAATCAGTAAGGAGGGACCCAGGCTAAGAAGGC
AATCCTGGGATTCTGGAAGAAAAGATGTTTTTAGTTTTTATAGAAAACACTACTACATTCTTG
ATCTACAACTCAATGTGGTTTAATGAATTTGAAGTTGCCAGTAAATGTACTTCCTGGTTGTTA
AAGAATGGTATCAAAGGACAGTGCTTAGATCCGAGGTGAGTGTGAGAGGACAGGGGCTGG
GGTATGGATACGCAGAAGGAAGGCCACAGCTGTACAGAATTGAGAAAGAATAGAGACCTG
CAGTTGAGGCCAGCAGGTCGGCTGGACTAACTCTCCAGCCACAGTAATGACCCAGACAGA
GAAAGCCAGACTCATAAAGCTTGCTGAGCAAAATTAAGGGAACAAGGTTGAGAGCCCTAGT
AAGCGAGGCTCTAAAAAGCACAGCTGAGCTGAGATGGGTGGGCTTCTCTGAGTGCTTCTA
AAATGCGCTAAACTGAGGTGATTACTCTGAGGTAAGCAAAGCTGGGCTTGAGCCAAAATGA
AGTAGACTGTAATGAACTGGAATGAGCTGGGCCGCTAAGCTAAACTAGGCTGGCTTAACC
GAGATGAGCCAAACTGGAATGAACTTCATTAATCTAGGTTGAATAGAGCTAAACTCTACTGC
CTACACTGGACTGTTCTGAGCTGAGATGAGCTGGGGTGAGCTCAGCTATGCTACGCTGTG
TTGGGGTGAGCTGATCTGAAATGAGATACTCTGGAGTAGCTGAGATGGGGTGAGATGGGG
TG (SEQ ID NO: 4)

FIG. 14B

| | |
|---|---|
| MOUSE_REGION_2_gRNA__1 | CCGAAACCAGGCACCGCAAATGG (SEQ ID NO: 65) |
| MOUSE_REGION_2_gRNA__2 | CACCGCAAATGGTAAGCCAGAGG (SEQ ID NO: 66) |
| MOUSE_REGION_2_gRNA__3 | GGCTTACCATTTGCGGTGCCTGG (SEQ ID NO: 67) |
| MOUSE_REGION_2_gRNA__4 | TGCGGTGCCTGGTTTCGGAGAGG (SEQ ID NO: 68) |
| MOUSE_REGION_2_gRNA__5 | CAGCTATGCTACGCTGTGTTGGG (SEQ ID NO: 69) |
| MOUSE_REGION_2_gRNA__6 | AAGGACAGTGCTTAGATCCGAGG (SEQ ID NO: 70) |
| MOUSE_REGION_2_gRNA__7 | TCAGTCAGTCAGTGACGTGAAGG (SEQ ID NO: 71) |
| MOUSE_REGION_2_gRNA__8 | CATGCTGGTTGGTGGTTGAGAGG (SEQ ID NO: 72) |
| MOUSE_REGION_2_gRNA__9 | TCTTTTGAGTACCGTTGTCTGGG (SEQ ID NO: 73) |
| MOUSE_REGION_2_gRNA__10 | TGGCCCATTCAACAATAAGCAGG (SEQ ID NO: 74) |
| MOUSE_REGION_2_gRNA__11 | CTGGGCCGCTAAGCTAAACTAGG (SEQ ID NO: 75) |
| MOUSE_REGION_2_gRNA__12 | GCCAGCCTAGTTTAGCTTAGCGG (SEQ ID NO: 76) |
| MOUSE_REGION_2_gRNA__13 | TGAAGTAGACTGTAATGAACTGG (SEQ ID NO: 77) |
| MOUSE_REGION_2_gRNA__14 | GACCTGGGAATGTATGGTTGTGG (SEQ ID NO: 78) |
| MOUSE_REGION_2_gRNA__15 | GGTATGGATACGCAGAAGGAAGG (SEQ ID NO: 79) |
| MOUSE_REGION_2_gRNA__16 | GTTGAGAGCCCTAGTAAGCGAGG (SEQ ID NO: 80) |
| MOUSE_REGION_2_gRNA__17 | GCCGCTAAGCTAAACTAGGCTGG (SEQ ID NO: 81) |
| MOUSE_REGION_2_gRNA__18 | TCAGCTATGCTACGCTGTGTTGG (SEQ ID NO: 82) |
| MOUSE_REGION_2_gRNA__19 | TTTTAGAGCCTCGCTTACTAGGG (SEQ ID NO: 83) |
| MOUSE_REGION_2_gRNA__20 | CTCTATGATTATTGGTTAACAGG (SEQ ID NO: 84) |

FIG. 14B (cont'd)

| | |
|---|---|
| MOUSE_2_gRNA__1 | CCGAAACCAGGCACCGCAAA (SEQ ID NO: 347) |
| MOUSE_2_gRNA__2 | CACCGCAAAUGGUAAGCCAG (SEQ ID NO: 348) |
| MOUSE_2_gRNA__3 | GGCUUACCAUUUGCGGUGCC (SEQ ID NO: 349) |
| MOUSE_2_gRNA__4 | UGCGGUGCCUGGUUUCGGAG (SEQ ID NO: 350) |
| MOUSE_2_gRNA__5 | CAGCUAUGCUACGCUGUGUU (SEQ ID NO: 351) |
| MOUSE_2_gRNA__6 | AAGGACAGUGCUUAGAUCCG (SEQ ID NO: 352) |
| MOUSE_2_gRNA__7 | UCAGUCAGUCAGUGACGUGA (SEQ ID NO: 353) |
| MOUSE_2_gRNA__8 | CAUGCUGGUUGGUGGUUGAG (SEQ ID NO: 354) |
| MOUSE_2_gRNA__9 | UCUUUUGAGUACCGUUGUCU (SEQ ID NO: 355) |
| MOUSE_2_gRNA__10 | UGGCCCAUUCAACAAUAAGC (SEQ ID NO: 356) |
| MOUSE_2_gRNA__11 | CUGGGCCGCUAAGCUAAACU (SEQ ID NO: 357) |
| MOUSE_2_gRNA__12 | GCCAGCCUAGUUUAGCUUAG (SEQ ID NO: 358) |
| MOUSE_2_gRNA__13 | UGAAGUAGACUGUAAUGAAC (SEQ ID NO: 359) |
| MOUSE_2_gRNA__14 | GACCUGGGAAUGUAUGGUUG (SEQ ID NO: 360) |
| MOUSE_2_gRNA__15 | GGUAUGGAUACGCAGAAGGA (SEQ ID NO: 361) |
| MOUSE_2_gRNA__16 | GUUGAGAGCCCUAGUAAGCG (SEQ ID NO: 362) |
| MOUSE_2_gRNA__17 | GCCGCUAAGCUAAACUAGGC (SEQ ID NO: 363) |
| MOUSE_2_gRNA__18 | UCAGCUAUGCUACGCUGUGU (SEQ ID NO: 364) |
| MOUSE_2_gRNA__19 | UUUUAGAGCCUCGCUUACUA (SEQ ID NO: 365) |
| MOUSE_2_gRNA__20 | CUCUAUGAUUAUUGGUUAAC (SEQ ID NO: 366) |

FIG. 23A
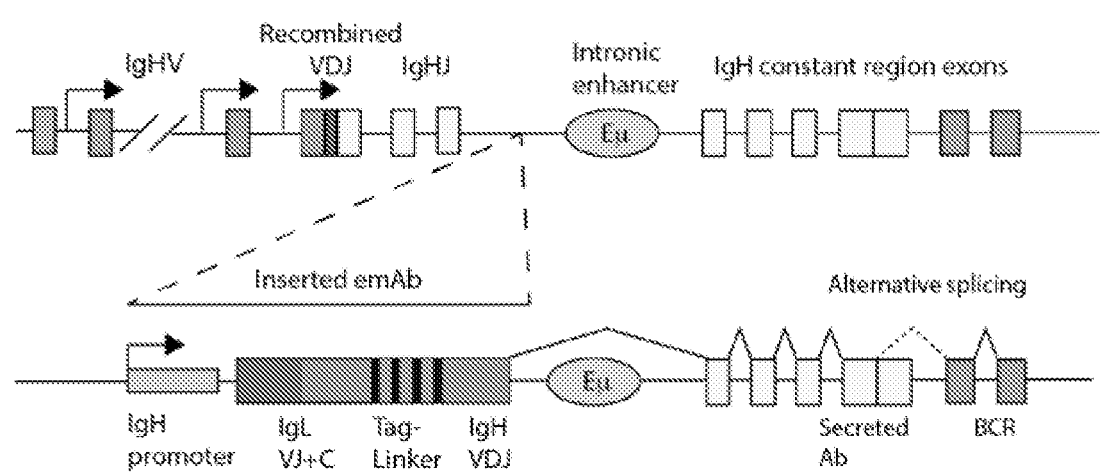

FIG. 25A sgRNA sequences:

Mouse: sgRNA-mIgH_3: UUAUACAGUAUCCGAUGCAU (SEQ ID NO: 87)
Human: sgRNA-hIgH-6: GCAUUGCAGGUUGGUCCUCG (SEQ ID NO: 88)
      sgRNA-hIgH-7: GUCUCAGGAGCGGUGUCUGU (SEQ ID NO: 89)

Mouse (for sgRNA-mIgH_3) Genome Homology Regions:
Upstream: CATCGGATACTGTATAAATGCTGTCACAGAGGTGGT (SEQ ID NO: 90)
Downstream: CATAGGGACAAAGAGTGGAGTGGGGCACTTTCTTTA (SEQ ID NO: 91)

Human (for sgRNA-hIgH-7) Genome Homology Regions:
GACACCGCTCCTGAGACACATTCCTCAGCCATCACT (SEQ ID NO: 92)
TGTAGGACTGCAAGATCGCTGCACAGCAGCGAATCG (SEQ ID NO: 93)

Human (for sgRNA-hIgH-6) Genome Homology Regions:
GGGACCAACCTGCAATGCTCAGGAAACCCCACAGGCA (SEQ ID NO: 94)
TTCGGGGCATGTTCCGAGGGGACCTGGGCGGACTGGC (SEQ ID NO: 95)

Splicing oligonucleotides (homology to genome indicated in bold):

Mouse (for sgRNA-mIgH_3):
Upstream:CTTCGAGACATGTACAGACCATTTAGATGTAGTATCAAAGCCTAATATCTCAATCTT
AAAATAGAATCCTAACCTGAGACACTCACTTGTC**CATCGGATACTGTATAAATGCTGTCACA
GAGGTGGT** (SEQ ID NO: 96)
Downstream:CTTCTCCCATTCTAAATGCATGTTGGGGGGATTCTGGGCCTTCAGGACCAC**ATA
GGGACAAAGAGTGGAGTGGGGCACTTTCTTTA** (SEQ ID NO: 97)

Human (for sgRNA-hIgH-7):
Upstream:GTGCACAGCGCTCTTCCCGCTGCAGAACAAACCCCAACCCCAGGATGCACTCCTC
ACTGTGAACCCACATTTTATTGGCCTAAAGATTACG**GACACCGCTCCTGAGACACATTCCTC
AGCCATCACT** (SEQ ID NO: 98)
Downstream:GTCTGGGGATAGCGGGGAGCCAGGTGTACTGGGCCAGGCAAGGGCTTTGG**TG
TAGGACTGCAAGATCGCTGCACAGCAGCGAATCG** (SEQ ID NO: 99)

Human (for sgRNA-hIgH-6):
Upstream:GTGCACAGCGCTCTTCCCGCTGCAGAACAAACCCCAACCCCAGGATGCACTCCTC
ACTGTGAACCCACATTTTATTGGCCTAAAGATTACG**GGGACCAACCTGCAATGCTCAGGAAA
CCCCACAGGCA** (SEQ ID NO: 100)
Downstream:GTCTGGGGATAGCGGGGAGCCAGGTGTACTGGGCCAGGCAAGGGCTTTGG**TT
CGGGGCATGTTCCGAGGGGACCTGGGCGGACTGGC** (SEQ ID NO: 101)

FIG. 25B
human anti-RSV emAb AAV (2531 bp)

```
TGTGAGGCCGGAGAGAAGGGTCTCTGGGTGGACTGGGTTTTTGTGGGTGAGGATGGACATTCTGCCATTGTGATTACTACTACTACTACATGGAGCGTCTGGG
                                             Human T7 Upstream Homology
         20           40           60           80          100

GCAAAGGGACCACGGTCACCGTCTCCTCAGGTAAGAATGGCCACTCTAGGGCCTTTGTTTCTGCTACTGCCTGTGGGGTTTCCTGAGCATTGCAGGTTGGTCCTCG
                                             Human T7 Upstream Homology
        120          140          160          180          200

GGGACTCAGGTGTTCCGAGGGGACCTGGGCCGGATGGGCACTGGGGTGCCTTGAGGATCTGGGAGCCTCTGTGGATTTTCCGATGCCTTTGGAAAATG
                                             Human T7 Upstream Homology
        220          240          260          280          320

GGACTCAGGTGGTGCCTCTGATGGAGTAACTGAGCCTGGGGAGCCCACATTTGGACGAGATGCCTGAACAACCAGGGTCTTAGTGATGGCTGAGGA
                                             Human T7 Upstream Homology
        340          360          380          400          420

ATGTGTCTCAGGAGCGGTGTCTGATCGTAATCTTTAGGCCCAATAAAATGTGGGTTCACAGTGAGGAGTGCATCCTGGGGTTGGGGTTTGTTCTGCAGCGGGAAGAGC
                                             IgWH1-69 Promoter
        440          460          480          500          520
```

>Human T7 upstream homology region in human anti-RSV emAb AAV
TGTGACGCCCGGAGAGACAGAAGGTCTCTGGGTGGCTGGGTTTTGTGGGTGAGGATGGACATTCTGCCATTGTGATTACTACTA
CTACTACTACATGACGTCTGGGCAAAGGACCACGTCCTCAGTAAGAATGGCCACTCTAGGGCCTTTGTTT
CTGCTACTGCCTGTGGGGTTCCTGAGCATTGCAGGTTGGTCCTGGAGGACCATGTCCGAGGGGACCTGGCCAG
GAGGGGACTGGCACTGGGGTGCCTTGAGGATCTGGGAGCCTCTGTGGATTTTCCGATGCCTTTGGAAAATGGGACTCAGGTTG
GGTGCGTCTGATGAGTAACTGAGCCTGGGGGCTTGGGAGCCACATTTGGAACGAGATGCCTG

FIG. 25B (cont'd)

>hRSV variable light chain coding sequence in human anti-RSV emAb AAV
GACATCCAGATGACACAGAGCCCTAGCACACTGTCTGCCAGCGTGGGCGACAGAGTGACCATCACATGCAAGTGCCAGCTGAG
CGTGGGCTACATGCACTGGTATCAGCAAAAGCCCGGCAAGGCCCCTAAGCTGCTGATCTACGATACCTCCAAGCTGGCCTCTG
GCGTGCCCTCCAGATTTTCTGGCAGCGGCAGCGGAACCGAGTTCACCCTGACCATCTCAAGCCTGCAGCCTGACGACTTCGCT
ACGTACTACTGCTTCCAAGGCAGCGGCTACCCCTTCACATTTGGCGGCGGAACAAAGCTGGAAATCAAGCGG (SEQ ID NO: 114)

>kappa constant light chain coding sequence in human anti-RSV emAb AAV
ACTGTGGCCGCTCCTAGCGTGTTCATCTTTCCACCTAGCGACGAGCAGCTGAAGTCTGGCACTGCCTCTGTCGTGTGCCTGCTG
AACAACTTCTACCCTCGAGAGGCCAAGGTGCAGTGGAAAGTGGACAATGCCCTGCAGAGCGGCAACAGCCAAGAGTCTGTGAC
CGAGCAGGACTCCAAGGATTCCACCTACAGCCTGTCTAGCACCCTGACTCTGAGCAAGGCCGACTACGAGAAGCACAAGGTGT
ACGCCTGCGAAGTGACACACCAGGGACTGAGCAGCCCTGTGACCAAGAGCTTCAATCGGGGCGAGTGC (SEQ ID NO: 115)

>GSSG-streptag linker coding sequence in human anti-RSV emAb AAV
GGAGGAAGTAGTGGCAGCGGGAGTGGGTCCAATTGGAGTCATCCTCAATTTGAGAAAGGAGGGGGAGGGTCCAATTGGTCTCA
TCCGCAGTTTGAGAAGGGCGGCGGCGGCTCCAATTGGTCCCATCCCCAGTTTGAAAAAGGCTCTGGTGGAGGTGGTAGTGCTG
GTGGG (SEQ ID NO: 116)

>hRSV variable heavy chain coding sequence in human anti-RSV emAb AAV
CAAGTGACCCTGAGAGAGTCTGGACCTGCTCTGGTCAAGCCCACACAGACCCTGACACTGACCTGCACCTTCAGCGGCTTTAG
CCTGAGCACAAGCGGCATGAGCGTCGGCTGGATTAGACAGCCTCCTGGCAAAGCCCTGGAATGGCTGGCCGACATTTGGTGG
GACGACAAGAAGGACTACAACCCCAGCCTGAAGTCCCGGCTGACCATCAGCAAGGACACCAGCAAGAACCAGGTGGTGCTGAA
AGTGACCAACATGGACCCTGCCGACACCGCCACCTACTACTGTGCCAGATCCATGATCACCAACTGGTACTTCGACGTGTGGGG
AGCCGGCACCACAACCGTCTCTTCA (SEQ ID NO: 117)

>signal peptide amino acid sequence in human anti-RSV emAb AAV
MATGSRTSLLLAFGLLCLPWLQEGSA (SEQ ID NO: 118)

FIG. 25B (cont'd)

>hRSV light chain amino acid sequence in human anti-RSV emAb AAV
MATGSRTSLLLAFGLLCLPWLQEGSADIQMTQSPSTLSASVGDRVTITCKCQLSVGYMHWYQQKPGKAPKLLIYDTSKLASGVPSRFS
GSGSGTEFTLTISSLQPDDFATYYCFQGSSGYPFTFGGGTKLEIKRTVAAPSVFIFPPSDEQLKSGTASVVCLLNNFYPREAKVQWKVD
NALQSGNSQESVTEQDSKDSTYSLSSTLTLSKADYEKHKVYACEVTHQGLSSPVTKSFNRGEC (SEQ ID NO: 119)

>hRSV variable light chain amino acid sequence in human anti-RSV emAb AAV
DIQMTQSPSTLSASVGDRVTITCKCQLSVGYMHWYQQKPGKAPKLLIYDTSKLASGVPSRFSGSGSGTEFTLTISSLQPDDFATYYCF
QGSSGYPFTFGGGTKLEIKR (SEQ ID NO: 120)

>kappa constant light chain amino acid sequence in human anti-RSV emAb AAV
TVAAPSVFIFPPSDEQLKSGTASVVCLLNNFYPREAKVQWKVDNALQSGNSQESVTEQDSKDSTYSLSSTLTLSKADYEKHKVYACEV
THQGLSSPVTKSFNRGEC (SEQ ID NO: 121)

>GSSG-streptag linker amino acid sequence in human anti-RSV emAb AAV
GGSSGSGSGSNWSHPQFEKGGGGSNWSHPQFEKGGGGSNWSHPQFEKGSGGGGSAGG (SEQ ID NO: 122)

>hRSV variable heavy chain amino acid sequence in human anti-RSV emAb AAV
QVTLRESGPALVKPTQTLTLTCTFSGFSLSTSGMSVGWIRQPPGKALEWLADIWWDDKKD
YNPSLKSRLTISKDTSKNQVVLKVTNMDPADTATYYCARSMITNWYFDVWGAGTTTVSS (SEQ ID NO: 123)

>splice junction with flanking sequence in human anti-RSV emAb AAV
CAGGTAAGTCTGTCTGGGGATAGCGGGGGAGCCAGGTGCTGGGCCAGGCAAGGGCTTTGGATC (SEQ ID NO: 124)

>Human T7 downstream homology in human anti-RSV emAb AAV
GTAGGACTGCAAGATCGCTGCACAGCAGCGAATCGTGAAATATTTTCTTAGAATTATGAGGTGCGCTGTGTGTCAACCTGCATC
TAAATTCTTTATTGGCTGGAAAGAGAACTGTCGGAGTGGGTGAATCCAGCCAGAGGACGCGTAGCCCCCGGTCTTGATGAGA
GCAGGGTTGGGGGCAGGGTAGCCCAGAAACGGTGCTGCCGTCCTGACGAGGGCTTAGGGAGGCTCCAGGACCTCAGTGC
CTTGAAGCTGGTTTCCATGAGAAAAGGATTGTTTATCTTAGGAGGCATGCTTACTGTTAAAAGACAGGATATGTTGAAGTGGCTT
CTGAGAAAAATGGTTAAGAAAATTATGACTTAAAAATGTGAGAGATTTTCAAGTATATTAATTTTTTAACTGTCCAAGTATTTGAAA
TTCTTATCATTTGATTAACACCCATG (SEQ ID NO: 125)

FIG. 25B (cont'd)

>hRSV light chain coding sequence without signal sequence in human anti-RSV emAb AAV
GACATCCAGATGACACAGAGCCCTAGCACACTGTCTGCCAGCGTGGGCGACAGAGTGACCATCACATGCAAGTGCCAGCTGAG
CGTGGGCTACATGCACTGGTATCAGCAGAAGCCCGGCAAGGCCCCTAAGCTGCTGATCTACGATACCTCCAAGCTGGCCTCTG
GCGTGCCCTCCAGATTTTCTGGCAGCGGCAGCGGAACCGAGTTCACCCTGACCATCTCAAGCCTGCAGCCTGACGACTTCGCT
ACGTACTACTGCTTCCAAGGCAGCGGGCTACCCCTTCACATTTGGCGGAACAAAGCTGGAAATCAAGCGGACTGTGGCCGC
TCCTAGCGTGTTCATCTTTCCACCTAGCGACGAGCAGCTGAAGTCTGGCACTGCCTCTGTCGTGTGCCTGCTGAACAACTTCTA
CCCTCGAGAGGCCAAGGTGCAGTGGAAAGTGGACAATGCCCTGCAGAGCGGCAACAGCCAAGAGAGCGTGACCGAGCAGGAC
TCCAAGGATTCCACCTACAGCCTG FIG. 25C
mouse anti-RSV emAb AAV (3134 bp)

CCAGGGGTGATTCTAGTCAGACTCTGGGGTTTTTGTCGGGTATAGAGGAAAAATCCACTATTGTGATTACTATGCTATGGACTACTGGGGTCAAGGAACCTCAGTCA
mB3 Balb/C Upstream
20 40 60 80 100

CCGTCTCCTCAGGTAAGAATGGCCTCTCCAGGTCTTTATTTTTAACCTTTGTTATGGAGTTTTCTGAGCATTGCAGACTAATCTTGGATATTTGTCCCTGAGGGAGC
mB3 Balb/C Upstream
120 140 160 180 200

CGGCTGAGAGAAGTTGGGAAATAAACTGTCTAGGGATCTCAGAGCCTTTAGGACAGATTATCTCCACATCTTTGAAAAACTAAGAATCTGTGTGATGGTGTTGGTGG
mB3 Balb/C Upstream
220 240 260 280 300 320

AGTCCCTGGATGATGGGATAGGGACTTTGGAGGCTCATTTGAGGGAGATGCTAAAACAATCCTATGGCTGGAGGGATAGTTGGGGCTGTAGTTGGAGATTTTCAGTT
mB3 Balb/C Upstream
340 360 380 400 420

TTTAGAATAAAAGTATTAGTTGTGGAATATACTTCAGGACCACCTCTGTGACAGCATTTATACAGTATCCGATGGATGACAAGTGAGTGTCTCAGGTTAGGATTCTA
mB3 Balb/C Upstream J558H10 Promoter
440 460 480 500 520

FIG. 25C (cont'd)

>Mouse mB3 Balb/C upstream region in mouse anti-RSV emAb AAV
CCAGGGGTGATTCTAGTCAGACTCTGGGTTTTTGTCGGTATAGAGGAAAAATCCACTATTGTGATTACTATGCTATGGACTAC
TGGGGTCAAGGAACCTCAGTCACCGTCTCCTCAGGTAAGAATGGCCTCTCCAGGTCTTTATTTTAACCTTTGTTATGGAGTTTC
TGAGCATTGCAGACTAATCTTGGATATTGTCCCTGAGGGAGCCGGCTGAGAGAAGTTGGGAAATAAACTGTCTAGGGATCTCA
GAGCCTTTAGGACAGATTATCTCCACATCTTTGAAAAACTAAGAATCTGTGTGATGGTCCTGATGATGGAT
AGGGACTTTGGAGGCTCATTTGAGGGAGATGCTAAAACAATCCTATGGCTGGGAGGGATAGTTGGGGCTGTAGTTGGAGATTTTC
AGTTTTTAGAATAAAAGTATTAGTTGTGTGGAATATACTTCAGGACCACCTCTGTGACAGCATTTATACAGTATCCGATG (SEQ ID
NO: 127)

>J558H10 promoter in mouse anti-RSV emAb AAV
GACAAGTGAGTGTCTCAGGTTAGGATTCTATTTAAGATTGAGATATTAGGCTTTGATACTACATCTAAATGGTCTGTACATGTCT
CGAAGAAAGTTCTTCAGACAGAGTTAGGACTTGGATCCAGGAGTAGGACTTGGACTCTAGTTCTTCTTC
TCCAGCTGGAATGTCCTTATGTAAGAAAAGCCTTGCCTCATGAATCATGTGCAATCATGTGCGACTGTGATGATTAATATAGGGATAT
CCACACCAAACATCATATGAGCCTATCTTCTACAGACACTGAATCTCAAGGTCCTTACA (SEQ ID NO: 128)

>Signal peptide coding sequence in mouse anti-RSV emAb AAV
ATGGAAACCGACACACTGCTGCTGTGGGTGCTGCTTCTTTGGGTGCCCGGAAGCACAGGC (SEQ ID NO: 129)

>mRSV kappa light chain coding sequence in mouse anti-RSV emAb AAV
ATGGAAACCGACACACTGCTGCTGTGGGTGCTGCTTCTTTGGGTGCCCGGAAGCACAGGC
GACATCCAGCTGACACAGAGCCCTGCCATCATGTCTGCTAGCCCTGGCGAGAAAGTGACAATGACCTGTTCCGCCAGCAGCTC
CGTGTCCTACATGCACTGGTATCAGCAGAAGTCTAGCACAAGCCCTAAGCTGTGGATCTACGACACACCTCCAAGCTGGCCTCTG
GCGTGCCAGGCAGATTTCTGGAAGCGGCAGCGGCTACCCCTTCACATTTGGCTGCACATGGAAATCAAGGCCGATGCCGCTCC
ACCTACTACTGCTTCAGAGGCAGCCATTAGCAGCCTGAGATCTGGGGGAGCCTCTGTGTGCTTCCTGAACAACTTCTACCCT
AAGGACATCAACGTCAAGTGGAAGATCGACGGCAGCGAGCGGCGGCTCCGAGAGCAGAAGGACAGCACTGACTCTGAACCTGCCTGTGTCCAACAGGAGACAGCAA
GGATAGCACCTACAGCATGAGCAGCACACTCTGACCCTGACAAGCAGCACTGACCAGCAGCAGCGAGAGGCACACGCCACATGCGAGGTG
CACACAAGACCAGCACATCCCCAATCGTGAAGTCCTTCAACCGGAACGAGT

FIG. 25C (cont'd)

>mPalivizumab variable light chain coding sequence in mouse anti-RSV emAb AAV
GACATCCAGCTGACACAGAGCCCTGCCATCATGTCTGCCTCAGCAGTCGCCCTGGCGAGAAAGTGACAATGACCTGTTCCGCCAGCAGCTC
CGTGAGCTACATGCACTGGTATCAGCAGAAGTCTAGCACAGCCCAAGCCCTGTGGATCTACGACACATCCAAGCTGGCCTCTG
GCGTGCCAGGCAGATTTCTGGAAGCGGCAGCGGCAACAGCTACAGCCTGACTATCAGCTCCATCCAGGCCGAGGATGTGGCT
ACCTACTACTGCTTCCAGAGGCAGCGGCTACCCCTTCACATTTGGCCAGGGCACCAAGCTGGAAATCAAG (SEQ ID NO: 131)

>mIgL kappa constant light chain coding sequence in mouse anti-RSV emAb AAV
GCCGATGCCGCTCCTACCGTGTCTATCTTTCCACCTAGCAGCGAGCAGCTGACATCTGGGCGAGCCTCTGTCGTGTGCTTCCTG
AACAACTTCTACCCTAAGGACATCAACGTCAAGTGGAAGATCGACGGCTCCGAGAGACAGAACGGCGTGCTGAACTCTTGACC
GACCAGGACAGCAAGGATAGCACCTACAGCCTGAGCAGCACTCTGACCCTGAAGGACGAGTACGAGAGGCACAACTCCTA
CACATGCGAGGCCACACACAAGACCAGCACATCCCCAATGCTGAAGTCCTTCAACCGGAACGAGTGC (SEQ ID NO: 132)

>GSSG-streptag linker coding sequence in mouse anti-RSV emAb AAV is SEQ ID NO: 116

>mPalivizumab variable heavy chain coding sequence in mouse anti-RSV emAb AAV
CAGGTGCAGCTGGAACTGCAAGAAGCGGCCCTGGCATCCTGCAGCCTTCTCAGACACTGAGCCTGACCTGTAGCTTCAGCGGCTTCAG
CCTGAGCACAAGCGGCATGTCTGTCGGCTGGATCAGACAGCCTTCTGGCAAGGGACTGGAATGGCTGGCCGACATTTGGTGGG
ACGACAAGAAGGACTACAACCCCAGCCTGAAGTCCAAGCCAGCATCAGCAAGGACAACAGCAAGAACCAGGTGTTCCTGAAG
ATCACCGGCGTGGACACAGCCGATACCGCCACCTATTACTGCGCCAGATCCATGATCACCAACTGGTACTTCGACGTGTGGGG
CGCTGGCACCACAGTGACCGTCTCCTCA (SEQ ID NO: 133)

>Signal peptide amino acid sequence in mouse anti-RSV emAb AAV
METDTLLLWVLLLWVPGSTG (SEQ ID NO: 134)

>mRSV kappa light chain amino acid sequence in mouse anti-RSV emAb AAV
METDTLLLWVLLLWVPGSTGDIQLTQSPAIMSASPGEKVTMTCSASSSVGYMHWYQQKSSTSPKLWIYDTSKLASGVPGRFSGSGSG
NSYSLTISSIQAEDVATYYCFRGSGYPFTFGQGTKLEIKADAAPTVSIFPPSSEQLTSGGASVVCFLNNFYPKDINVKWKIDGSERQNGV
LNSWTDQDSKDSTYSMSSTLTLTKDEYERHNSYTCEATH

FIG. 25C (cont'd)

>mPalivizumab variable light chain amino acid sequence in mouse anti-RSV emAb AAV
DIQLTQSPAIMSASPGEKVTMTCSASSSVGYMHWYQQKSSTSPKLWIYDTSKLASGVPGRFSGSGSGNSYSLTISSIQAEDVATYYCF
RGSGYPFTFGQGTKLEIK (SEQ ID NO: 136)

>mIgL kappa constant light chain amino acid sequence in mouse anti-RSV emAb AAV
ADAAPTVSIFPPSSEQLTSGGASVVCFLNNFYPKDINVKWKIDGSERQNGVLNSWTDQDSKDSTYSMSSTLTLTKDEYERHNSYTCEA
THKTSTSPIVKSFNRNEC (SEQ ID NO: 137)

>GSSG-streptag linker amino acid sequence in mouse anti-RSV emAb AAV is SEQ ID NO: 122

>mPalivizumab variable heavy chain amino acid sequence mouse anti-RSV emAb AAV
QVELQESGPGILQPSQTLSLTCSFSGFSLSTSGMSVGWIRQPSGEGLEWLADIWWDDKKDYNPSLKSRLTISKDTSSNQVFLKITGVD
TADTATYYCARSMITNWYFDVWGAGTTVTVSS (SEQ ID NO: 138)

>splice junction with flanking sequence in mouse anti-RSV emAb AAV
CAGGTGAGTCCTAACTTCTCCCATTCTAAATGCATGTTGGGGGGATTCTGGGCCTTCAGGACCA (SEQ ID NO: 139)

>Mouse mB3 Balb/C downstream region in mouse anti-RSV emAb AAV
CATAGGGACAAAGAGTGGAGTGGGGCACTTTCTTTAGATTTGTGAGGAATGTTCCGCACTAGATTGTTTAAAACTTCATTTGTTG
GAAGGAGAGCTGTCTTAGTGATTGAGTCAAGGGAGAAAGGCATCTAGCCTCGGTCTCAAAAGGGTAGTTGCTGTCTAGAGAGGT
CTGGTGGAGCCTGCAAAAGTCCAGCTTTCAAAGGAACACAGAAGTATGTGTATGGAATATTAGAAGATGTTGCTTTTACTCTTAA
GTTGGTTCCTAGGAAAAATAGTTAAATACTGTGACTTTAAAATGTGAGAGGGTTTTCAAGTACTCATTTTTTTAAATGTCCAAAATT
TTTGTCAATCAGTTTGAGGTCTTGTTTGTGTAGAACTGATATTACTTAAAGTTTAACCGAGGAATGGGAGTGAGGCTCTCTCATAA
CCTATTCAGAACTGACTTTTAACAATAATAAATTAAGTTTAAAATATTTTTAAATGAATTGAGCAATGTTGAGTTGGAGTCAAGATG
GCCGATCAGAACCAGAACACCTGCAGCAGCTGGCAGGAAGCAGGTCATGTGGCAAGGCTATTTGGGGAAGGGAAAATAAAACC
ACTAGGTAAACTTGTAGCTGTGGTTTGAAGAAGTGGTTTTGAAACACTCTGTCCAGCCCCACCAAACCGAAAGTCCAGGCTGAG
CAAAACACCACCTGGGTAATTTGCATTTCTAAAATAAGTTGAGGATTCAGCCGAAACTGGAGAGGTCCTCTTTTAACTTATTGAGT
TCAACCTTTTAATTTTAGCTTGAGTAGTTCTAGTTTCCCCAAACTTAAGTTTATCGACTTCTAAAATGTATTTAGAATTCATTTTCAA
AATTAGGTTATGTAAGAAATTGAAGGACTTTAGTGTCTTTAATTTCTAATATATTTAGAAAACTTCTTAAAATTACTCTATTATTCTTC
CCTCTGATTATTGGTCTCCATTCA (SEQ ID NO: 140)

FIG. 25C (cont'd)

>mRSV kappa light chain coding sequence without signal sequence in mouse anti-RSV emAb AAV
GACATCCAGCTGACACAGAGCCCTGCCATCATGTCTGCTAGCCTGGCGAGAAAGTGACAATGACCTGTTCCGCCAGCAGCTC
CGTGGGCTACATGCACTGGTATCAGCAGAAGTCTAGCACAAGCCCCAAGCTGTGGATCTACGACACATCCAAGTGGCCTCTG
GCGTGCCAGGCAGATTTTCTGGAAGCGGCAGCGGCTACCCCTTCACATTTGGCCAGGGCACCAAGCTGGAAATCAAGGCCGCTCC
ACCTACTGTCTATCTTTCCACCTAGCGAGCAGCTGACATCTGGGGAGCCTCTGTGTCTGTGTGCTTCCTGAACAACTTCTACCCT
AAGGACATCAACGTCAAGTGGAAGATCGACGGCTCCGAGAGACAGAACGGCGTGCTGAACTCTTGGACCGACCAGGACAGCAA
GGATAGCACCTACAGCATGAGCAGCACTCTGACCCTGACAAGGACGAGTACGAGAGGCACACAACTCCTACACACATGCGAGGCCA
CACACAAGACCACATCCCCAATCGTGAAGTCCTTCAACCGGAACGAGTGC (SEQ ID NO: 281)

>mRSV kappa light chain amino acid sequence without signal peptide in mouse anti-RSV emAb AAV
DIQLTQSPAIMSASPGEKVTMTCSASSSVGYMHWYQQKSSTSPKLWIYDTSKLASGVPGRFSGSGSGNSYSLTISSIQAEDVATYYCF
RGSGYPFTFGQGTKLEIKADAAPTVSIFPPSSEQLTSGGASVVCFLNNFYPKDINVKWKIDGSERQNGVLNSWTDQDSKDSTYSMSST
LTLTKDEYERHNSYTCEATHKTSTSPIVKSFNRNE

FIG. 25D (cont'd)

```
TGACACAGAGCCCTGCCATCATGTCTGCTAGCCCTGGCGAGAAAGTGACAATGACCTGTTCCGCCAGCAGCTCCGTGGCTACATGCACTGGTATCAGCAGAAGTCT
 L  T  Q  S  P  A  I  M  S  A  S  P  G  E  K  V  T  M  T  C  S  A  S  S  S  V  G  Y  M  H  W  Y  Q  Q  K  S
                                                    mRSV-kappa1
                                 mPalivizumab variable light chain
           440                      460                     480                     500                520
```

```
AGCACAAGCCCCCAAGCTGCTGATCTACGACACCTCCAAGCTGGCCTCTGGCGTGCCAGGCAGATTTCTGGAAGGGCGGCAAACAGCTACAGACTGACTATCAG
 S  T  S  P  K  L  W  I  Y  D  T  S  K  L  A  S  G  V  P  G  R  F  S  G  S  G  S  G  N  S  Y  S

FIG. 25D (cont'd)

ATTCTAAATGCATGTTGGGGGATTCTGGGCCTTCAGGACCACCATGTACCAAAAGCCATAACGATCGGTGGGAGTATTCATTGTGTCAAGATCCATAGGGACAAA

Intronsplice | Extra Sequence 1,620  1,640  1,660  1,680  1,700

GAGTGGAGTGGGGCACTTTCTTTA (SEQ ID NO: 104)

>Upstream homology sequence (F primer) in ms-emAb-RSV-dsDNA

ACCACCTCTGTGACAGCATTTATACAGTATCCGATGGAT (SEQ ID NO: 142)

>J558H10 promoter in ms-emAb-RSV-dsDNA is SEQ ID NO: 128

>Signal peptide coding sequence in ms-emAb-RSV-dsDNA is SEQ ID NO: 129

>mPalivizumab light chain coding sequence in ms-emAb-RSV-dsDNA is SEQ ID NO: 130

>mPalivizumab variable light chain coding sequence in ms-emAb-RSV-dsDNA is SEQ ID NO: 131

>mPalivizumab kappa constant light chain coding sequence in ms-emAb-RSV-dsDNA is SEQ ID NO: 132

>GSSG-streptag linker coding sequence in ms-emAb-RSV-dsDNA is SEQ ID NO: 116

>mPalivizumab variable heavy chain coding sequence in ms-emAb-RSV-dsDNA is SEQ ID NO: 133

>Signal peptide amino acid sequence in ms-emAb-RSV-dsDNA is SEQ ID NO: 134

>mPalivizumab light chain amino acid sequence in ms-emAb-RSV-dsDNA is SEQ ID NO: 135

>mPalivizumab variable light chain amino acid sequence in ms-emAb-RSV-dsDNA is SEQ ID NO: 136

>mPalivizumab kappa constant light chain amino acid sequence in ms-emAb-RSV-dsDNA is SEQ ID NO: 137

>GSSG-streptag linker amino acid sequence in ms-emAb-RSV-dsDNA is SEQ ID NO: 122

>mPalivizumab variable heavy chain amino acid sequence in ms-emAb-RSV-dsDNA is SEQ ID NO: 138

>splice junction with flanking sequence in in ms-emAb-RSV-dsDNA is SEQ ID NO: 139

>Downstream homology sequence in ms-emAb-RSV-dsDNA
ATCCATAGGGACAAAGAGTGGAGTGGGGCACTTTCTTTA (SEQ ID NO: 143)

>mPalivizumab light chain coding sequence without signal sequence in ms-emAb-RSV-dsDNA is SEQ ID NO: 281

>mPalivizumab light chain amino acid sequence without signal peptide in ms-emAb-RSV-dsDNA is SEQ ID NO: 286

FIG. 25E
hu-emAb-VRC01-AAV (2551 bp)

TGTGACGCCCGGAGACAGAAGGTCTCTGGGTGGCTGGGTTTTTGTGGGGTGAGGATGGACATTCTGCCATTGTGATTACTACTACTACTACTACATGGACGTCTGGG
Human T7 Upstream Homology
20 40 60 80 100

GCAAAGGGACCACGGTCACCGTCTCCTCAGGTAAGAATGGCCACTCTAGGGCCTTTGTTTTCTGCTACTGCCTGTGGGGTTTCCTGAGCATTGCAGGTTGGTCCTCG
Human T7 Upstream Homology
120 140 160 180 200

GGGCATGTTCCGAGGGGACCTGGGCGGACTGGCCAGGAGGGGATGGGCACTGGGGTGCCTTGAGGATCTGGGAGCCTCTGTGGATTTTCCGATGCCTTTGGAAAATG
Human T7 Upstream Homology
220 240 260 280 300 320

GGACTCAGGTTGGGTGCGTCTGATGGAGTAACTGAGCCTGGGGGCTTGGGGAGCCACATTTGGACGAGATGCCTGAACAAACCAGGGGTCTTAGTGATGGCTGAGGA
Human T7 Upstream Homology
340 360 380 400 420

ATGTGTCTCAGGAGCGGTGTCTGATCGTAATCTTTAGGCCAATAAAATGTGGGTTCACAGTGAGGAGTGCATCCTGGGGTTGGGGTTTGTTCTGCAGCGGGAAGAGC
IGVH1-69 promoter
440 460 480 500 520

ATATTTCTTTAGAATTATGAGGTGCGCTGTGTGTCAACCTGCATCTTAAATTCTTTATTGGCTGGAAAGAGAACTGTCGGAGTGGGTGAATCCAGCCAGGAGGGAC

GCCTAGCCCCGGTCTTCGATCGAGAGCAGGGTTGGGGCAGGGTAGCCCAGAGAACGGTGGCTGCCGTCCTGACAGGGCTTAGGGAGGCTCCAGGACCTCAGTGCCTT

GAAGCTGGTTCCATGAGAAAAGGATTGTTTATCTTAGCAGGCATGCTTACTGTTAAACACAGGATATGTTTGAAGTGGCTTCTGAGAAAATGGTTAAGAAAATT

ATGACTTAAAAATGTGAGAGATTTCAAGTATATTAATTTTTTTAACTGTCCAAGTATTTGAAATTCTTATCATTTGATTAACACCCATG (SEQ ID NO: 105)

FIG. 25E (cont'd)

>Human T7 upstream homology in Hu-emAb-VRC01-AAV is SEQ ID NO: 110

>IgVH1-69 promoter in Hu-emAb-VRC01-AAV is SEQ ID NO: 111

>Signal peptide coding sequence in Hu-emAb-VRC01-AAV is SEQ ID NO: 112

>VRC01 light chain coding sequence in Hu-emAb-VRC01-AAV
ATGGCTACCGGCAGCAGAACAAGCCTGCTGCTGCTTTTGGACTGCTGCTCTGTCTCCCCTGGTTGCAAGAAGGCAGGCGCCGAAATT
GTGTTGACACAGTCTCCAGGCACCCTGTCTTTGTCTCCAGGGGAAACAGCCATCATCTCTTGTCGGACCAGTCAGTATGGTTCC
TTAGCCTGGTATCAACAGAGGCCCGGCCAGGCTCTCATCTATTCGGGCTCTACTCGGGCCGTGGCATCCAGA
CAGGTTCAGCGGCAGTGGTGGGCAGGGACAGACTTCACTCTCACCATCAGCAACCTGAGTGAGTGTGACAACTTAAGCGCACTTAAGCGCACTGCCTGAACAACTTCTACCCTCGAGAGGCAAGG
TCCACCTAGCGACGAGCAGTTGGACAGCTGAAGTCGCCCTGCAGAGCGGCAACAGCCAAGAGTCTGTGACCAAGAGTCTGTGCTAACCTCAGGAGAGGCAAG
TGCAGTGGAAAGTGGACACCCTGCTCTAGCACCCTCTGACTCTGAGCAAGCCCCAAGAGAAGGAAGCCCGACTCTGACCAAGGTGACGCCTGAAGTCTGACGGACAGAGATTCGACCAGGGAGT
GAGCAGCAGCCCCTGTGACCAAGAGCTTCAATCGGGGCGAGTGC (SEQ ID NO: 145)

>VRC01 variable light chain coding sequence in Hu-emAb-VRC01-AAV
GAAATTGTGTTGACACAGTCTCCAGGCACCCTGTCTTTGTCTCCAGGGGAAACAGCCACCCTCTCTTGTCGGACCAGTCAGTATG
GTTCCTTAGCCTGGTATCAACAGAGGCCCGGCCAGGCTCTCGTCATCTATTCGGGCTCTACTCGGGCCGTGGCATC
CCAGACAGGTTCAGCGGCAGTGGATCGGGGACAGACTTCACTCTCACCATCAGCAACCTGGAGTGAGGATTTTGCAGTGTATTA
TTGTGCCAGCAGTATGATGAATTTTTGCAGGGACCAAGGTCCAGGTCCAGGACATTAAGCGC (SEQ ID NO: 146)

>Kappa constant light chain coding sequence in Hu-emAb-VRC01-AAV is SEQ ID NO: 115

>GSSG-streptag linker coding sequence in Hu-emAb-VRC01-AAV is SEQ ID NO: 116

>VRC01 variable heavy chain coding sequence in Hu-emAb-VRC01-AAV
CAGGTGCAGCTGGTGCAGTCGGGGGTGCAGGTCAAGAAGCCTGGCGAGTCGATGAGAATTTCTTGTCGGGCTTCTGGATATGA
ATTTATTGATTGTACGCTAAATTGATTCGTCTGGCCCCGGGAAAAGGCCTGGAGTGGATGGGCTGAAGCCTCGAGGTGG
CGCGGTCAACTACGCACGTCCACTTCAGGGCAGAGAGTGACCATGAGCAGCAGACGTTTATTCCGACACAGCCTTTGGAGCTGCG
CTCGTTGACAGTAGAGACGACAGCGGCCGTCTACTTTTGTACTAGGGGAAAAACTGTGATTACAATTGGGACTTCGAACACTGGGG
CCGGGGCACCCCGGTCATCGTCTCATCA (SEQ ID NO: 147)

FIG. 25E (cont'd)

>Signal peptide amino acid sequence in Hu-emAb-VRC01-AAV is SEQ ID NO: 118

>VRC01 light chain amino acid sequence in Hu-emAb-VRC01-AAV
MATGSRTSLLLAFGLLCLPWLQEGSAEIVLTQSPGTLSLSPGETAIISCRTSQYGSLAWYQQRPGQAPRLVIYSGSTRAAGIPDRFSGS
RWGPDYNLTISNLESGDFGVYYCQQYEFFGQGTKVQVDIKRTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNRGEC (SEQ ID NO: 148)

>VRC01 variable light chain amino acid sequence in Hu-emAb-VRC01-AAV
EIVLTQSPGTLSLSPGETAIISCRTSQYGSLAWYQQRPGQAPRLVIYSGSTRAAGIPDRFSGSRWGPDYNLTISNLESGDFGVYYCQQ
YEFFGQGTKVQVDIKR (SEQ ID NO: 149)

>Kappa constant light chain amino acid sequence in Hu-emAb-VRC01-AAV is SEQ ID NO: 121

>GSSG-streptag linker amino acid sequence in Hu-emAb-VRC01-AAV is SEQ ID NO: 122

>VRC01 variable heavy chain amino acid sequence in Hu-emAb-VRC01-AAV
QVQLVQSGGQMKKPGESMRISCRASGYEFIDCTLNWIRLAPGKRPEWMGWLKPRGGAVNYARPLQGRVTMTRDVYSDTAFLELRSL
TVDDTAVYFCTRGKNCDYNWDFEHWGRGTPVIVSS (SEQ ID NO: 150)

>splice junction with flanking sequence in constructs of the disclosure
CAGGTGAGTTGGCTTTCCTTCTGCCTCCTTTCTCTGGGCCCAGGTCCTCTGACCTGGAGCTGGGAGATAATGTCCGGGGCT
CCTT (SEQ ID NO: 151)

>Human T7 downstream homology in Hu-emAb-VRC01-AAV is SEQ ID NO: 125

FIG. 25E (cont'd)

>VRC01 light chain coding sequence without signal sequence in Hu-emAb-VRC01-AAV
GAAATTGTGTTGACACAGTCTCCAGGCACCCTGTCTTTGTCTCCAGGGGAAACAGCCACCATCATCTCTTGTCGGACCAGTCAGTATG
GTTCCTTAGCCTGGTATCAACAGAGAGCCCGGCCAGGCTCGTCTACTCGGGCCTGCATC
CCAGACAGGTTCAGCGGCAGTCGGTGGGCCAGTACAATCTCACCATCAGCAACCTGGAGTCGGGAGATTTTGGTGTTA
TTATTGCCAGCAGTATGAATTTTTGGCAGGGACCAAGGCTGGAGATCAAGCGCCTCCTAGCGTGT
CATCTTTCCACCTAGCGAGCAGCTGAAGTCTGGCACTGCCTCTGTGGTGTGCCTGCTGAACAACTTCTACCCTGAGAGGC
CAAGGTGCAGTGGAAGTGGACAATGCCCTGCAGAGCGGCAACAGCCAAGAGTCTGTGACCGAGCAGGACTCAAGGATTCCA
CCTACAGCCTGTCTAGCACCCTGACCCTGAGCAAGGCCGACTACGAGAAGCACAAGGTGTACGCCTGCGAAGTGACACACCAG
GGACTGAGCAGCCCCGTGACCAAGAGCTTCAATCGGGGCGAGTGC (SEQ ID NO: 282)

>VRC01 light chain amino acid sequence without signal peptide in Hu-emAb-VRC01-AAV
EIVLTQSPGTLSLSPGETAIISCRTSQYGSLAWYQQRPGQAPRLVIYSGSTRAAGIPDRFSGSRWGPDYNLTISNLESGDFGVYYCQQ
YEFFGQGTKVQVDIKRTVAAPSVFIFPPSDEQLKSGTASVVCLLNNFYPREAKVQWKVDNALQSGNSQESVTEQDSKDSTYSLSSTLT
LSKADYEKHKVYACEVTHQGLSSPVTKSFNRGEC (SEQ ID NO: 287)

hu-emAb-Medi8852-AAV (2544 bp)

>human T7 upstream homology region in constructs of disclosure
TGTGACGCCCGAGACAGAAGGTCTCTGGGTGGCTGGTTTTTGTGGGTGAGGATGGACATTCTGCCATTGTGATTACTACTA
CTACTACTACTGACGTCTGGGGCAAAGGGACCACGGTCACCGTCTCCTCAGTGAAGAATGGCCACTCTAGGGCCTTTGTTT
CTGCTACTACTGCCTCTGTGGGTTTCCTGAGGGCATGTTCCGAGGGACCTGGGCGGACTGGACTCAGTTGGGTGCTCTGAGTAACT
GCCTTGAGGATCTGGGAGCCTCTGTGGATTTTCCGATGCCTTGGAAAATGGGACTCAGTTGGGTGCGTCTGATGGAGTAACT
GAGCCTGGGGGCTTGGGGAGCCACATTTGACGAGATGCCTGAACAAACCAGGGGTCTTAGTGATGGCTGAGGAATGTGTCTC
AGGAGCGGGTGTCT (SEQ ID NO: 153)

>IgVH1-69 promoter in hu-emAb-Medi8852-AAV is SEQ ID NO: 111

>Signal peptide coding sequence in hu-emAb-Medi8852-AAV is SEQ ID NO: 112

>Medi8852 light chain coding sequence in hu-emAb-Medi8852-AAV
ATGGCTACCGGCGACAGCAGCAGCAACAAGCCTGCTGCTGCTGTCTCCCCTGGTTGCAAGAAGGCAGCGCCGATATT
CAGATGACCCAGAGCCCCTCCAGCCTGTCCGCTTCAGTGGGGATCGAGTGACCATTACCTGCCGAACCAGCCAGAGCCTGAG
CTCCTACACGCACTGGTATCAGCAGAAGCCCGGCAAAGCCCAAGCTGCTGATCTACGCCGCTTCTAGTCGGGGGTCCGGAG
TGCCAAGCCGGTTCTCCGGATCTGGGAGTGGACAGGGCACTGACTTTCACCCTGACAATTCAGCCTGACAGTGTGGAGGATTTCGCTACAT
ACTACTGTCAGCAGAGCAGAGAACTTTCGGCAGGGCACTAAGGTGGAGATCAAACGGACTGTGGCCGCTCCTAGCGTGTTCATC
TTTCCACCTAGCGACGAGCAGCTGAAGTCTGGCACTGCCTCTGTGGTGTGCCTGCTGAACAACTTCTACCCTCGAGAGGCCAAG
GTGCAGTGGAAAGTGGACAATGCCCTGCAGAGCGGCAACAGCCAAGAGTCTGTGACCGAGCAGGACTCCAAGGATTCCACCTA
CAGCCTGTCTAGCACCCTGACCCTGAGCAAAGCCGACTACGAGAAGCACAAGGTGTACGCCTGCGAAGTGACACACCAGGGAC
TGAGCAGCCCTGTGACCAAGAGCTTCAATCGGGGAGAGTGC (SEQ ID NO: 154)

>MEDI8852-VK anti-stem HA variable light chain coding sequence in hu-emAb-Medi8852-AAV
GATATTCAGATGACCCAGAGCCCCTCCAGCCTGTCCGCTTCAGTGGGGATCGAGTGACCATTACCTGCCGAACCAGCCAGAG
CCTGAGCTCCTACACGCACTGGTATCAGCAGAAGCCCGGCAAAGCCCAAGCTGCTGATCTACGCCGCTTCTAGTCGGGGT
CCGGAGTGCCAAGCCGGTTCTCCGGATCTGGGAGTGGACAGGGCACTGACTTTCACCCTGACAATTCAGCCTGACAGTGTGGAG
GCTACATACTACTGTCAGCAGAGCAGAGAACTTTCGGGCAGGGCACTAAGGTGGAGATCAAA (SEQ ID NO: 155)

>Kappa constant light chain coding sequence in hu-emAb-Medi8852-AAV is SEQ ID NO: 115

>GSSG-streptag linker coding sequence in hu-emAb-Medi8852-AAV is SEQ ID NO: 116

FIG. 25F (cont'd)

>anti-stem HA variable heavy chain coding sequence in hu-emAb-Medi8852-AAV
CAGGTCCAGCTGCAGGAGAGCGGGCCCCGGACTGGTCAAGCCTTCACAGACACTGAGCCTGACATGCGCCATTAGCGGAGATAG
CGTGAGCTCCTACAATGCCGTGTGGAACTGGATCAGGCAGTCTCCAAGTGCAGTCAGGACTGGAGTGGCTGGGACGAACATACTATA
GATCCGGGTGGTACAATGACTATGCTGAATCAGTGAAAAGCCGATTACTATCAACCCGATACCTCCAAGAATCAGTTCTCT
GCAGCTGAACAGTGTGACCCCTGAGGACACAGCCGTGTACTACTGCGCCAGAAGCGGCCATATCACCGTCTTTGGCGTCAATG
TGGATGCTTTCGATATGTGGGGCCAGGGGACTATGGTCACCGTCTCTTCA (SEQ ID NO: 156)

>Signal peptide amino acid sequence in hu-emAb-Medi8852-AAV is SEQ ID NO: 118

>Medi8852 light chain amino acid sequence in hu-emAb-Medi8852-AAV
MATGSRTSLLLAFGLLCLPWLQEGSADIQMTQSPSSLSASVGDRVTITCRTSQSLSSYTHWYQQKPGKAPKLLIYAASSRGSGVPSRF
SGSGSGTDFTLTISSLQPEDFATYYCQQSRTFGQGTKVEIKRTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNRGEC (SEQ ID NO: 157)

>MEDI8852-VK anti-stem HA variable light chain amino acid sequence in hu-emAb-Medi8852-AAV
DIQMTQSPSSLSASVGDRVTITCRTSQSLSSYTHWYQQKPGKAPKLLIYAASSRGSGVPSRFSGSGSGTDFTLTISSLQPEDFATYYC
QQSRTFGQGTKVEIK (SEQ ID NO: 158)

>Kappa constant light chain amino acid sequence in hu-emAb-Medi8852-AAV is SEQ ID NO: 121

>GSSG-streptag linker amino acid sequence in hu-emAb-Medi8852-AAV is SEQ ID NO: 122

>anti-stem HA variable heavy chain amino acid sequence in hu-emAb-Medi8852-AAV
QVQLQQSGPGLVKPSQTLSLTCAISGDSVSSYNAVWNWIRQSPSRGLEWLGRTYYRSGWYNDYAESVKSRITINPDTSKNQFSLQLN
SVTPEDTAVYYCARSGHITVFGVNVDAFDMWGQGTMVTVSS (SEQ ID NO: 159)

>splice junction with flanking sequence in hu-emAb-Medi8852-AAV is SEQ ID NO: 151

>Human T7 downstream homology in hu-emAb-Medi8852-AAV is SEQ ID NO: 125

FIG. 25F (cont'd)

>Medi8852 light chain coding sequence without signal sequence in hu-emAb-Medi8852-AAV
GATATTCAGATGACCCAGAGCCCCTTCCAGCCTGTCCGCTTCAGTGGGGGATCGAGTGACCATTACCTGCGAACCAGCCAGAG
CCTGAGCTCCTACACGCACTGGTATCAGCAGAAGCCCGGCAAAGCCCCTAAGCTGCTGATCTACGCCGCTTCTAGTCGGGGGT
CCGGAGTGCCAAGCCGGTTCTCCGGATCTGGGAGTGGAACCGACTTTACCCTGACAATTTCAAGCCTGCAGCCCGAGGATTTC
GCTACATACTACTGTCAGCAGAGCAGAACTTTCGGGCAGGGCACTAAGGTGGAGATCAAACGGACTGTGGCCGCTCCTAGCGT
GTTCATCTTTCCACCTAGCGACGAGCAGCTGAAGTCTGGCACTGCCTCTGTGTGCCTGCTGAACAACTTCTACCCTCGAGA
GGCCAAGGTGCAGTGGAAAGTGGACAATGCCCTGCAGAGCGGCAACAGCCAAGAGAGTCTGACGAGCAGGACTCCAAGGAT
TCCACCTACAGCCTGTCTAGCACCCTGACCACTGCCTGAGCAAGGCCGACTACGAGAAGCACAAGGTGTACGCCTGCGAAGTGACACA
CCAAGGGACTGAGCAGCCCTGTGACGCGCTTCAATCGGGGCGAGTGC (SEQ ID NO: 283)

>Medi8852 light chain amino acid sequence without signal peptide in hu-emAb-Medi8852-AAV
DIQMTQSPSSLSASVGDRVTITCRTSQSLSSYTHWYQQKPGKAPKLLIYAASSRGSGVPSRFSGSGSGTDFTLTISSLQPEDFATYYC
QQSRTFGQGTKVEIKRTVAAPSVFIFPPSDEQLKSGTASVVCLLNNFYPREAKVQWKVDNALQSGNSQESVTEQDSKDSTYSLSSTLT
LSKADYEKHKVYACEVTHQGLSSPVTKSFNRGEC (SEQ ID NO: 288)

hu-emAb-AMM01-AAV (2555 bp)

```
gaaggcagatagcagccccgtcaaggcggggagtggagaccaccaccctccaaacaaagcaacaacaagtacgcggccagcagctacctgagcctgacgcctgagc
 E  A  D  S  S  P  V  K  A  G  V  E  T  T  T  P  S  K  Q  S  N  N  K  Y  A  A  S  S  Y  L  S  L  T  P  E
```
AMM01 light chain
Lambda Constant 1,300    1,320    1,340    1,360    1,380

```
agtggaagtcccacagaagctacagctgccagagtcacgcgcatgaaggcgacgtggcccctacagaatgtgccccctacagaatgttcaGGAGGAAGTAGTGGCAGCGGG
 Q  W  K  S  H  R  S  Y  S  C  Q  V  T  H  E  G  S  T  V  E  K  T  V  A  P  T  E  C  S  G  G  S  S  G
```
AMM01 light chain
Lambda Constant 1,400    1,420    1,440    1,460    1,480

```
AGTGGGGTCAAATTGGAGTCATCCTCAATTTGAAAAAGGAGGGGAGGGTCCAATTGGTCTCATCGGCAGTTTGAGAAGGCGGCGGCGGCTCCAATTGGTCCATCC
 S  G  S  N  W  S  H  P  Q  F  E  K  G  G  G  S  N  W  S  H  P  Q  F  E  K  G  G  G  G  S  N  W  S  H  P
```
GSSG-streptag linker 1,500    1,520    1,540    1,560    1,580

```
CCAGTTTGAAAAAGGCTCTGGTGGCAGTGGCTGGTGGGcaggttcagctggtgcagtctggggctgatgtgaagaagcctggggcctcagtgaaggtctcct
 Q  F  E  K  G  S  G  G  S  A  G  G  Q  V  Q  L  V  Q  S  G  A  D  V  K  K  P  G  A  S  V  K  V  S
```
GSSG-streptag linker
AMM01 HC Variable 1,620    1,640    1,660    1,680    1,700

FIG. 25G (cont'd)

TGAAATATTTTCTTTAGAATTATGAGGTGCCCTGTGTGTCAACCTGCATCTTAAATTCTTTATTGGCTGAAAGAGAACTGTCGGAGTGGGTGAATCCAGCCAGGAG

Human T7 Downstream Homology

GGACGCGTAGCCCCGGTCTTGATCAGAGACAGGGTTGGGGGCAGGGGTAGCCCAGAAACGGTGGCTGCCGTCCTGACAGGGGCTTAGGGAGGCTCCAGGACCTCAGTG

Human T7 Downstream Homology

CCTTGAAGCTGGTTTCCATGAGAAAAGGATTGTTATCTTAGGAGGGCATGCTTACTGTTAAAGACAGGATATGTTTGAAGTGGCTTCTGAGAAAATGGTTAAGAA

Human T7 Downstream Homology

AATTATGACTTAAAAATGTGAGAGATTTTCAAGTATATTAATTTTTTAACTGTCCAAGTATTTGAAATTCTTATCATTGATTAACACCCATG(SEQ ID NO: 107)

Human T7 Downstream Homology

FIG. 25G (cont'd)

>human T7 upstream homology region in hu-emAb-AMM01-AAV is SEQ ID NO: 153

>IgVH1-69 promoter in hu-emAb-AMM01-AAV is SEQ ID NO: 111

>Signal peptide coding sequence in hu-emAb-AMM01-AAV is SEQ ID NO: 112

>AMM01 light chain coding sequence in hu-emAb-AMM01-AAV
ATGGCTACCGGCAGCAGACAAGCCTGCTGCTCTGTCTCCCCTGGTTGCAAGAAGGCAGGCCTCCTAT
GAGCTGACTCAGCCACCCTCAGTGCTGCTGGCCCCGGGGCAGAGGCCACACTGTGGGGGACACAACATCGGAGCTA
AAATGTCCACTGGTACCAGCAGAAGCCAGGCCAGGCACGCCCTGTCATCCAATATGATAGCGACCGGCCCTCAGGATC
CCTGAGCGATCGGATTCTCTGGCTCCAACTCTGGGGACAGCACGGCACGCGGGATCGGGGCAAGTCGAAGCCGAGCGACT
ATTACTGTGCAGGTGGGATAGTGGTCGTGGGACATCCCCTTATGTCTTCGGAGGTGGGACCAAGGTCACCGTCCTAGGTCAGC
CAAGGCCAACCCACTGTCACTCTGTTCCCACCCTCGAGTGAGGAGCTTCAAGCCAACAAGGCCACACTGGTGTGTCTCATAA
GTGACTTCTACCCGGGAGCCGTGACAGTGGCCGTGACAAGTACGCGGCCAGTGGAGACCACCACCAC
CTCCAAACAAAGCAACAACAAGTATACGCGGCCAGTGGAAGTCCCACAGAAGCTACA
GCTGCCAGTGGTCACGCATGAAGGGAGCACCGTGGAGAAGACCAGAATCTTCA (SEQ ID NO: 161)

>AMM01 lambda variable light chain coding sequence in hu-emAb-AMM01-AAV
TCCTATGAGCTGACTCAGCCACCCTCAGTGCTGCTTGGCCCCGGGGCAGAGGGCCACAATTACCTGTGGGGACACAACATCGG
AGCTAAAAATGTCCACTGGTACCAGCAGAAGCCACAGGGCCCCTGTCCTGGTCATCCAATATGATAGCGACGGCCCTCAG
GGATCCCTGAGCGATCGGATTCTCTGGCTCCAACTCTGGGAGCACGGCACCATCAGCAGGTCGAAGCCGGGATGAGGC
CGACTATTACTGTGCAGGTGCGATAGTGGTCGTGGGACATCCCTTTATGTCTTCGGAGGTGGGACCAAGGTCACCGTCCTAGG
TCAGCCCCAAGGCCAACCCCACTGTCACTCTGTTCCCACCCC (SEQ ID NO: 162)

>lambda constant light chain coding sequence in hu-emAb-AMM01-AAV
TCGAGTGAGGAGCTTCAAGCCAACAAGGCCACACTGGTGTGTCTCATAAGTGACTTCTACCCGGGAGCCGTGACAGTGGCCTG
GAAGGCAGATAGCAGCCCCGTCAAGGCGGGAGTGGAGACCACCACCACCCTCCAAACAAAGCAACAACAAGTACGGCGGCCAGC
AGCTACCTGAGCCTGACGCCTGAGCGACGAGCAGTGGAAGTCCCACAGAAGCTACAGCTGCCAGTGGTCACGCATGAAGGGAGCACCGTGG
AGAAGACAGTGGCCCCTACAGAATGTTCA (SEQ ID NO: 163)

>GSSG-streptag linker coding sequence in hu-emAb-AMM01-AAV is SEQ ID NO: 116

FIG. 25G (cont'd)

>AMM01 variable heavy chain coding sequence in hu-emAb-AMM01-AAV
CAGGTTCAGCTGGTGCAGTCTGGAGCTGATGTGAAGAAGCCTGGGGCCTCAGTGAAGGTCTCCTGCAAGGCTTCTGGTTACAC
CTTTATTCATTTGGTATCAGTTGGGTGCGACAAGGCCCCTGGACAAGGGCTTGAGTGGATGGATCGACACTAATAATGG
TAACACAAACTATGCACAGAGTCTCCAGGGCAGAGTCACCATGACCACAGATACATCCACGGGCACAGCCTACATGGAGCTGAG
GAGCCTCTCGACTGACGACACGGCCGTGTATTTCTGTGCGCGAGCTCTGGAAATGGGGCATAGAAGTGGCTTCCCATTGACTA
CTGGGGCCAGGGAGTCCTGGTCACCGTCTCCCCA (SEQ ID NO: 164)

>Signal peptide amino acid sequence in hu-emAb-AMM01-AAV is SEQ ID NO: 118

>AMM01 light chain amino acid sequence in hu-emAb-AMM01-AAV
MATGSRTSLLLAFGLLCLPWLQEGSASYELTQPPSVSVAPGQRATITCGGHNIGAKNVHWYQQKPGQAPVLVIQYDSDRPSGIPERFS
GSNSGSTATLTISRVEAGDEADYYCQVWDSGRGHPLYVFGGGTKVTVLGQPKANPTVTLFPPSSEELQANKATLVCLISDFYPGAVTV
AWKADSSPVKAGVETTTPSKQSNNKYAASSYLSLTPEQWKSHRSYSCQVTHEGSTVEKTVAPTECS (SEQ ID NO: 165)

>AMM01 variable light chain amino acid sequence in hu-emAb-AMM01-AAV
SYELTQPPSVSVAPGQRATITCGGHNIGAKNVHWYQQKPGQAPVLVIQYDSDRPSGIPERFSGSNSGSTATLTISRVEAGDEADYYCQ
VWDSGRGHPLYVFGGGTKVTVLGQPKANPTVTLFPP (SEQ ID NO: 166)

>AMM01 lambda constant light chain amino acid sequence in hu-emAb-AMM01-AAV
SSEELQANKATLVCLISDFYPGAVTVAWKADSSPVKAGVETTTPSKQSNNKYAASSYLSLTPEQWKSHRSYSCQVTHEGSTVEKTVA
PTECS (SEQ ID NO: 167)

>GSSG-streptag linker amino acid sequence in hu-emAb-AMM01-AAV is SEQ ID NO: 122

>AMM01 variable heavy chain amino acid sequence in hu-emAb-AMM01-AAV
QVQLVQSGADVKKPGASVKVSCKASGYTFIHFGISWVRQAPGQGLEWMGWIDTNNGNTNYAQSLQGRVTMTTDTSTGTAYMELRSL
STDDTAVYFCARALEMGHRSGFPFDYWGQGVLVTVSP (SEQ ID NO: 168)

>splice junction with flanking sequence in hu-emAb-AMM01-AAV is SEQ ID NO: 151

>Human T7 downstream homology in hu-emAb-AMM01-AAV is SEQ ID NO: 125

FIG. 25G (cont'd)

>AMM01 light chain coding sequence without signal sequence in hu-emAb-AMM01-AAV
TCCTATGAGCTGACTCAGCCACCCTCAGTGTCAGTGTCAGTGGCCCCGGGACAGAGGGCCACAATTACCTGTGGGGGACACAACATCGG
AGCTAAAAATGTCCACTGGTACCAGCAGAAGCCAGGCCAGGCCCCTGTCCTGGTCATCCAATATGATAGCGACCGGCCCTCAG
GGATCCCTGAGCGATTCTCTGGCTCCAACTCTGGGAACACAGGACACGGCCAGGGTGGGACCAAGGTCACCGTCCTAGG
CGACTATTACTGTGCAGGTGCGGATAGTGGTCACTCTGTTCCCACCCCTGAGTGAGGAGCTTCAAGCCAACAAGGCCACACTGGTGTCT
TCAGCCAAGGCCAACCCCACTGTCACTCTGTTCCCACCCCTGAGTGAGGAGCTTCAAGCCAACAAGGCCACACTGGTGTCT
CATAAGTGACTTCTACCCGGGAGCCGTGACAGTGGCCTGGAAGGCAGATAGCAGCCCTGAGCCTGAGCAGTGGAAGTCCCACAGAAG
ACACCCTCCAAACAAAGCAACAACAAGTACGCGGCAGCAGTACCTGAGCCTGAGCAGTGGAAGTCCCACAGAAG
CTACAGCTGCCAGGTCACGCATGAAGGGAGCACCGTGGAGAGACAGTGGCCCCTACAGAATGTTCA (SEQ ID NO: 284)

>AMM01 light chain amino acid sequence without signal peptide in hu-emAb-AMM01-AAV
SYELTQPPSVSVAPGQRATITCGGHNIGAKNVHWYQQKPGQAPVLVIQYDSDRPSGIPERFSGSNSGSTATLTISRVEAGDEADYYCQ
VWDSGRGHPLYVFGGGTKVTVLGQPKANPTVTLFPPSSEELQANKATLVCLISDFYPGAVTVAWKADSSPVKAGVETTTPSKQSNNK
YAASSYLSLTPEQWKSHRSYSCQVTHEGSTVEKTVAPTECS (SEQ ID NO: 289)

FIG. 25H
Balb/C mRSV-Splice Integration (2261 bp)

```
CTACTGGGGTCAAGGAACCTCAGTCACCGTCTCCTCAGGTAAGAATGGCCTCTCCAGGTCTTATTTTTAACCTTTGTTATGGAGTTTTCTGAGCATTGCAGACTAA
         20              40              60              80             100

TCTTGGATATTTGTCCCTGAGGAGCCGGCTGAGAGAAGTTGGGAAATAAACTGTCTAGGAGATCTCAGAGCCTTTAGGACAGATTATCTCCACATCTTTGAAAAACT
         120             140             160             180             200

AAGAATCTGTGTGATGGTGTTGGTGGAGTCCCTGGATGGGATAGGGACTTTGGAGGCTCATTTGAAGAAGATGCTAAAACAATCCTATGGCTGGAGGGATAGT
         220             240             260             280             300             320

GGGGCTGAGTTGGAGATTTTCAGTTTTTAGAGAATAAAAGTATTAGTGGTGGAATATACTTCAGGACCACCTCTGTGACAGCATTTATACAGTATCCGATGGACAAGT
                                                                     FlankingGenomic
         340             360             380             400             420

GAGTGTCTCAGGAGGATTCTATTTTAAGATTGAGATATTAGCTTTGATACTACATCTAAATGGTCTGTACATGTCCGAAGAAAGTTCTTCAGACAGAGTTAGG
                                                    J558H10 Promoter
         440             460             480             500             520

ACTTGGATCCAGGAGTTAGGACTCGACTCAGGAGGACTCTAGTTTCTTCTCTCCAGCTGGAATGTCCTTATGTAAGAAAAGCCTTGCCTCATGAGTATGCA
                       J558H10 Promoter
         540             560             580             600             620             640
```

FIG. 25H (cont'd)

TCAAGGGAGAAAGGCATCTAGCCTCGGTCTCAAAAGGGTAGTTGCTGTCTAGAGAGGTCTGGTGGAGCTTGCAAAAGTCCAGCTTTCAAAGGAACACAGAAGTATGT
GTATGGAATATTAG (SEQ ID NO: 108)

FIG. 25H (cont'd)

>upstream flanking genomic DNA in Balb/C mRSV-Splice Integration
AGGACCACCTCTGTGACAGCATTATACAGTATCCGATG (SEQ ID NO: 170)

>J558H10 promoter in Balb/C mRSV-Splice Integration is SEQ ID NO: 128

>Signal peptide coding sequence in Balb/C mRSV-Splice Integration is SEQ ID NO: 129

>mPalivizumab light chain coding sequence in Balb/C mRSV-Splice Integration is SEQ ID NO: 130

>mPalivizumab variable light chain coding sequence in Balb/C mRSV-Splice Integration is SEQ ID NO: 131

>mPalivizumab kappa constant light chain coding sequence in Balb/C mRSV-Splice Integration is SEQ ID NO: 132

>GSSG-streptag linker coding sequence in Balb/C mRSV-Splice Integration is SEQ ID NO: 116

>mPalivizumab variable heavy chain coding sequence in Balb/C mRSV-Splice Integration is SEQ ID NO: 133

>Signal peptide amino acid sequence in Balb/C mRSV-Splice Integration is SEQ ID NO: 134

>mPalivizumab light chain amino acid sequence in Balb/C mRSV-Splice Integration is SEQ ID NO: 135

>mPalivizumab variable light chain amino acid sequence in Balb/C mRSV-Splice Integration is SEQ ID NO: 136

>mPalivizumab kappa constant light chain amino acid sequence in Balb/C mRSV-Splice Integration is SEQ ID NO: 137

>GSSG-streptag linker amino acid sequence in Balb/C mRSV-Splice Integration is SEQ ID NO: 122

>mPalivizumab variable heavy chain amino acid sequence in Balb/C mRSV-Splice Integration is SEQ ID NO: 138

>splice junction with flanking sequence in in Balb/C mRSV-Splice Integration is SEQ ID NO: 139

>downstream flanking genomic DNA in Balb/C mRSV-Splice Integration
CATAGGGACAAAGAGTGGAGTGGGGCACTTTCTTTAGATTT (SEQ ID NO: 171)

>mPalivizumab light chain coding sequence without signal sequence in Balb/C mRSV-Splice Integration is SEQ ID NO: 281

>mPalivizumab light chain amino acid sequence without signal peptide in Balb/C mRSV-Splice Integration is SEQ ID NO: 286

FIG. 25I
TT-hRSV-T7-integrated (1707 bp)

>upstream flanking genomic DNA sequence in TT-hRSV-T7-integrated
GTCTTAGTGATGGCTGAGGAATGTGTCTCAGGAGCGGTGTC (SEQ ID NO: 173)

>IgVH1-69 promoter in TT-hRSV-T7-integrated is SEQ ID NO: 111

>Signal peptide coding sequence in TT-hRSV-T7-integrated is SEQ ID NO: 112

>hRSV light chain coding sequence in TT-hRSV-T7-integrated is SEQ ID NO: 113

>hRSV variable light chain coding sequence in TT-hRSV-T7-integrated is SEQ ID NO: 114

>kappa constant light chain coding sequence in TT-hRSV-T7-integrated is SEQ ID NO: 115

>GSSG-streptag linker coding sequence in TT-hRSV-T7-integrated is SEQ ID NO: 116

>hRSV variable heavy chain coding sequence in TT-hRSV-T7-integrated is SEQ ID NO: 117

>signal peptide amino acid sequence in TT-hRSV-T7-integrated is SEQ ID NO: 118

>hRSV light chain amino acid sequence in TT-hRSV-T7-integrated is SEQ ID NO: 119

>hRSV variable light chain amino acid sequence in TT-hRSV-T7-integrated is SEQ ID NO: 120

>kappa constant light chain amino acid sequence in TT-hRSV-T7-integrated is SEQ ID NO: 121

>GSSG-streptag linker amino acid sequence in TT-hRSV-T7-integrated is SEQ ID NO: 122

>hRSV variable heavy chain amino acid sequence in TT-hRSV-T7-integrated is SEQ ID NO: 123

>splice junction with flanking sequence in TT-hRSV-T7-integrated is SEQ ID NO: 124

>downstream flanking genomic DNA sequence in TT-hRSV-T7-integrated
TGTAGGACTGCAAGATCGCTGCACAGCAGCGAATCGTGAAA (SEQ ID NO: 174)

FIG. 25I (cont'd)

>hRSV light chain coding sequence without signal sequence in TT-hRSV-T7-integrated is SEQ ID NO: 280

>hRSV light chain amino acid sequence without signal sequence in TT-hRSV-T7-integrated is SEQ ID NO: 285

FIG. 27A
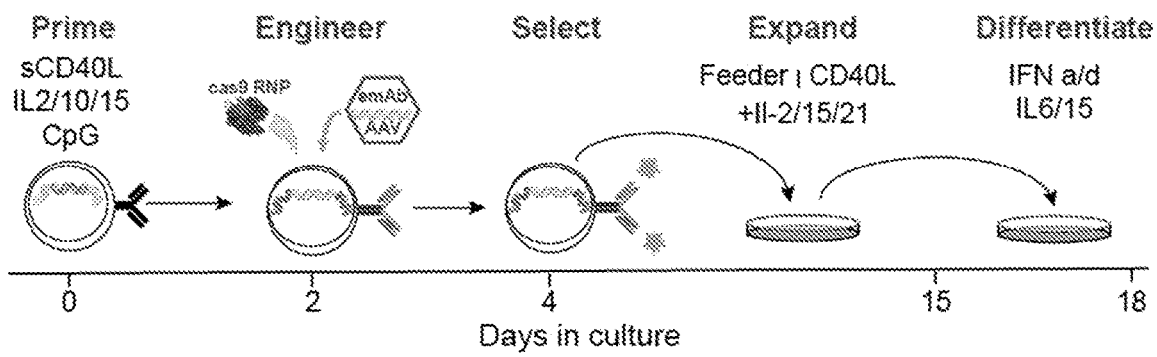
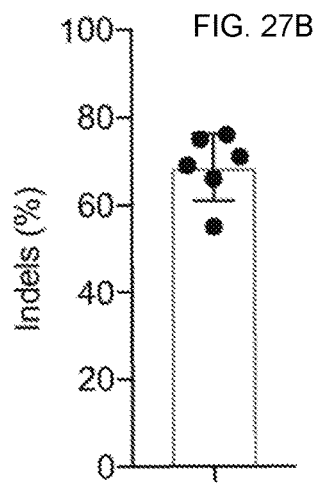
FIG. 27B
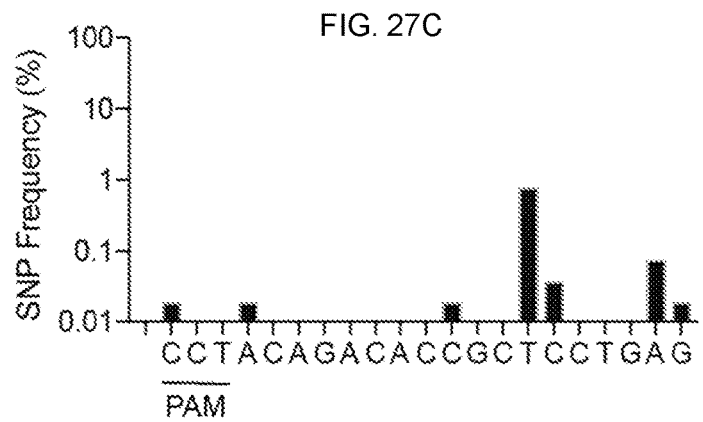
FIG. 27C
FIG. 27D
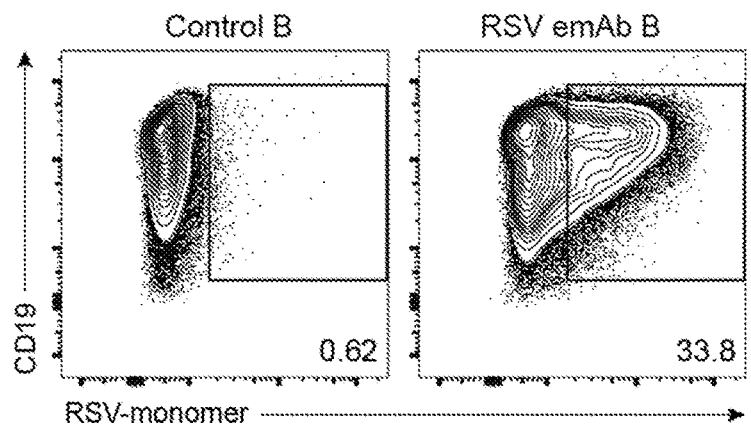

SYSTEMS AND METHODS TO PRODUCE B CELLS GENETICALLY MODIFIED TO EXPRESS SELECTED ANTIBODIES

CROSS-REFERENCE TO RELATED APPLICATIONS

This application is a U.S. National Phase Patent Application based on PCT/US2018/056789, filed Oct. 19, 2018, which claims priority to U.S. Provisional Patent Application No. 62/575,275 filed Oct. 20, 2017, to U.S. Provisional Patent Application No. 62/580,303 filed Nov. 1, 2017, and to U.S. Provisional Patent Application No. 62/623,371 filed Jan. 29, 2018, each of which is incorporated by reference herein.

STATEMENT REGARDING SEQUENCE LISTING

The Sequence Listing associated with this application is provided in text format in lieu of a paper copy and is hereby incorporated by reference into the specification. The name of the text file containing the Sequence Listing is 2A68074_ST25.txt. The text file is 184 KB, was created on Apr. 18, 2020, and is being submitted electronically via EFS-Web.

FIELD OF THE DISCLOSURE

The current disclosure provides systems and methods to genetically modify B cells to express selected antibodies. The systems and methods can be used to: obviate the need for classical vaccinations; provide protection against infectious agents for which no vaccinations are currently available; provide protection against infectious agents when patients are otherwise immune-suppressed; and/or provide a benefit provided by a therapeutic antibody, such as in the treatment of autoimmune disorders.

BACKGROUND OF THE DISCLOSURE

Vaccines are designed to increase the immunity of a subject against a particular infection by stimulating B cells to produce antibodies against the targeted infectious agent. Routine pediatric vaccination is a long established clinical intervention with comparatively low risk and high efficacy. Unfortunately, however, vaccinations are not available for all infectious agents. As one example, every year in the United States, millions of children visit a doctor or emergency room due to infections with Respiratory Syncytial Virus (RSV).

For decades, researchers have been trying to develop a vaccine that can induce B cells to produce antibodies that are effective to protect against viruses such as RSV, human immunodeficiency virus (HIV), and Zika virus. But all efforts to induce protective antibodies have failed. The only RSV vaccine tested widely actually made infection worse: antibodies generated following vaccination did not disable the virus, but instead, enhanced its ability to infect cells. Besides RSV, HIV, and Zika virus there are a number of other infectious agents for which no effective vaccines are available.

In addition to combating infections, antibodies can also be useful as treatments for other conditions such as autoimmune diseases. However, these antibody-based therapies typically require repeated injections of the antibodies to maintain protection.

Also of note, numerous patients undergo bone marrow or hematopoietic stem cell transplants as treatments for hematological malignancies (e.g., leukemia, lymphoma, myeloma). Other patients receive infusions of genetically-modified hematopoietic stem cells that provide a therapeutic gene that the patient lacks. All of these treatments require that the patient's existing immune system be removed before administration of the transplant or genetically-modified hematopoietic stem cells, leaving a dangerous window of immune suppression before the patient's immune system repopulates following the treatment. During this time of immune suppression, patients are incredibly susceptible to infections, such as RSV, influenza, parainfluenza, and metapneumovirus (MPV). These infections are a high risk factor and associated with numerous fatalities following these treatments.

SUMMARY OF THE DISCLOSURE

The current disclosure provides systems and methods to genetically modify B cells to express selected antibodies. In particular embodiments, the selected antibodies reduce or obviate the need for existing vaccinations. In particular embodiments, the selected antibodies protect against infection from viruses for which no effective vaccination strategies are currently available (e.g., RSV, HIV, Zika). In particular embodiments, the selected antibodies reduce or obviate the need for therapeutic antibody injections, such as those administered to treat various autoimmune disorders. In particular embodiments, the selected antibodies protect immune-suppressed patients from infections. In particular embodiments, methods of the disclosure can be used to reprogram B cells to protect against hundreds of different infectious agents or pathogens, all via a single laboratory manipulation encompassing a few days.

In particular embodiments, the current disclosure provides these benefits through the targeted insertion of a genetic construct into a particular area of the B cell's endogenous genome. Importantly, the genetic modification of B cells is difficult due to the high variability of genetic sequences within these cells that are required for antibody diversity. This high degree of genetic variability makes directly targeting antibody coding regions for genetic manipulation impractical. Moreover, removing and replacing coding portions of the B cell's genome is also not effective because this approach negatively affects B cell function.

Additional challenges regarding genetically modifying B cells to express selected antibodies arise because antibodies are formed from discrete protein units, referred to as heavy chains and light chains. The different chains are encoded by different portions of the B cell genome, yet must come together to form a functioning antibody.

The current disclosure overcomes the noted challenges, among others, by identifying a constant region of the B cell genome that can be reliably targeted for genetic insertion and that, when modified, results in preferential expression of an inserted genetic construct over corresponding portions of the B cell's natural genome. This strategy overcomes sequence variability associated with the B cell genome and also overcomes the need to remove and replace portions of the endogenous B cell genome to achieve functional expression of the selected antibody. Overcoming the need to remove and replace portions of the endogenous B cell genome preserves B cell function after the genetic manipulation.

In particular embodiments, the noted area targeted for genetic insertion is an intronic region upstream or downstream of an Eμ enhancer element of SEQ ID NO: 85 (human) or SEQ ID NO: 86 (mouse). In particular embodiments, the area targeted for genetic insertion is a constant intronic region selected from SEQ ID NO: 1 or 2 (human) or SEQ ID NO: 3 or 4 (mouse). In particular embodiments, human DNA sequences within SEQ ID NO: 1 to target for genetic insertion include SEQ ID NOs: 5-24. In particular embodiments, human DNA sequences within SEQ ID NO: 2 to target for genetic insertion include SEQ ID NOs: 25-44. In particular embodiments, mouse DNA sequences within SEQ ID NO: 3 to target for genetic insertion include SEQ ID NOs: 45-64. In particular embodiments, mouse DNA sequences within SEQ ID NO: 4 to target for genetic insertion include SEQ ID NOs: 65-84. Genetic sequences particularly capable of targeting these sites for genetic modification are described within the current disclosure as guide RNA (gRNA) SEQ ID NOs: 87-89, and 290-366.

In particular embodiments, the placement and components of an inserted genetic construct result in preferential expression of the inserted genetic construct over corresponding portions of the B cell's endogenous genome. These embodiments also include elements that overcome challenges associated with portions of antibodies being encoded by different regions of the endogenous B cell genome.

In particular embodiments, the genetic constructs are inserted into one of SEQ ID NO: 1, 2, 3, and 4 and include (i) a promoter; (ii) a signal peptide; (iii) a transgene encoding an entire light chain of a selected antibody; (iv) a flexible linker or a skipping element; (v) the variable portion of the heavy chain of a selected antibody; and (vi) a splice junction that results in expression of the B cell's endogenous heavy chain constant region. In these embodiments, expressing the selected antibody as a single construct overcomes challenges associated with portions of antibodies being encoded by different areas of the endogenous B cell genome. Inclusion of a flexible linker physically links the light chain portion and the heavy chain portion of the expressed selected antibody in a manner that allows them to form a functional unit and at the same time reduces the risk of the antibody portions binding with other potentially expressed antibody chains from the B cell's endogenous genome. Use of a skipping element does not physically link the light chain portion and the heavy chain portion, but their expression in close proximity also results in association to form a functional unit while at the same time reducing the risk of the antibody portions binding with other potentially expressed antibody chains from the B cell's endogenous genome. Inclusion of a splice junction results in the selected antibody including a heavy chain constant region appropriate for the B cell's current activation and/or maturation state. In other words, the selected expressed antibodies can be expressed having any of the B cell's endogenous heavy chain constant regions, and the heavy chain constant region expressed with the selected antibody can naturally change over time.

The current disclosure also provides methods to ensure that only B cells that have been effectively genetically modified to express a selected antibody are collected for formulation and administration to patients. For example, before genetic modification, a B cell will naturally express antibodies that include either a kappa light chain or a lambda light chain. The B cell can be modified to express a light chain that is different from the kappa or lambda chain that it naturally expresses, and only those B cells that express the replacement chain are selected for formulation and administration.

The current disclosure also provides numerous additional strategies to effectively modify B cells to provide the benefits described herein. These and other strategies are described more fully in the Detailed Description below.

BRIEF DESCRIPTION OF THE FIGURES

(FIG. 2A) formalin-inactivated RSV vaccine; (FIG. 2B) "improved" RSV vaccines; and (FIG. 2C) RSV epitope scaffold vaccine.

(FIG. 3A) palivizumab injection; (FIG. 3B) adenovirus-mediated palivizumab expression; and (FIG. 3C) stem cell genetic modification and differentiation.

(FIG. 4A) B cell modification to protect against RSV; and (FIG. 4B) strategy for simultaneous protection.

(FIG. 8A) An approach for endogenous IgH targeting and a resulting chimera including portions of a selected antibody (e.g., Palivizumab). (FIG. 8B) An approach for IgL inactivation. In the depicted approaches, a stop codon can be placed upstream (or as part of) the inserted genetic construct.

In FIG. 9, the constant regions are individually denoted to highlight that the inserted genetic construct can be expressed with any of the potential heavy chain constant regions.

FIG. 11A, 11B. (FIG. 11A) the human Eμ intronic enhancer (SEQ ID NO: 85) and human DNA sequence to target for genetic insertion including from IGHJ6 to Eμ intronic enhancer (SEQ ID NO: 1); (FIG. 11B) exemplary associated gRNA (e.g., sgRNA) target sites (SEQ ID NOs. 5-24) and gRNA sequences (SEQ ID NOs: 88, 89, and 290-307).

FIGS. 12A, 12B. (FIG. 12A) Human DNA sequence to target for genetic insertion including from Eμ intronic enhancer to switch region (SEQ ID NO: 2); (FIG. 12B) exemplary associated gRNA (e.g., sgRNA) target sites (SEQ ID NOs. 25-44) and gRNA sequences (SEQ ID NOs: 308-327).

FIGS. 13A, 13B. (FIG. 13A) the mouse Eμ intronic enhancer (SEQ ID NO: 86) and mouse DNA sequence to target for genetic insertion including from IGHJ4 to Eμ intronic enhancer (SEQ ID NO: 3); (FIG. 13B) exemplary associated gRNA (e.g., sgRNA) target sites (SEQ ID NOs. 45-64) and gRNA sequences (SEQ ID NOs: 87, and 328-346).

FIGS. 14A, 14B. (FIG. 14A) Mouse DNA sequence to target for genetic insertion including from Eμ intronic enhancer to switch region (SEQ ID NO: 4); (FIG. 14B) exemplary associated gRNA (e.g., sgRNA) target sites (SEQ ID NOs. 65-84) and gRNA sequences (SEQ ID NOs: 347-366).

FIG. 15A is a schematic depicting insertion of a genetic construct encoding an anti-RSV antibody into an endogenous heavy chain locus, utilizing a CRISPR/Cas9 gene-editing system. The genetic construct can include homology arms or stitches, which are nucleotide overhangs that are homologous to genomic DNA at the insertion site. FIG. 15B depicts additional examples of DNA repair templates including sequences flanked by sgRNA target sites to generate double stranded DNA breaks flanking an inserted sequence in concert with Cas9/sgRNA cutting of the genome (top), single stranded DNA containing long homology arms flanking an inserted sequence (middle), and short homology arms flanking an inserted sequence produced by annealing of a DNA oligo (bottom).

FIGS. 18A-18C. Efficient Cas9 cutting of a targeted intronic region in mouse and human B cells. Electroporation with Cas9/sgRNA ribonuclear protein complexes mediated effective cutting in mouse and human B cells. Cells were electroporated with Cas9/sgRNA complexes. Editing efficiency was assessed at 3 days post electroporation by Tracking of Indels by Decomposition (TIDE) in: (FIG. 18A) mouse B cell line (A20); (FIG. 18B) primary B cells; and (FIG. 18C) human B cell line (Ramos).

(FIG. 22A) Primary B cells were primed 24 hours, co-incubated with adeno-associated virus (AAV) for 12 hours, washed and either electroporated or transferred directly into secondary culture for 3 days before analysis of mCherry expression. (FIG. 22B) Primary B cells were primed for 24 hours, mock electroporated, or electroporated with template+Cas9/sgRNA and transferred to secondary culture for 5 days before analysis of mCherry expression.

FIGS. 23A-23E. Insertion of a novel genetic construct encoding a functional antibody into mouse and human B cell lines enables expression of surface bound and secreted antibody. (FIG. 23A) Diagram of the IgH locus showing site for insertion of partial antibody construct, as well as depictions of a surface bound and secreted antibody. emAb=synthetic antibody, herein used interchangeably with synAb. (FIG. 23B) Staining of unmodified or anti-RSV synthetic antibody (αRSV synAb) modified mouse A20 B cell lines with the RSV-prefusion-F protein tetramer (RSV-Tetramer) and anti-Streptag II tetramer (αTagAb Tetramer). (FIG. 23C) Staining of unmodified or anti-RSV synAb modified human RAMOS B cell lines with the RSV-prefusion tetramer and anti-Streptag II antibody tetramer. (FIG. 23D) ELISA for binding of antibody to RSV prefusion F protein from the culture media of unmodified or anti-RSV synAb modified A20 cell cultures. Palivizumab was used as a positive control. (FIG. 23E) ELISA for binding of antibody to RSV prefusion F protein from the culture media of unmodified or anti-RSV synAb modified RAMOS cell cultures. Palivizumab was used as a positive control.

(FIG. 24A) Surface staining of mock treated (top) or anti-RSV synAb modified mouse B cell lines (bottom) with anti-Streptag II tetramer before enrichment (left panel) and after enrichment and expansion with anti-Streptag II tetramer (middle panel) and RSV-prefusion viral protein tetramers (right panel). (FIG. 24B) ELISA for binding of antibody to RSV prefusion F protein from the culture media of unmodified or anti-RSV synAb modified mouse B cell cultures. Palivizumab was used as a positive control. Antibody binding detected with a 1:1 mixture of polyclonal anti-human Ig and anti-mouse Ig bound to HRP. (24C) Rapid expansion of enriched B synAb cells in culture with 3T3-CD40L feeder cells and IL-21.

FIGS. 25A-25I. Exemplary sequences. (FIG. 25A) Exemplary sgRNA sequences (SEQ ID NOs: 87, 88, 89), genome homology regions (SEQ ID NOs: 90-95), and splicing oligonucleotides (SEQ ID NOs: 96-101); (FIG. 25B) human anti-RSV-emAb AAV (2531 bp (SEQ ID NO: 102) and associated nucleotide and protein sequences (SEQ ID NOs: 110-126, 280, 285)); (FIG. 25C) mouse anti-RSV-emAb AAV (3134 bp (SEQ ID NO: 103) and associated nucleotide and protein sequences (SEQ ID NOs: 127-141, 281, 286)); (FIG. 25D) mouse emAb-RSV-dsDNA (1736 bp (SEQ ID NO: 104) and associated nucleotide and protein sequences (SEQ ID NOs: 142-144)); (FIG. 25E) human emAb-VRC01-AAV (2551 bp (SEQ ID NO: 105) and associated nucleotide and protein sequences (SEQ ID NOs: 145-152, 282, 287)); (FIG. 25F) human-emAb-Medi8852-AAV (2544 bp (SEQ ID NO: 106) and associated nucleotide and protein sequences (SEQ ID NOs: 153-160, 283, 288)); (FIG. 25G) human-emAb-AMM01-AAV (2555 bp (SEQ ID NO: 107) and associated nucleotide and protein sequences (SEQ ID NOs: 161-169, 284, 289)); (FIG. 25H) Balb/C mRSV-splice integration sequence (2261 bp (SEQ ID NO: 108) and associated nucleotide and protein sequences (SEQ ID NOs: 170-172)); and (FIG. 25I) TT-hRSV-T7-integrated sequence (1707 bp (SEQ ID NO: 109) and associated nucleotide and protein sequences (SEQ ID NOs: 173-175)).

(FIG. 26A) Targeted area upstream of the Eµ enhancer for insertion of a new antibody cassette; by targeting this region, inserted emAb genes can be driven by a native (but inserted) IgH promoter, maximizing the native control of immunoglobin expression. To enable one-hit insertion and minimize off-target interactions, emAb constructs were expressed as a single chain fusion. This fusion consists of a full light chain sequence, linked to the variable region of the heavy chain with a 57 amino acid glycine-serine linker. Physically linking the light and heavy chains minimizes the possibility of misspairing between an inserted emAb and endogenous light chain. An optimized splice junction allows emAbs to splice to downstream endogenous IgH constant regions. This allows emAbs to be expressed as any of the heavy chain isotype classes. (FIG. 26B) The Burkitts-lymphoma derived B cell line natively expresses surface and secreted forms of IgM paired with a lambda light chain. Expression of an engineered αRSV-emAb derived from Palivizumab was detected using monomeric RSV-F protein and streptactin, a modified streptavidin with high affinity for the Streptag II motifs in the linker. αRSV-emAb modified RAMOS cells expressed the engineered RSV-specific antibody, which could be detected on the surface of cells. (FIG. 26C) The engineered RSV-specific antibody was also detected in secreted form in the supernatant. (FIG. 26D) αRSV-emAb modified cells but not control cells exhibited rapid and sustained calcium signaling in response to protein antigen.

FIGS. 27A-27G. Human B cells are efficiently genetically-modified to express single chain emAb by paired cas9-sgRNA and AAV template delivery. (FIG. 27A) Schematic representation of human cell engineering process. Day 0: B cells are isolated from PBMC and primed with CD40L, IL2, IL10, IL15, and CpG oligonucleotides. Day 2: cells are electroporated with cas9/sgRNA RNP and treated with AAV encoding the emAb HR template 1 hr post electroporation, followed by culture as described for day 0. Day 4: cells are selected on antigen binding or tag expression. Day 4-15L: selected cells are expanded on irradiated feeder cells expressing CD40L, IL2, and IL21, supplemented with IL15. Days 15-18: Cells transitioned to feeder-free differentiation culture with IL6, IL15, and IFNγ. (FIG. 27B) Indel frequency in B cells from 6 independent PBMC donors treated with emAb-targeting Cas9/sgRNA RNPs. (FIG. 27C) All human SNPs with an reported frequency across the targeting sgRNA site. (FIG. 27D) Representative FACS for binding of RSV-F prefusion monomer to control cultured or RSV-emAb genetically-modified human B cells at day 4 of culture. (FIG. 27E) Frequency of RSV-emAb B cells after engineering of B cells from 6 independent donors. (FIG. 27F) FACS for plasma cell markers (CD19, CD27, CD38 and CD138) in primed cells (Day 2) and cells differentiated in vitro (Day 18). (FIG. 27G) ELISA for secreted anti-HA-stem antibody in the culture media of control B cells or influenza targeted MEDI8852-emAb B cells at day 18 of culture.

(FIG. 29A) Diagram of RAMOS IgH alleles: one productive allele containing an emAb target site, and one allele with a c-myc translocation eliminating the emAb target site. (FIG. 29B) Flow cytometry showing surface expression of lambda light chain and RSV-F antigen binding in input RAMOS cells (gated on CD79b+), and αRSV-emAb engineered RAMOS cells (gated on CD79b+/RSV-F+). (FIG. 29C) Diagram of primary IgH alleles: one productive allele, and one non-productive allele without functional recombined VDJ, both of which contain an emAb target site. (FIG. 29D) Flow cytometry showing surface expression of λ light chain and RSV-F antigen binding on input sorted λ light chain+B cells (gated on CD79b+) and αRSV-emAb engineered B cells (gated on CD79b+/RSV-F+).

(FIG. 30B) Indel percentage in B cells treated with IgH targeting cas9/sgRNA RNP. (FIG. 30C) Representative FACS for binding to monomeric prefusion-RSV-F protein in control B cells, or emAb B cells engineered using a dsDNA or AAV template. (FIG. 30D) Frequency of emAb cells in B cells engineered with dsDNA or AAV templates. (FIG. 30E) Anti-RSV specific secreted antibody in the supernatant of control B cells, or B cells engineered with using a dsDNA or AAV template.

(FIG. 31A) Schematic representation of antiviral protection by transferred emAb cells. Day 0: $1.5 \times 10^7$ enriched RSV-emAb B cells are transferred via I.P. injection. Day 5: Palivizumab I.P. injection at 15 mg/kg. Day 6: Blood draw to measure antiviral Ab titers. Day 7: intranasal challenge with $10^6$ pfu RSV virus. Day 12: measurement of viral titer in lungs. (FIG. 31B) Surface expression of RSV-emAb receptor before or 24 hours after transfer of RSV-emAb cells measured with RSV-F monomer and streptactin tag binding. (FIG. 31C) Plasma titer of αRSV-F antibodies in mice at day 6. (FIG. 31D) Viral titers of RSV in the lungs of mice with no cells transferred, with αRSV-emAb B cells, with control B cells, or with 15 mg/kg Palivizumab delivered I.P. 48 hours prior to infection.

(FIG. 32B) ELISA for serum titers of anti-RSV-F and anti-HA-stem antibodies in mice which received emAb cells (Dual transfer) versus control serum (no transfer).

DETAILED DESCRIPTION

Vaccines are designed to increase the immunity of a subject against a particular infection by stimulating B cells to produce antibodies against the targeted infectious agent. Antibodies are proteins that can provide protection against pathogens. Antibodies can bind to a pathogen and are protective when this binding interferes with the normal function of a pathogen. For example, many protective antibodies bind to a portion of a pathogen that blocks the pathogen from entering cells. Antibodies can be attached to the surface of B cells (known as B cell receptors), but exert most of their protective functions when secreted into the blood.

Pathogen can refer to any substance that can cause disease, and pathogenic can refer to the ability of a substance to cause disease. Examples of pathogens include viruses, bacteria, and fungi that can infect a host and cause disease. Other examples of pathogens include host-derived proteins or other host-derived substances that cause disease, such as tumor necrosis factor alpha (TNFα), an inflammatory molecule associated with numerous autoimmune conditions (e.g., arthritis) and beta amyloid plaques, which are fibrous proteins that accumulate in the brain during Alzheimer's disease. In particular embodiments, cancer cells and/or tumors can also be referred to as pathogens or pathogenic substances, based on their ability to cause disease.

Upon exposure to a vaccine or a natural pathogen, an epitope provided in the vaccine and/or present on the pathogen can bind to a B cell receptor present on a naïve B cell. This binding can lead to activation of the B cell and production of protective antibodies.

Figure 1:
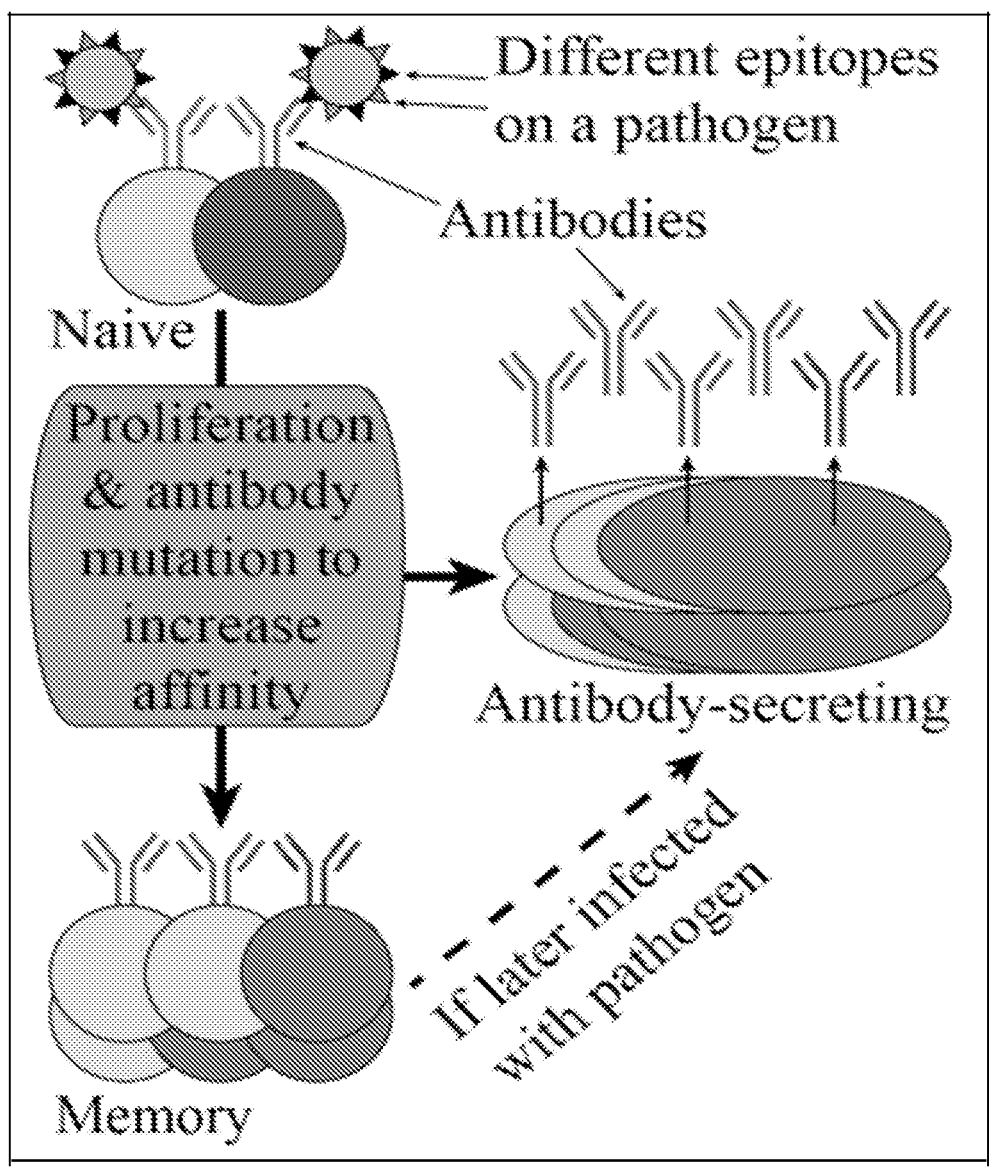
FIG. 1. Schematic of B cell response to classical vaccination strategies.

A naïve B cell refers to a B cell before it has come in contact with its epitope. Each naïve B cell expresses a unique antibody with unique epitope specificity. The unique antibody expressed by each naïve B cell is generated randomly through genetic recombination. Naïve B cells express membrane-bound antibodies (i.e., B cell receptors) and upon epitope binding, can rapidly proliferate. During proliferation and maturation, the antibody genes undergo somatic mutation, which serves to increase the affinity of epitope binding. The increase in affinity of epitope binding that occurs during B cell maturation is required for effective protection against the pathogen. A single naïve B cell is able to undergo dozens of cell divisions to create thousands of antibody-secreting B cells and memory B cells (FIG. 1) expressing the same antibody, or a related antibody that has been mutated to improve binding to the pathogen.

In addition to active antibody-secreting B cells, memory B cells are important for protection against pathogens. Memory B cells do not normally actively secrete antibodies but can rapidly differentiate into antibody-secreting cells. The rapid differentiation of memory B cells into antibody-secreting cells can help the immune system mount a rapid response to a secondary infection or a pathogen that has previously been encountered through vaccination (McHeyzer-Williams et al., Nat Rev Immunol. 2011; 12(1): 24-34; Taylor et al., Trends Immunol. 2012; 33(12):590-7). For example, memory B cells maintain protection against Hepatitis B virus when the level of antibody produced by antibody-secreting B cells has diminished (Williams et al., Vaccine. 2001; 19(28-29):4081-5; Bauer et al., Vaccine. 2006; 24(5):572-7). Thus, successful vaccines stimulate the generation of antibody-secreting B cells and long-lived memory B cells, all capable of expressing antibodies that bind to an epitope on the pathogen with high affinity.

Unfortunately, there are many infectious agents for which no vaccines are available. Examples of infectious agents without an available effective vaccine strategy include RSV, HIV, and Zika virus.

Figure 2A:
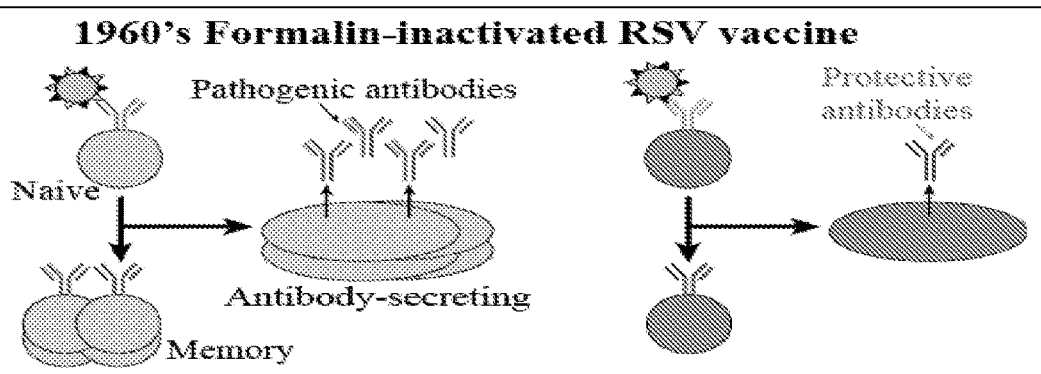
FIGS. 2A-2C. Schematics of prior art vaccination strategies against Respiratory Syncytial Virus (RSV)

Regarding RSV, the disastrous failure of a formalin-inactivated RSV vaccine in the 1960s was likely not due to a failure to induce antibody-secreting B cells and memory B cells targeting RSV. It is likely that the vaccine induced the production of antibodies that did not neutralize RSV, but instead enhanced RSV infection (FIG. 2A) (Blanco et al., Hum Vaccin. 2010; 6(6):482-92; Broadbent et al., Influenza Other Respir Viruses. 2015; 9(4):169-78). This highlights the delicate balance that must be achieved by vaccines: induction of the production of "protective" antibodies targeting certain epitopes while avoiding stimulating the production of "pathogenic" antibodies targeting the incorrect epitopes (FIG. 2A).

Figure 2B:
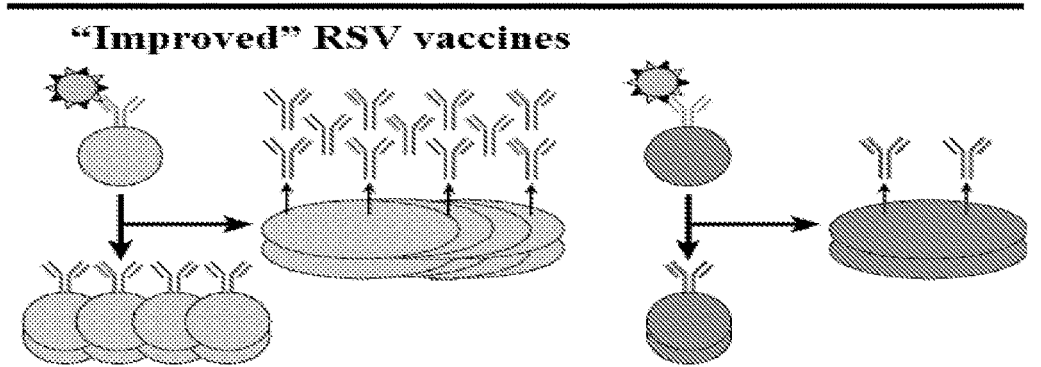

A 2015 analysis of the World Health Organization International Clinical Trials Registry Platform identified nine candidate RSV vaccines evaluated clinically since 2008, none of which progressed beyond Phase 2 of testing (Broadbent et al., Influenza Other Respir Viruses. 2015; 9(4):169-78). Amongst these, only three trials have been completed and only one has reported results. That vaccine, called MEDI-559, appears to reduce RSV infection, but respiratory symptoms were too high for further testing (Malkin et al., PLoS One. 2013; 8(10):e77104). These data suggest that while MEDI-559 induced the production of protective antibodies, it likely also induced the production of pathogenic antibodies (FIG. 2B).

Other "improved" vaccination strategies involve changing the formulation that is administered to patients. These include alternative methods to inactivate/attenuate the virus, and changes to the adjuvant aimed at increasing the inflammatory response (Broadbent et al., Influenza Other Respir Viruses. 2015; 9(4):169-78; Garg et al., The Journal of general virology. 2014; 95(Pt 5):1043-54; Swanson et al., J Virol. 2014; 88(20):11802-10; Widjaja et al., PLoS One. 2015; 10(6):e0130829; Stewart-Jones et al., PLoS One. 2015; 10(6):e0128779). Some of these approaches have yielded increases in protective antibodies in animal models, but the possibility of inducing pathogenic antibodies makes it likely that these "improved" RSV vaccines would suffer the same fate as MEDI-559.

Figure 2C:
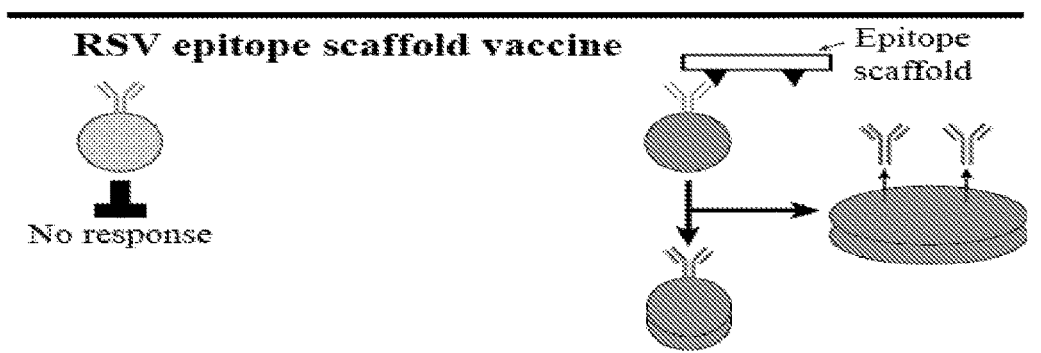
Figures 3A, 3B, 3C:
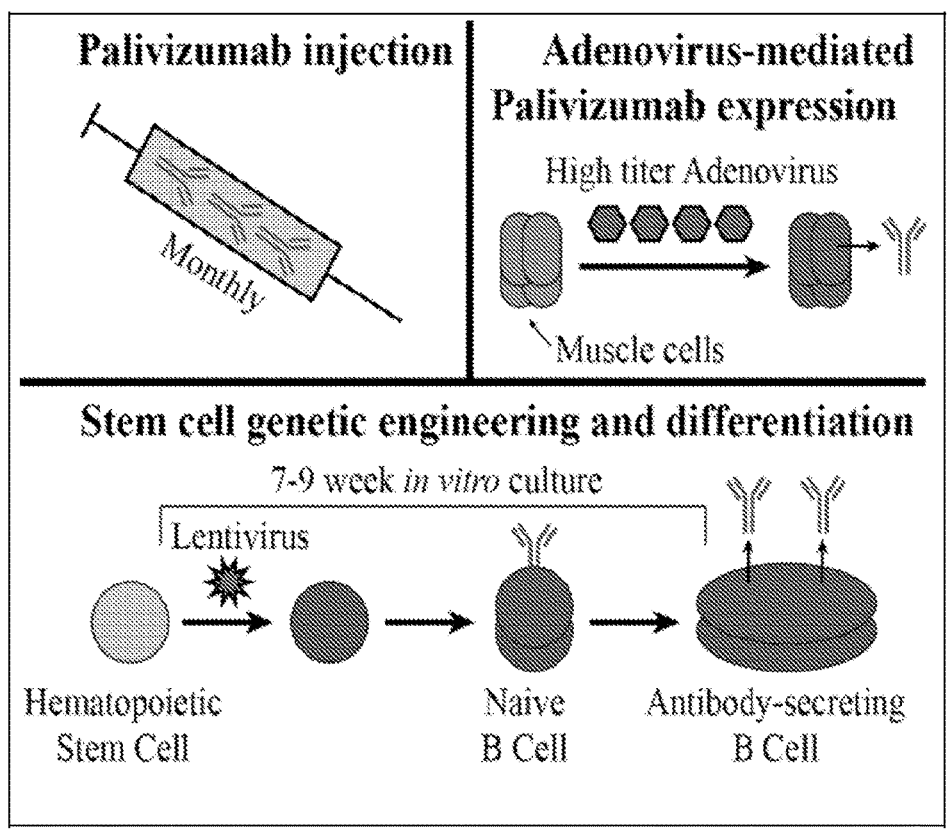
FIGS. 3A-3C. Summary of previous efforts to bypass vaccination and directly provide protective antibodies against RSV.
Figure 4A:
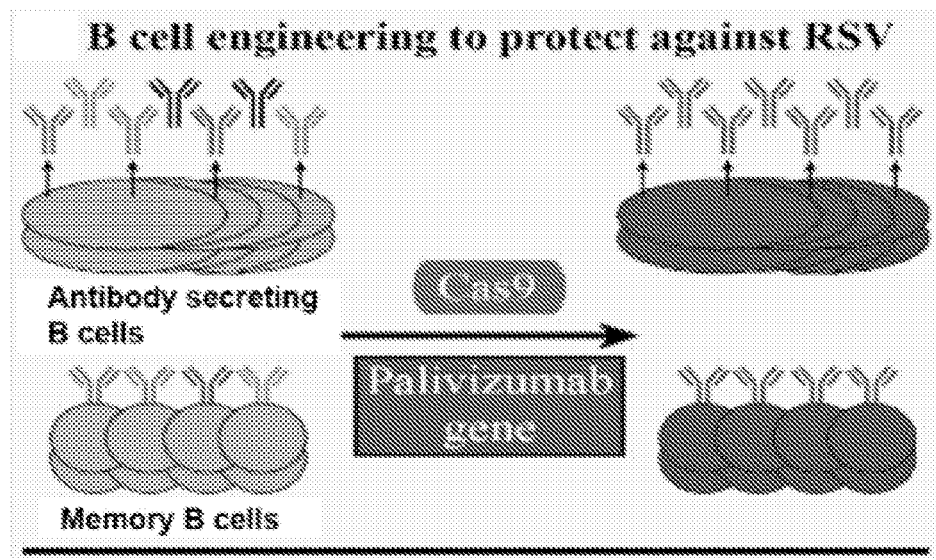
FIGS. 4A, 4B. Schematics for particular embodiments of protection strategies disclosed herein.
Figure 4B:
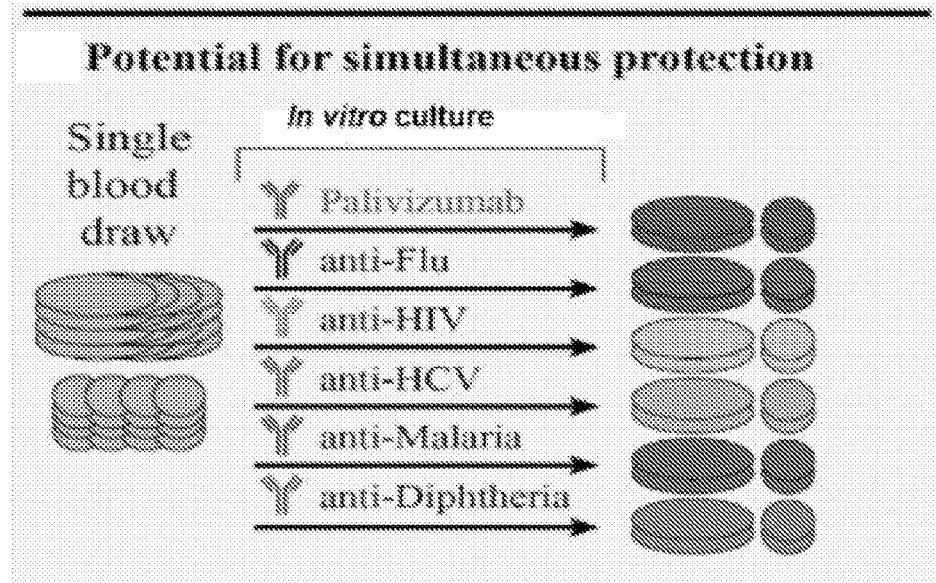
Figure 5:
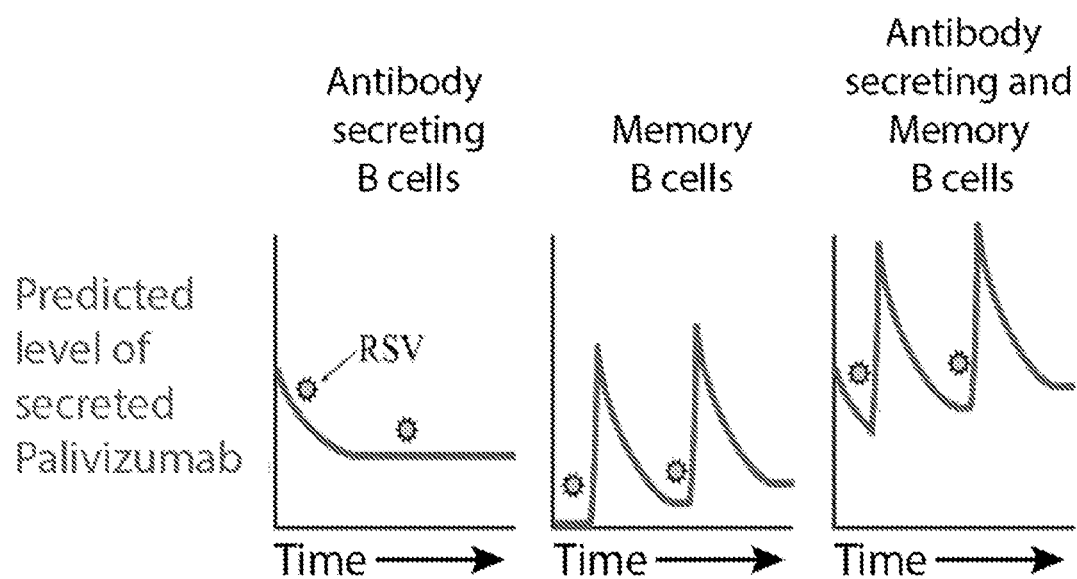
FIG. 5. Hypothesized secretion of palivizumab by B cell subtypes in the presence and absence of infection.

In an effort to focus the immune response to the epitopes targeted by protective antibodies, a recent approach has been to graft a single RSV epitope onto a non-RSV scaffold (FIG. 2C). This approach eliminates the possibility of pathogenic antibodies specific for other RSV epitopes since they are absent from the scaffold. RSV epitope scaffold vaccination of rhesus macaque resulted in the production of neutralizing antibodies by some animals, but only after 3-5 injections (Correia et al., Nature. 2014; 507(7491):201-6).

Approaches to bypass vaccination and directly provide protective antibodies have also been developed. The only clinically approved prophylactic treatment for RSV is the injection of the high affinity RSV-specific protective antibody Palivizumab (FIG. 3A) (The PREVENT Study Group. Pediatrics. 1997; 99(1):93-9; The IMpact-RSV Study Group. Pediatrics. 1998; 102(3 Pt 1):531-7). Unfortunately, the $10,000 cost of a 5-month series of Palivizumab has limited its use to children at high-risk for severe RSV infection (Meissner & Kimberlin, Pediatrics. 2013; 132(5): 915-8). Other RSV-specific antibodies designed to last up to a year are currently undergoing clinical evaluation (Influenza Other Respir Viruses. 2015; 9(4):169-78). However, yearly antibody re-injection is not feasible for life-time protection.

To eliminate the need for life-long injections, methods have been developed in which an adenoviral vector is used to transfer a gene encoding a protective antibody into muscle cells (FIG. 3B) (Schnepp & Johnson, Curr Opin HIV AIDS. 2014; 9(3):250-6). Promisingly, adenovirus-mediated expression of Palivizumab partially protected mice from RSV infection (Skaricic et al., Virology. 2008; 378(1):79-85). A limitation of this approach, however, is the high costs of manufacturing the high doses of virus necessary to achieve protective levels of antibody (24). The high doses are necessary because the expression of antibody by a muscle cell is low compared to the estimated 10,000 antibodies secreted per second by a single B cell (Helmreich et al., J Biol Chem. 1961; 236:464-73; Hibi & Dosch, Eur J Immunol. 1986; 16(2):139-45). B cells achieve this high rate of secretion by completely reprogramming their protein production machinery to focus upon antibody secretion. Without a revolution in manufacturing capability, adenovirus-mediated antibody gene transfer into muscle cells is not a realistic option for RSV prevention.

Another approach uses a lentiviral vector to incorporate the genes encoding protective antibodies into the genome of hematopoietic stem cells, which would be subsequently induced to differentiate into antibody-secreting B cells (FIG. 3C). One limitation of this approach is that antibody gene insertion is random, which introduces the risk of off-target genetic effects resulting in disease. A second limitation of this approach is the long two-month in vitro culture conditions necessary to induce differentiation of antibody-secreting cells from hematopoietic stem cells (Luo et al., Blood. 2009; 113(7):1422-31). A final limitation is that this strategy will not generate a source of antibody that can be augmented upon infection. Therefore, if the antibody-secreting cells are not present in high numbers, or are not long-lived, protection against infection will be inadequate In particular embodiments, the current disclosure provides bypassing vaccination and/or eliminating the need for repeated therapeutic antibody injections by genetically engineering B cells to express a selected antibody (e.g., an antibody against an infectious agent (e.g., palivizumab; FIG. 4A)). Types of B cells that are particularly useful to genetically engineer include existing antibody-secreting B cells, memory B cells, naïve B cells, B1 B cells, and marginal zone B cells. Naive B cells have the greatest proliferative and functional potential and can enter the germinal center response and improve their binding ability. B1 B cells express BCR and migrate to different locations such as the peritoneal cavity. B1 B cells rapidly differentiate into antibody-secreting cells upon stimulation through the BCR, and do not require signals for T cells for optimal function. Marginal zone B cells are largely located in the marginal zone of the spleen and rapidly differentiate into antibody-secreting cells upon stimulation through the BCR. Marginal zone B cells also do not require signals from T cells for optimal function. Genetically engineering one or more of these subsets of B cells can create a baseline level of antibody to treat ongoing or immediate infection, and a long-lived source of inducible antibody in case of future re-infection. FIG. 4B demonstrates an associated strategy for simultaneous protection against numerous pathogens utilizing the teachings of the current disclosure while FIG. 5 depicts hypothesized secretion of palivizumab by exemplary B cell subtypes in the presence and absence of infection.

The current disclosure provides genetic engineering of B cells by inserting a genetic construct including a transgene into an endogenous antibody gene locus specifically chosen to take advantage of the structure and function of the endogenous B cell genome. For example, inserting a transgene encoding at least a portion of a selected antibody into an endogenous antibody gene locus can allow for robust production of the selected antibody by taking advantage of the endogenous antibody expression regulatory machinery. Transgene may refer to a section of DNA that encodes a foreign (i.e., exogenous) protein. Genetic construct may refer to an artificially constructed segment of nucleic acid which is intended for introduction into a cell to allow expression of the foreign protein.

In particular embodiments, the current disclosure provides B cells that are modified to express a selected antibody. Antibodies are produced from two genes, a heavy chain gene and a light chain gene. Generally, an antibody includes two identical copies of a heavy chain, and two identical copies of a light chain (see, e.g., FIG. 6B). The heavy chains are the larger subunits of the two and each heavy chain includes a VDJ segment and a constant region (shown as "C" in FIG. 6B). The VDJ segment (or VDJ) refers to the unique pairing of V, D and J gene segments that encode the unique portion of the antibody heavy chains that bind to an epitope on a pathogen. Thus, V refers to one of the gene segments that randomly pairs with a D and J segment to encode the unique portion of the antibody heavy chain that binds to an epitope on the pathogen. Similarly, D refers to one of the gene segments that randomly pairs with a V and J segment to encode the unique portion of the antibody heavy chain that binds to an epitope on the pathogen. Finally, J refers to one of the gene segments that randomly pairs with a V and D segment to encode the unique portion of the antibody heavy chain that binds to an epitope on the pathogen. There are several V segments, D segments, and J segments that can come together in a variety of distinct combinations to form the particular VDJ segment of a particular heavy chain (see, e.g. FIG. 7).

Each B cell pairs just a single VDJ combination with a conserved constant, C, region to form a full-length heavy chain. The heavy chain C region can interact with other immune proteins, such as Fc receptors to activate other immune cells. All naive B cells express the same C region segments, but can change to express different C region segments following activation, and different C regions give antibodies different functions. For example, one C gene segment encodes ε, and antibodies expressing E are "IgE". IgE-type antibodies bind to cells of the body and often mediate allergic reactions. Antibodies expressing an a C region are IgA antibodies; antibodies expressing a γ C region are IgG antibodies and antibodies expressing a μ C region are IgM antibodies. The human genome includes a single heavy chain locus, which is present on chromosome 14.

Again referring to FIG. 6B, the light chain of an antibody (IgL) includes a variable region and a constant region. The light chain variable region includes V and J gene segments, and the light chain constant region can include a single immunoglobulin constant domain. Humans express two different light chains: Igκ, which is encoded by the immunoglobulin kappa locus on chromosome 2; and Igλ, which is encoded by the immunoglobulin lambda locus on chromosome 22.

Figure 6A:
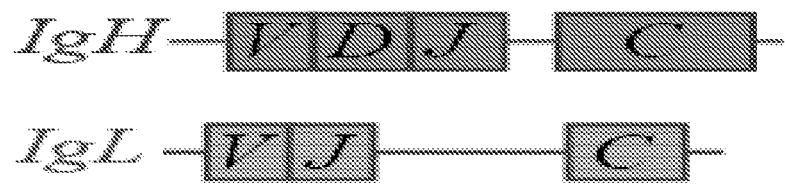
FIGS. 6A, 6B. The structure of (FIG. 6A) antibody genes and (FIG. 6B) antibody proteins, highlighting a technical challenge of the disclosure: that antibodies are proteins made from two separate gene products. In particular embodiments, synthetic genetic constructs encoding selected antibodies disclosed herein utilize skipping elements (e.g., self-cleaving peptides) to address this challenge.
Figure 8A:
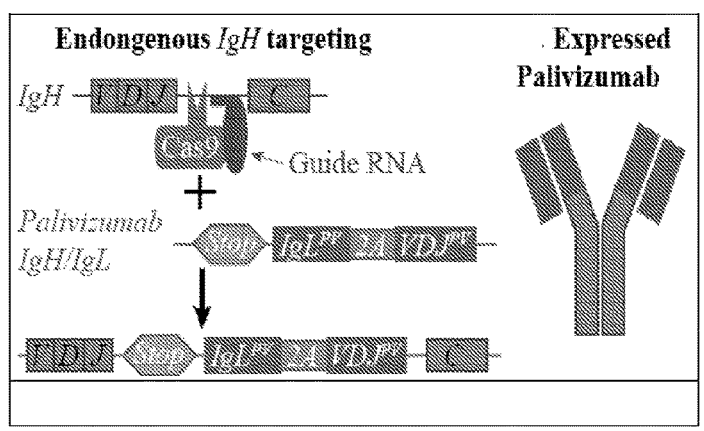
FIGS. 8A, 8B. Because two proteins come together to form an antibody, it can be desirable to target or inactivate the B cell's endogenous antibody heavy chain (IgH) and/or endogenous antibody light chain (IgL). In the absence of such targeting or inactivation, undesired hybrid antibodies could form (i.e., an endogenous light chain pairing with a selected antibody heavy chain or vice versa).
Figure 8B:
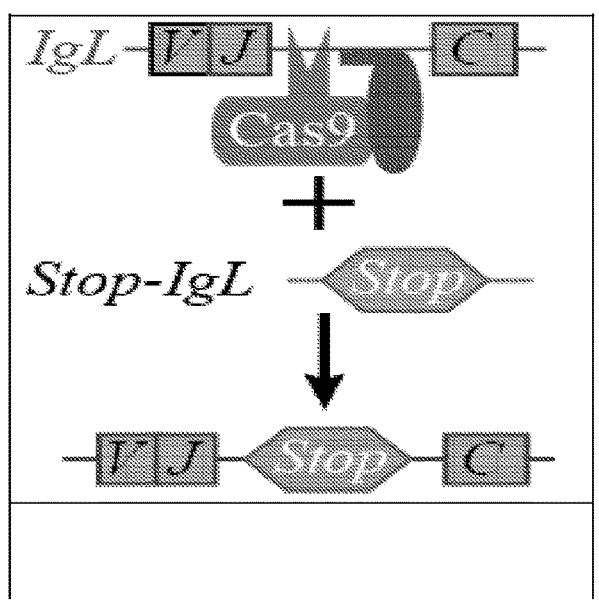

FIG. 6A depicts schematics of the endogenous B cell genome that encode an IgH chain and an IgL chain. FIGS. 8A and 8B depict initial schematics of where exogenous genetic constructs according to the current disclosure can be inserted to achieve expression of a selected antibody. FIG. 8A depicts inserting a genetic construct including [a stop signal, an IgL chain of a selected antibody (here, PV), a skipping element (here, 2A), and the VDJ segment of a heavy chain] into the endogenous IgH genome between the endogenous VDJ segment and the endogenous C region coding segments. This approach leads to expression of an entire exogenous IgL chain, an exogenous VDJ segment of a heavy chain, and an endogenous C region of the heavy chain. Expression of an antibody that includes an endogenous C region can be useful, for example, because it can allow a modified B cell to modulate C region expression based on natural B cell activation and maturation state. For example, alternative splicing in the constant region of the heavy chain gene locus can allow a modified B cell to switch between expression of a membrane-bound antibody and expression of a secreted antibody. This approach also allows expression of an exogenous VDJ without requiring excision of the endogenous VDJ. This feature is beneficial because the VDJ is a relatively large segment of DNA and its excision can negatively affect cellular function.

Figure 9:
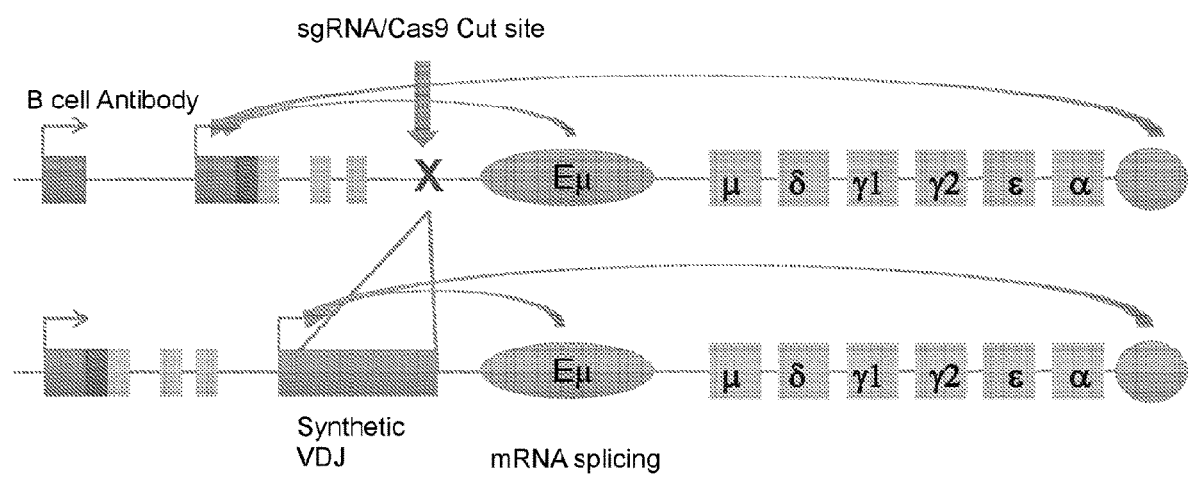
FIG. 9. Schematic depicting interactions of heavy chain enhancers with (top) an endogenous VDJ or (bottom) a synthetic VDJ encoded by an inserted genetic construct. Promoters are depicted as arrows. Nucleic acid is depicted as boxes. B cells naturally express nucleic acid that is downstream of the promoter that is closest to the Eμ enhancer. In the endogenous B cell genome depicted in FIG. 9, the first upstream promoter closest to the Eμ enhancer then drives expression of the endogenous heavy chain VDJ segments. Inserting a genetic construct that includes a promoter between the Eμ enhancer and the first endogenous promoter, results in the B cell expressing the inserted genetic construct rather than the endogenous heavy chain VDJ segments. This inserted gene could be a VDJ variable region of a heavy chain, a paired full antibody light chain together with the heavy chain variable VDJ, or another synthetic gene capable of being expressed as a fusion with a B cell heavy chain constant region.

FIG. 9 depicts a similar schematic with more detail regarding the structure and function of the endogenous B cell genome, and how the current disclosure utilizes this structure and function to achieve expression of selected antibodies. Promoter regions are necessary to achieve transcription of a gene segment. Heavy chain variable region ($V_H$) promoters are selectively active in the B cell lineage, and include a TATA box, an Inr element, and an octamer element within 100 base pair (bp) of the transcriptional initiation site. $V_H$ promoter activity is under proximity-dependent regulation by the endogenous B cell genome's Eμ enhancer element (gray oval), and an enhancer element positioned at the 3' end of the heavy chain gene locus, proximal to the heavy chain a constant gene (gray circle). The Eμ enhancer element is an intronic region of DNA (40 to 1500 bp in length) within the 700-bp intron between the J heavy chain segment and the C mu (μ) segment of the immunoglobulin heavy chain gene locus. It can bind an activator protein to increase or activate transcription of the heavy chain gene. The sequence of the human Eμ enhancer element is provided in FIG. 11A as SEQ ID NO: 85. The sequence of the mouse Eμ enhancer element is provided in FIG. 13A as SEQ ID NO: 86.

Inserting a genetic construct that includes a $V_H$ promoter between an endogenous heavy chain variable region and an endogenous Eμ enhancer may reduce or block transcription activation from the endogenous $V_H$ promoter because the Eμ enhancer will initiate transcription at the most proximal upstream promoter. In this manner, expression of the endogenous VDJ can be blocked without requiring the removal of such a large DNA segment (which, as indicated, is problematic for cell function and survival). In particular embodiments, VDJ recombination removes genetic material between the $V_H$ promoter and the Eμ enhancer, which positions the enhancer at the appropriate distance from an exogenous promoter of a genetic construct disclosed herein to activate transcription starting from the promoter in the inserted genetic construct. In particular embodiments, no endogenous genetic material is removed. In particular embodiments, less than 50 base pairs are removed. In particular embodiments, $V_H$ promoters within exogenous genetic constructs include the native light chain promoter for IgK or IgL, a native human IgH promoter, the spleen focus forming viral promoter SFFV, the J558 h10 promoter or the IgVH1-69 promoter.

Figure 10:
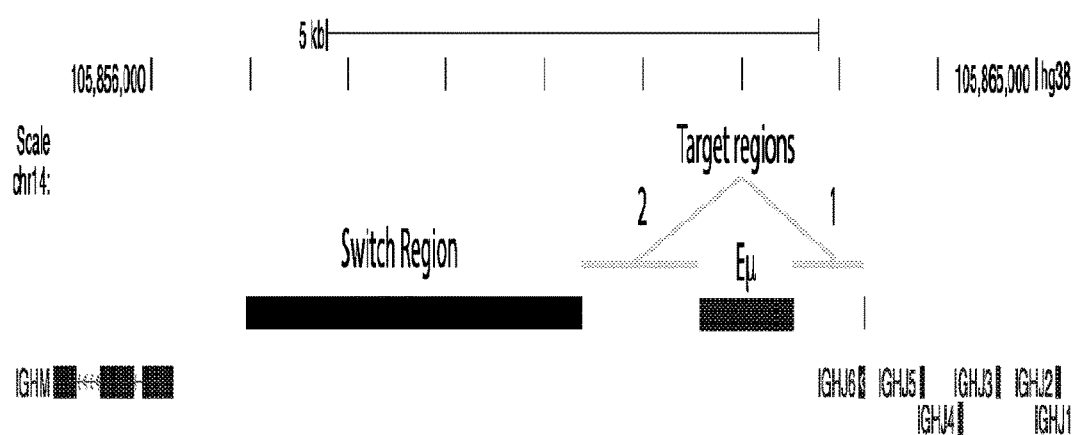
FIG. 10. Target regions for insertion (Human). Regions for genetic construct insertion into the genome: #1: From the terminal J region (IGHJ6 in human, IGHJ4 in mouse) to the Eμ enhancer, or #2: From the Eμ enhancer to the repetitive sequences of the constant domain switch region.

FIG. 10 provides an additional schematic for target areas for genetic construct insertion. These target areas encompass two conserved regions present in all B cells: from the terminal J gene segment (IGHJ6 in humans, IGHJ4 in mice) to the heavy chain intronic enhancer (Eμ), and from Eμ to the repetitive sequences associated with DNA switch recombination.

In particular embodiments, the area of the endogenous B cell genome that is targeted for insertion of the genetic construct is upstream of the Eμ enhancer of SEQ ID NOs: 85 or 86. FIGS. 11A-14B provide particular sequences that can be targeted for genetic construct insertion to achieve expression of a selected antibody as disclosed herein.

Figure 25B:
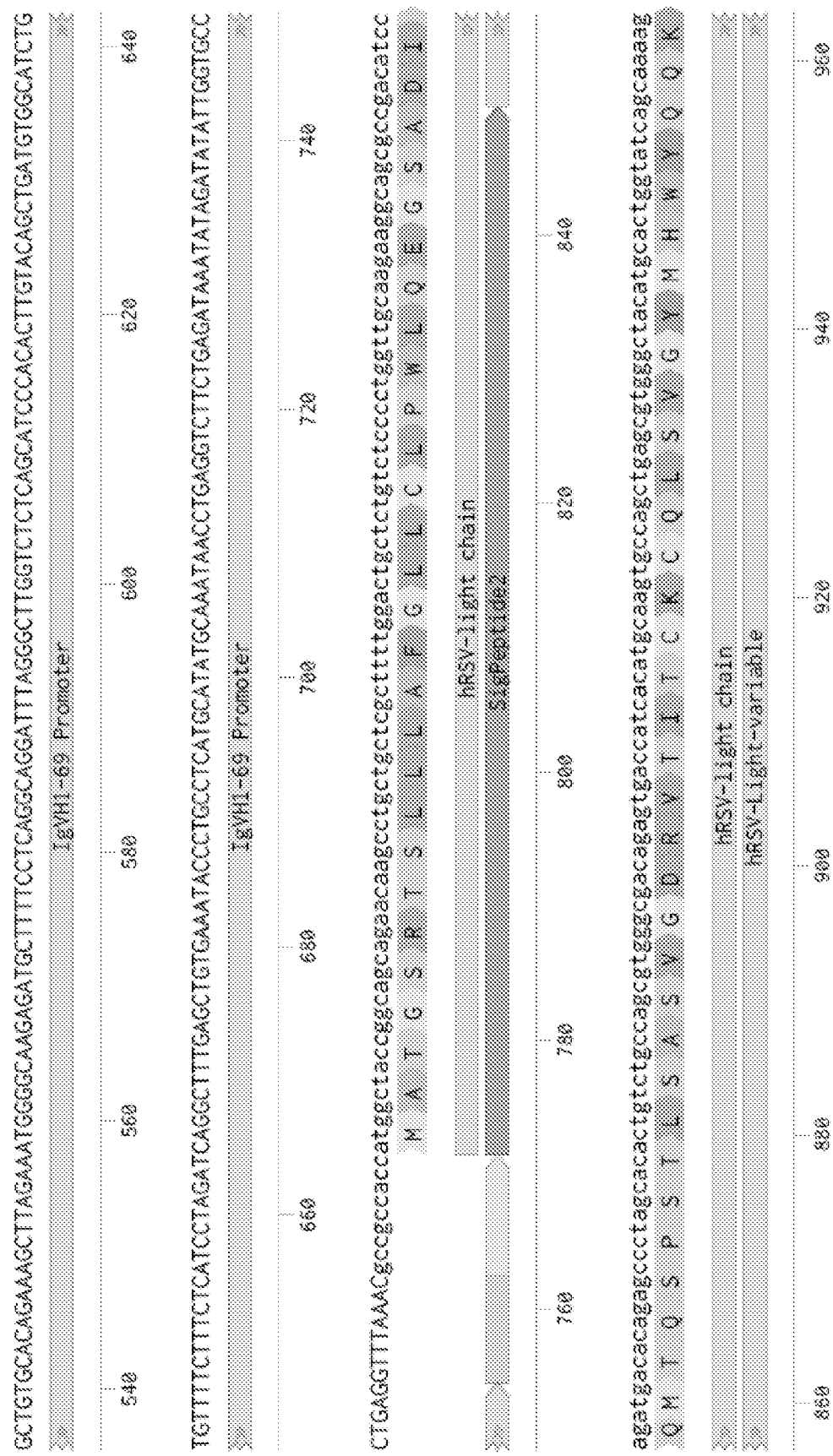
Figure 25B:
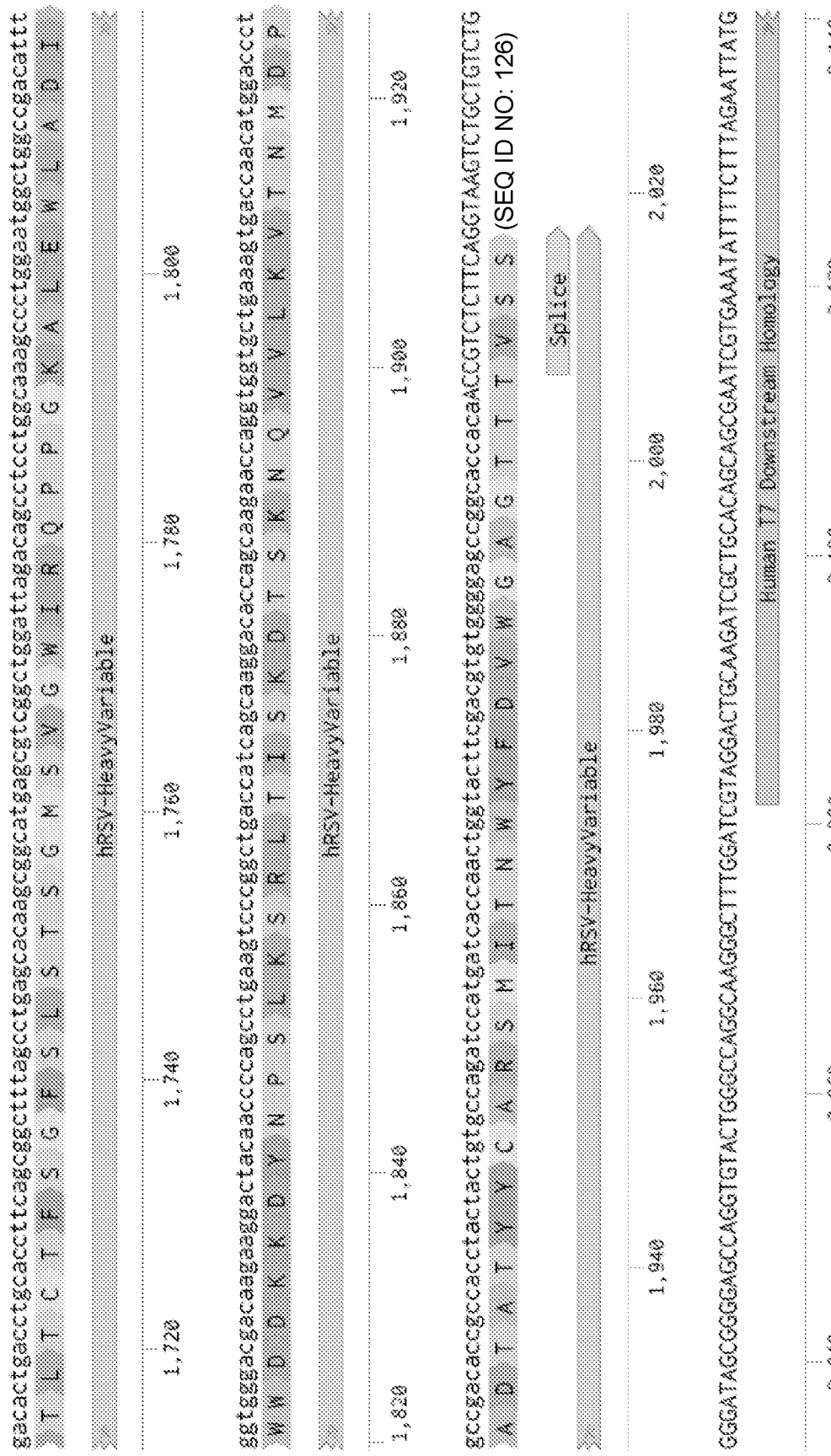
Figure 25B:
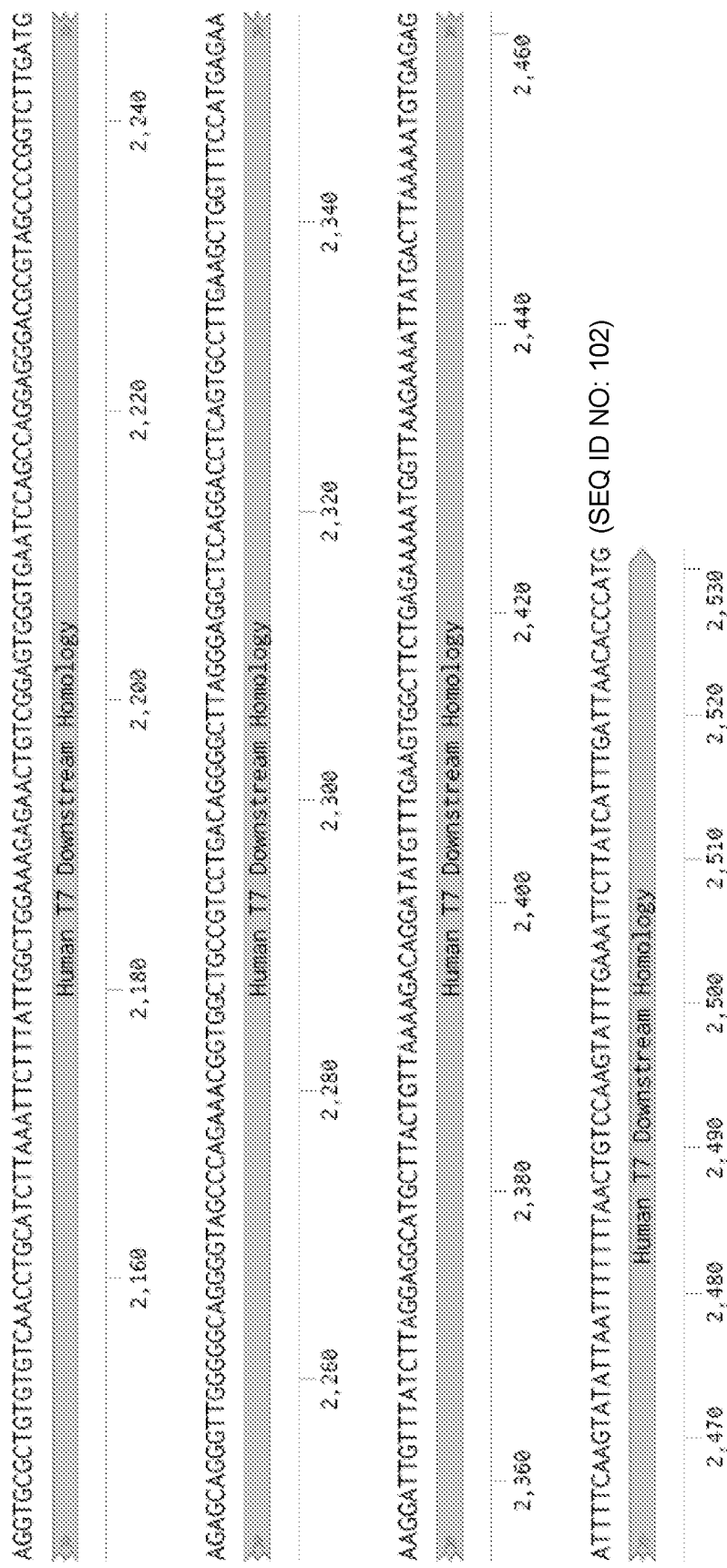
Figure 25C:
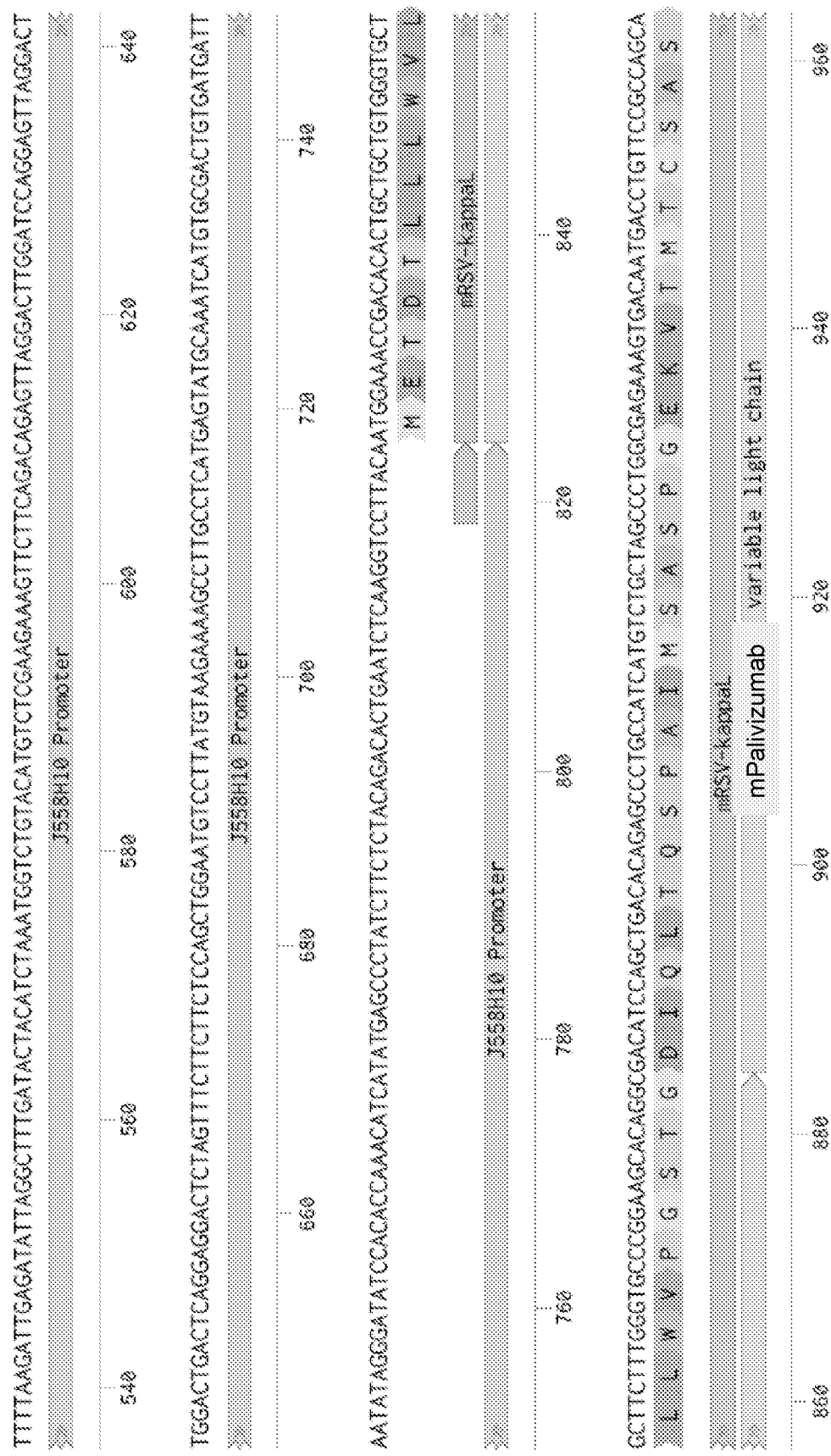
Figure 25C:
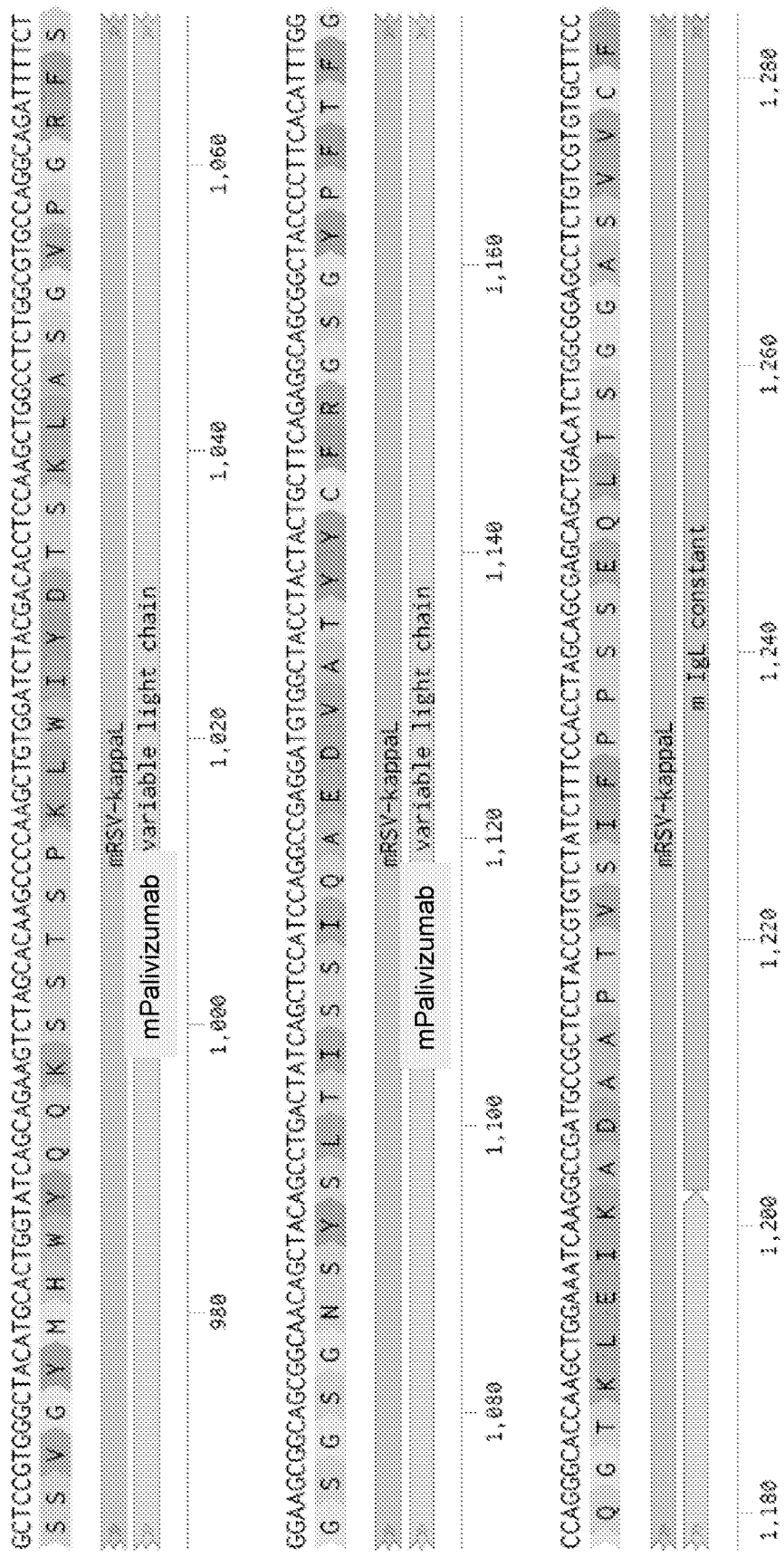
Figure 25C:
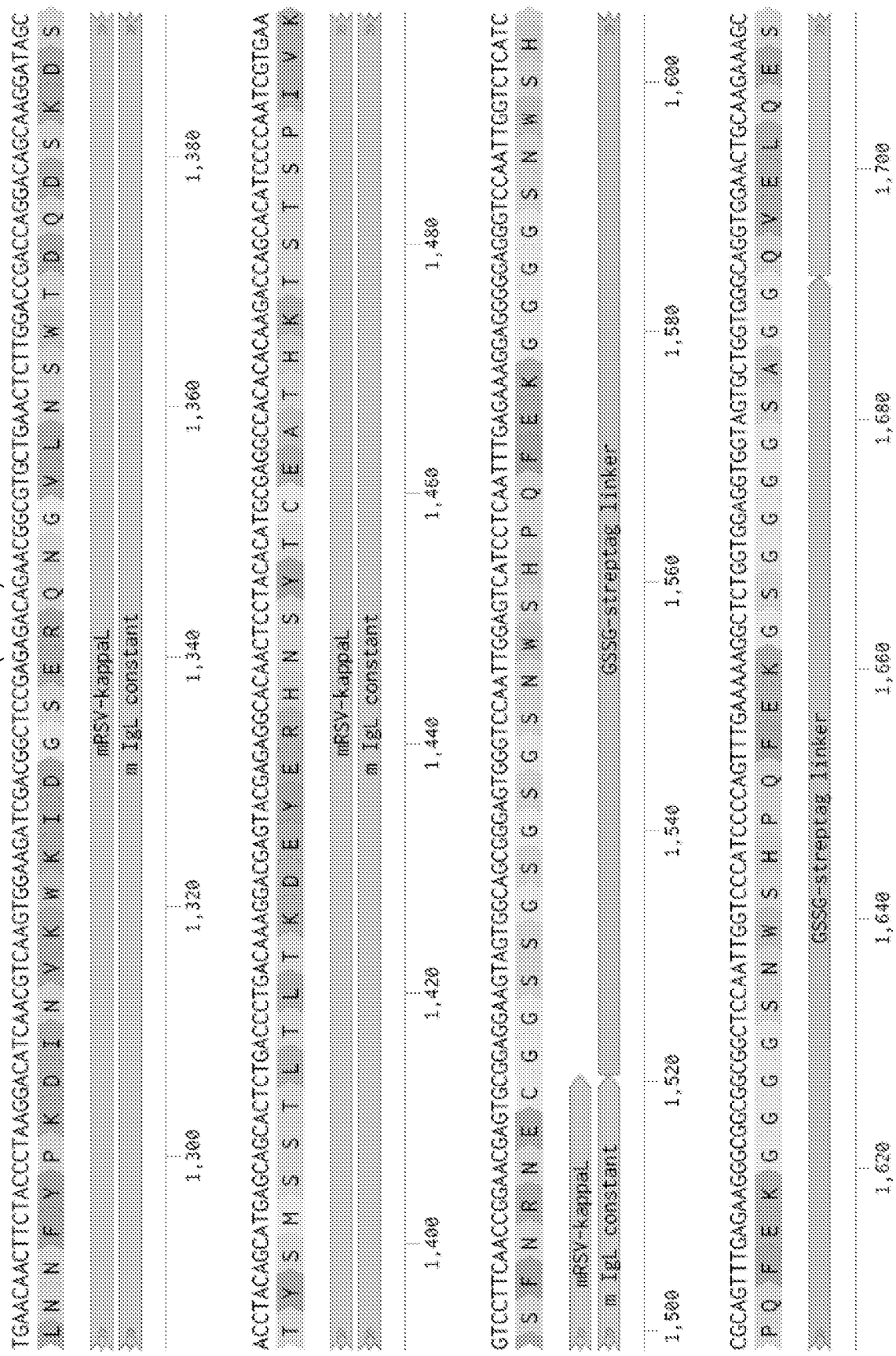
Figure 25C:
Figure 25C:
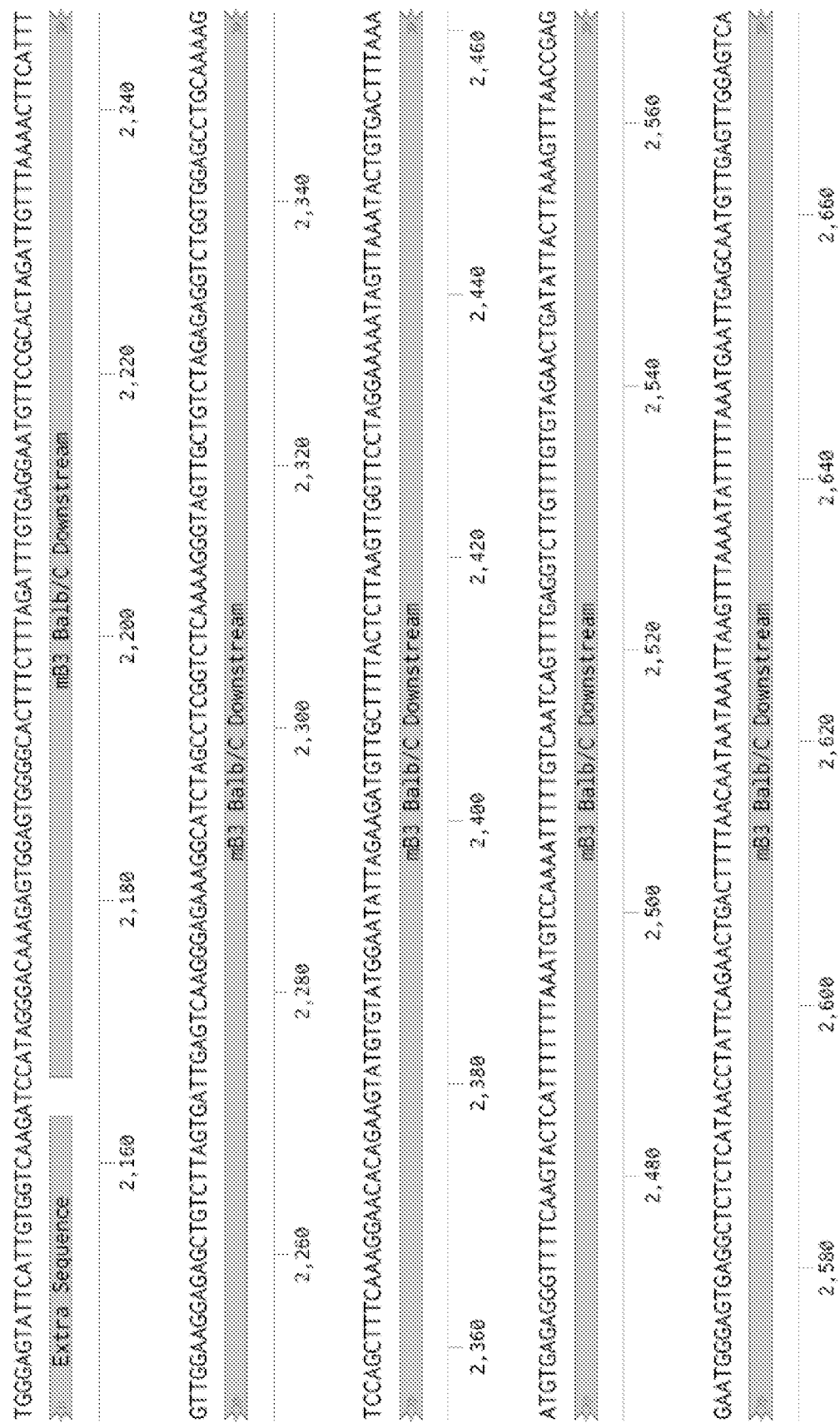
Figure 25C:
Figure 25D:
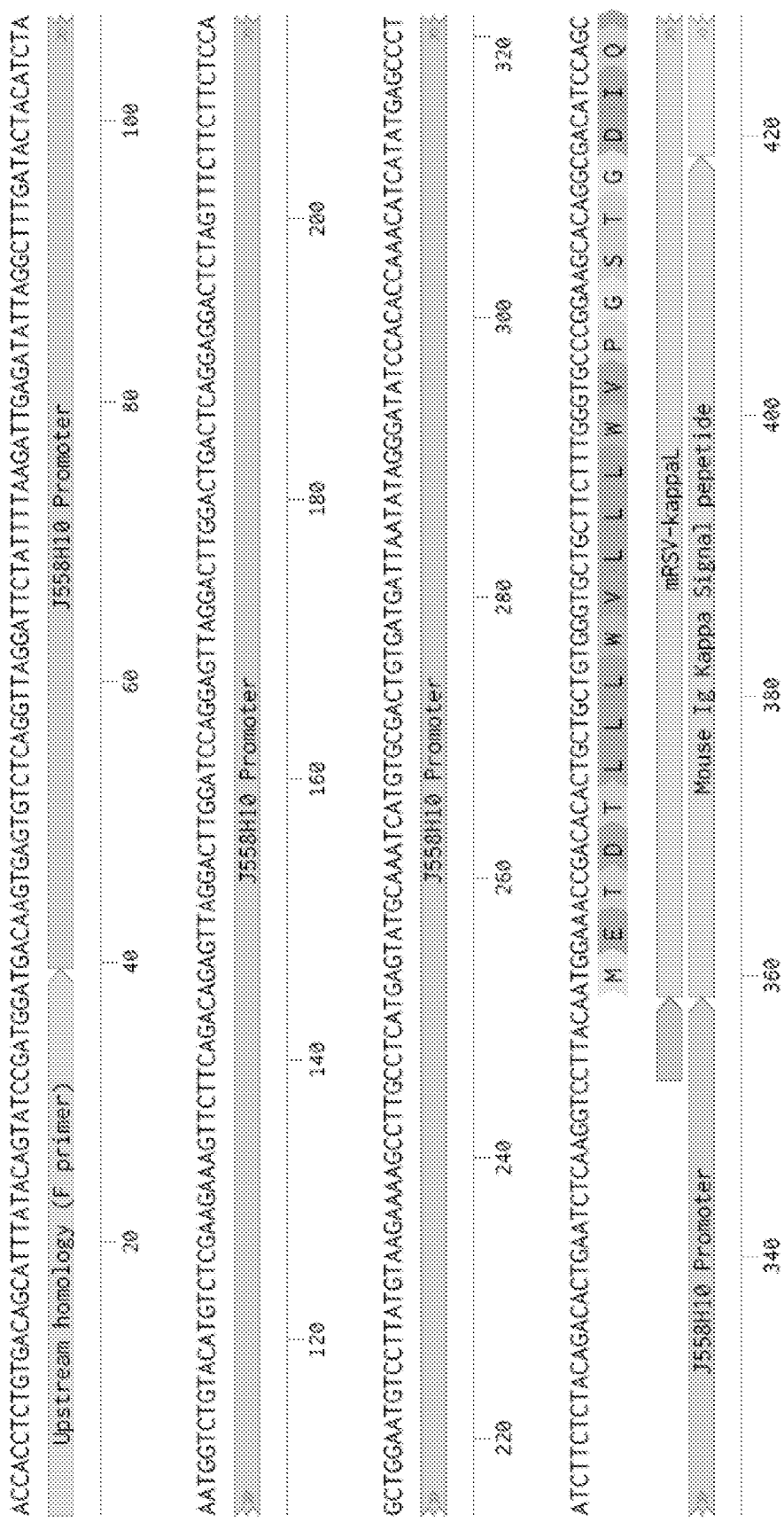
Figure 25D:
Figure 25D:
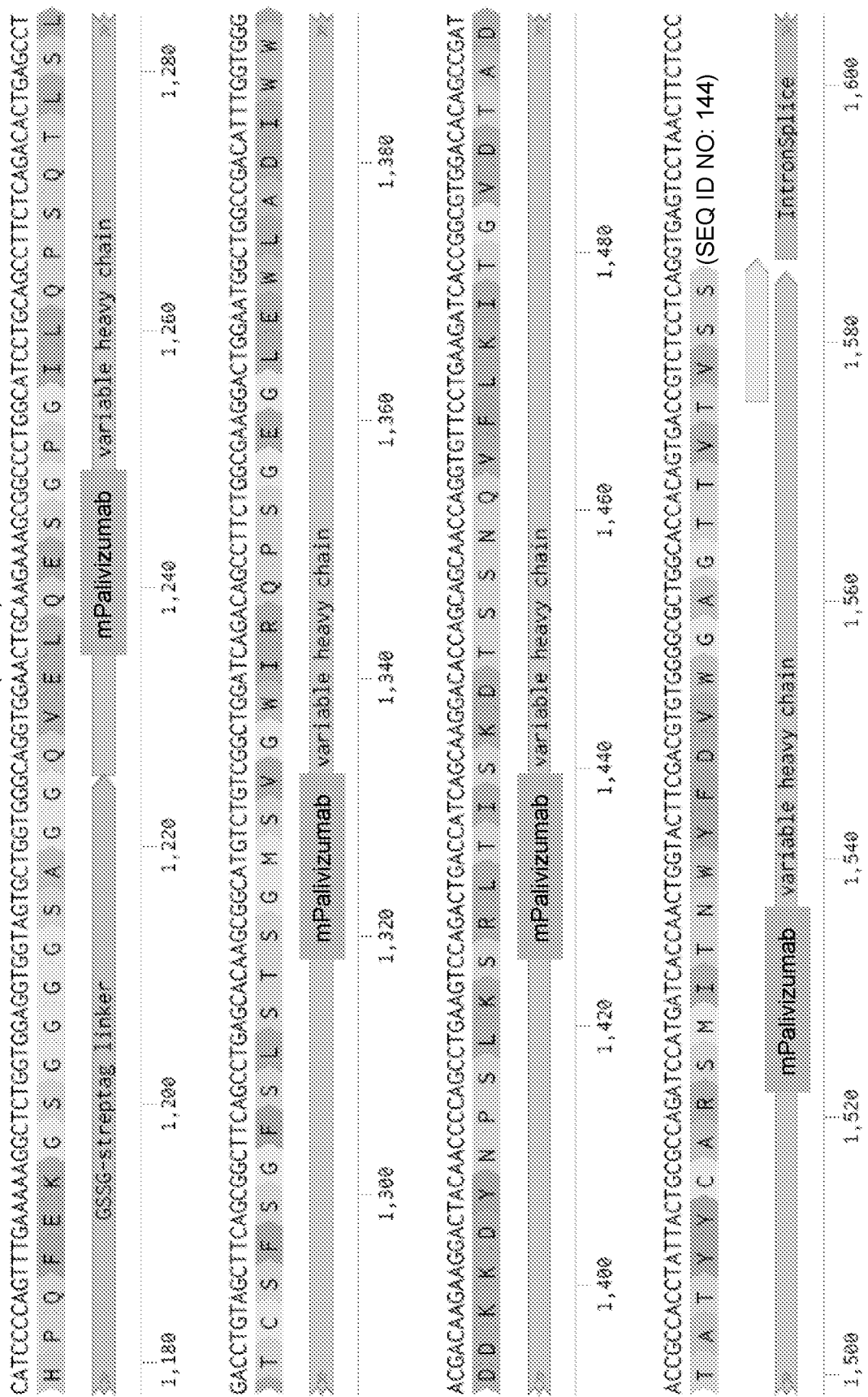
Figure 25E:
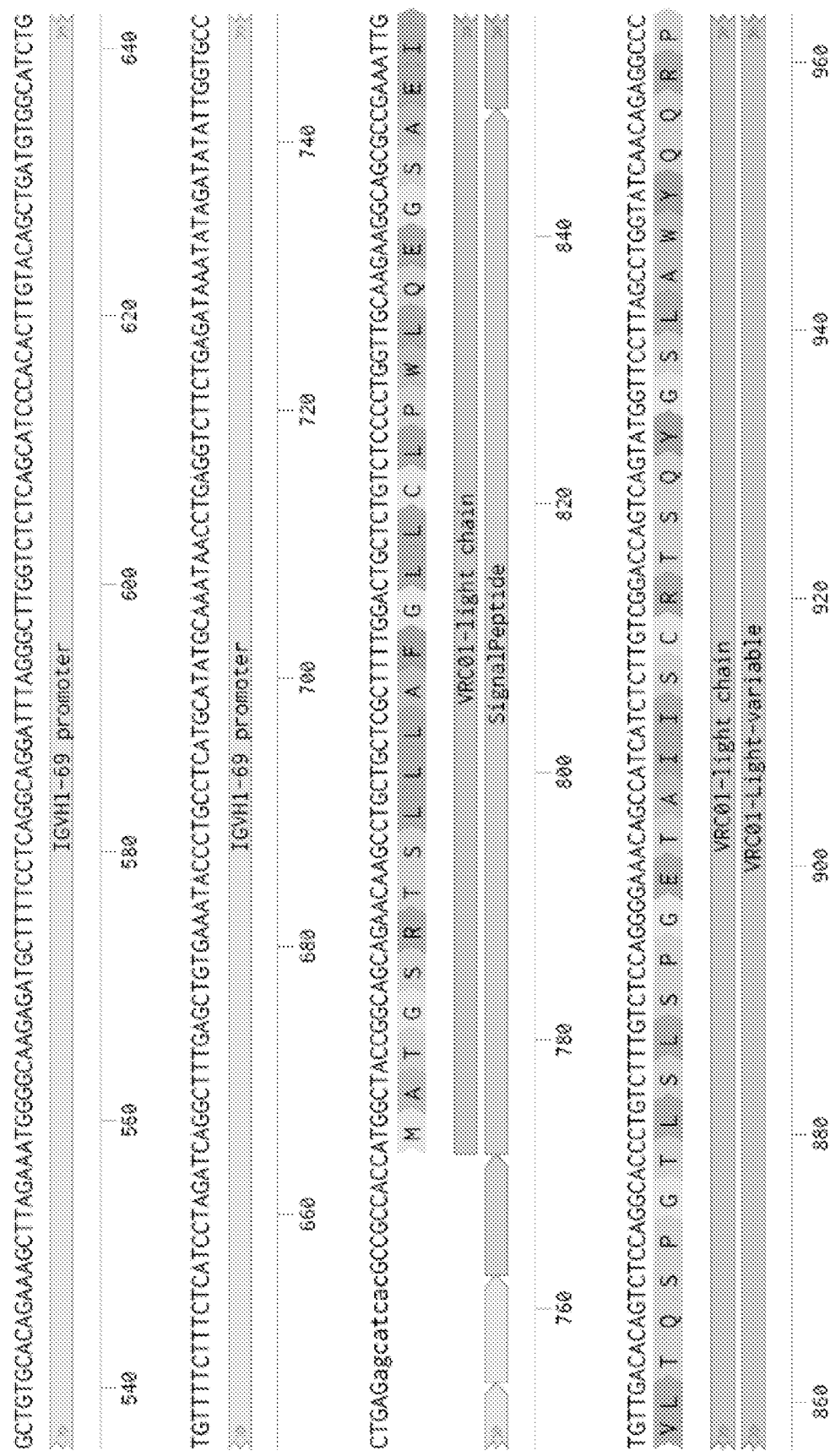
Figure 25E:
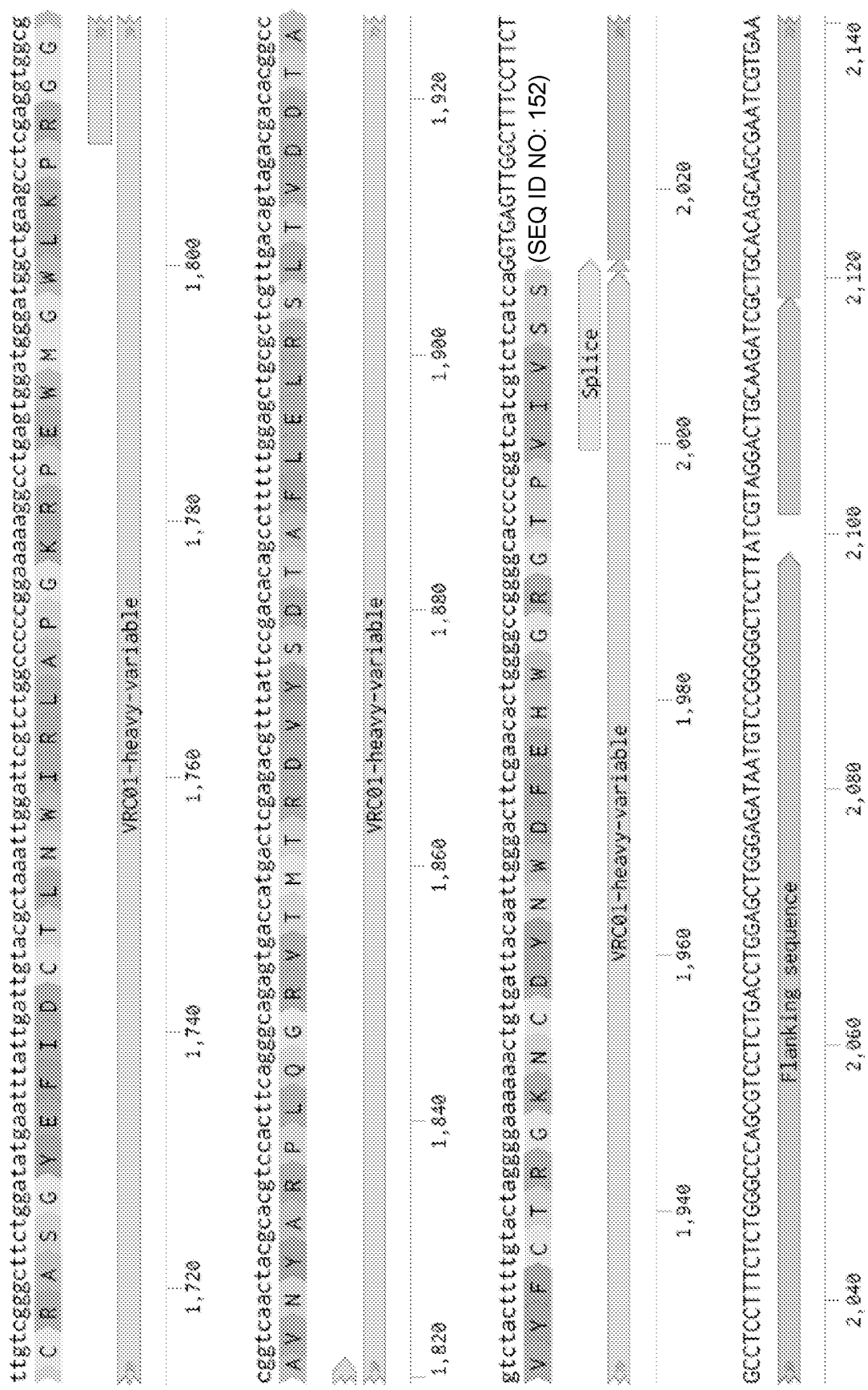
Figure 25F:
Figure 25F:
Figure 25F:
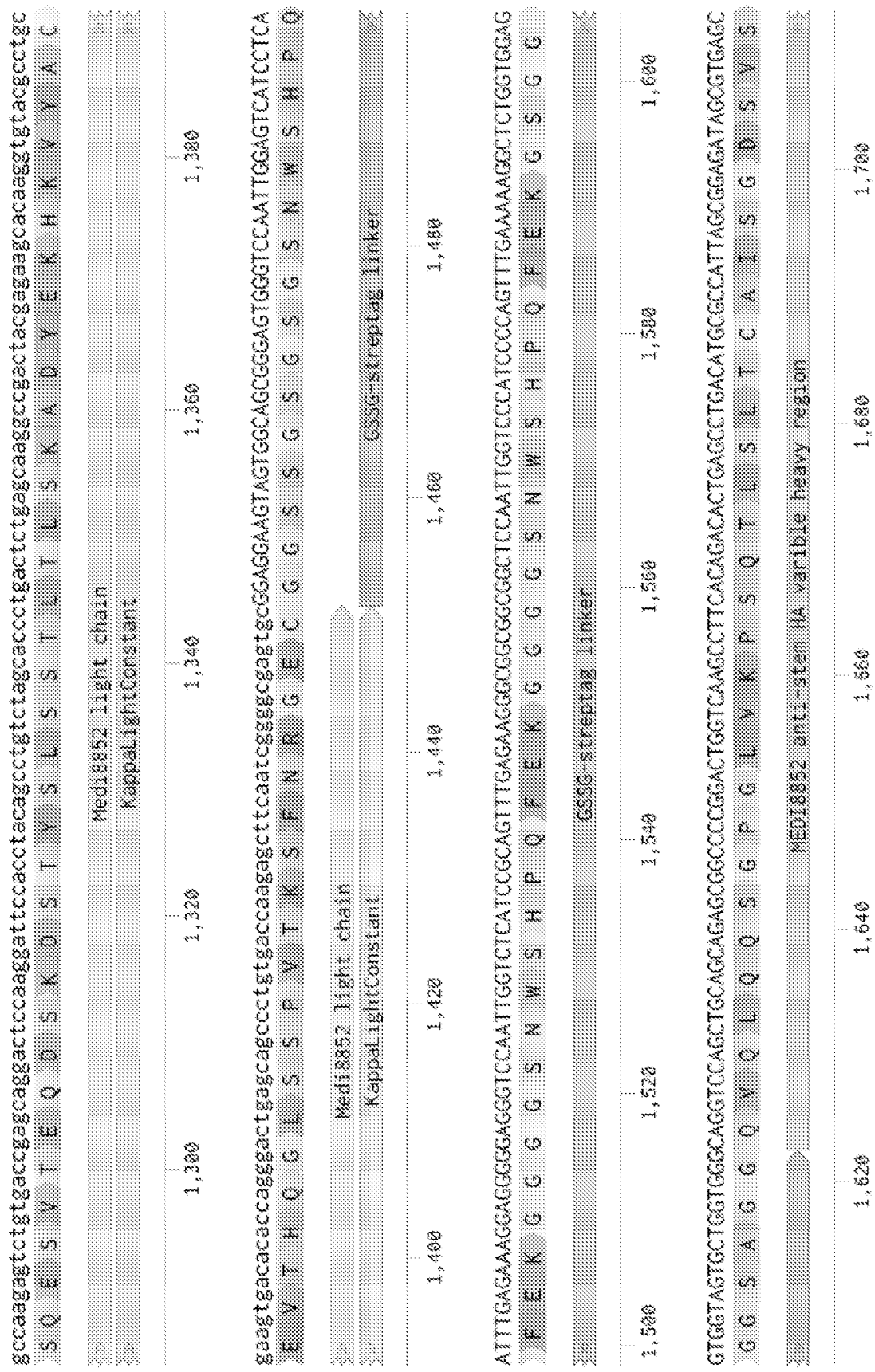
Figure 25F:
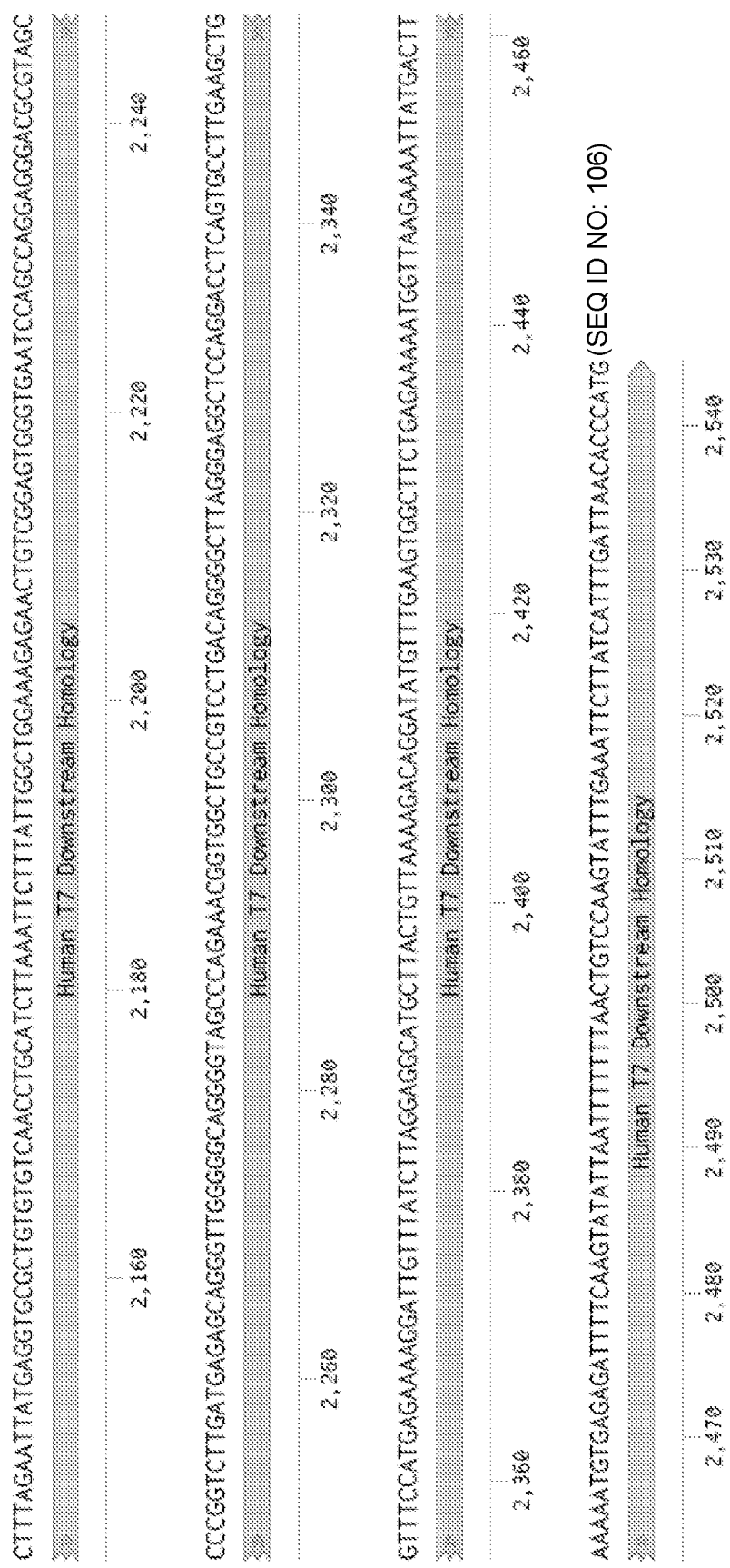
Figure 25G:
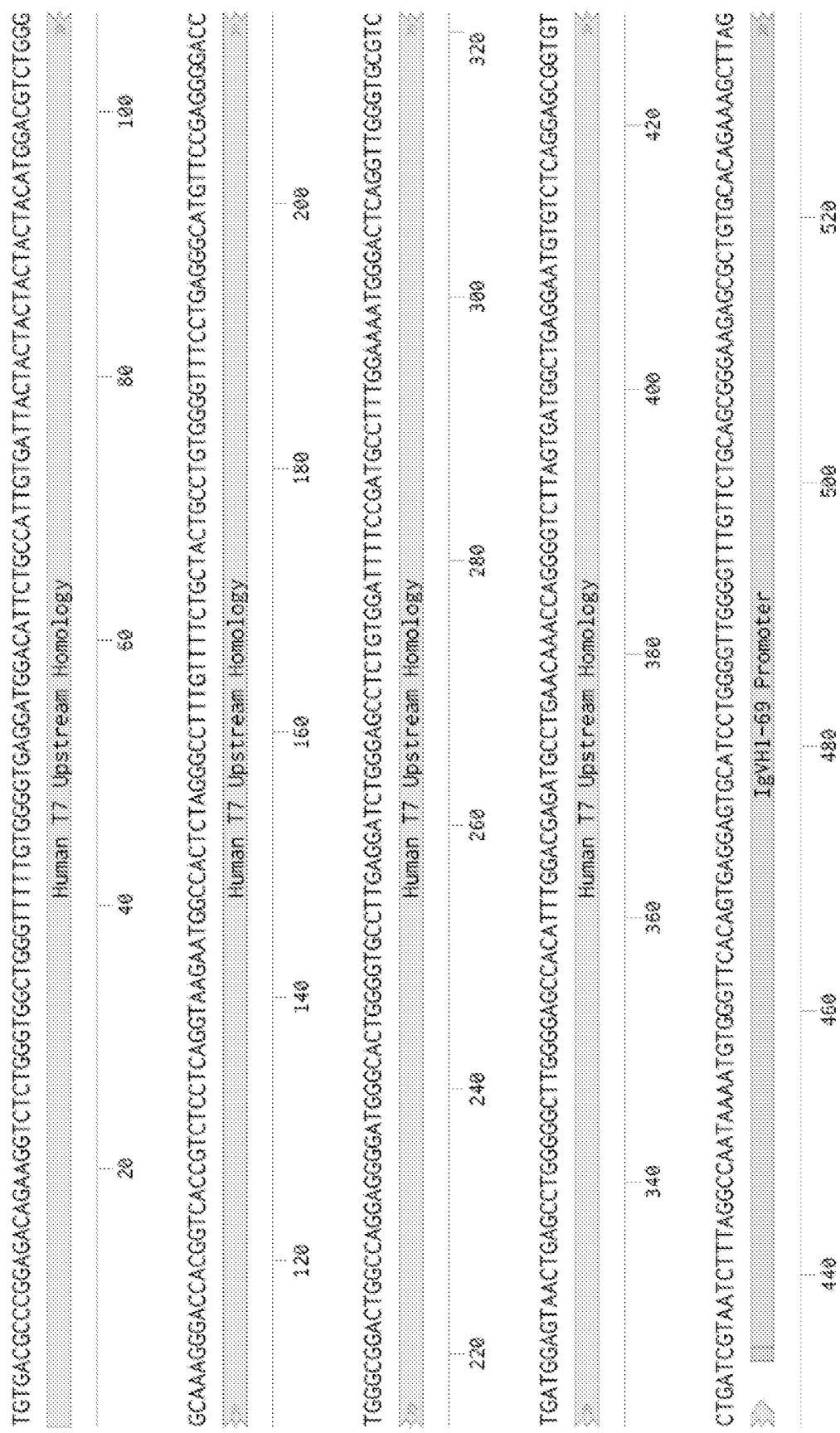
Figure 25G:
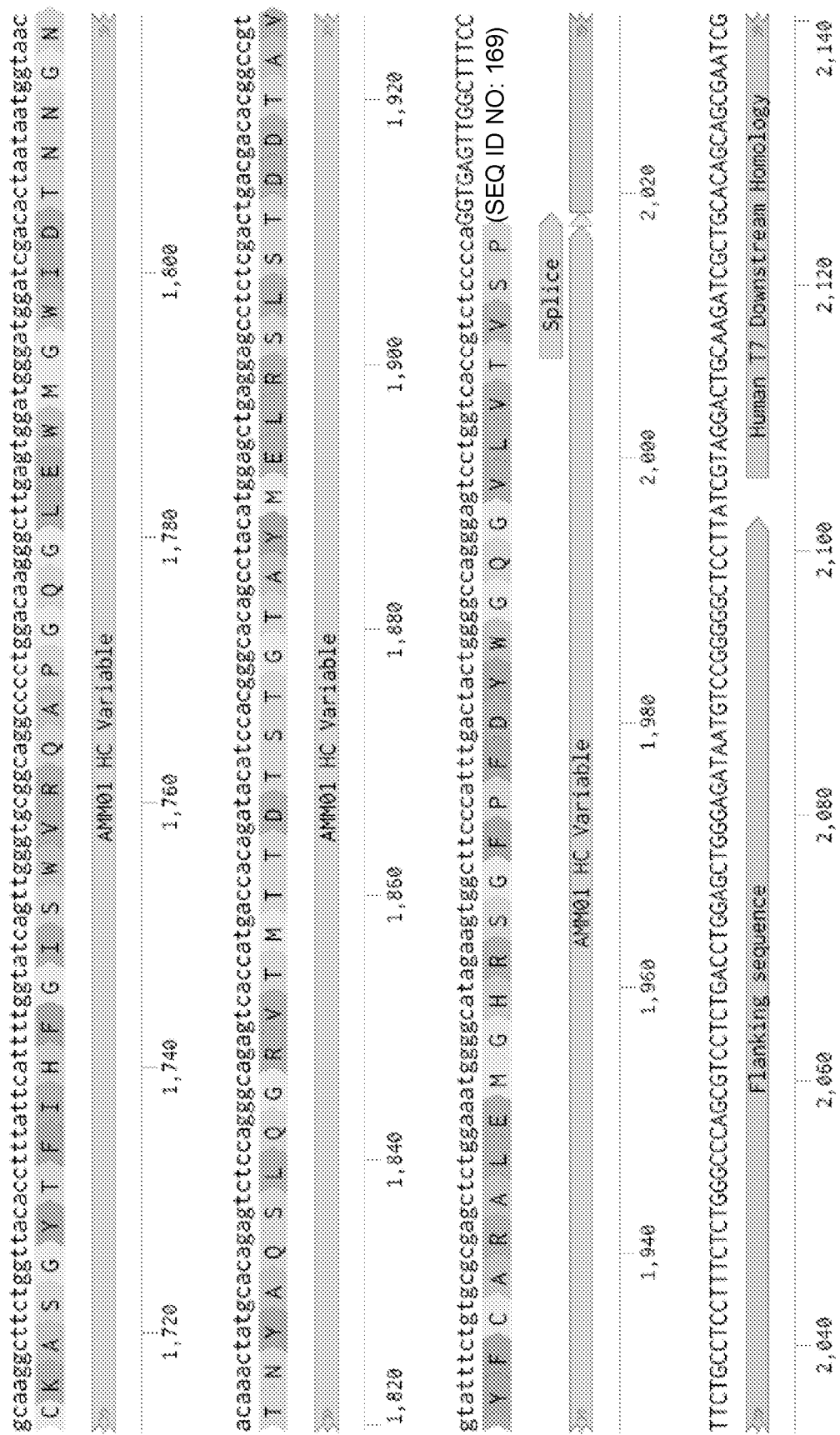
Figure 25H:
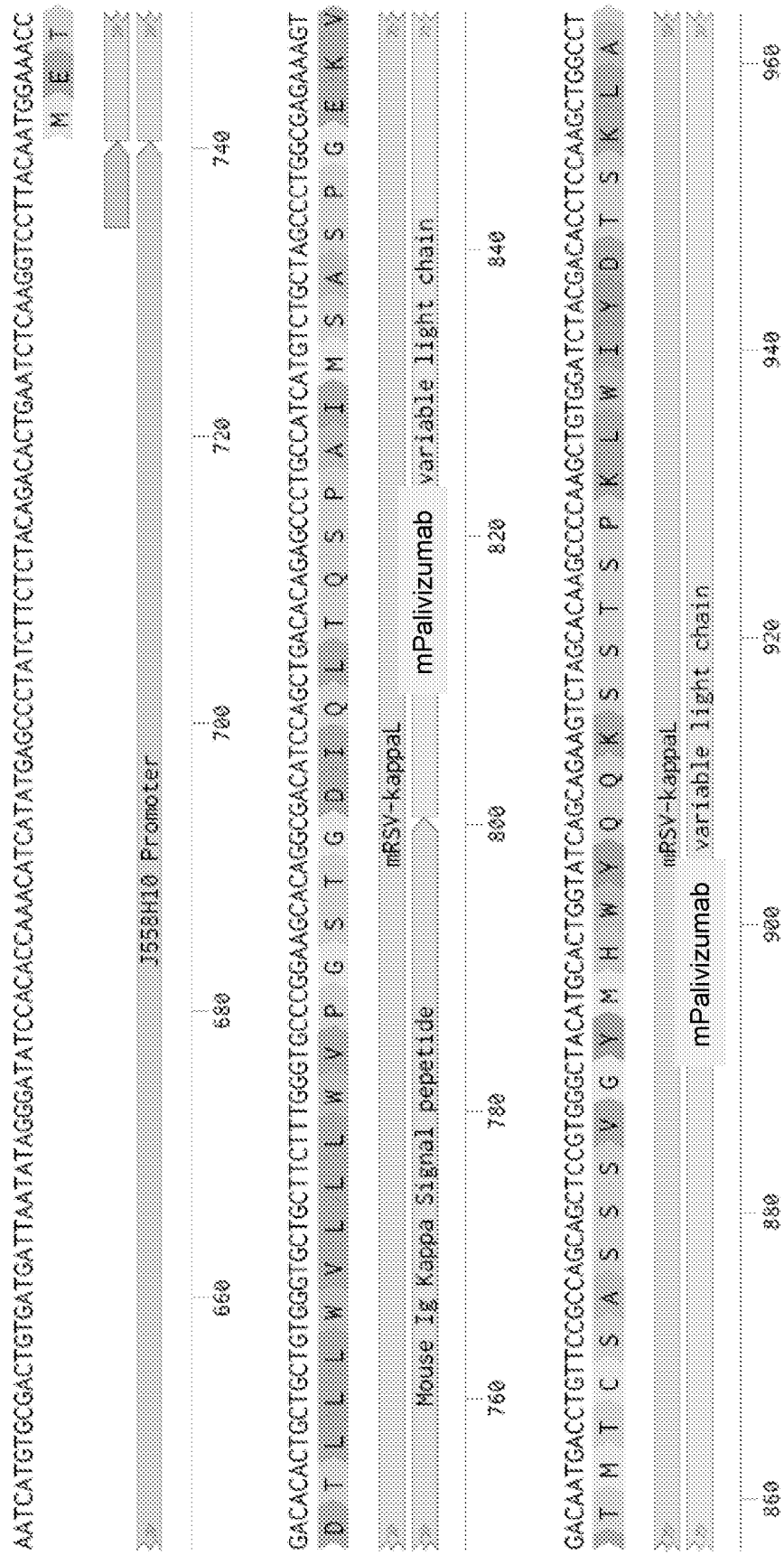
Figure 25H:
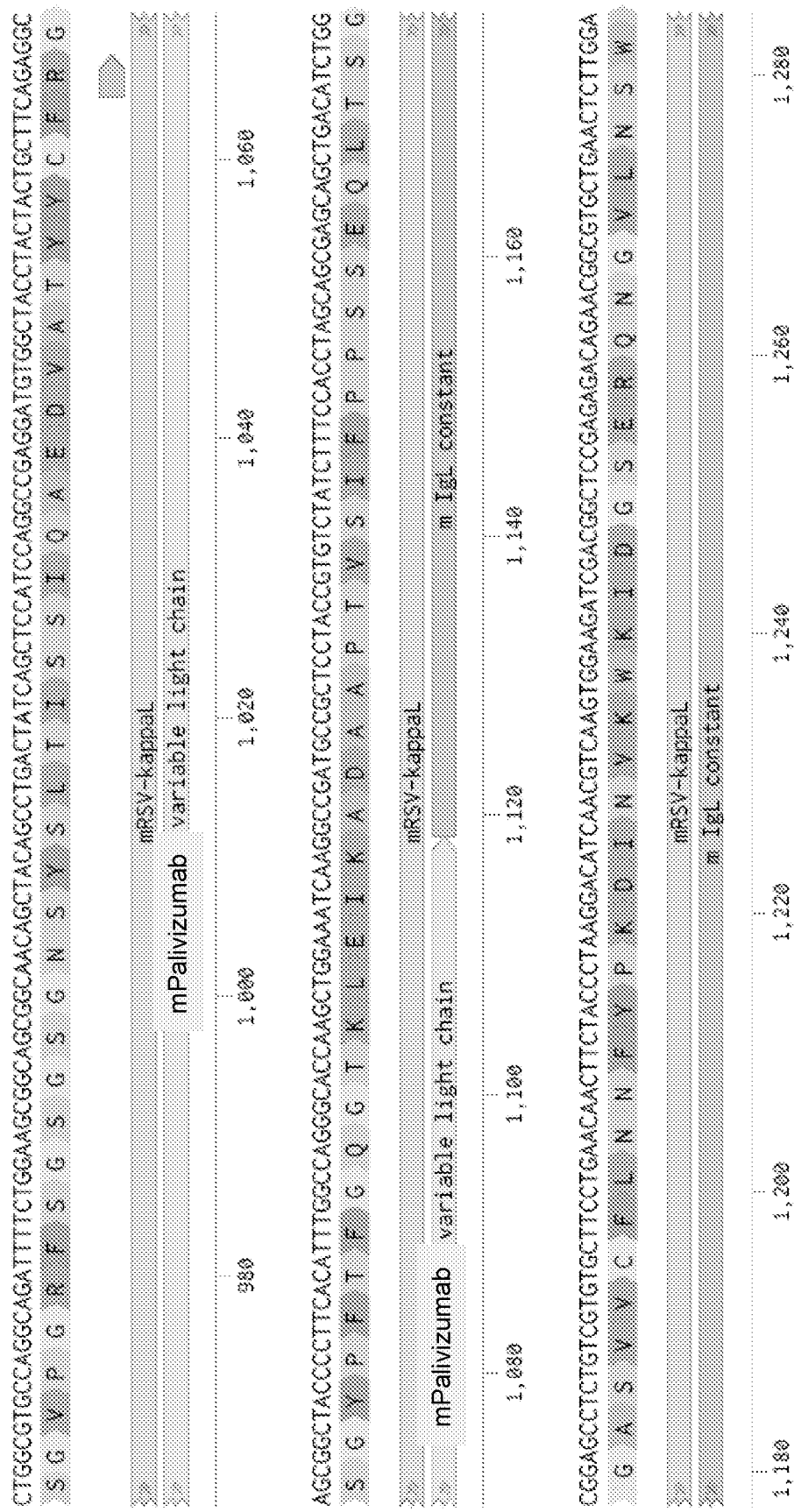
Figure 25H:
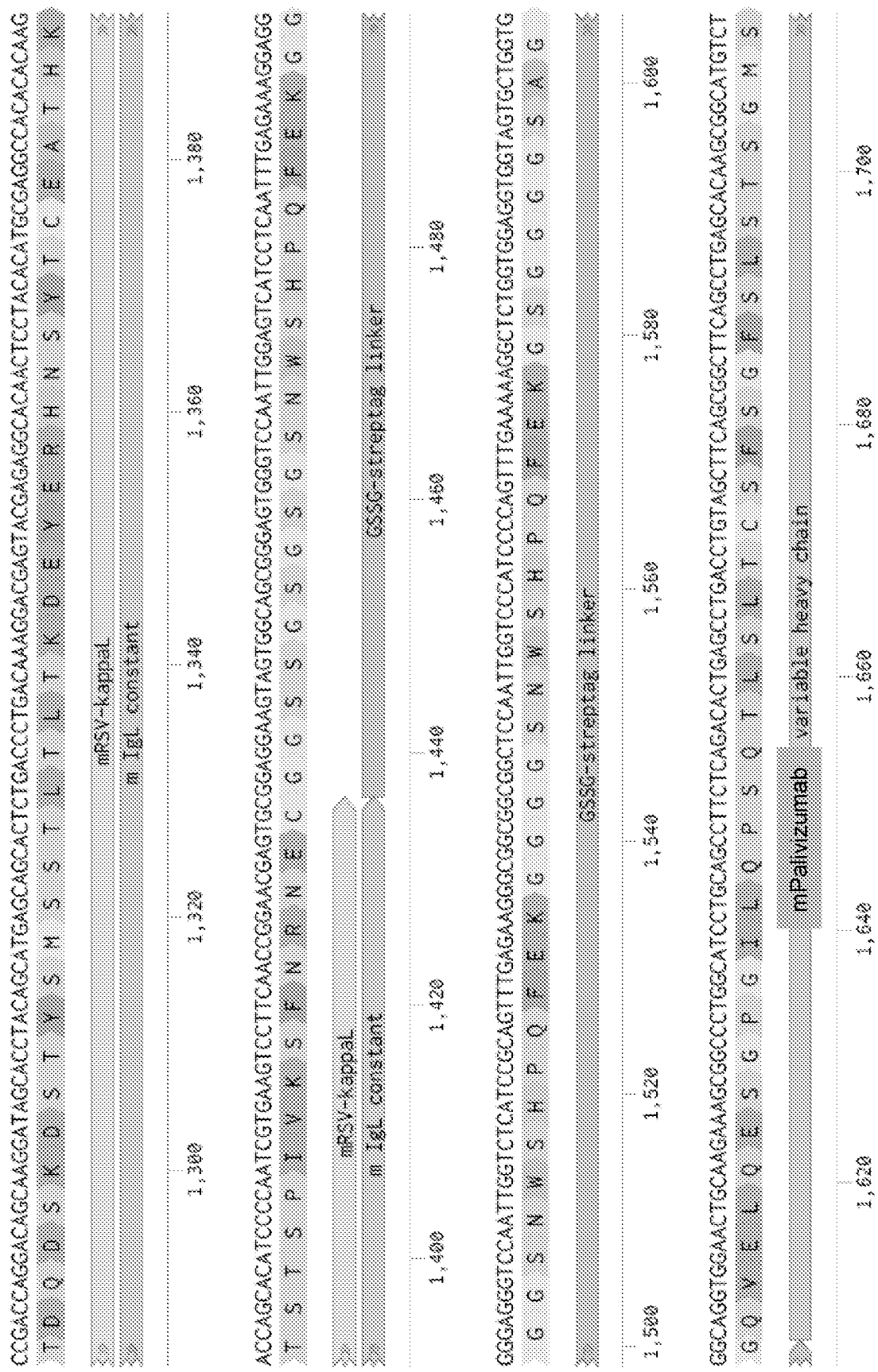
Figure 25H:
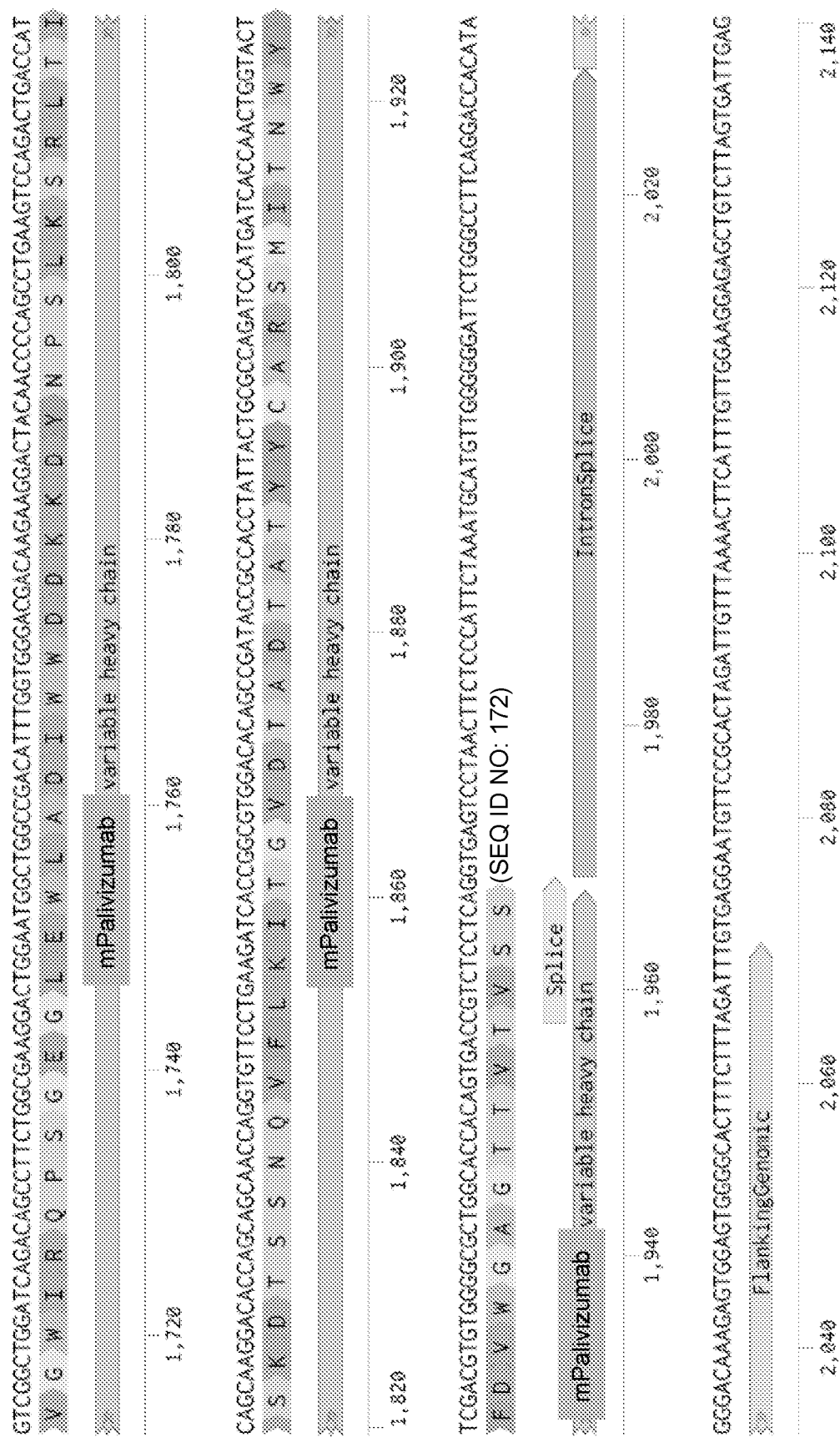
Figure 25I:
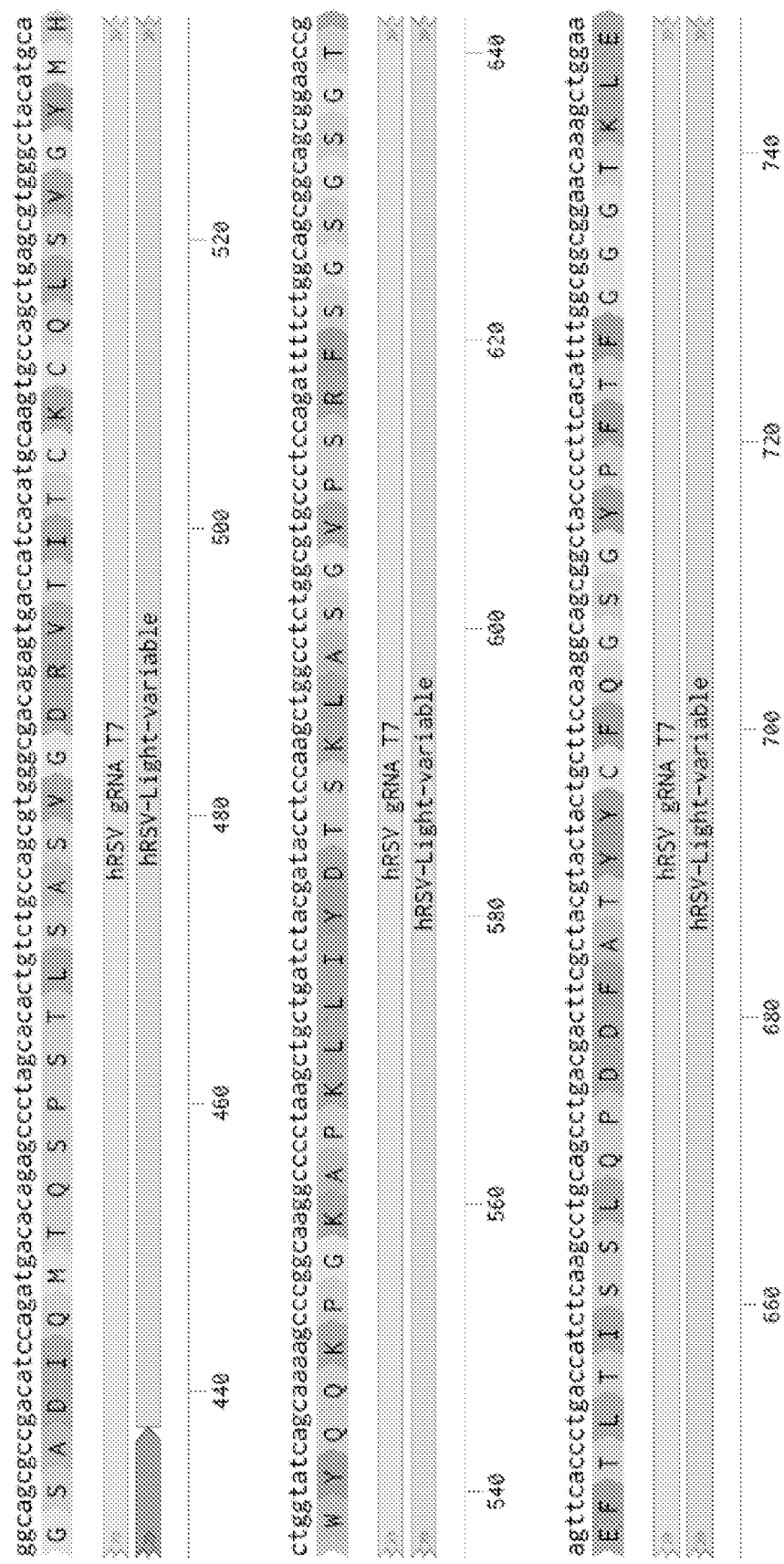
Figure 25I:
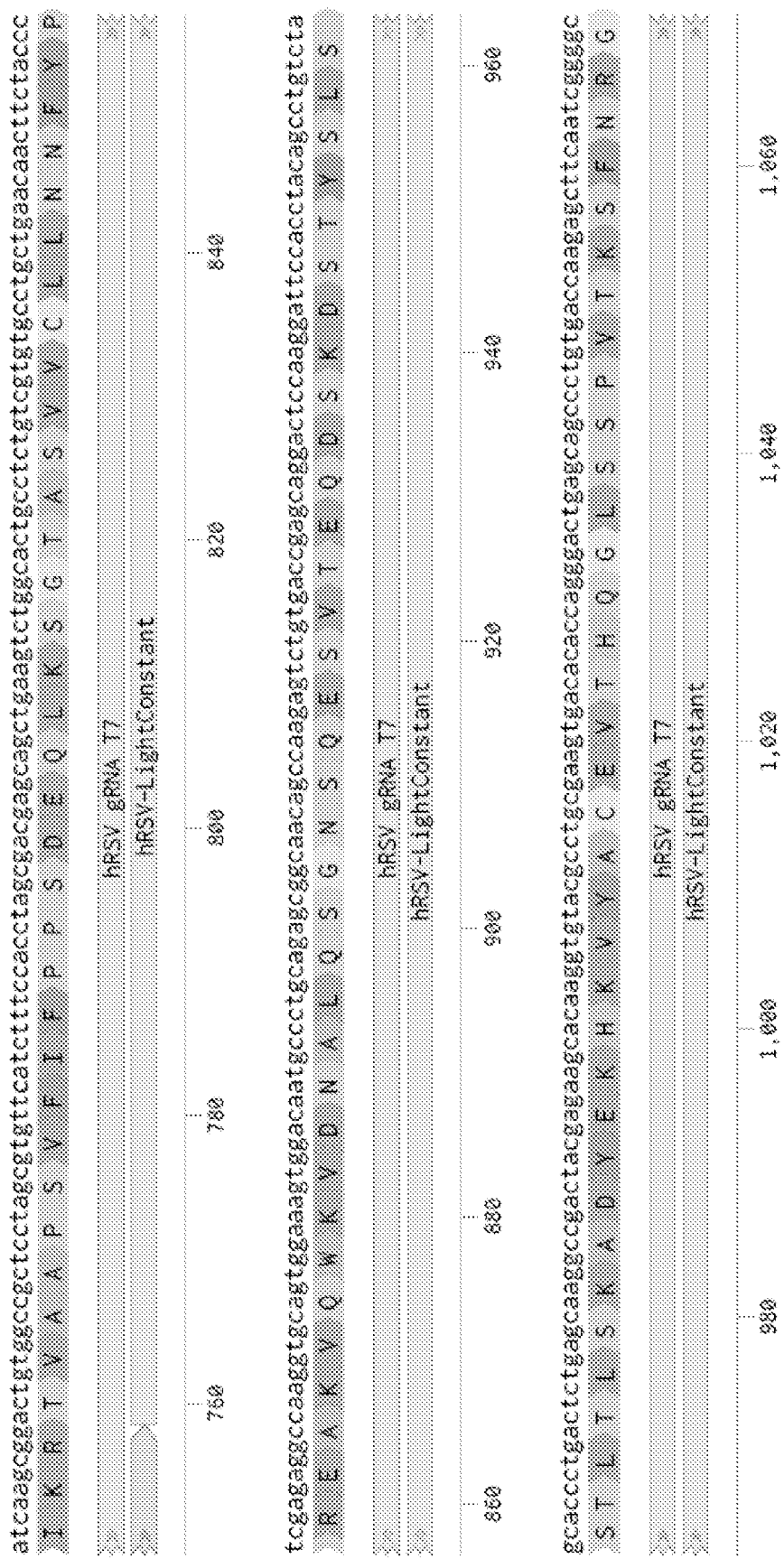
Figure 25I:
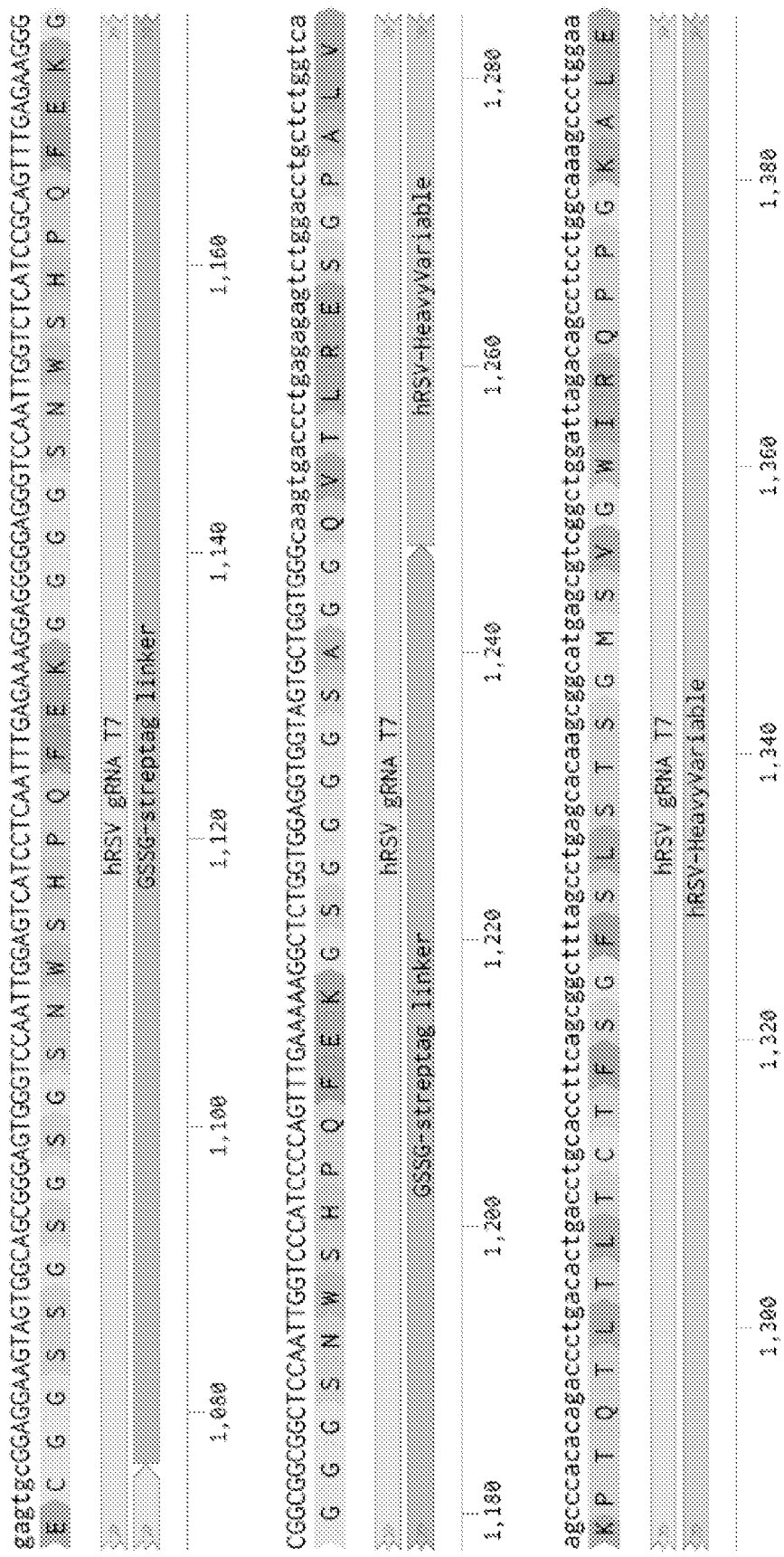
Figure 26A:
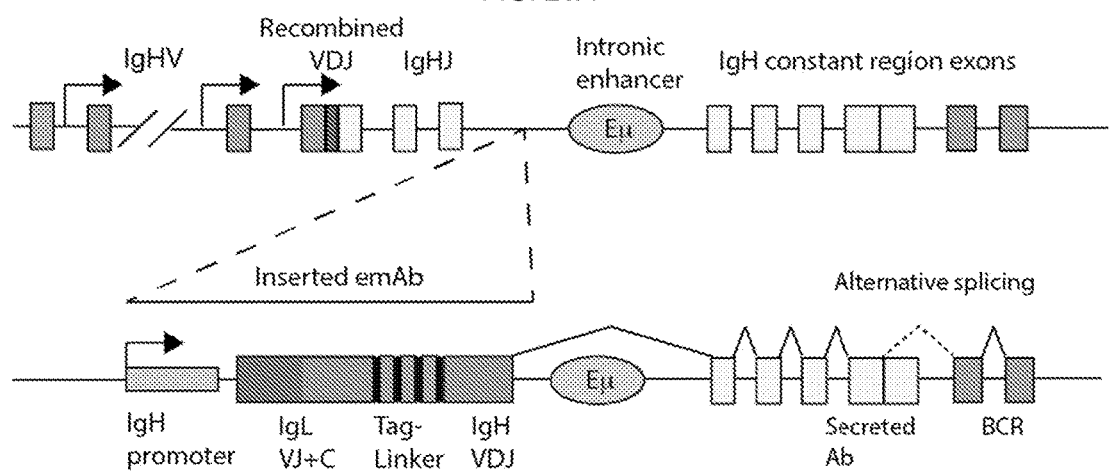
FIGS. 26A-26D.
Figure 26B:
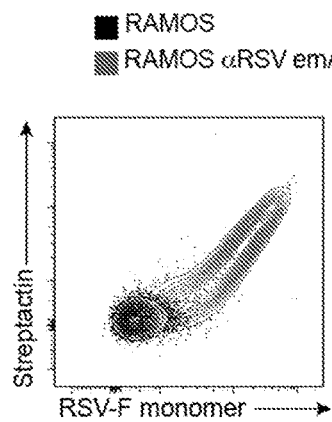
Figure 26C:
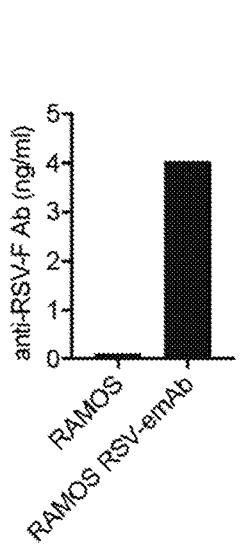
Figure 26D:
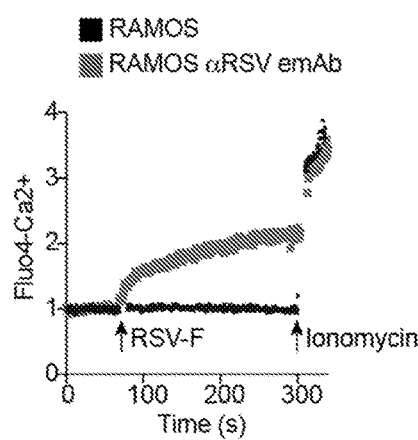
Figure 27E:
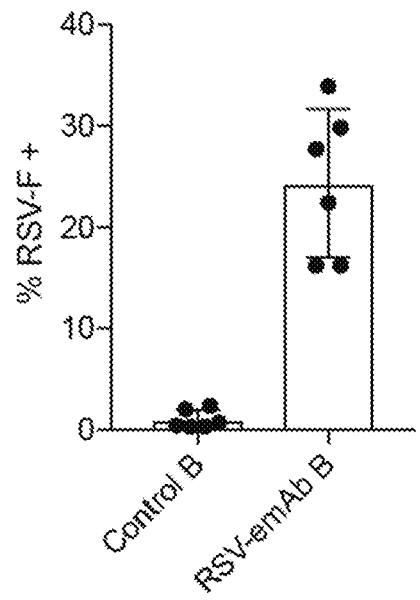
Figure 27F:
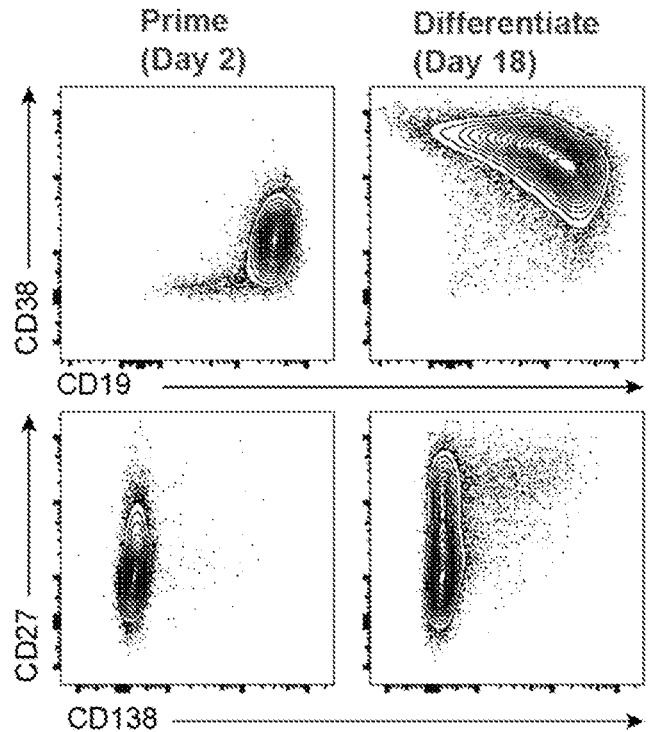
Figure 27G:
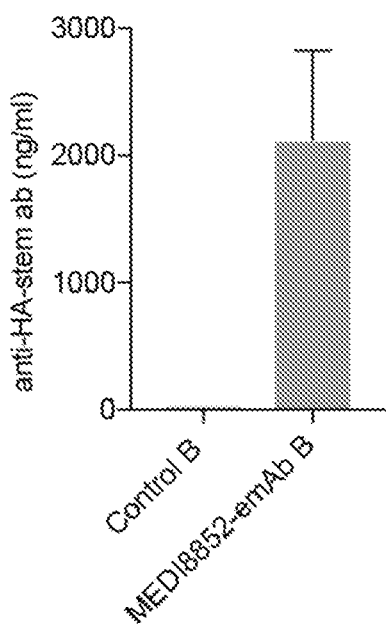

FIG. 11A provides the human DNA sequence of IGHJ6 to Eμ intronic enhancer (SEQ ID NO: 1; >hg38_dna range=chr14:105862523-105863244 5'pad=0 3'pad=0 strand=-repeatMasking=none). FIG. 11B provides exemplary ranges to target (e.g., gRNA sites) within this sequence including SEQ ID NOs: 5-24 and associated gRNA sequences (SEQ ID NOs: 88, 89, and 290-307). As examples, in particular embodiments, sgRNA of SEQ ID NO: 88 (see also FIG. 25A) can be used to target gRNA site of SEQ ID NO: 7. In particular embodiments, sgRNA of SEQ ID NO: 89 (see also FIG. 25A) can be used to target gRNA site of SEQ ID NO: 10.

FIG. 12A provides the human DNA sequence for Region 2: Eμ intronic enhancer to switch region (SEQ ID NO: 2; >hg38_dna range=chr14:105860383-105861690 5'pad=0 3'pad=0 strand=--). FIG. 12B provides exemplary ranges to target (e.g., gRNA sites) within this sequence including SEQ ID NOs: 25-44 and associated gRNA sequences (SEQ ID NOs: 308-327).

FIG. 13A provides the mouse DNA sequence for region 1: from IGHJ4 to Eμ intronic enhancer (SEQ ID NO: 3; >mm10_dna range=chr12:113427973-113428554 5'pad=0 3'pad=0 strand=-repeatMasking=none). FIG. 13B provides exemplary ranges to target (e.g., gRNA sites) within this sequence including SEQ ID NOs: 45-64 and associated gRNA sequences (SEQ ID NOs: 87, and 328-346). As an example, in particular embodiments, sgRNA of SEQ ID NO: 87 (see also FIG. 25A) can be used to target gRNA site of SEQ ID NO: 46.

FIG. 14A provides the Mouse DNA sequence for region 2: from Eμ intronic enhancer to switch region (SEQ ID NO: 4; >mm10_dna range=chr12:113425446-113426973

5'pad=0 3'pad=0 strand=−repeatMasking=none). FIG. 14B provides exemplary ranges to target (e.g., gRNA sites) within this sequence including SEQ ID NOs. 65-84 and associated gRNA sequences (SEQ ID NOs: 347-366).

Thus, in particular embodiments, the current disclosure provides targeted insertion of a genetic construct including (i) a promoter and (ii) a transgene encoding a portion of a selected antibody at an intronic region that is constant in all B cells (before and after recombination) and (i) positioned relative to an enhancer element that interacts with the promoter; and (ii) in a configuration such that the B cells' endogenous heavy chain VDJ sequence is not expressed. In particular embodiments, the encoded portion of the selected antibody includes the entire light chain of the antibody and the VDJ segment of the heavy chain. These portions of the selected antibody can be expressed with a heavy chain constant region expressed by the modified B cell at any given time. Particular embodiments of the genetic construct may also include or encode a signal peptide, a flexible linker, a skipping element, and or a splice junction.

Figure 6B:
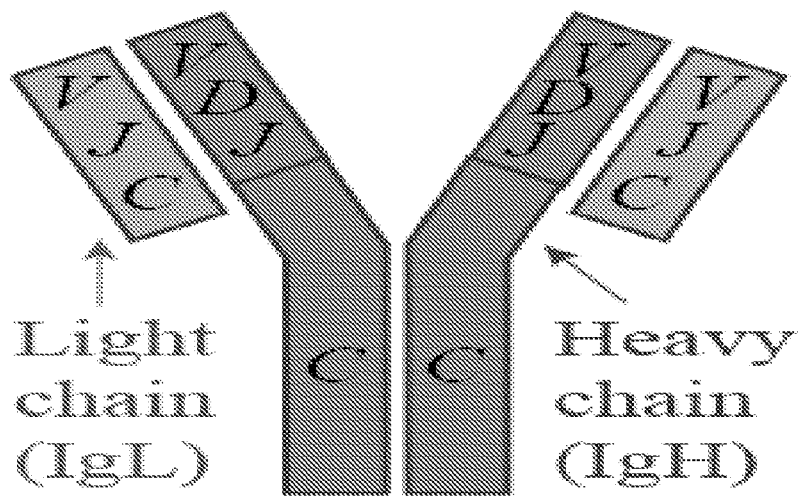

One technical challenge of the current disclosure is that an antibody is a protein made from two separate gene products, the heavy chain (IgH) and the light chain (IgL) (FIGS. 6A, 6B). This means that, in particular embodiments, both genetic locations must be simultaneously modified in order to properly express a selected antibody. However, the current disclosure also provides strategies to produce functional selected antibodies without necessitating modifying both genetic locations. One approach that allows this is through the use of sequences that allow antibody expression through a single construct. In particular embodiments, this is achieved by including a skipping element within the genetic construct. One example of a skipping element is a self-cleaving peptide, such as a self-cleaving "2A" peptide. 2A peptides function by causing the ribosome to skip the synthesis of a peptide bond at a defined location, leading to production of two proteins from one mRNA. The 2A sequences are short (e.g., 20 amino acids), facilitating use in size-limited constructs, and proteins are produced at a 1:1 ratio. Particular examples include T2A (GSG) EGRGSLLTCGDVEENPGP (SEQ ID NO: 176); P2A (GSG)ATNFSLLKQAGDVEENPGP (SEQ ID NO: 177); E2A (GSG)QCTNYALLKLAGDVES NPGPP (SEQ ID NO: 178); and F2A (GSG)VKQTLNFDLLKLAGD-VESNPGP (SEQ ID NO: 179).

In particular embodiments, the genetic constructs include an internal ribosome entry site (IRES) sequence. The IRES can be positioned upstream of the heavy chain VDJ of the genetic construct. IRES are non-coding structured RNA sequences that allow ribosomes to initiate translation at a second internal site on a mRNA molecule, leading to production of two proteins from one mRNA. However, IRES driven translation is less efficient than 2A driven translation, leading to lower expression of the second protein in the transcript.

In particular embodiments, the genetic constructs encode a flexible linker between the light chain portion of the selected antibody and the heavy chain portion of the selected antibody. A linker can be a series of amino acids that flexibly link one protein domain to another protein domain in a way that allows the linked sequences to interact to form a functional unit.

In particular sequences, flexible linkers can include one or more series of combinations of glycine and serine, which provide flexibility to the linker sequence. Exemplary Gly-Ser linkers include (GGS)n (SEQ ID NO: 180), (GGGS)n (SEQ ID NO: 181), and (GGGGS)n (SEQ ID NO: 182) wherein n=1-100 and every integer therebetween. In particular embodiments, n=10, 11, 12, 13, 14, 15, 16, 17, 18, 19, 20, 21, 22, 23, 24, 25, 26, 27, 28, 29, or 30. In particular embodiments, a Gly-Ser linker includes 50-80 amino acids. In particular embodiments, the Gly-Ser linker includes 54, 57, or 60 amino acids. In particular embodiments, the Gly-Ser linker is encoded by SEQ ID NO: 116. In particular embodiments, the Gly-Ser linker includes SEQ ID NO: 122.

Additional examples of flexible linkers include (KES-GSVSSEQLAQFRSLD)n (SEQ ID NO: 183) and (EGKSSGSGSESKST)n (SEQ ID NO: 184). In these linkers the Gly and Ser residues in the linker were designed to provide flexibility, whereas Glu and Lys were added to improve the solubility. Bird, R E et al. Science, 1988, 242:423-426. In particular embodiments, n=1-100 and every integer therebetween. In particular embodiments, n=10, 11, 12, 13, 14, 15, 16, 17, 18, 19, 20, 21, 22, 23, 24, 25, 26, 27, 28, 29, or 30. In particular embodiments, these linkers includes 50-80 amino acids.

Particular embodiments include a splice junction that allows splicing between RNA encoded by the genetic construct and RNA encoded by the endogenous heavy chain constant region. In particular embodiments, the genetic constructs include a splice junction sequence at the 3' end. Splicing can refer to the removal of introns and joining together of exons by an RNA/protein complex known as the spliceosome. A splice junction refers to an intronic sequence directly flanking an exon. A splice junction at the 3' end of an exon can include a splice donor site. Splice donor site sequences typically begin with "GU". In particular embodiments, the splice junction may include 40-80 bp of an intron following the last exon of a VDJ. In particular embodiments, the splice junction includes 40-80 bp of the intron flaking the 3' end of the human IGHJ1 gene segment or the mouse IGHJ3 gene. In particular embodiments, the splice junction includes CAG/gtaagt, with the cut and splice taking place after the uppercase G (indicated by the "splice" annotation). In particular embodiments, the splice junction includes CAG/gtgagt. The CA form the end of a serine codon, and the G begins the first codon from the constant region. In particular embodiments, a splice junction with flanking sequence includes SEQ ID NOs: 124 or 151 in genetic constructs for insertion into a human locus. In particular embodiments, a splice junction with flanking sequence includes SEQ ID NO: 139 in genetic constructs for insertion into a mouse locus.

Genetic constructs disclosed herein can also encode signal peptides. Exemplary signal peptides include signal peptides derived from human IgH heavy chains, such as MELGLS-WIFLLAILKGVQC (SEQ ID NO: 185); MEL-GLRWVFLVAILEGVQC (SEQ ID NO: 186); MKHLWF-FLLLVAAPRWVLS (SEQ ID NO: 187); MDWTWRILFLVAAATGAHS (SEQ ID NO: 188); MDWTWRFLFVVAAATGVQS (SEQ ID NO: 189); MEFGLSWLFLVAILKGVQC (SEQ ID NO: 190); MEFGLSWVFLVALFRGVQC (SEQ ID NO: 191); and MDLLHKNMKHLWFFLLLVAAPRWVLS (SEQ ID NO: 192); and signal peptides derived from human IgL light chains, such as MDMRVPAQLLGLLLLWLSGARC (SEQ ID NO: 193); and MKYLLPTAAAGLLLLAAQPAMA (SEQ ID NO: 194). In particular embodiments, a signal peptide is encoded by SEQ ID NO: 112 and includes SEQ ID NO: 118 in genetic constructs for insertion into a human locus. In particular embodiments, a signal peptide is encoded by SEQ ID NO: 129 and includes SEQ ID NO: 134 in genetic constructs for insertion into a mouse locus. See also FIGS. 25B-25I and Haryadi R et al., tPLoS One v. 10(2); 2015 PMC4338144.

As indicated, particular embodiments of the disclosure utilize insertion of exogenous genetic constructs at a targeted location within the endogenous B cell genome. In particular embodiments, such targeted insertion can be facilitated by including homology regions on one or both ends of the genetic construct. Homology regions (i.e., homology stitches or homology arms) are homologous to sequences at a desired insertion site. In particular embodiments, homology arms refer to segments of DNA included in a genetic construct that are 100% identical to a region of DNA that is being modified. In particular embodiments, 100% identity may not be required to achieve targeted insertion (e.g., at least 90% identity may be sufficient).

Figure 15A:
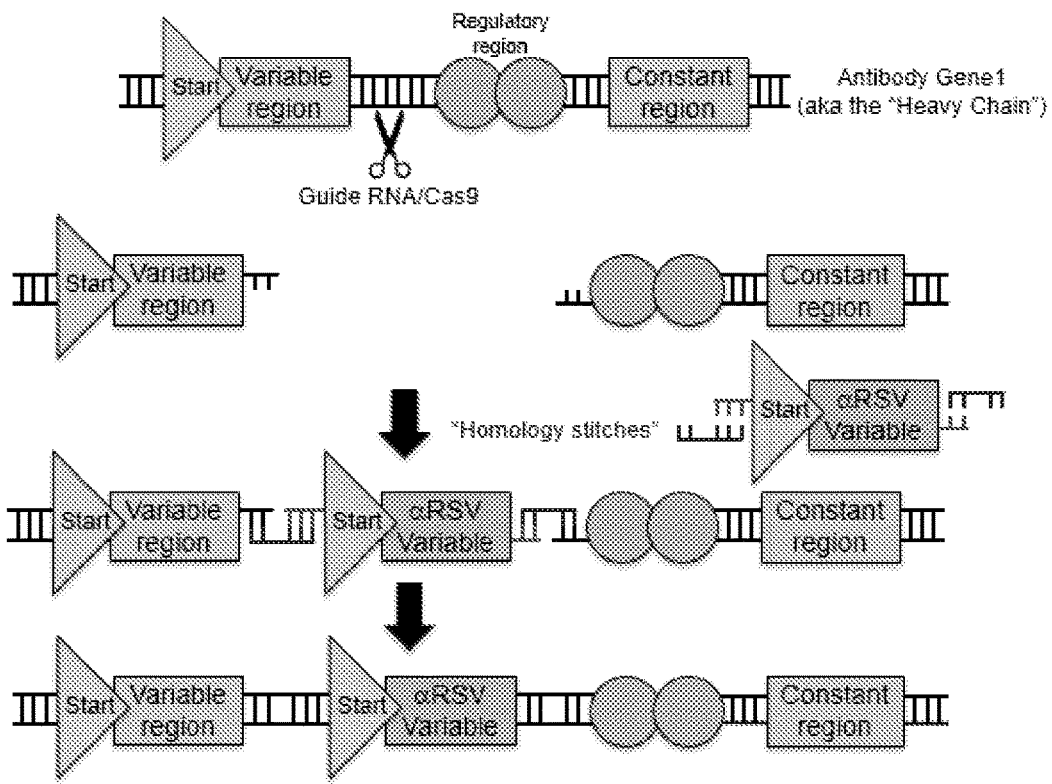
FIGS. 15A, 15B.

Homology regions cause the genetic construct to align next to the targeted genetic region, and portions of DNA from the genetic construct are swapped into the region cut by gene editing techniques. In particular embodiments, a genetic construct may include an upstream genome homology end with 20 to 1,500 bp of genome homology, and a downstream genome homology end with 20 to 1,500 bp of genome homology. The regions of homology may, for example, provide "homology stitches" as shown in FIG. 15A, which can mediate insertion of the genetic construct into the targeted insertion site. In particular embodiments, the upstream genome homology end and the downstream genome homology end may include sequences with homology to genome sequences between a heavy chain VDJ region and a heavy chain Eµ enhancer element. In particular embodiments, regions of homology may particularly include 20-50 base pairs; 300-500 base pairs; 350-550 base pairs; 900-1,000 base pairs, or 400-600 base pairs. In particular embodiments, regions of homology may particularly include 30-40 base pairs (e.g., 36 base pairs); 445-455 base pairs (e.g., 450 base pairs); 495-510 base pairs (e.g., 503 base pairs); and/or 960-980 base pairs (e.g., 968 base pairs). In particular embodiments, homology regions for use in mouse genetic constructs include SEQ ID NOs: 90, 91, 96, 97, 127, 140, 142, 143, 170, and 171. In particular embodiments, homology regions for use in human genetic constructs include SEQ ID NOs: 92-95, 98-101, 110, 125, 153, 173, and 174.

In particular embodiments, the genetic constructs also encode a tag sequence. Tag sequences may be useful, for example, so that cells expressing the genetic construct may be identified and/or sorted during genetic modification processes and/or so that they can be controlled following administration to a subject. For example, in particular embodiments, it may be useful to track and/or terminate genetically modified cells following administration to a subject. Exemplary tags include STREPTAG® (GmbH, LLC, Gottingen, Del.), STREP® tag II (WSHPQFEK (SEQ ID NO: 195)), or any variant thereof; see, e.g., U.S. Pat. No. 7,981,632), His tag, Flag tag (DYKDDDDK (SEQ ID NO:196)), Xpress tag (DLYDDDDK (SEQ ID NO: 197)), Avi tag (GLNDIFEAQKIEWHE (SEQ ID NO: 198)), Calmodulin tag (KRRWKKNFIAVSAANRFKKISSSGAL (SEQ ID NO: 199)), Polyglutamate tag, HA tag (YPYDVPDYA (SEQ ID NO: 200)), Myc tag (EQKLISEEDL (SEQ ID NO: 201)), Nus tag, S tag, SBP tag, Softag 1 (SLAELLNAGLGGS (SEQ ID NO: 202)), Softag 3 (TQDPSRVG (SEQ ID NO: 203)), and V5 tag (GKPIPNPLLGLDST (SEQ ID NO: 204)).

In particular embodiments, the current disclosure provides a genetic construct for selected antibody expression including or encoding (i) a heavy chain promoter, and/or (ii) an immunoglobulin light chain, and/or (iii) a heavy chain variable region, and/or (iv) a stop codon; and/or (v) a skipping element and/or (vi) a splice junction and/or (vii) homology arms and/or (viii) a linker and/or (ix) a tag.

Particular embodiments include or encode: (i) a heavy chain promoter; (ii) a signal peptide; (iii) an entire light chain of a selected antibody; (iv) a flexible linker or a skipping element; (v) the variable region of a selected antibody heavy chain; and (vi) a splice junction.

Particular embodiments include or encode: (i) a heavy chain promoter; (ii) a signal peptide; (iii) an entire light chain of a selected antibody; (iv) a flexible linker or a skipping element; (v) the variable region of a selected antibody heavy chain; (vi) a splice junction, and (vii) homology arms.

Particular embodiments include or encode: (i) a heavy chain promoter; (ii) a signal peptide; (iii) an entire light chain of a selected antibody; (iv) a flexible linker or a skipping element; (v) the variable region of a selected antibody heavy chain; (vi) a splice junction, (vii) homology arms; and (viii) a tag.

Figure 15B:
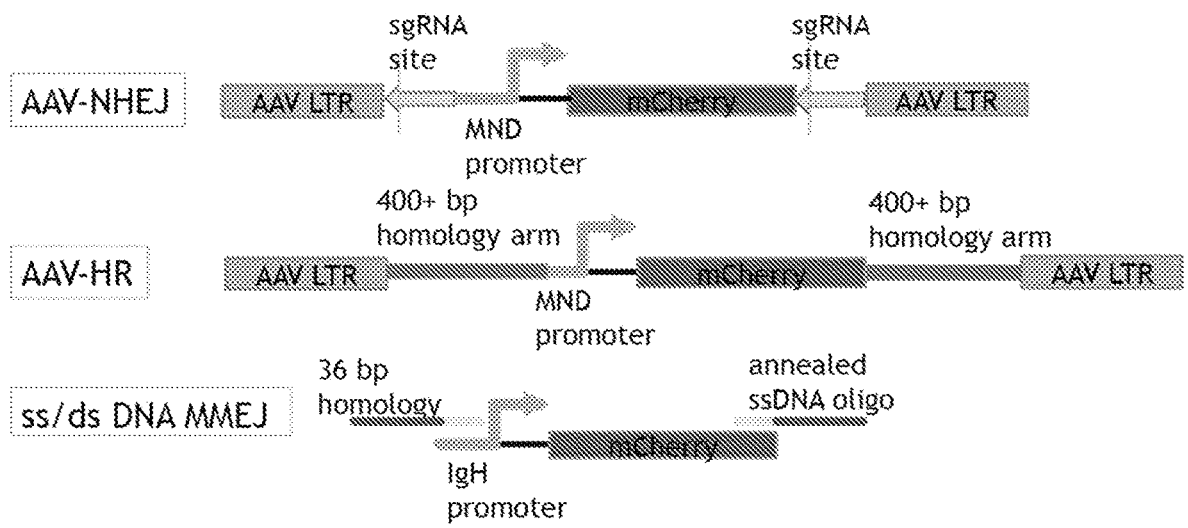

FIG. 15B depicts additional examples of DNA repair templates. Examples of DNA repair templates that can also be used include synthetic DNA templates and adeno-associated viruses. In particular embodiments, synthetic DNA templates can include double stranded DNA (dsDNA) including or encoding a promoter and selected antibody portion flanked by 20-1,500 base pairs of homology to the target site in the genome. In particular embodiments, synthetic DNA templates can include single stranded DNA (ssDNA) including or encoding a promoter and selected antibody portion flanked by 10-80 base pairs, or 400-1000 base pairs of homology to the target site in the genome. In particular embodiments, synthetic DNA templates can include both dsDNA and ssDNA, terminally modified by phosphorylation to increase DNA ligation efficiency. In particular embodiments, both dsDNA and ssDNA can be terminally modified with phosphorothioate bonds to increase stability and prevent endonuclease digestion.

In particular embodiments, an adeno-associated virus can include a segment encoding a synthetic antibody portion flanked by 20-1,500 base pairs of homology to the target site in the genome. In particular embodiments, the promoter and synthetic antibody portion encoding sequence can be flanked by matching homology sequences to the target site in the genome.

In particular embodiments, the genetic construct including a DNA repair mechanism (e.g., homology stitches, synthetic DNA template) may be delivered utilizing a gene editing system, such as CRISPR, TALENs, megaTALs, zinc finger nucleases and/or an adeno-associated virus as described in more detail below. For example, a genome targeting element, a genome cutting element, and a genetic construct described herein can be administered to a B cell.

As a particular example of an application of the current disclosure, B cells may be modified to express the palivizumab antibody. The B cells may be modified with a genetic construct that includes 80 bp homology arms flanking a heavy chain promoter upstream of the complete light chain (IgLPV) and VDJ heavy chain gene segments (VDJPV) from palivizumab separated by a 2A peptide. Here, the 2A peptide is included in order to induce a ribosomal skipping event (Donnelly et al., The Journal of general virology. 2001; 82(Pt 5):1013-25), which allows for the heavy chain and light chain to be produced as separate subunits that will associate normally to form the selected antibody. In particular embodiments, a stop codon can be included upstream of the inserted heavy chain promoter to halt any potential transcription of the endogenous heavy chain variable region.

Figure 16:
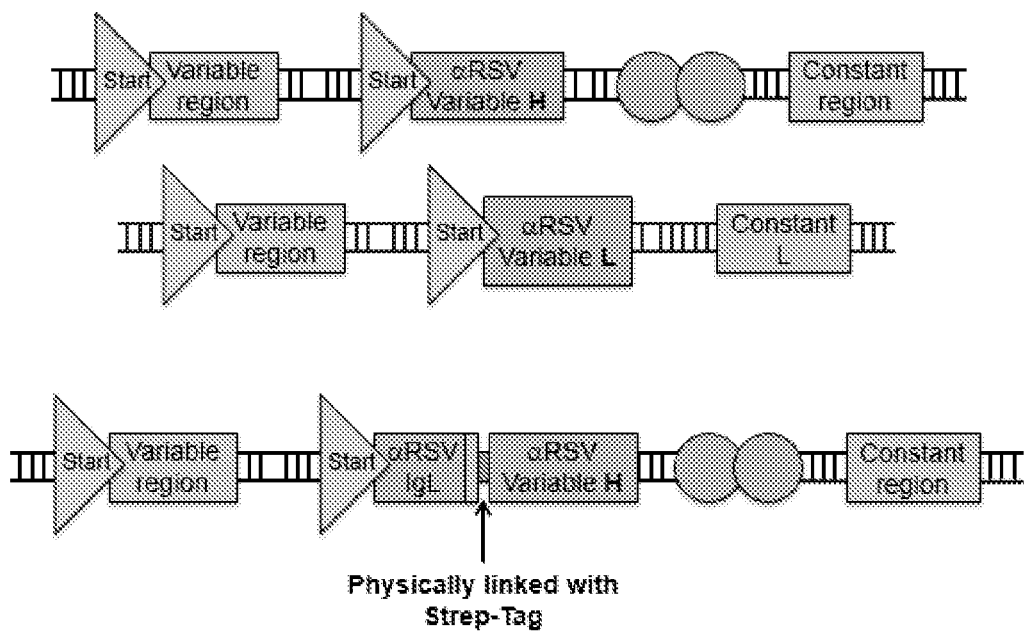
FIG. 16. Schematic depicting: (top) a modified heavy chain locus, modified with a genetic construct encoding a heavy chain variable region of an anti-RSV antibody; (middle) a modified light chain locus, modified with a genetic construct encoding a light chain variable region of an anti-RSV antibody; and (bottom) a modified heavy chain locus, modified with a genetic construct encoding a light chain (i.e., IgL) of an anti-RSV antibody, and a heavy chain variable region of an anti-RSV antibody, with a linker (including a Strep-Tag) between the light chain and the heavy chain variable region.
Figure 17:
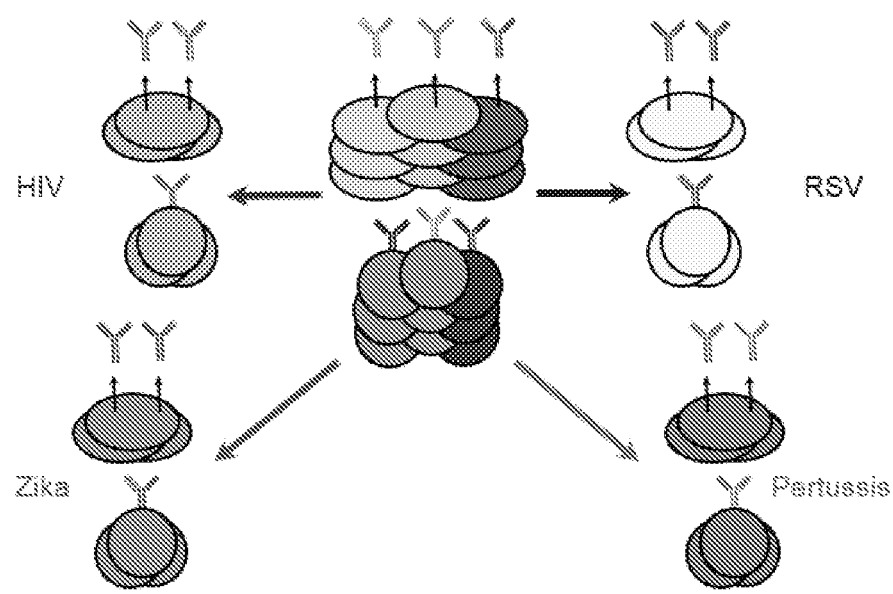
FIG. 17. Schematic of simultaneous protection against multiple pathogens by modified memory B cells and modified antibody-secreting B cells, as disclosed herein.
Figure 18:
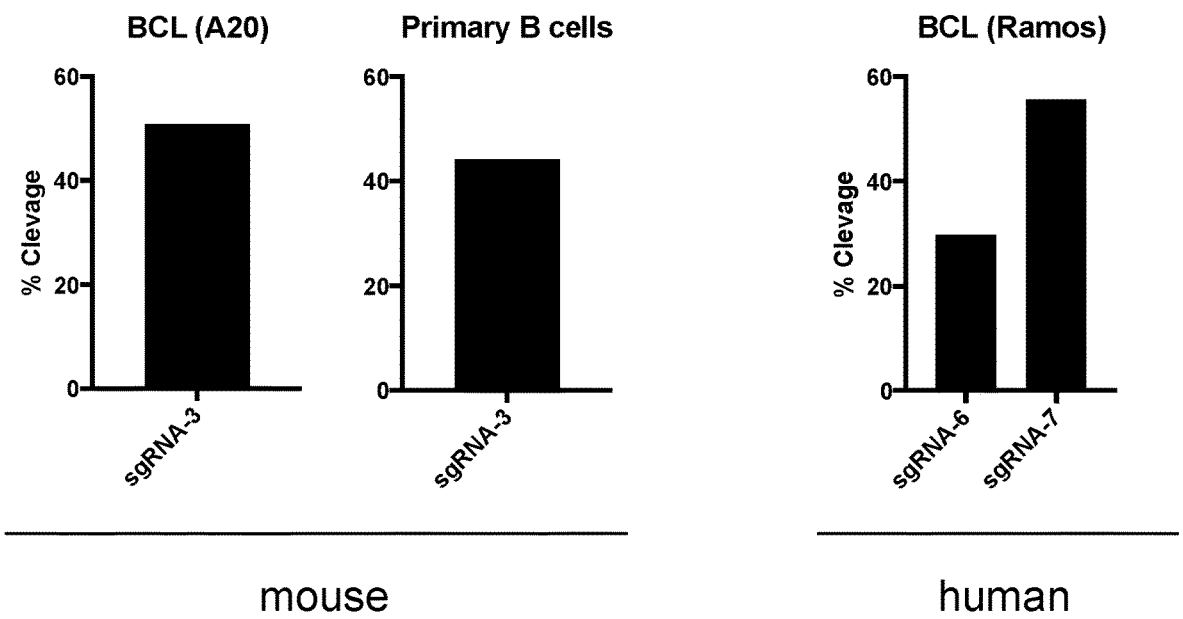
Figure 19:
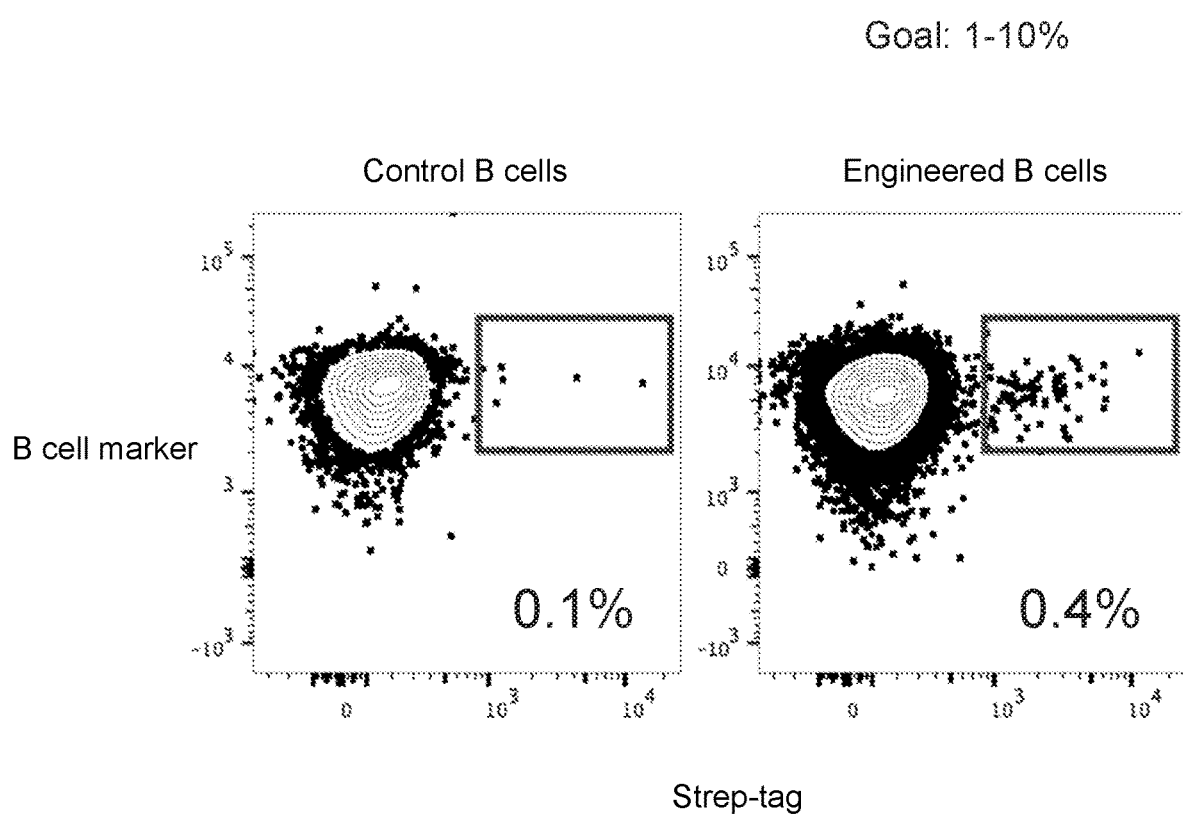
FIG. 19. Insertion of a genetic construct encoding an RSV-specific antibody into mouse B cells.
Figure 20:
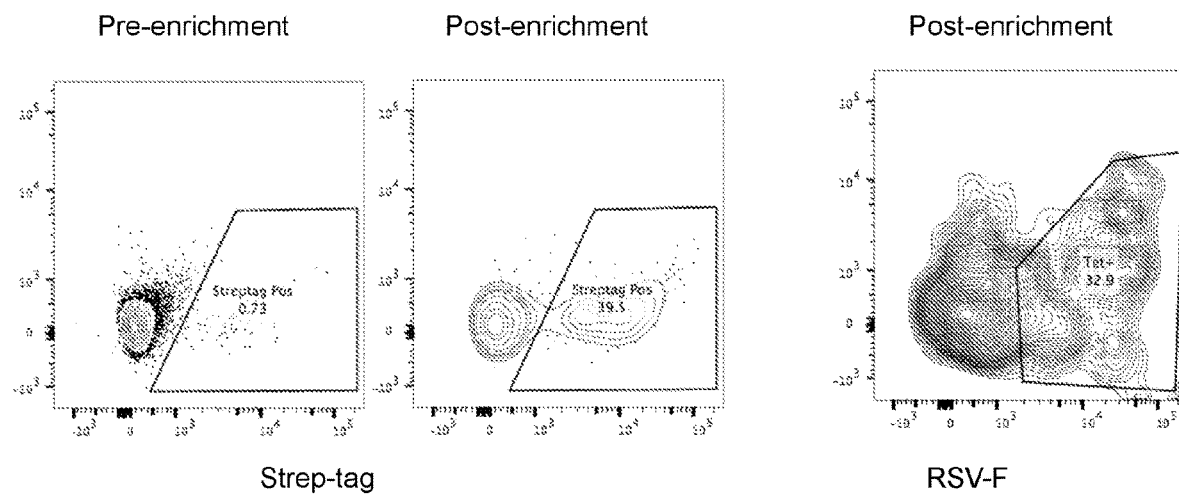
FIG. 20. Enrichment and analysis of genetically-modified B cells.
Figure 21:
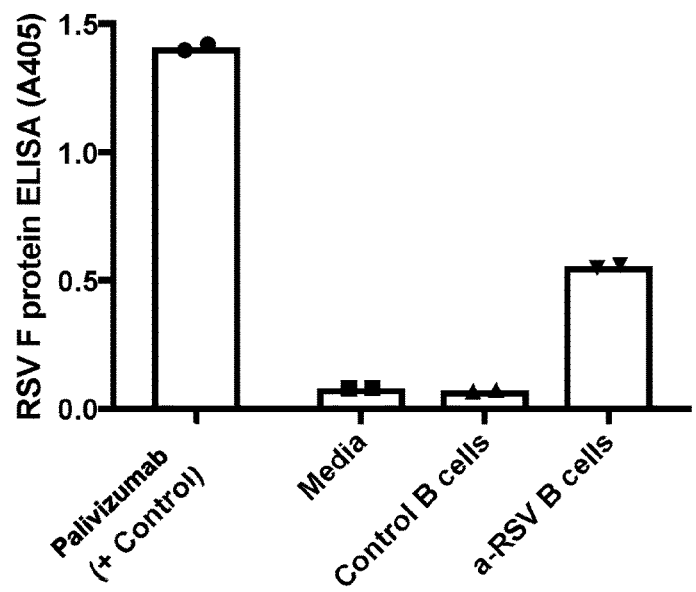
FIG. 21. Genetically-modified B cells secrete RSV binding antibody.
Figure 22A:
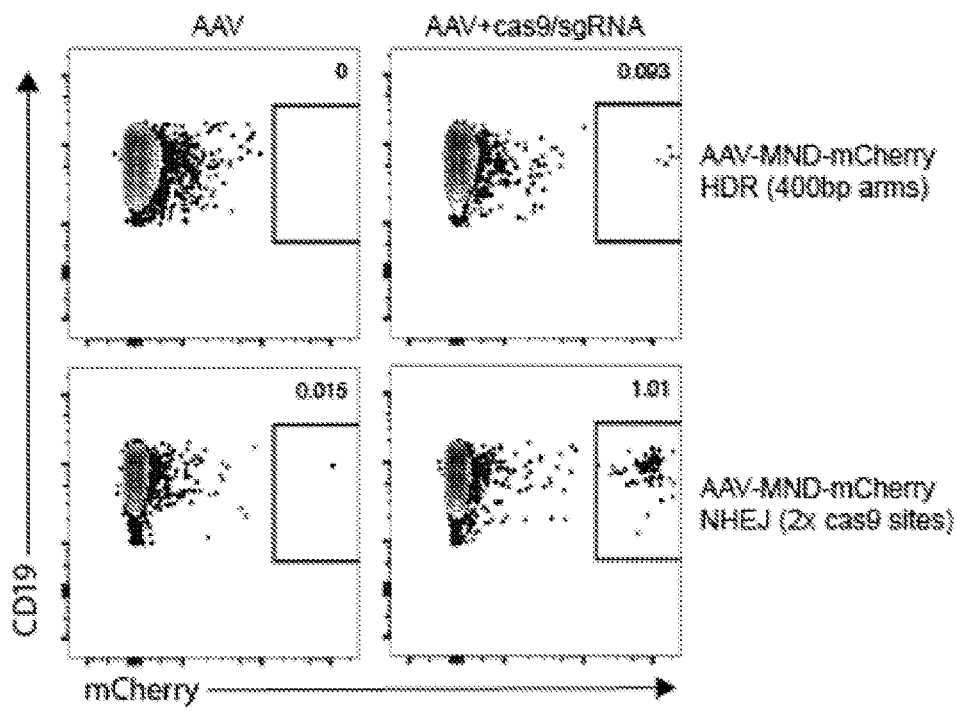
FIGS. 22A, 22B. Non-homologous end joining (NHEJ) and micro-homology mediated end joining (MMEJ) approaches offer alternatives to long-homology-directed repair (HDR) for genome engineering of primary mouse B cells.
Figure 22B:
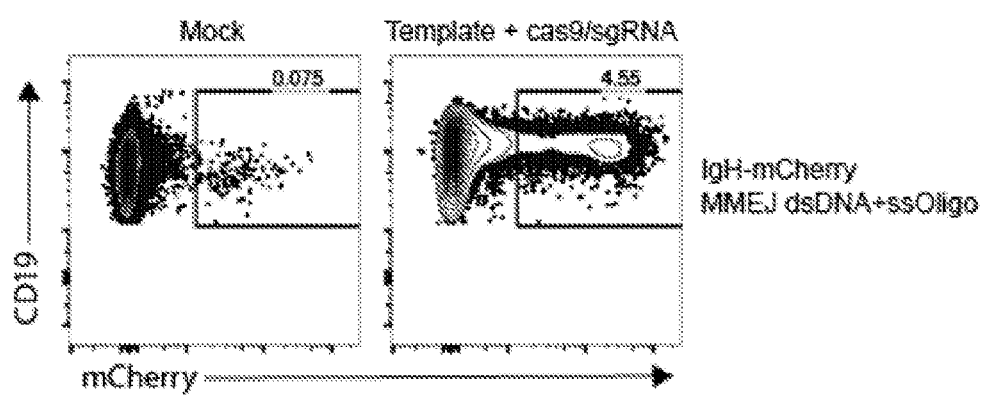
Figure 23B:
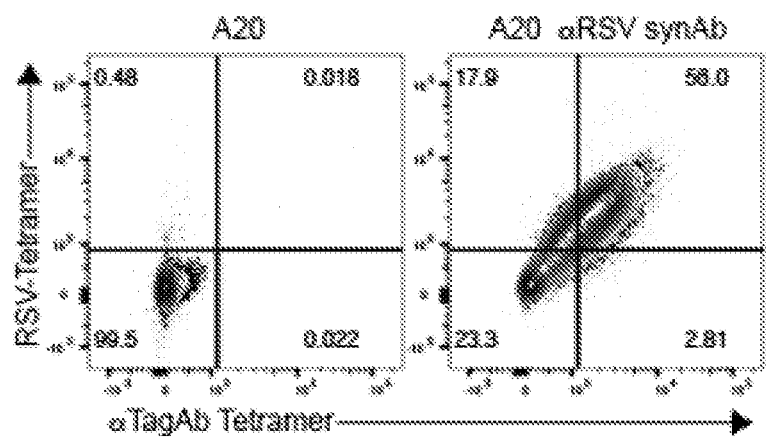
Figure 23C:
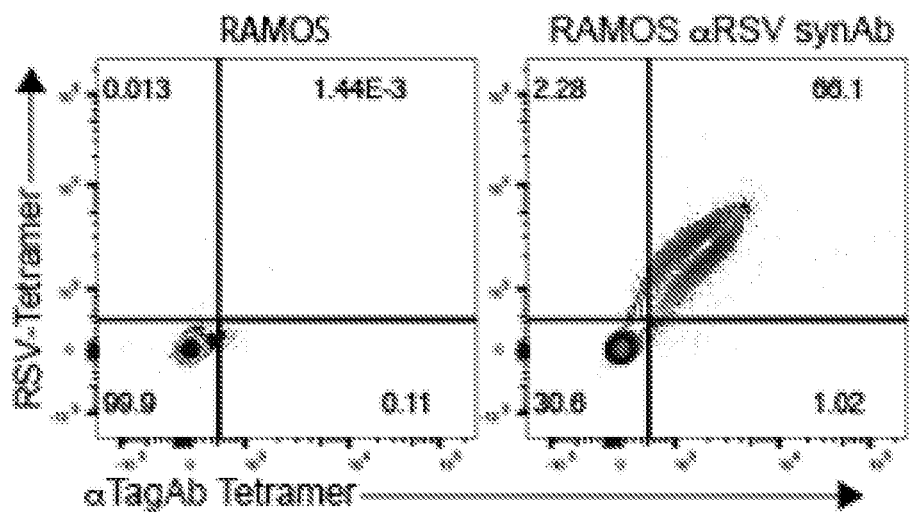
Figure 23D:
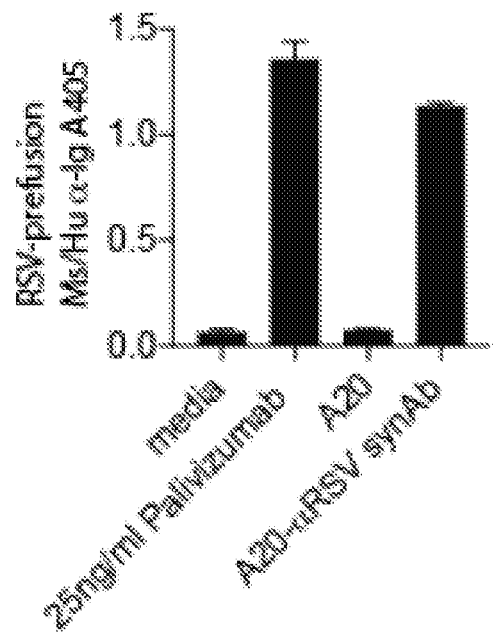
Figure 23E:
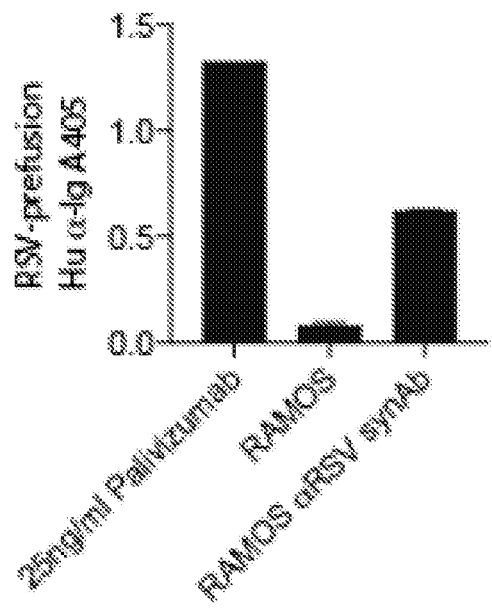
Figure 24A:
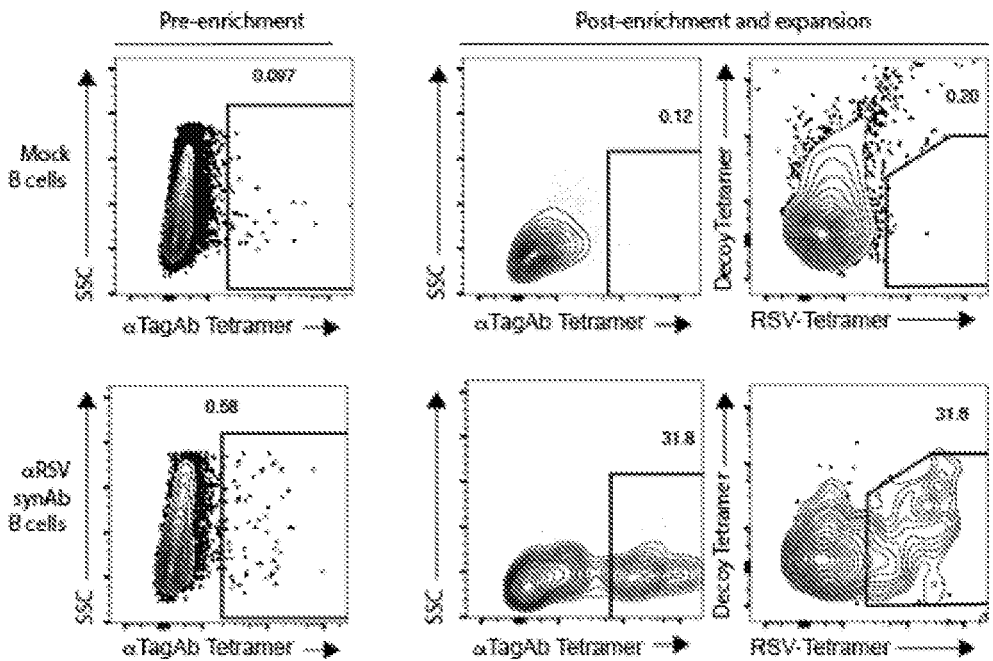
FIGS. 24A-24C. Production of primary mouse B cells with a novel specificity.
Figure 24B:
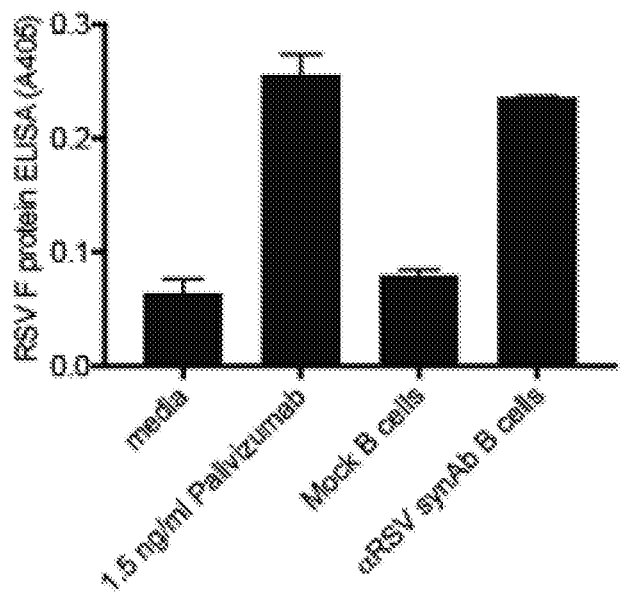
Figure 24C:
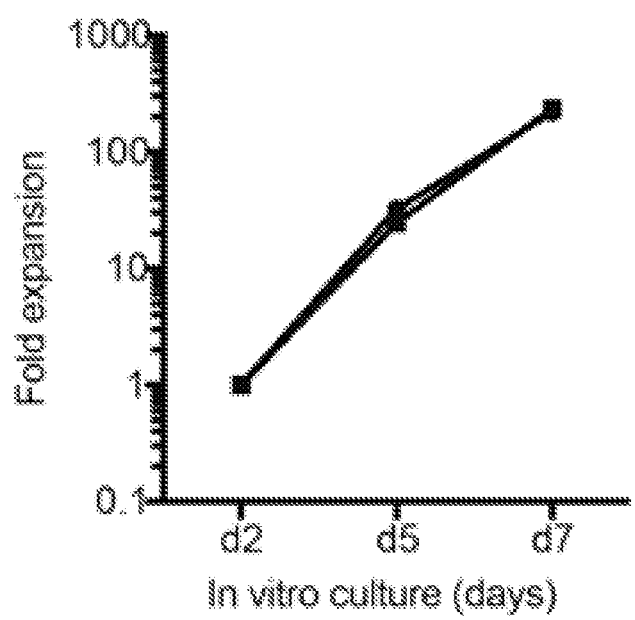

FIG. 16 depicts an example of an "as-modified" B cell genome, while FIG. 17 depicts resulting B cell populations expressing selected antibodies.

The following paragraphs provide a more detailed description regarding (i) Exemplary Selected Antibodies and Sequences; (ii) Gene Editing Techniques and Cell Sorting; (iii) Formulation of Modified B cells; and (iv) Methods of Use.

(i) Exemplary Selected Antibodies and Sequences. In particular embodiments, a selected antibody is an antibody that can provide a protective effect against a pathogen or condition (e.g., autoimmune disease). In particular embodiments, the selected antibody is an anti-RSV antibody, an anti-HIV antibody, an anti-Dengue virus antibody, an anti-*Bordatella pertussis* antibody, an anti-hepatitis C antibody, an anti-influenza virus antibody, an anti-parainfluenza virus antibody, an anti-metapneumovirus (MPV) antibody, an anti-cytomegalovirus antibody, an anti-Epstein Barr virus antibody; an anti-herpes simplex virus antibody, an anti-*Clostridium difficile* bacterial toxin antibody, or an anti-tumor necrosis factor (TNF) antibody.

In particular embodiments, the selected antibodies are chimeric antibodies. In particular embodiments, chimeric antibodies refer to a synthetic antibody that includes: (i) at least one portion that is encoded by a B cell's endogenous genome, and (ii) at least one portion that is encoded by an inserted genetic construct. In particular embodiments, the chimeric antibody includes an endogenous heavy chain constant domain, an exogenous immunoglobulin variable and constant light chain, and an exogenous variable heavy chain.

The following antibodies and sequences are useful to provide selected antibodies with targeted binding against pathogens or antigens of interest (unless noted, Kabat numbering is intended):

An exemplary anti-RSV antibody is palivizumab, which targets the RSV fusion protein and is used to prevent or reduce RSV infections.

In particular embodiments, an anti-RSV antibody is mouse palivizumab that includes a variable heavy chain sequence including:

```
                                      (SEQ ID NO: 138)
QVELQESGPGILQPSQTLSLTCSFSGFSLSTSGMSVGWIRQPSGEGLEWL
ADIWWDDKKDYNPSLKSRLTISKDTSSNQVFLKITGVDTADTATYYCARS
MITNWYFDVWGAGTTVTVSS;

and a variable light
chain sequence including:             (SEQ ID NO: 205)
DIQLTQSPAIMSASPGEKVTMTCSASSSVGYMHWQQKLSTSPKLQIYDTS
KLASGVPGRFSGSGSGNSYSLTISSIQAEDVATYYCFRGSGYPFTFGQGT
KLEIK
```

An additional exemplary anti-RSV antibody is human palivizumab and includes a variable light chain sequence including:

```
                                      (SEQ ID NO: 206)
DIQMTQSPSTLSASVGDRVTITCKCQLSVGYMHWYQQKPGKAPKLLIYDT
SKLASGVPSRFSGSGSGTEFTLTISSLQPDFATYYCFQGSGYPFTFGGGT
KLEIKR;

and a variable heavy
chain sequence including:             (SEQ ID NO: 123)
QVTLRESGPALVKPTQTLTLTCTFSGFSLSTSGMSVGWIRQPPGKALEWL
ADIWWDDKKDYNPSLKSRLTISKDTSKNQVVLKVTNMDPADTATYYCARS
MITNWYFDVWGAGTT.
```

Within a variable heavy chain and variable light chain, segments referred to as complementary determining regions (CDRs) dictate epitope binding. Each heavy chain has three CDRs (i.e., CDRH1, CDRH2, and CDRH3) and each light chain has three CDRs (i.e., CDRL1, CDRL2, and CDRL3)

An additional exemplary anti-RSV antibody is described in U.S. Pat. No. 9,403,900. This anti-RSV antibody includes a variable heavy chain including a CDRH1 sequence including GASINSDNYYWT (SEQ ID NO: 207), a CDRH2 sequence including HISYTGNTYYTPSLKS (SEQ ID NO: 208), and a CDRH3 sequence including CGAYVLIS-NCGWFDS (SEQ ID NO: 209); and a variable light chain including a CDRL1 sequence including QASQDISTYLN (SEQ ID NO: 210), a CDRL2 sequence including GASNLET (SEQ ID NO: 211), and a CDRL3 sequence including QQYQYLPYT (SEQ ID NO: 212).

Exemplary anti-RSV antibodies also include AB1128 (available from MILLIPORE) and ab20745 (available from ABCAM).

An example of an anti-HIV antibody is 10E8, which is a broadly neutralizing antibody that binds to gp41. The 10E8 anti-HIV antibody includes a variable heavy chain including a CDRH1 sequence including GFDFDNAW (SEQ ID NO: 213), a CDRH2 sequence including ITGPGEGWSV (SEQ ID NO: 214), and a CDRH3 sequence including TGKYYDFWSGYPPGEEYFQD (SEQ ID NO: 215); and a variable light chain including a CDRL1 sequence including TGDSLRSHYAS (SEQ ID NO: 216), a CDRL2 sequence including GKNNRPS (SEQ ID NO: 217), and a CDRL3 sequence including SSRDKSGSRLSV (SEQ ID NO: 218).

An additional example of an anti-HIV antibody is VRC01, which is a broadly neutralizing antibody that binds to the CD4 binding site of gp120. The VRC01 antibody includes a variable heavy chain including a CDRH1 sequence including GYEFIDCT (SEQ ID NO: 219), a CDRH2 sequence including KPRGGAVN (SEQ ID NO: 220), and a CDRH3 sequence including RGKNCDYNWDFEHW (SEQ ID NO: 221); and a variable light chain including a CDRL1 sequence including QYGS, a CDRL2 sequence including SGS, and a CDRL3 sequence including QQYEF (SEQ ID NO: 222).

Exemplary anti-HIV antibodies also include ab18633 and 39/5.4A (available from ABCAM); and H81E (available from THERMOFISHER).

An example of an anti-Dengue virus antibody is antibody 55 described in U.S. 20170233460 and includes a variable heavy chain including a CDRH1 sequence including EVQLHQSGAELVKPGASVKLSCTVSGFNIK (SEQ ID NO: 223), a CDRH2 sequence including WVKQRPEQGLEWI (SEQ ID NO: 224), and a CDRH3 sequence including ATIKADTSSNTAYLQLISLTSEDTAVYYCAF (SEQ ID NO: 225); and a variable light chain including a CDRL1 sequence including DIQMTQSPASLSVSVGETVTITC (SEQ ID NO: 226), a CDRL2 sequence including WYQQKQGKSPQLLVY (SEQ ID NO: 227), and a CDRL3 sequence including GVPSRFSGSGSGTQYSLKINSLQSEDFGTYYC (SEQ ID NO: 228).

An additional example of an anti-Dengue virus antibody is DB2-3 described in U.S. Pat. No. 8,637,035 and includes a variable heavy chain including a CDRH1 sequence including YTFTDYAIT (SEQ ID NO: 229), a CDRH2 sequence including GLISTYYGDSFYNQKFKG (SEQ ID NO: 230), and a CDRH3 sequence including TIRDGKAMDY (SEQ ID NO: 231); and a variable light chain including a CDRL1 sequence including RSSQSLVHSNGNTYLH (SEQ ID NO: 232), a CDRL2 sequence including KVSNRFS (SEQ ID NO: 233), and a CDRL3 sequence including SQSTHVPYT (SEQ ID NO: 234). Examples of anti-Dengue virus antibodies also include ab155042 and ab80914 (both available from ABCAM).

An example of an anti-pertussis antibody is described in U.S. Pat. No. 9,512,204 and includes a variable heavy chain including QVQLQQPGSELVRPGASVKLSCK-ASGYKFTS YWMHWVKQRPGQGLEWIGNIFPGSG-STNYDEKFNSKATLTVDTSSNTAYMQLSSLTSEDSAV YYCTRWLSGAYFDYWGQGTTVTVSS (SEQ ID NO: 235) and a variable light chain including QIVLTQSPALM-SASPGEKVTMTCSASSSVSFMYWYQQKPRSSPKP-WIYLTSNLPSGVPARFSG SGSGTSYSLTISSMEAE-DAATYYCQQWSSHPPTFGSGTKLEIK (SEQ ID NO: 236).

An example of an anti-hepatitis C antibody includes a variable heavy chain including a CDRH1 sequence including SYGMHW (SEQ ID NO: 237), a CDRH2 sequence including VIWLDGSNTYYADSVKGR (SEQ ID NO: 238), and a CDRH3 sequence including ARDIFTVARGVIIYFDY (SEQ ID NO: 239); and a variable light chain including a CDRL1 sequence including RASQSVSSYLA (SEQ ID NO: 240), a CDRL2 sequence including DASNRAT (SEQ ID NO: 241), and a CDRL3 sequence including QQRSNWVT (SEQ ID NO: 242). Examples of anti-hepatitis C antibodies also include MAB8694 (available from MILLIPORE) and C7-50 (available from ABCAM).

An example of an anti-influenza virus antibody is described U.S. Pat. No. 9,469,685 and includes a variable heavy chain including a CDRH1 sequence including GMTSNSLA (SEQ ID NO: 243), a CDRH2 sequence including IIPVFETP (SEQ ID NO: 244), and a CDRH3 sequence including ATSAGGIVNYYLSFNI (SEQ ID NO: 245); and a variable light chain including a CDRL1 sequence including QTITTW (SEQ ID NO: 246), a CDRL2 sequence including KTS, and a CDRL3 sequence including QQYSTYSGT (SEQ ID NO: 247). An example of an anti-influenza virus antibody also includes C102 (available from THERMOFISHER).

An exemplary anti-MPV antibody includes MPE8.

Exemplary anti-CMV antibodies includes MCMV5322A, MCMV3068A, LJP538, and LJP539. RG7667 includes a mixture of MCMV5322A and MCMV3068A while CSJ148 includes a mixture of LJP538, and LJP539. See also, for example, Deng et al., Antimicrobial Agents and Chemotherapy 62(2) e01108-17 (February 2018); and Dole et al., Antimicrobial Agents and Chemotherapy 60(5) 2881-2887 (May 2016).

An example of an anti-EBV antibody includes a variable heavy chain including an AMM01 CDRH1 sequence including YTFIHFGISW (SEQ ID NO: 248), an AMM01 CDRH2 sequence including IDTNNGNTNYAQSLQG (SEQ ID NO: 249), and an AMM01 CDRH3 sequence including RALEMGHRSGFPFDY (SEQ ID NO: 250); and a variable light chain including an AMM01 CDRL1 sequence including GGHNIGAKNVH (SEQ ID NO: 251), an AMM01 CDRL2 sequence including YDSDRPS (SEQ ID NO: 252), and an AMM01 CDRL3 sequence including CQVWDS-GRGHPLYV (SEQ ID NO: 253).

An example of an anti-HSV antibody includes HSV8-N and MB66.

Exemplary anti-*Clostridium difficile* antibodies include actoxumab and bezlotoxumab. See also, for example, Wilcox et al., N Engl J Med 376(4) 305-317 (2017).

Commercially available anti-TNF antibodies include infliximab (Remicade® Centocor, Inc., Malvern, Pa. with biosimilars Inflectra® Pfizer, Kent, UK and Ixifi® Pfizer, New York, N.Y.), adalimumab (Humira® Abbott Laboratories, Abbott Park, Ill. with biosimilars Amjevita® Amgen, Thousand Oaks, Calif. and Cyltezo® Boehringer Ingelheim Int'l, Ingelheim, Del.), golimumab (Simponi® Johnson & Johnson Corp., New Brunswick, N.J.), etanercept (Enbrel® Immunex Corp, Thousand Oaks, Calif. with biosimilar Erelzi® Novartis AG, Basel, CH), and certolizumab-pegol (Cimzia® UCB Pharma, Brussels, BE).

In particular embodiments, the CDRs of infliximab include: heavy chain residues 26-37, 52-70, and 103-116 and light chain residues 24-39, 55-61, and 94-102. In particular embodiments, the heavy chain of infliximab begins with EVKLEESGGGLVQPGGSMK (SEQ ID NO: 254) and the light chain begins with DILLTQSPAILSVSPGER (SEQ ID NO: 255).

In particular embodiments, infliximab includes a variable heavy chain including a CDRH1 sequence including IFSNHW (SEQ ID NO: 256), a CDRH2 sequence including RSKSINSATH (SEQ ID NO: 257), and a CDRH3 sequence including NYYGSTY (SEQ ID NO: 258); and a variable lightchain including a CDRL1 sequence including FVGSSIH (SEQ ID NO: 259), a CDRL2 sequence including KYASESM (SEQ ID NO: 260), and a CDRL3 sequence including QSHSW (SEQ ID NO: 261).

In particular embodiments, adalimumab includes a variable heavy chain including a CDRH1 sequence including TFDDYA (SEQ ID NO: 262), a CDRH2 sequence including TWNSGHID (SEQ ID NO: 263), and a CDRH3 sequence including VSYLSTASSL (SEQ ID NO: 264); and a variable light chain including a CDRL1 sequence including GIR-NYLA (SEQ ID NO: 265), a CDRL2 sequence including YAASTLQ (SEQ ID NO: 266), and a CDRL3 sequence including RYNRA (SEQ ID NO: 267).

In particular embodiments, certolizumab includes a variable heavy chain including a CDRH1 sequence including VFTDYG (SEQ ID NO: 268), a CDRH2 sequence including NTYIGEPI (SEQ ID NO: 269), and a CDRH3 sequence including GYRSYAM (SEQ ID NO: 270); and a variable light chain including a CDRL1 sequence including NVGTNVA (SEQ ID NO: 271), a CDRL2 sequence including YSASFLY (SEQ ID NO: 272), and a CDRL3 sequence including QYNIY (SEQ ID NO: 273).

Numerous additional antibody sequences are available and known to those of ordinary skill in the art that can be used within the teachings of the current disclosure. Sequence information for commercially available antibodies may be found in the Drug Bank database, the CAS Registry, and/or the RSCB Protein Data Bank. Moreover, nucleic acid sequences encoding portions of selected antibodies described herein can be easily derived by one of ordinary skill in the art.

(ii) Gene Editing Techniques and Cell Sorting. Gene editing systems allow control over the target sites of genetic therapies. Within the teachings of the current disclosure, any gene editing system capable of precise sequence targeting and modification can be used. These systems typically include a targeting element for precise targeting and a cutting element for cutting the targeted genetic site. Guide RNA is one example of a targeting element while various nucleases provide examples of cutting elements. Targeting elements and cutting elements can be separate molecules or linked, for example, by a nanoparticle. Alternatively, a targeting element and a cutting element can be linked together into one dual purpose molecule. When insertion of a therapeutic nucleic acid sequence is intended, the systems can also include homology-directed repair templates (i.e., homology arms as described above) associated with the genetic construct. As detailed further below, however, different gene editing systems can adopt different components and configurations while maintaining the ability to precisely target, cut, and modify selected genomic sites.

Particular embodiments utilize zinc finger nucleases (ZFNs) as gene editing agents. ZFNs are a class of site-specific nucleases engineered to bind and cleave DNA at specific positions. ZFNs are used to introduce double strand breaks (DSBs) at a specific site in a DNA sequence which enables the ZFNs to target unique sequences within a genome in a variety of different cells. Moreover, subsequent to double-stranded breakage, homology-directed repair (HDR) or non-homologous end joining (NHEJ) takes place to repair the DSB, thus enabling genome editing.

ZFNs are synthesized by fusing a zinc finger DNA-binding domain to a DNA cleavage domain. The DNA-binding domain includes three to six zinc finger proteins which are transcription factors. The DNA cleavage domain includes the catalytic domain of, for example, FokI endonuclease. The FokI domain functions as a dimer requiring two constructs with unique DNA binding domains for sites on the target sequence. The FokI cleavage domain cleaves within a five or six base pair spacer sequence separating the two inverted half-sites.

For additional information regarding ZFNs, see Kim, et al. Proceedings of the National Academy of Sciences of the United States of America 93, 1156-1160 (1996); Wolfe, et al. Annual review of biophysics and biomolecular structure 29, 183-212 (2000); Bibikova, et al. Science 300, 764 (2003); Bibikova, et al. Genetics 161, 1169-1175 (2002); Miller, et al. The EMBO journal 4, 1609-1614 (1985); and Miller, et al. Nature biotechnology 25, 778-785 (2007).

Particular embodiments can use transcription activator like effector nucleases (TALENs) as gene editing agents. TALENs refer to fusion proteins including a transcription activator-like effector (TALE) DNA binding protein and a DNA cleavage domain. TALENs are used to edit genes and genomes by inducing DSBs in the DNA, which induce repair mechanisms in cells. Generally, two TALENs must bind and flank each side of the target DNA site for the DNA cleavage domain to dimerize and induce a DSB. The DSB is repaired in the cell by NHEJ or HDR if an exogenous double-stranded donor DNA fragment is present.

As indicated, TALENs have been engineered to bind a target sequence of, for example, an endogenous genome, and cut DNA at the location of the target sequence. The TALEs of TALENs are DNA binding proteins secreted by *Xanthomonas* bacteria. The DNA binding domain of TALEs include a highly conserved 33 or 34 amino acid repeat, with divergent residues at the $12^{th}$ and $13^{th}$ positions of each repeat. These two positions, referred to as the Repeat Variable Diresidue (RVD), show a strong correlation with specific nucleotide recognition. Accordingly, targeting specificity can be improved by changing the amino acids in the RVD and incorporating nonconventional RVD amino acids.

Examples of DNA cleavage domains that can be used in TALEN fusions are wild-type and variant FokI endonucleases. For additional information regarding TALENs, see Boch, et al. Science 326, 1509-1512 (2009); Moscou, & Bogdanove, Science 326, 1501 (2009); Christian, et al. Genetics 186, 757-761 (2010); and Miller, et al. Nature biotechnology 29, 143-148 (2011).

Particular embodiments utilize MegaTALs as gene editing agents. MegaTALs have a single chain rare-cleaving nuclease structure in which a TALE is fused with the DNA cleavage domain of a meganuclease. Meganucleases, also known as homing endonucleases, are single peptide chains that have both DNA recognition and nuclease function in the same domain. In contrast to the TALEN, the megaTAL only requires the delivery of a single peptide chain for functional activity.

In particular embodiments, the endogenous B cell genome can be targeted using CRISPR gene editing systems. The CRISPR nuclease system is a prokaryotic immune system that confers resistance to foreign genetic elements such as plasmids and phages and provides a form of acquired immunity. CRISPRs are DNA loci containing short repetitions of base sequences. In the context of a prokaryotic immune system, each repetition is followed by short segments of spacer DNA belonging to foreign genetic elements that the prokaryote was exposed to. This CRISPR array of repeats interspersed with spacers can be transcribed into RNA. The RNA can be processed to a mature form and associate with a nuclease, such as cas (CRISPR-associated) nuclease. A CRISPR-Cas system including an RNA having a sequence that can hybridize to the foreign genetic elements and Cas nuclease can then recognize and cut these exogenous genetic elements in the genome.

A CRISPR-Cas system does not require the generation of customized proteins to target specific sequences, but rather a single Cas enzyme can be programmed by a short guide RNA molecule (crRNA) to recognize a specific DNA target. The CRISPR-Cas systems of bacterial and archaeal adaptive immunity show extreme diversity of protein composition and genomic loci architecture. The CRISPR-Cas system loci have more than 50 gene families and there are no strictly universal genes, indicating fast evolution and extreme diversity of loci architecture. So far, adopting a multi-pronged approach, there is comprehensive cas gene identification of 395 profiles for 93 Cas proteins. Classification includes signature gene profiles plus signatures of locus architecture. A new classification of CRISPR-Cas systems is proposed in which these systems are broadly divided into two classes, Class 1 with multi-subunit effector complexes and Class 2 with single-subunit effector modules exemplified by the Cas9 protein.

At least three different Cas9 nucleases have been developed for genome editing. The first is the wild type Cas9 which introduces double strand breaks (DSBs) at a specific DNA site, resulting in the activation of DSB repair machinery. DSBs can be repaired by non-homologous end joining (NHEJ), homology-directed repair (HDR), or microhomology mediated repair (MMEJ). NHEJ can involve repair of a DSB with no homology (<5 bp) between the two ends joined during repair; HDR can involve repair of a DSB with a large region of homology between the ends joined during repair (100 or more nucleotides); and MMEJ can involve repair of a DSB with a small (5 to 50 bp) region of homology between the ends joined during repair. Another type of Cas9 includes a mutant Cas9, known as the Cas9D10A, with only nickase activity, which means that it only cleaves one DNA strand and does not activate NHEJ. Thus, the DNA repairs proceed via the HDR pathway only. The third is a nuclease-deficient Cas9 (dCas9) which does not have cleavage activity but is able to bind DNA. Therefore, dCas9 is able to target specific sequences of a genome without cleavage. By fusing dCas9 with various effector domains, dCas9 can be used either as a gene silencing or activation tool.

In addition to the Class 1 and Class 2 CRISPR-Cas systems, more recently a putative Class 2, Type V CRISPR-Cas class exemplified by Cpf1 has been identified Zetsche et al. (2015) Cell 163(3): 759-771. The Cpf1 nuclease particularly can provide added flexibility in target site selection by means of a short, three base pair recognition sequence (TTN), known as the protospacer-adjacent motif or PAM. Cpf1's cut site is at least 18 bp away from the PAM sequence, thus the enzyme can repeatedly cut a specified locus after indel (insertion and deletion) formation, increasing the efficiency of HDR. Moreover, staggered DSBs with sticky ends permit orientation-specific donor template insertion.

Additional information regarding CRISPR-Cas systems and components thereof are described in, U.S. Pat. Nos. 8,697,359, 8,771,945, 8,795,965, 8,865,406, 8,871,445, 8,889,356, 8,889,418, 8,895,308, 8,906,616, 8,932,814, 8,945,839, 8,993,233 and 8,999,641 and applications related thereto; and WO2014/018423, WO2014/093595, WO2014/093622, WO2014/093635, WO2014/093655, WO2014/093661, WO2014/093694, WO2014/093701, WO2014/093709, WO2014/093712, WO2014/093718, WO2014/145599, WO2014/204723, WO2014/204724, WO2014/204725, WO2014/204726, WO2014/204727, WO2014/204728, WO2014/204729, WO2015/065964, WO2015/089351, WO2015/089354, WO2015/089364, WO2015/089419, WO2015/089427, WO2015/089462, WO2015/089465, WO2015/089473 and WO2015/089486, WO2016205711, WO2017/106657, WO2017/127807 and applications related thereto.

Particular embodiments combine tracrRNA and crRNA into a single synthetic single guide RNA (sgRNA utilizing e.g., SEQ ID NOs: 87-89, or 290-366). In particular embodiments, an sgRNA can include a twenty nucleotide sequence that is analogous to the crRNA, and a tracrRNA sequence. For certain gene editing systems, the target sequence may be adjacent to a PAM (e.g., 5'-20nt target-NGG-3'). In particular embodiments, a target sequence can include a PAM (SEQ ID NOs: 5-84). In particular embodiments, guide RNA (gRNA) includes a target site adjacent to the PAM targeted by the genome editing complex. The gRNA can include at least the 16, 17, 18, 19, 20, 21, or 22 nucleotides adjacent to the PAM.

In particular embodiments, a cutting element is directed to the targeted DNA location with the assistance of engineered gRNAs (FIG. 25A (Sternberg et al., Mol Cell. 2015; 58(4): 568-74)). Genetic constructs with homology arms flanking the cut genomic region are efficiently inserted into this location by the homology-directed DNA repair mechanism (see., e.g., FIG. 15B (Elliott et al., Mol Cell Biol. 1998; 18(1):93-101). Using this approach expression of the endogenous antibody will be eliminated and genes encoding the selected antibody will be inserted into the targeted genetic location. This targeted insertion eliminates or significantly reduces the possibility of off-target effects resulting from random genetic insertion.

Figure 7:
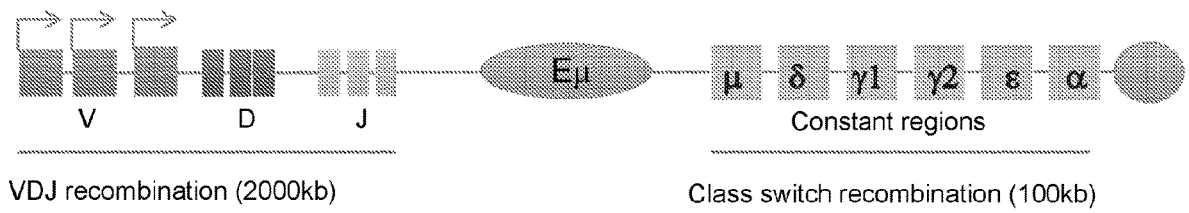
FIG. 7. Schematic depicting an endogenous heavy chain gene locus, including V, D, and J segments that recombine, enhancer elements, shown as a circle and an oval, and 6 potential constant regions that can be expressed. B cells start by expressing the μ/δ constant regions, but can switch to using γ, α, or ε constant regions by deleting intervening DNA. Also note that each V segment is associated with a heavy chain promoter denoted by an arrow that drives expression of the heavy chain following recombination.

In particular embodiments, sgRNA targeting the mouse or human IgH of each endogenous antibody targets the region 100 bp downstream of the J region (FIG. 9). In the experimental examples, this region was targeted to express a version of the selected antibody palivizumab containing the C region from the endogenous genome (FIGS. 7 and 9). The crispr.mit.edu algorithm (Hsu et al., Nat Biotechnol. 2013; 31(9):827-32) identified 22 targeting sequences for this region that are predicted to have little, if any, off-target binding. Individual targeting sequences can be inserted into the full-length sgRNA and mixed with a nuclease such as Cas9 immediately prior to incubation as described (Schumann et al., Proc Natl Acad Sci USA. 2015; 112(33):10437-42) and electroporated into B cells (Kim et al., J Immunol. 1979; 122(2):549-54). Since cellular repair of DNA cut by Cas9 often results in loss of gene function (Symington & Gautier, Annu Rev Genet. 2011; 45:247-71), efficient sgR-NAs targeting antibody coding regions are expected to result in the appearance of some B cells lacking antibody, which can be easily assessed by flow cytometry. The activity of sgRNAs targeting intronic sequences can be assessed by sequencing, or through enzymatic assays such as the T7 endonuclease assay.

In particular embodiments, genome targeting and cutting elements can be administered through electroporation, nanoparticle-mediated delivery and/or viral vector delivery. Electroporation can be useful, for example, to deliver targeting elements and/or cutting elements because the membrane of the cell does not normally allow such foreign molecules into the cell. Electroporation sends an electric shock to the cells that temporarily allows such foreign molecules to pass through the cell membrane.

In particular embodiments, genetic constructs for insertion can be administered through electroporation, nanoparticle-mediated delivery and/or viral vector delivery. Adeno-associated viral vectors include those derived from e.g., adenovirus 5 (Ad5), adenovirus 35 (Ad35), adenovirus 11 (Ad11), adenovirus 26 (Ad26), adenovirus 48 (Ad48) or adenovirus 50 (Ad50)), and adeno-associated virus (AAV; see, e.g., U.S. Pat. No. 5,604,090; Kay et al., Nat. Genet. 24:257 (2000); Nakai et al., Blood 91:4600 (1998)).

In particular embodiments, genome targeting and cutting elements can be administered through electroporation and genetic constructs for insertion can be administered through AAV-mediated delivery. In particular embodiments, genome targeting and cutting elements can be administered through nanoparticle-mediated delivery and genetic constructs for insertion can be administered through AAV-mediated delivery.

In particular embodiments, the genetic construct including a transgene can be mixed with a targeting element (e.g., sgRNA) and a cutting element (e.g., Cas9 or cpf1) immediately or shortly before electroporation. Selected antibody expression can be confirmed later (e.g., 3 days later) by measuring cell binding to fluorescently tagged target proteins by flow cytometry. Enrichment and analysis methodologies for detecting and analyzing epitope-specific B cells can be used. Pape et al., Science. 2011; 331(6021):1203-7; Taylor et al., J Exp Med. 2012; 209(3):597-606; Taylor et al., J Exp Med. 2012; 209(11):2065-77; Haasken et al., J Immunol. 2013; 191(3):1055-62; Taylor et al., J Immunol Methods. 2014; 405:74-86; Nanton et al., Eur J Immunol. 2015; 45(2):428-41; Hamilton et al., J Immunol. 2015; 194(10): 5022-34; Taylor et al., Science. 2015; 347(6223):784-7). These methodologies allow detection of selected antibody-expressing B cells at frequencies as extraordinarily low as 0.00002% of the total B cell population (Taylor et al., Science. 2015; 347(6223):784-7).

In particular embodiments, cells can be identified and/or sorted based on marker expression, before or after delivering the genetic construct. For example, it may be useful to isolate a particular type of B cells (e.g., memory B cells, antibody-secreting B cells, naïve B cells, B1 B cells, marginal zone B cells) from a sample prior to delivering the genetic construct. As another example, it may be useful to isolate B cells from other cells present in a blood sample. CD19 is an example of a protein expressed by B cells but few other cells of the body. By marking CD19 with a fluorescent molecule, B cells can be specifically identified. B220 is a useful marker to identify mouse B cells.

CD27 is an example of a protein expressed by memory but not naïve human B cells. By marking CD27 with a fluorescent molecule, memory B cells can be identified.

CD21 is an example of a protein not expressed (or expressed to a low degree) by some memory human B cells with the capacity to quickly secrete antibody following infection. Low CD21 expression can be used to define B cells primed for plasma cell differentiation. By marking CD21 with a fluorescent molecule, these B cells can be specifically identified by for example, negative selection.

Human naïve B cells can be identified by the marker profile IgM+IgD+CD27−. Mouse naïve B cells can be identified by the marker profile CD38+GL7−IgM+IgD+. Human B1 B cells can be identified by the marker profile CD5+CD43+. Mouse B1 B cells can be identified by the marker profile CD43+B220LOW. Human marginal zone B cells can be identified by the marker profile CD21+++IgM++IgD−CD27+. Mouse marginal zone B cells can be identified by the marker profile CD21+++IgM++IgD−.

Particular embodiments may utilize the $CD19^+CD27^+CD21^{lo}$ marker profile.

CD45 is a marker used for identifying and/or isolating cell types used in the experiments described herein. Different mouse strains express different versions of the protein called CD45, termed CD45.1 and CD45.2. In experiments disclosed herein, B cells from a mouse that expresses CD45.2 will be taken and transferred into a mouse that expresses CD45.1. By marking CD45.1 and CD45.2 with different fluorescent molecules, one can identify the cells that came from the donor animal because they express CD45.2 but not CD45.1.

Particular embodiments include sorting B cells after genetic modification based on expression of an exogenous light chain. For example, B cells that naturally express a kappa light chain can be modified to express a selected antibody that includes a lambda light chain. B cells that naturally express a lambda light chain can be modified to express a selected antibody that includes a kappa light chain. Sorting based on expression of an exogenous light chain will allow for isolation of only those B cells expressing the selected antibody. In particular embodiments, only those B cells that completely lack surface expression of their endogenous light chain are isolated for formulation and administration to a subject.

In particular embodiments, cells may be identified and/or isolated using flow cytometry. Flow cytometry is a sensitive and powerful analysis approach that uses lasers to individually analyze the fluorescent molecules marking millions of individual cells. By analyzing the combination of fluorescent molecules each cell is marked with, different B cell subtypes can be identified. Flow cytometry can be used to identify B cell subsets and analyze the expression of selected antibodies (e.g., palivizumab) within these cells.

In particular embodiments, methods of modifying B cells can include obtaining hematopoietic stem cells (HSC), and/or delivering the genetic constructs to HSC. HSC can refer to a type of stem cell that naturally produces B cells as well as all other cells of the immune system. HSC can be obtained, for example, from cord blood.

Particular experimental results described herein utilized A20 cells to develop the genetic modification methodology prior to moving on to freshly-isolated B cells. A20 is an immortalized cell line made from a mouse B cell.

In particular embodiments, B cells may be obtained from a human subject and obtained B cells or a subset thereof may be modified ex vivo.

Formulations of Modified B Cells. Once modified, cells can be harvested from a culture medium, and washed and concentrated into a carrier in a therapeutically-effective amount. Exemplary carriers include saline, buffered saline, physiological saline, water, Hanks' solution, Ringer's solution, Nonnosol-R (Abbott Labs), PLASMA-LYTE A® (Baxter Laboratories, Inc., Morton Grove, Ill.), glycerol, ethanol, and combinations thereof.

In particular embodiments, carriers can be supplemented with human serum albumin (HSA) or other human serum components or fetal bovine serum. In particular embodiments, a carrier for infusion includes buffered saline with 5% hyaluronic acid sodium salt (HAS) or dextrose. Additional isotonic agents include polyhydric sugar alcohols including trihydric or higher sugar alcohols, such as glycerin, erythritol, arabitol, xylitol, sorbitol, or mannitol.

Carriers can include buffering agents, such as citrate buffers, succinate buffers, tartrate buffers, fumarate buffers, gluconate buffers, oxalate buffers, lactate buffers, acetate buffers, phosphate buffers, histidine buffers, and/or trimethylamine salts.

Stabilizers refer to a broad category of excipients which can range in function from a bulking agent to an additive which helps to prevent cell adherence to container walls. Typical stabilizers can include polyhydric sugar alcohols; amino acids, such as arginine, lysine, glycine, glutamine, asparagine, histidine, alanine, ornithine, L-leucine, 2-phenylalanine, glutamic acid, and threonine; organic sugars or sugar alcohols, such as lactose, trehalose, stachyose, mannitol, sorbitol, xylitol, ribitol, myoinisitol, galactitol, glycerol, and cyclitols, such as inositol; PEG; amino acid polymers; sulfur-containing reducing agents, such as urea, glutathione, thioctic acid, sodium thioglycolate, thioglycerol, alpha-monothioglycerol, and sodium thiosulfate; low molecular weight polypeptides (i.e., <10 residues); proteins such as HSA, bovine serum albumin, gelatin or immunoglobulins; hydrophilic polymers such as polyvinylpyrrolidone; monosaccharides such as xylose, mannose, fructose and glucose; disaccharides such as lactose, maltose and sucrose; trisaccharides such as raffinose, and polysaccharides such as dextran.

Where necessary or beneficial, formulations can include a local anesthetic such as lidocaine to ease pain at a site of injection.

Exemplary preservatives include phenol, benzyl alcohol, meta-cresol, methyl paraben, propyl paraben, octadecyldimethylbenzyl ammonium chloride, benzalkonium halides, hexamethonium chloride, alkyl parabens such as methyl or propyl paraben, catechol, resorcinol, cyclohexanol, and 3-pentanol.

Formulations can include, for example, greater than $10^2$ modified B cells, greater than 103 modified b cells, greater than $10^4$ modified b cells, greater than $10^5$ modified b cells, greater than $10^6$ modified B cells, greater than $10^7$ modified B cells, greater than $10^8$ modified B cells, greater than $10^9$ modified B cells, greater than $10^{10}$ modified B cells, or greater than $10^{11}$ modified B cells.

Methods of Use. Methods disclosed herein include treating subjects (e.g., humans, veterinary animals (dogs, cats, reptiles, birds) livestock (e.g., horses, cattle, goats, pigs, chickens) and research animals (e.g., monkeys, rats, mice, fish) with formulations disclosed herein. Treating subjects includes delivering therapeutically effective amounts. Therapeutically effective amounts include those that provide effective amounts, prophylactic treatments and/or therapeutic treatments.

An "effective amount" is the amount of a composition necessary to result in a desired physiological change in the subject. Effective amounts are often administered for research purposes. Effective amounts disclosed herein can cause a statistically-significant effect in an animal model or in vitro assay relevant to the assessment of a condition's development, progression, and/or resolution.

A "prophylactic treatment" includes a treatment administered to a subject who does not display signs or symptoms of a condition or displays only early signs or symptoms of a condition such that treatment is administered for the purpose of diminishing or decreasing the risk of developing the condition. Thus, a prophylactic treatment functions as a preventative treatment against a condition. In particular embodiments, prophylactic treatments reduce, delay, or prevent the worsening of a condition. Particular embodiments include administration of a formulation described herein as prophylactic protection in the absence of a currently effective vaccine. Particular embodiments include administration of a formulation described herein as prophylactic protection as a replacement for conventional vaccination strategies. Particular embodiments include administration of a formulation described herein as prophylactic protection as a supplement to conventional vaccination strategies.

A "therapeutic treatment" includes a treatment administered to a subject who displays symptoms or signs of a condition and is administered to the subject for the purpose of diminishing or eliminating those signs or symptoms of the condition. The therapeutic treatment can reduce, control, or eliminate the presence or activity of the condition and/or reduce control or eliminate side effects of the condition.

In particular embodiments, the condition is an infection.

Function as an effective amount, prophylactic treatment or therapeutic treatment are not mutually exclusive, and in particular embodiments, administered dosages may accomplish more than one treatment type.

In particular embodiments, therapeutically effective amounts provide anti-pathogen effects. Anti-pathogen effects can include anti-infection effects. Anti-infection effects can include a decrease in the occurrence of infections, a decrease in the severity of infections, a decrease in the duration of infections, a decrease in the number of infected cells, a decrease in volume of infected tissue, an increase in life expectancy, induced sensitivity of infected cells to immune clearance, reduced infection-associated pain, and/or reduction or elimination of a symptom associated with the treated infection.

In particular embodiments, therapeutically effective amounts provide anti-inflammatory effects. Anti-inflammatory effects can include reduced inflammation-associated pain, heat, redness, swelling and/or loss of function.

In particular embodiments, therapeutically effective amounts provide anti-Crohn's disease effects or anti-ulcerative colitis effects. Anti-Crohn's disease effects or anti-ulcerative colitis effects can include reduced diarrhea, reduced rectal bleeding, reduced unexplained weight loss, reduced fever, reduced abdominal pain and cramping, reduced fatigue and feelings of low energy, and/or restored appetite.

In particular embodiments, therapeutically effective amounts provide anti-arthritis effects. Anti-arthritis effects can include reduced pain, stiffness, swelling, redness in the joints and/or a restored range of motion. Types of arthritis include rheumatoid arthritis (RA), ankylosing spondylitis, and psoriatic arthritis.

In particular embodiments, therapeutically effective amounts provide anti-plaque psoriasis effects. Anti-plaque psoriasis effects can include reduced red patches, scaling spots, itching, burning, soreness, nail bed abnormalities and/or swollen or stiff joints.

In particular embodiments, B cells may be obtained from a subject, a subset of the B cells may be modified ex vivo, and then the modified B cells may be formulated and administered to the subject. In particular embodiments, a first subset of the subject's B cells may be modified with a first genetic construct to produce a selected antibody against a first pathogen, and a second subset of the subject's B cells may be modified with a second genetic construct to produce a selected antibody against a second pathogen, thereby providing protective antibodies against two pathogens. As indicated, B cells against any number of pathogens can be formed and administered to a subject. In particular embodiments, the selected antibodies can be an anti-RSV antibody, an anti-HIV antibody, an anti-Dengue virus antibody, an anti-*Bordatella pertussis* antibody, an anti-hepatitis C antibody, an anti-influenza virus antibody, an anti-parainfluenza virus antibody, an anti-MPV antibody, an anti-cytomegalovirus antibody, an anti-Epstein Barr virus antibody; an anti-herpes simplex virus antibody, an anti-*Clostridium difficile* bacterial toxin antibody, and/or an anti-TNF antibody. In particular embodiments, the selected antibodies can be one or more of an anti-RSV antibody, an anti-influenza virus antibody, an anti-parainfluenza virus antibody, and/or an anti-MPV antibody. In particular embodiments, the selected antibodies can be an anti-RSV antibody, an anti-influenza virus antibody, an anti-parainfluenza virus antibody, and an anti-MPV antibody. In particular embodiments, the selected antibody is palivizumab.

In particular embodiments, B cells may be obtained from a bone marrow donor or a hematopoietic stem cell donor that has been immunologically matched to a recipient. In particular embodiments, a first subset of the donor's B cells may be modified with a first genetic construct to produce a selected antibody against a first pathogen, and a second subset of the donor's B cells may be modified with a second genetic construct to produce a selected antibody against a second pathogen, thereby providing protective antibodies against two pathogens. As indicated, B cells against any number of pathogens can be formed and administered to a subject. In particular embodiments, the selected antibodies can be an anti-RSV antibody, an anti-HIV antibody, an anti-Dengue virus antibody, an anti-*Bordatella pertussis* antibody, an anti-hepatitis C antibody, an anti-influenza virus antibody, an anti-parainfluenza virus antibody, an anti-MPV antibody, an anti-cytomegalovirus antibody, an anti-Epstein Barr virus antibody; an anti-herpes simplex virus antibody, an anti-*Clostridium difficile* bacterial toxin antibody, and/or an anti-TNF antibody. In particular embodiments, the selected antibodies can be one or more of an anti-RSV antibody, an anti-influenza virus antibody, an anti-parainfluenza virus antibody, and/or an anti-MPV antibody. In particular embodiments, the selected antibodies can be an anti-RSV antibody, an anti-influenza virus antibody, an anti-parainfluenza virus antibody, and an anti-MPV antibody. In particular embodiments, the selected antibody is palivizumab. The genetically-modified B cells can be administered to the recipient to provide protection against infection (e.g., an anti-infection effect) until the transplanted cells repopulate the recipient's own immune system.

In particular embodiments, the recipient is receiving bone marrow from a donor or a hematopoietic stem cell transplant as a treatment for a hematological malignancy. Examples of hematological malignancies include acute lymphocytic leukemia, B-cell prolymphocytic leukemia, Burkitt lymphoma/leukemia, chronic lymphocytic leukemia (CLL), diffuse large B-cell lymphoma, follicular lymphoma (grades I, II, III, or IV), Hodgkin's lymphoma, intravascular large B-cell lymphoma, lymphoma, lymphoplasmacytic lymphoma, mantle cell lymphoma, marginal zone lymphoma (extra-nodal and nodal), mediastinal (thymic) large B-cell lymphoma, multiple myeloma, non-Hodgkin's lymphoma, POEMS syndrome/osteosclerotic myeloma, primary effusion lymphoma, splenic marginal zone lymphoma, small lymphocytic lymphoma, smoldering multiple myeloma (SMM), and Waldenstrom's macroglobulinemia.

In particular embodiments, the recipient is receiving genetically-modified hematopoietic stem cells that provide a gene the recipient is lacking. These recipients may have a primary or secondary immunodeficiency that can be treated with the provision of a therapeutic gene through hematopoietic stem cells. More than 80 primary immune deficiency diseases are recognized by the World Health Organization. These diseases are characterized by an intrinsic defect in the immune system in which, in some cases, the body is unable to produce any or enough antibodies against infection. In other cases, cellular defenses to fight infection fail to work properly. Typically, primary immune deficiencies are inherited disorders. X-linked severe combined immunodeficiency (SCID-X1) is another example of a primary immune deficiency. X-linked SCID results in both a cellular and humoral immune depletion caused by mutations in the common gamma chain gene (γC), which result in the absence of T and natural killer (NK) lymphocytes.

Secondary, or acquired, immune deficiencies are not the result of inherited genetic abnormalities, but rather occur in individuals in which the immune system is compromised by factors outside the immune system. Examples include trauma, viruses, chemotherapy, toxins, and pollution. Acquired immunodeficiency syndrome (AIDS) is an example of a secondary immune deficiency disorder caused by a virus, the human immunodeficiency virus (HIV), in which a depletion of T lymphocytes renders the body unable to fight infection.

In particular embodiments, B cells may be obtained from a subject, a subset of the B cells may be modified ex vivo, and then the modified B cells may be formulated and administered to the subject. In particular embodiments, a first subset of the subject's B cells may be modified with a first genetic construct to produce a selected antibody against an inflammatory molecule, such as an inflammatory cytokine, thereby providing antibodies that protect against inflammation. In particular embodiments, the selected antibodies can be anti-TNF antibodies and/or anti-IL-1 antibodies. In particular embodiments, the selected antibody is infliximab, adalimumab, and/or golimumab and/or an approved biosimilar thereof.

For administration, therapeutically effective amounts (also referred to herein as doses) can be initially estimated based on results from in vitro assays and/or animal model studies. Such information can be used to more accurately determine useful doses in subjects of interest. The actual dose amount administered to a particular subject can be determined by a physician, veterinarian or researcher taking into account parameters such as physical and physiological factors including age, previous vaccinations (if any), target, body weight, severity of condition, type of condition, stage of condition, previous or concurrent therapeutic interventions, idiopathy of the subject and route of administration.

As indicated, in particular embodiments, modified B cells express a tag that allows, for example, tracking and/or elimination after administration to a subject Exemplary doses can include greater than $10^2$ modified B cells, greater than $10^3$ modified B cells, greater than $10^4$ modified B cells, greater than $10^5$ modified B cells, greater than $10^6$ modified B cells, greater than $10^7$ modified B cells, greater than $10^8$ modified B cells, greater than $10^9$ modified B cells, greater than $10^{10}$ modified B cells, or greater than $10^{11}$ modified B cells.

In particular embodiments, the effects of selected antibodies can be measured using viral titers. Viral titer refers to the amount of virus that can be detected. High viral titers mean high levels of infection. An optimal protective response is observed with titers that fall to zero.

As will be understood by one of ordinary skill in the art, while particular embodiments have been described, additional embodiments may also be utilized within the scope of the disclosure. The following description provides description and enablement of representative additional embodiments.

Exemplary Embodiments

1. A method of genetically engineering B cells to express a selected antibody including targeted insertion of a genetic construct including (i) a promoter and (ii) a transgene encoding a portion of a selected antibody at an intronic region that is constant in all B cells and that is (i) positioned relative to an enhancer element that interacts with the promoter to drive expression of the transgene; and (ii) in a configuration such that a portion of the B cells' endogenous antibody-encoding genome is not expressed.

2. A method of genetically engineering B cells to express a selected antibody including inserting into SEQ ID NO: 1, SEQ ID NO: 2, SEQ ID NO: 3, or SEQ ID NO: 4, a genetic construct including or encoding (i) a heavy chain promoter, (ii) a signal peptide, (iii) the full length light chain of the selected antibody; (iv) a flexible linker or a skipping element; (v) the variable region of the heavy chain of the selected antibody; and (vi) a splice junction, thereby genetically engineering the B cells to express the selected antibody.

3. A method of embodiment 1 or 2, wherein the B cells' endogenous variable heavy chain encoding genome is not excised during the genetic modification.

4. A method of any of embodiments 1-3, wherein the selected antibody is an anti-Respiratory Syncytial Virus (RSV) antibody, an anti-human immunodeficiency virus (HIV) antibody, an anti-Dengue virus antibody, an anti-*Bordatella pertussis* antibody, an anti-hepatitis C antibody, an anti-influenza virus antibody, an anti-parainfluenza virus antibody, an anti-metapneumovirus (MPV) antibody, an anti-cytomegalovirus antibody, an anti-Epstein Barr virus antibody; an anti-herpes simplex virus antibody, an anti-*Clostridium difficile* bacterial toxin antibody, or an anti-tumor necrosis factor (TNF) antibody.

5. A method of any of embodiments 1-4, wherein the genetic construct includes SEQ ID NOs: 102-175, 278, 279, or 280-289.

6. A method of any of embodiments 2-5, wherein the flexible linker is between the full length light chain of the selected antibody and the variable region of the heavy chain of the selected antibody.

7. A method of any of embodiments 2-6, wherein the flexible linker is selected from SEQ ID NOs: 180-184.

8. A method of any of embodiments 2-7, wherein the flexible linker is a Gly-Ser linker including 50-80 amino acids.

9. A method of any of embodiments 2-8, wherein the flexible linker is a Gly-Ser linker including 57 amino acids.

10. A method of any of embodiments 2-6, 8, or 9, wherein the flexible linker is SEQ ID NO: 122.

11. A method of any of embodiments 2-10, wherein the skipping element is between the full length light chain of the selected antibody and the variable region of the heavy chain of the selected antibody.
12. A method of any of embodiments 2-11, wherein the skipping element is a self-cleaving peptide.
13. A method of embodiment 12, wherein the self-cleaving peptide is selected from SEQ ID NOs: 176-179.
14. A method of any of embodiments 2-13, wherein the skipping element is an internal ribosome entry site (IRES).
15. A method of any of embodiments 2-14, wherein the heavy chain promoter is selected from SEQ ID NOs: 111 and 128.
16. A method of any of embodiments 2-15, wherein the heavy chain promoter is IgVH1-69 or J558H10.
17. A method of any of embodiments 2-16, wherein the signal peptide is selected from SEQ ID NOs: 118, 134, and 185-194.
18. A method of any of embodiments 2-17, wherein the signal peptide is derived from human IgH heavy chain or human IgL light chain.
19. A method of any of embodiments 1-18, wherein the genetic construct includes homology arms.
20. A method of embodiment 19, wherein the homology arms include SEQ ID NOs: 90-101, 110, 125, 127, 140, 142, 143, 153, 170, 171, 173, 174, 278, or 279.
21. A method of any of embodiments 1-20, wherein the genetic construct encodes a tag.
22. A method of embodiment 21, wherein the tag includes STREPTAG®, STREP® tag II, His tag, Flag tag, Xpress tag, Avi tag, calmodulin tag, polyglutamate tag, HA tag, Myc tag, Nus tag, S tag, SBP tag, Softag 1, Softag 3, or V5 tag.
23. A method of embodiment 21 or 22, wherein the tag includes SEQ ID NOs: 122, or 195-204.
24. A method of any of embodiments 1-23, further including delivering a guide RNA (gRNA) sequence selected from one or more of SEQ ID NOs: 87-89, and 290-366, and a nuclease to the B cells.
25. A method of embodiment 24, wherein the delivering is through electroporation, a nanoparticle, or viral-mediated delivery.
26. A method of any of embodiments 1-25, wherein the genetic construct is part of an adeno-associated viral vector.
27. A method of any of embodiments 24-26, wherein the gRNA and nuclease are delivered through electroporation and the genetic construct is delivered as part of an adeno-associated viral vector.
28. A method of any of embodiments 24-27, wherein the nuclease is Cas9 or Cpf1.
29. A method of any of embodiments 24-28, wherein a target sequence targeted by one or more of the gRNA sequence is selected from one or more of SEQ ID NOs: 5-84 and the gRNA is selected from one or more of SEQ ID NOs: 87-89, and 290-366.
30. A method of any of embodiments 1-29, wherein the selected antibody is an anti-RSV antibody including palivizumab, AB1128, or ab20745.
31. A method of any of embodiments 1-30, wherein the selected antibody is: palivizumab including a heavy chain including SEQ ID NO: 138 and a light chain including SEQ ID NO: 136; palivizumab including a heavy chain including SEQ ID NO: 138 and a light chain including SEQ ID NO: 205; an anti-RSV antibody including a heavy chain including SEQ ID NO: 123 and a light chain including SEQ ID NO: 120; or an anti-RSV antibody including a heavy chain including SEQ ID NO: 123 and a light chain including SEQ ID NO: 206.
32. A method of any of embodiments 1-30, wherein the selected antibody is an anti-RSV antibody including a CDRH1 including SEQ ID NO: 207, a CDRH2 including SEQ ID NO: 208, a CDRH3 including SEQ ID NO: 209; a CDRL1 including SEQ ID NO: 210, a CDRL2 including SEQ ID NO: 211, and a CDRL3 including SEQ ID NO: 212.
33. A method of any of embodiments 1-29, wherein the selected antibody is an anti-HIV antibody including 10E8, VRC01, ab18633 or 39/5.4A.
34. A method of any of embodiments 1-29 or 33, wherein the selected antibody is an anti-HIV antibody including a heavy chain including SEQ ID NO: 150 and a light chain including SEQ ID NO: 149.
35. A method of any of embodiments 1-29 or 33, wherein the selected antibody is an anti-HIV antibody including a CDRH1 including SEQ ID NO: 213, a CDRH2 including SEQ ID NO: 214, a CDRH3 including SEQ ID NO: 215, a CDRL1 including SEQ ID NO: 216, a CDRL2 including SEQ ID NO: 217, and a CDRL3 including SEQ ID NO: 218 or a CDRH1 including SEQ ID NO: 219, a CDRH2 including SEQ ID NO: 220, a CDRH3 including SEQ ID NO: 221, a CDRL1 including QYGS, a CDRL2 including SGS, and a CDRL3 including SEQ ID NO: 222.
36. A method of any of embodiments 1-29, wherein the selected antibody is an anti-Dengue virus antibody including antibody 55, DB2-3, ab155042 or ab80914.
37. A method of any of embodiments 1-29 or 36, wherein the selected antibody is an anti-Dengue virus antibody including a CDRH1 including SEQ ID NO: 223, a CDRH2 including SEQ ID NO: 224, a CDRH3 including SEQ ID NO: 225; a CDRL1 including SEQ ID NO: 226, a CDRL2 including SEQ ID NO: 227, and a CDRKL3 including SEQ ID NO: 228 or a CDRH1 including SEQ ID NO: 229, a CDRH2 including SEQ ID NO: 230, a CDRH3 including SEQ ID NO: 231, a CDRL1 including SEQ ID NO: 232, a CDRL2 including SEQ ID NO: 233, and a CDRL3 including SEQ ID NO: 234.
38. A method of any of embodiments 1-29, wherein the selected antibody is an anti-pertussis antibody including a heavy chain including SEQ ID NO: 235 and a light chain including SEQ ID NO: 236.
39. A method of any of embodiments 1-29, wherein the selected antibody is an anti-hepatitis C antibody including MAB8694 or C7-50.
40. A method of any of embodiments 1-29 or 39, wherein the selected antibody is an anti-hepatitis C antibody including a CDRH1 including SEQ ID NO: 237, a CDRH2 including SEQ ID NO: 238, a CDRH3 including SEQ ID NO: 239, a CDRL1 including SEQ ID NO: 240, a CDRL2 including SEQ ID NO: 241, and a CDRL3 including SEQ ID NO: 242.
41. A method of any of embodiments 1-29, wherein the selected antibody is an anti-influenza virus antibody including C102.
42. A method of any of embodiments 1-29 or 41, wherein the selected antibody is an anti-influenza virus antibody including a heavy chain including SEQ ID NO: 159 and a light chain including SEQ ID NO: 158.
43. A method of any of embodiments 1-29 or 41, wherein the selected antibody is an anti-influenza virus antibody including a CDRH1 including SEQ ID NO: 243, a CDRH2 including SEQ ID NO: 244, a CDRH3 including SEQ ID NO: 245, a CDRL1 including SEQ ID NO: 246, a CDRL2 including KTS, and a CDRL3 including SEQ ID NO: 247.
44. A method of any of embodiments 1-29, wherein the selected antibody is an anti-MPV antibody including MPE8.

45. A method of any of embodiments 1-29, wherein the selected antibody is an anti-CMV antibody including MCMV5322A, MCMV3068A, LJP538, or LJP539.

46. A method of any of embodiments 1-29, wherein the selected antibody is an anti-EBV antibody including a heavy chain including SEQ ID NO: 168 and a light chain including SEQ ID NO: 166.

47. A method of any of embodiments 1-29, wherein the selected antibody is an anti-EBV antibody including a CDRH1 including SEQ ID NO: 248, a CDRH2 including SEQ ID NO: 249, a CDRH3 including SEQ ID NO: 250, a CDRL1 including SEQ ID NO: 251, a CDRL2 including SEQ ID NO: 252, and a CDRL3 including SEQ ID NO: 253.

48. A method of any of embodiments 1-29, wherein the selected antibody is an anti-HSV antibody including HSV8-N and MB66.

49. A method of any of embodiments 1-29, wherein the selected antibody is an anti-*Clostridium difficile* antibody including actoxumab or bezlotoxumab.

50. A method of any of embodiments 1-29, wherein the selected antibody is an anti-TNF antibody including infliximab, adalimumab, etanercept, certolizumab, or accepted biosimilars thereof.

51. A method of any of embodiments 1-29 or 50, wherein the selected antibody is an anti-TNF antibody including a heavy chain including SEQ ID NO: 254 and a light chain including SEQ ID NO: 255; a CDRH1 including SEQ ID NO: 256, a CDRH2 including SEQ ID NO: 257, and a CDRH3 including SEQ ID NO: 258; a CDRL1 including SEQ ID NO: 259, a CDRL2 including SEQ ID NO: 260, and a CDRL3 including SEQ ID NO: 261; a CDRH1 including SEQ ID NO: 262, a CDRH2 including SEQ ID NO: 263, and a CDRH3 including SEQ ID NO: 264; a CDRL1 including SEQ ID NO: 265, a CDRL2 including SEQ ID NO: 266, and a CDRL3 including SEQ ID NO: 267; a CDRH1 including SEQ ID NO: 268, a CDRH2 including SEQ ID NO: 269, and a CDRH3 including SEQ ID NO: 270; or a CDRL1 including SEQ ID NO: 271, a CDRL2 including SEQ ID NO: 272, and a CDRL3 including SEQ ID NO: 273.

52. A method of any of embodiments 1-51, wherein the genetic modification utilizes a sequence including any of SEQ ID NOs: 87, 88, 89, 90-175, 278-366.

53. A method of any of embodiments 1-52, wherein the B cell is an antibody-producing B cell, a memory B cell, a naïve B cell, a B1 B cell or a marginal zone B cell.

54. A B cell modified according to a method of any one of embodiments 1-53.

55. A B cell of embodiment 54, wherein the B cell is an antibody-secreting B cell, a memory B cell, a naïve B cell, a B1 B cell or a marginal zone B cell.

56. A method of providing an anti-infection effect in a subject in need thereof including administering a therapeutically effective amount of a B cell of embodiment 54 or 55 to the subject thereby providing an anti-infection effect.

57. A method of embodiment 56, wherein the providing obviates the need for a vaccination.

58. A method of embodiment 56 or 57, wherein the administering replaces a vaccination protocol.

59. A method of any of embodiments 56-58, wherein the subject is immune-suppressed.

60. A method of any of embodiments 56-59, wherein the subject is immune-suppressed as part of a treatment regimen including a bone marrow transplant, hematopoietic stem cell transplant, or administration of genetically modified hematopoietic stem cells.

61. A method of providing an anti-inflammatory effect in a subject in need thereof including administering a therapeutically effective amount of a B cell of embodiment 54 or 55 to the subject thereby providing an anti-inflammatory effect.

62. A genetic construct for modifying a B cell to express a selected antibody, the genetic construct including or encoding (i) a heavy chain promoter, (ii) a signal peptide, (iii) the full length light chain of the selected antibody; (iv) a flexible linker or a skipping element; (v) the variable region of the heavy chain of the selected antibody; and (vi) a splice junction.

63. A genetic construct of embodiment 62, including SEQ ID NOs: 102-175, or 280-289.

64. A genetic construct of embodiment 62 or 63, wherein the flexible linker is between the full length light chain of the selected antibody and the variable region of the heavy chain of the selected antibody.

65. A genetic construct of any of embodiments 62-64, wherein the flexible linker is selected from SEQ ID NOs: 180-184.

66. A genetic construct of any of embodiments 62-65, wherein the flexible linker is a Gly-Ser linker including 50-80 amino acids.

67. A genetic construct of any of embodiments 62-66, wherein the flexible linker is a Gly-Ser linker includes 57 amino acids.

68. A genetic construct of any of embodiments 62-64, 66 or 67, wherein the flexible linker is SEQ ID NO: 122.

69. A genetic construct of any of embodiments 62-68, wherein the skipping element is between the full length light chain of the selected antibody and the variable region of the heavy chain of the selected antibody.

70. A genetic construct of any of embodiments 62-69, wherein the skipping element is a self-cleaving peptide.

71. A genetic construct of embodiment 70, wherein the self-cleaving peptide is selected from SEQ ID NOs: 176-179.

72. A genetic construct of any of embodiments 62-69, wherein the skipping element is an internal ribosome entry site (IRES).

73. A genetic construct of any of embodiments 62-72, wherein the heavy chain promoter is selected from SEQ ID NOs: 111 and 128.

74. A genetic construct of any of embodiments 62-73, wherein the heavy chain promoter is IgVH1-69 or J558H10.

75. A genetic construct of any of embodiments 62-74, wherein the signal peptide is selected from SEQ ID NOs: 118, 134, and 185-194.

76. A genetic construct of any of embodiments 62-75, wherein the signal peptide is derived from human IgH heavy chain or human IgL light chain.

77. A genetic construct of any of embodiments 62-76, wherein the genetic construct includes homology arms.

78. A genetic construct of embodiment 77, wherein the homology arms include SEQ ID NOs: 90-101, 110, 125, 127, 140, 142, 143, 153, 170, 171, 173, 174, 278, or 279.

79. A genetic construct of any of embodiments 62-78, wherein the genetic construct encodes a tag.

80. A genetic construct of embodiment 79, wherein the tag includes STREPTAG®, STREP® tag II, His tag, Flag tag, Xpress tag, Avi tag, calmodulin tag, polyglutamate tag, HA tag, Myc tag, Nus tag, S tag, SBP tag, Softag 1, Softag 3, or V5 tag.

81. A genetic construct of embodiment 79 or 80, wherein the tag includes SEQ ID NOs: 122, or 195-204.

82. A genetic construct of any of embodiments 62-81, wherein the selected antibody is an anti-RSV antibody including palivizumab, AB1128, or ab20745.

83. A genetic construct of any of embodiments 62-82, wherein the selected antibody is: palivizumab including a heavy chain including SEQ ID NO: 138 and a light chain including SEQ ID NO: 136; palivizumab including a heavy chain including SEQ ID NO: 138 and a light chain including SEQ ID NO: 205; an anti-RSV antibody including a heavy chain including SEQ ID NO: 123 and a light chain including SEQ ID NO: 120; or an anti-RSV antibody including a heavy chain including SEQ ID NO: 123 and a light chain including SEQ ID NO: 206.

84. A genetic construct of any of embodiments 62-82, wherein the selected antibody is an anti-RSV antibody including a CDRH1 including SEQ ID NO: 207, a CDRH2 including SEQ ID NO: 208, a CDRH3 including SEQ ID NO: 209; a CDRL1 including SEQ ID NO: 210, a CDRL2 including SEQ ID NO: 211, and a CDRL3 including SEQ ID NO: 212.

85. A genetic construct of any of embodiments 62-81, wherein the selected antibody is an anti-HIV antibody including 10E8, VRC01, ab18633 or 39/5.4A.

86. A genetic construct of any of embodiments 62-81 or 85, wherein the selected antibody is an anti-HIV antibody including a heavy chain including SEQ ID NO: 150 and a light chain including SEQ ID NO: 149.

87. A genetic construct of any of embodiments 62-81 or 85, wherein the selected antibody is an anti-HIV antibody including a CDRH1 including SEQ ID NO: 213, a CDRH2 including SEQ ID NO: 214, a CDRH3 including SEQ ID NO: 215, a CDRL1 including SEQ ID NO: 216, a CDRL2 including SEQ ID NO: 217, and a CDRL3 including SEQ ID NO: 218 or a CDRH1 including SEQ ID NO: 219, a CDRH2 including SEQ ID NO: 220, a CDRH3 including SEQ ID NO: 221, a CDRL1 including QYGS, a CDRL2 including SGS, and a CDRL3 including SEQ ID NO: 222.

88. A genetic construct of any of embodiments 62-81, wherein the selected antibody is an anti-Dengue virus antibody including antibody 55, DB2-3, ab155042 or ab80914.

89. A genetic construct of any of embodiments 62-81 or 88, wherein the selected antibody is an anti-Dengue virus antibody including a CDRH1 including SEQ ID NO: 223, a CDRH2 including SEQ ID NO: 224, a CDRH3 including SEQ ID NO: 225; a CDRL1 including SEQ ID NO: 226, a CDRL2 including SEQ ID NO: 227, and a CDRKL3 including SEQ ID NO: 228 or a CDRH1 including SEQ ID NO: 229, a CDRH2 including SEQ ID NO: 230, a CDRH3 including SEQ ID NO: 231, a CDRL1 including SEQ ID NO: 232, a CDRL2 including SEQ ID NO: 233, and a CDRL3 including SEQ ID NO: 234.

90. A genetic construct of any of embodiments 62-81, wherein the selected antibody is an anti-pertussis antibody including a heavy chain including SEQ ID NO: 235 and a light chain including SEQ ID NO: 236.

91. A genetic construct of any of embodiments 62-81, wherein the selected antibody is an anti-hepatitis C antibody including MAB8694 or C7-50.

92. A genetic construct of any of embodiments 62-81 or 91, wherein the selected antibody is an anti-hepatitis C antibody including a CDRH1 including SEQ ID NO: 237, a CDRH2 including SEQ ID NO: 238, a CDRH3 including SEQ ID NO: 239, a CDRL1 including SEQ ID NO: 240, a CDRL2 including SEQ ID NO: 241, and a CDRL3 including SEQ ID NO: 242.

93. A genetic construct of any of embodiments 62-81, wherein the selected antibody is an anti-influenza virus antibody including C102.

94. A genetic construct of any of embodiments 62-81 or 93, wherein the selected antibody is an anti-influenza virus antibody including a heavy chain including SEQ ID NO: 159 and a light chain including SEQ ID NO: 158.

95. A genetic construct of any of embodiments 62-81 or 93, wherein the selected antibody is an anti-influenza virus antibody including a CDRH1 including SEQ ID NO: 243, a CDRH2 including SEQ ID NO: 244, a CDRH3 including SEQ ID NO: 245, a CDRL1 including SEQ ID NO: 246, a CDRL2 including KTS, and a CDRL3 including SEQ ID NO: 247.

96. A genetic construct of any of embodiments 62-81, wherein the selected antibody is an anti-MPV antibody including MPE8.

97. A genetic construct of any of embodiments 62-81, wherein the selected antibody is an anti-CMV antibody including MCMV5322A, MCMV3068A, LJP538, or LJP539.

98. A genetic construct of any of embodiments 62-81, wherein the selected antibody is an anti-EBV antibody including a heavy chain including SEQ ID NO: 168 and a light chain including SEQ ID NO: 166.

99. A genetic construct of any of embodiments 62-81, wherein the selected antibody is an anti-EBV antibody including a CDRH1 including SEQ ID NO: 248, a CDRH2 including SEQ ID NO: 249, a CDRH3 including SEQ ID NO: 250, a CDRL1 including SEQ ID NO: 251, a CDRL2 including SEQ ID NO: 252, and a CDRL3 including SEQ ID NO: 253.

100. A genetic construct of any of embodiments 62-81, wherein the selected antibody is an anti-HSV antibody including HSV8-N and MB66.

101. A genetic construct of any of embodiments 62-81, wherein the selected antibody is an anti-*Clostridium difficile* antibody including actoxumab or bezlotoxumab.

102. A genetic construct of any of embodiments 62-81, wherein the selected antibody is an anti-TNF antibody including infliximab, adalimumab, etanercept, certolizumab, or accepted biosimilars thereof.

103. A genetic construct of any of embodiments 62-81 or 102, wherein the selected antibody is an anti-TNF antibody including a heavy chain including SEQ ID NO: 254 and a light chain including SEQ ID NO: 255; a CDRH1 including SEQ ID NO: 256, a CDRH2 including SEQ ID NO: 257, and a CDRH3 including SEQ ID NO: 258; a CDRL1 including SEQ ID NO: 259, a CDRL2 including SEQ ID NO: 260, and a CDRL3 including SEQ ID NO: 261; a CDRH1 including SEQ ID NO: 262, a CDRH2 including SEQ ID NO: 263, and a CDRH3 including SEQ ID NO: 264; a CDRL1 including SEQ ID NO: 265, a CDRL2 including SEQ ID NO: 266, and a CDRL3 including SEQ ID NO: 267; a CDRH1 including SEQ ID NO: 268, a CDRH2 including SEQ ID NO: 269, and a CDRH3 including SEQ ID NO: 270; or a CDRL1 including SEQ ID NO: 271, a CDRL2 including SEQ ID NO: 272, and a CDRL3 including SEQ ID NO: 273.

104. A kit for genetically modifying a B cell including a genetic construct of any of embodiments 62-103 and a gRNA targeting SEQ ID NO: 1, SEQ ID NO: 2, SEQ ID NO: 3, or SEQ ID NO: 4.

105. A kit of embodiment 104, wherein the gRNA is selected from one or more of SEQ ID NOs: 87, 88, 89, and 290-366.

106. A kit of embodiment 104 or 105, further including a nuclease.

107. A kit of embodiment 106, wherein the nuclease is Cas9 or Cpf1.

108. A kit of any of embodiments 104-107, further including a nanoparticle or adeno-associated viral vector.

109. A kit of any of embodiments 104-108, wherein the gRNA and nuclease are associated with a nanoparticle.

110. A kit of any of embodiments 104-109, wherein the genetic construct is part of an adeno-associated viral vector.

Example 1. Providing Life-Long Protection Against Respiratory Syncytial Virus Infection without a Vaccine. Respiratory syncytial virus (RSV) is a leading cause of severe respiratory illness in young children, particularly infants with chronic lung disease, congenital heart disease or born prematurely. Humoral immunity can mediate effective protection against RSV, demonstrated by the therapeutic effects of the recombinant antibody Synagis® (MedImmune, Inc.)/palivizumab. However, both natural infection and previous vaccine trials have failed to induce a fully protective immune response against RSV.

For RSV and other difficult to vaccinate against diseases, bypassing vaccination through engineering primary B cells to elicit expression of a desired therapeutic antibody is extremely attractive. The immunoglobin (Ig) loci are extremely large, diverse, and subject to extensive genomic recombination and editing. In addition, the transcription of immunoglobin genes to produce both membrane and secreted forms relies on the regulation of mRNA splicing and polyadenylation by regulatory DNA elements. This complexity has made viral transduction, the traditional approach for cellular engineering of lymphocytes, technically impractical for the production of therapeutic B cells.

Particular embodiments include a platform for rapid and selective reprogramming of primary B cell antibody specificity by single hit immunogenetic engineering. This platform takes advantage of the high activity of the microhomology mediated end joining DNA repair pathway in primary B cells to insert a fully synthetic hybrid double stranded/single stranded DNA template after creation of DNA breaks by Cas9/sgRNA riboproteins. Key to this approach is preservation of endogenous regulatory elements, which allows for native control of surface bound and secreted antibody expression. Moreover, the strategy is not restricted to RSV. It can be possible to express antibodies protective against virtually any pathogen with just a single blood draw and subsequent cell infusion a few days later.

Materials and Methods. Design of sgRNA. sgRNAs targeting intronic sequences in the mouse and human IgH locus were designed using CrispRGold (crisprgold.mdc-berlin.de) and produced in a synthetic form incorporating 2'-O-methyl analogs and 3' phosphorothioate internucleotide linkages at the first three 5' and 3' terminal RNA residues (Synthego). Genome targeting sequences are as follows:

```
Mouse:                    (SEQ ID NO: 87)
UUAUACAGUAUCCGAUGCAU

Assessment of sgRNA activity by Tracking of Indels by Decomposition (TIDE). Total genomic DNA was isolated from mock and Cas9 treated cells at 3-5 days post electroporation. The 500-600 bp region flanking the cut site was amplified by PCR using the following oligos:

```
Mouse: For-         (SEQ ID NO: 274)
ward:
GGCTCCACCAGACCTCTCTA

Figure 28:
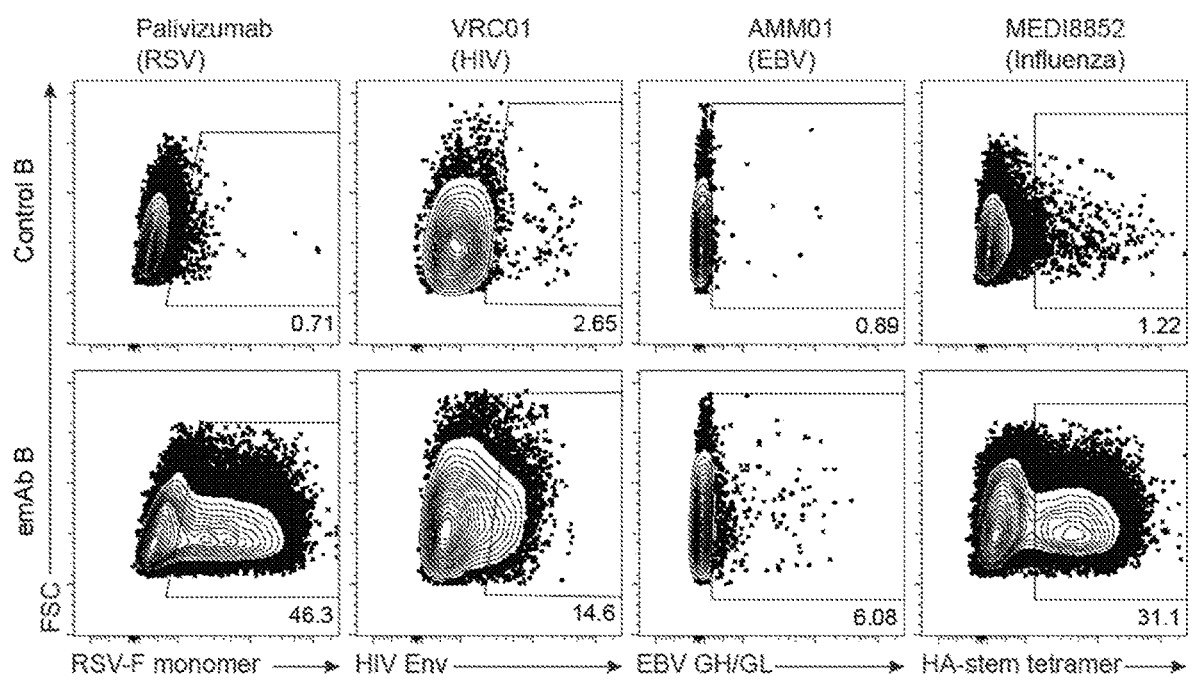
FIG. 28. Single chain emAb is a flexible platform for expression of antiviral antibodies. Human B cells were mock electroporated (Control B, top row) or genetically-modified with emAb constructs (bottom row) derived from the variable regions of the indicated broadly neutralizing antibody constructs and human kappa (Palivizumab, VRC01, and MEDI8852) or lambda (AMM01) light chains. Control and emAb engineered cells were stained with a matching antigen derived from the indicated pathogen: RSV-F monomer, or tetramers of HIV-ENV, EBV GH/GL, or HA-stem.

Reverse:            (SEQ ID NO: 275)
AACCTCAGTCACCGTCTCCT targeted VRC01, the EBV targeted AMM01, and the influenza HA-stem targeted MEDI8852. Primary B cells were efficiently reprogrammed with all 4 constructs, which included antibodies with both kappa (Palivizumab, VRC01, Medi8852) and lambda (AMM01) light chains (FIG. 28). These data demonstrate the flexible and broadly applicable nature of the emAb platform.

Figure 29A:
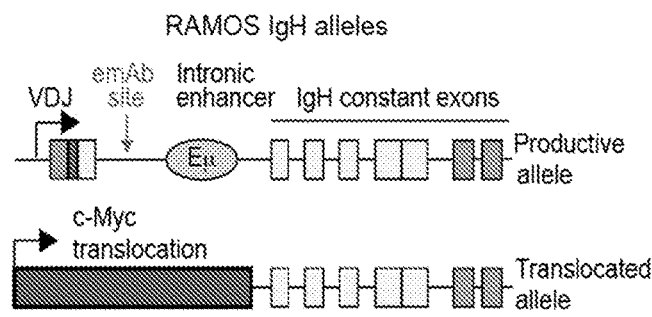
FIGS. 29A-29D. emAb insertion on the productive IgH allele can block endogenous IgH production.
Figure 29B:
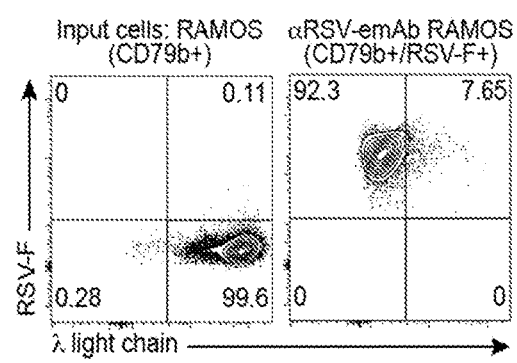
Figure 29C:
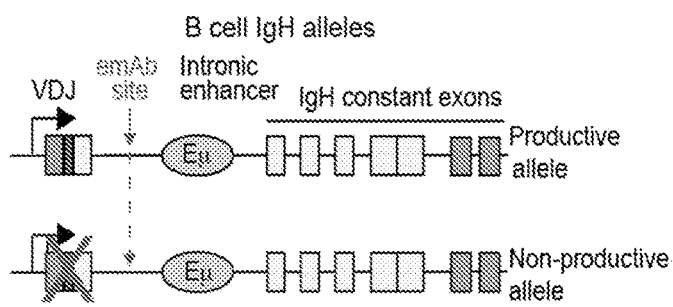
Figure 29D:
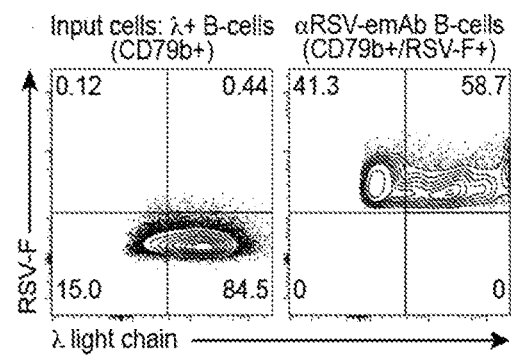

Blocking production of the endogenous Ig heavy chain is important to maximize the production of emAb and minimize the potential for production of unknown endogenous antibodies from genetically-modified cells. The RAMOS B cell line endogenously expresses an IgH paired with a lambda light chain. Engineering these cells with an αRSV-emAb linked to a kappa light chain enables use of surface lambda light chain expression as an effective measure of IgH expression. In addition, RAMOS cells have undergone a c-myc translocation, disrupting one IgH allele, such that any emAb insertion will by necessity be in the productive allele (FIG. 29A). Input RAMOS cells express high levels of lambda light chain on the surface, whereas cells expressing the αRSV-emAb have almost completely lost lambda expression (FIG. 29B). These data indicate that emAb insertion on the productive allele can effectively block expression of an endogenous IgH. In almost all primary B cells, one IgH allele possesses a productive VDJ rearrangement, whereas the other allele did not undergo VDJ recombination, or was unproductively recombined. However, both these alleles possess potential sites for emAb insertion (FIG. 29C). To test the effects of emAb insertion, purified lambda light chain expressing primary B cells were genetically-modified with αRSV-emAb. Input cells continued to express the endogenous antibody paired with lambda light chain on the surface. In contrast, half of αRSV-emAb engineered B cells have lost lambda light chain expression (FIG. 29D). The differential patterns of expression seen in RAMOS and primary B cells suggest that emAb insertion can block endogenous IgH expression if inserted into the productive allele. Differential expression of surface light chain is an avenue for purification of cells which exclusively express an emAb construct. Alternatively, the potential for insertion at either allele offers the possibility of producing dual-antibody expressing emAb cells by either selection of initial pool of anti-viral memory B cells for engineering, or by insertion of a different cassette on each allele.

Figure 30A:
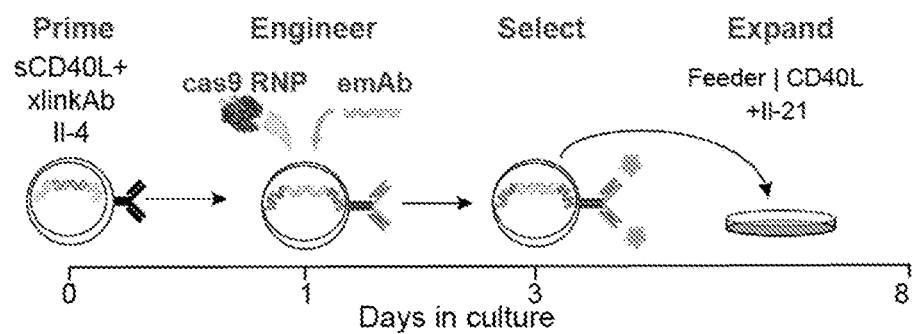
FIG. 30A-30E. Engineering of primary mouse B cells with an αRSV-emAb cassette (FIG. 30A) Schematic representation of the mouse B cell engineering process. Day 0: B cells are isolated from Spleen and peripheral lymph nodes (PLN) via negative selection and primed with CD40L-HA, anti-HA mAb, and IL4. Day 1: cells are electroporated with cas9/sgRNA RNP together with dsDNA (dsDNA condition), or cas9/sgRNA RNP alone followed by treatment with AAV containing the emAb HR template 1 hr post electroporation (AAV condition). Cells were then maintained in culture as described for day 0. Day 3: cells are selected on antigen binding or tag expression. Day 4-8L: selected cells are expanded on irradiated feeder cells expressing CD40L, supplemented with IL-21.
Figure 30B:
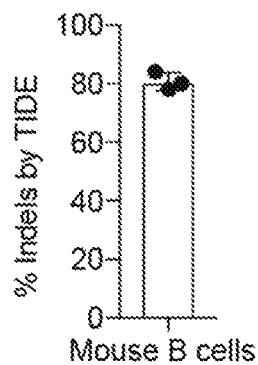
Figure 30C:
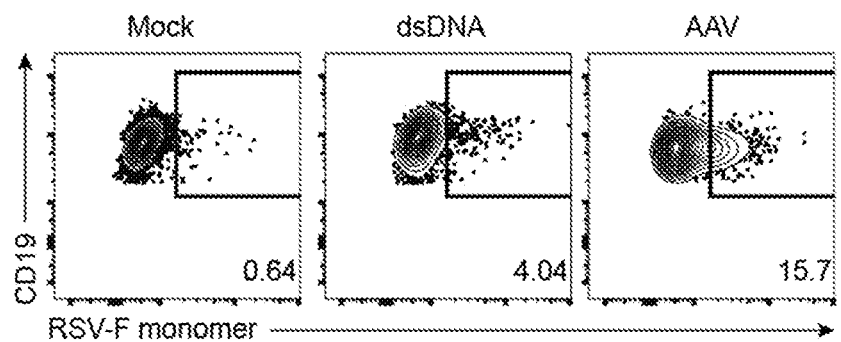
Figure 30D:
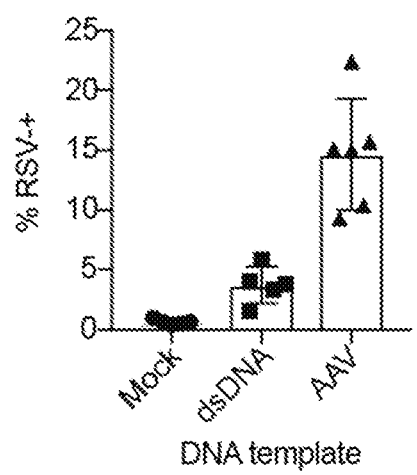
Figure 30E:
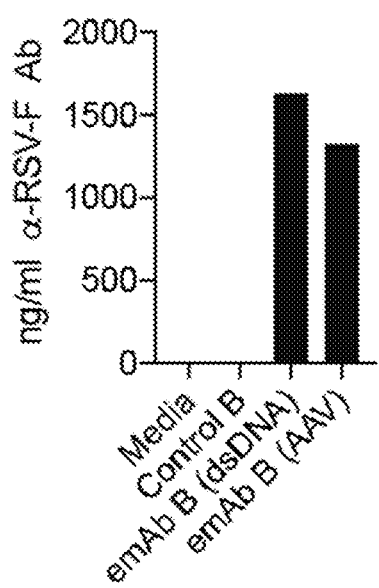

Having demonstrated the ability to engineer B cells, the protective capability of the cells in murine models of viral infection was next confirmed. Murine emAb B cells were produced using a process of priming, electroporation+emAb cassette delivery, and expansion similar to that used in human primary B cells (FIG. 30A). Electroporation in combination with pre-complexed guide RNA and Cas9, cutting was highly efficient, resulting in faulty repairs of this region in 80% of the DNA analyzed (FIG. 30B). Delivery of a murine αRSV-emAb cassette via AAV reproducibly modified mouse B cells, with 8-24% of murine B cells binding RSV-F (FIG. 30C, 30D). Insertion in 1-7% of cells was also achieved using double stranded DNA (dsDNA) containing short homology regions instead of AAV (FIG. 30C, 30D (see also Example 1), offering a potential for emAb engineering of B cells using purely synthetic components. High titers of secreted engineered antibodies could also be detected in culture supernatants produced by both methodologies (FIG. 30E).

Figure 31A:
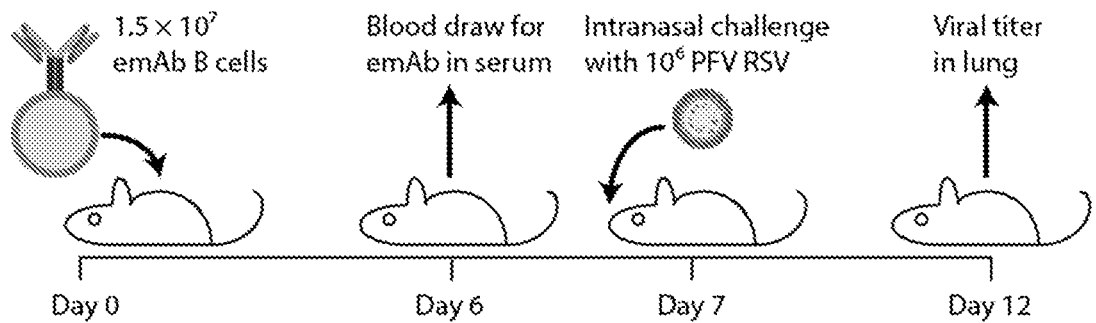
FIGS. 31A-31D. Protection from viral infection by engineered αRSV-emAb B cells.
Figure 31B:
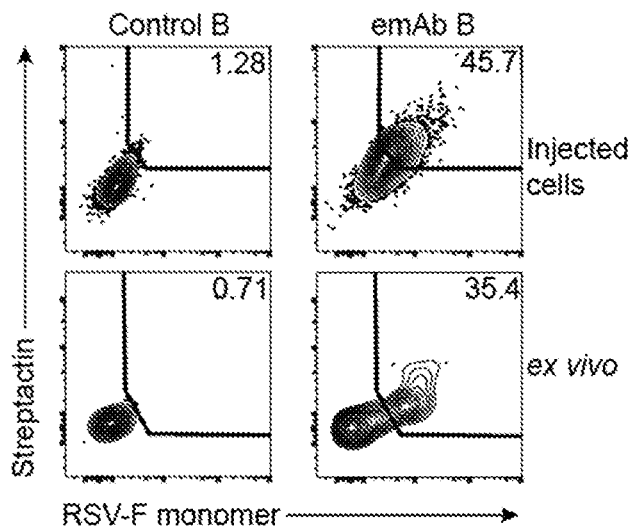
Figure 31C:
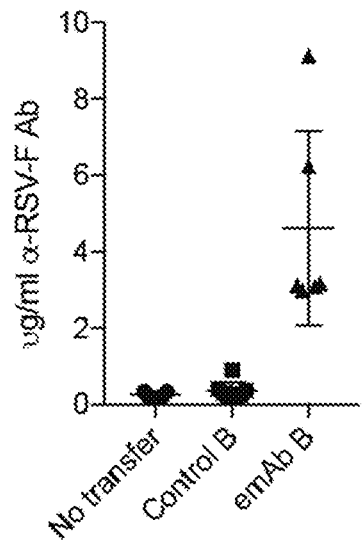
Figure 31D:
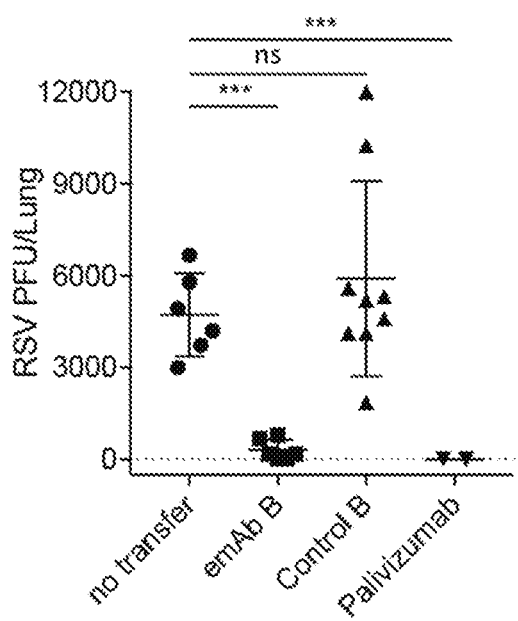
Figure 32A:
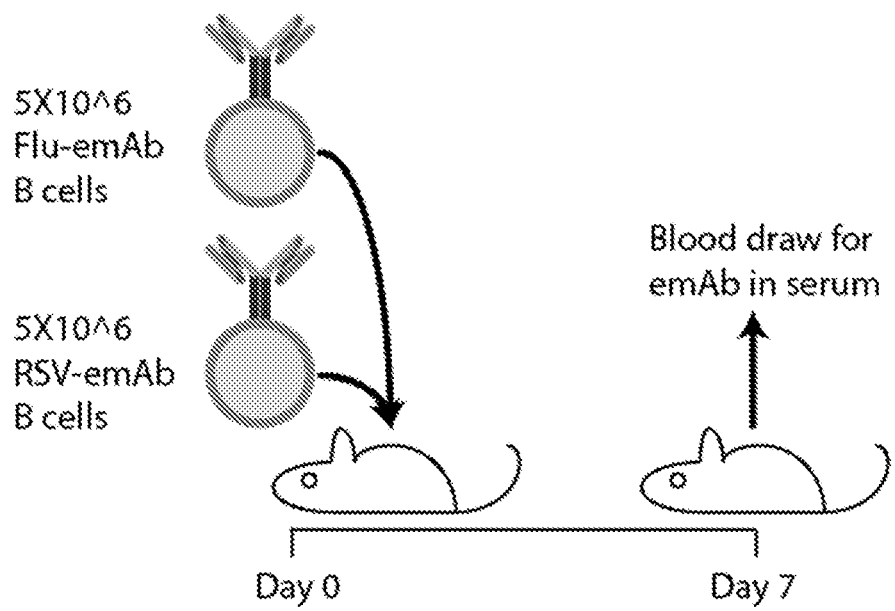
FIGS. 32A, 32B. Multiplex transfer of human antibody secreting cells to NSG mice (FIG. 32A) Schematic of transfer of human emAb B cells into NSG mice. Day 0: $5\times10^6$ anti-Flu emAb B cells and $5\times10^6$ anti-RSV emAb B produced as described in FIG. 27 were transferred via I.P. injection. Day 7: Blood draw for antibody production in serum.
Figure 32B:
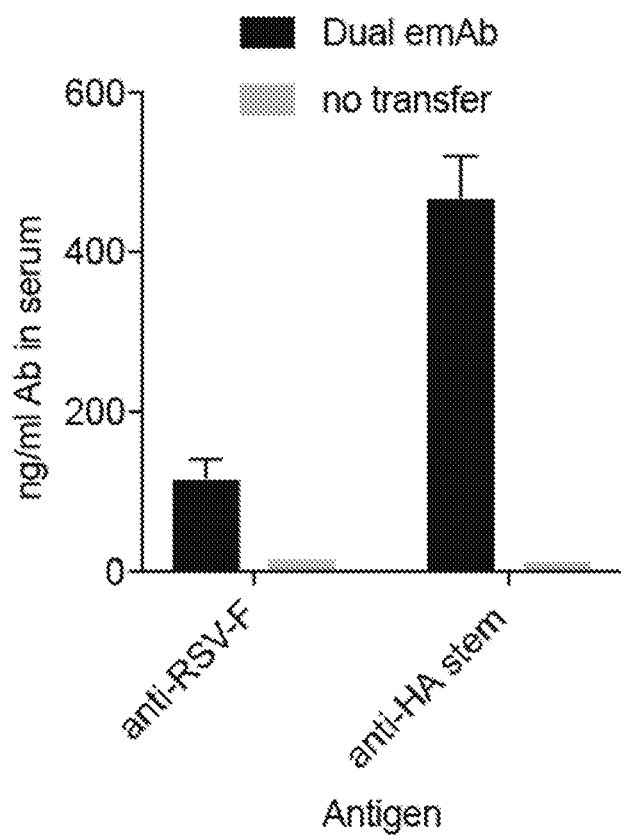
Figure 33A:
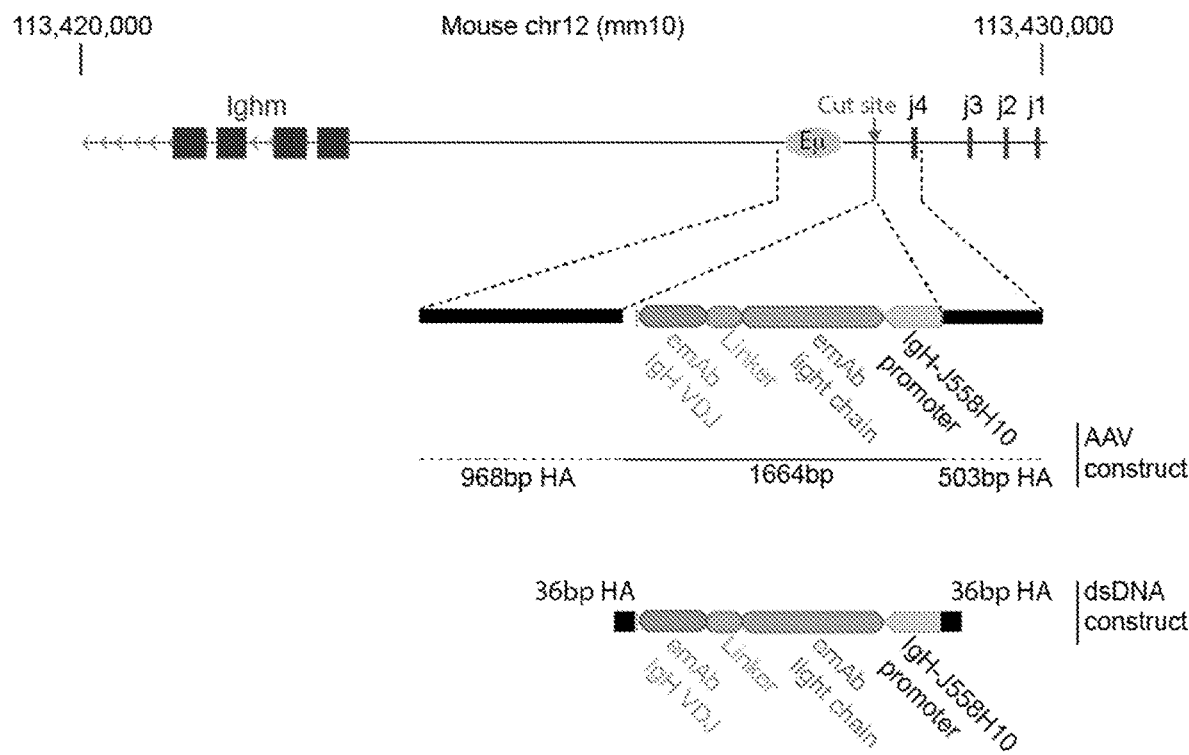
FIGS. 33A, 33B. Templates for long insertion of emAb cassettes into the mouse (FIG. 33A) and human (FIG. 33B) IgH locus. Indicated on the top row for each genome are the position of elements in germline IgH loci, including the final J regions, the Eμ intronic enhancer element, and the beginning of the μ constant domain. The position of the cas9/sgRNA target site is indicated (Cut site). Below is shown the positions of the targeting arms targeting homology arms included in the mouse AAV and dsDNA construct (FIG. 33A) as well as the human AAV construct (FIG. 33B). Also shown is the emAb cassette as inserted in the genome.
Figure 33B:
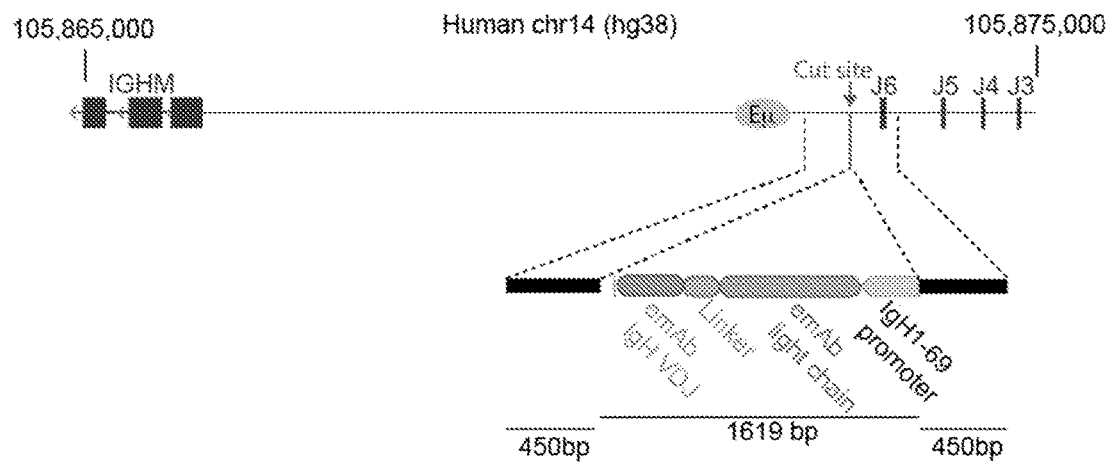

To test the potential for antiviral protection $1.5 \times 10^7$ genetically-modified mouse B cells were infused into wild-type Balbc/byJ mice, followed by a blood draw and RSV challenge (FIG. 31A). RSV-specific antibodies and genetically-modified B cells were present in the blood 6 days following the transfer of genetically-modified B cells (FIG. 31B, 31C). Importantly, mice receiving genetically-modified B cells were almost completely protected against RSV infection (FIG. 31D). This protection approached that afforded by the injection of Palivizumab 2 days before infection (FIG. 31D). Transfer of mixed human emAb cells targeting RSV and influenza to NOD-scid IL2Rgammanull (NSG) mice lead to serum titers of antibodies targeting both viruses (FIGS. 32A, 32B). These results show that genetically-modified B cells disclosed herein protect against viral infection.

Methods. Design of single-chain antibody templates sequences. Human: Antibody constructs included the IgVH1-69 heavy chain promoter region (SEQ ID NO: 111), full-length antibody light chain (e.g., SEQ ID NOs: 113, 145, 154, and 161 (nucleotide) and SEQ ID NOs: 119, 148, 157, and 165 (amino acid)), a 57 amino acid glycine-serine linker containing 3 tandem copies of the StreptagII motif (SEQ ID NO: 116 (nucleotide) and SEQ ID NO: 122 (amino acid)), variable region of the heavy chain (e.g., SEQ ID NOs: 117, 147, 156, and 164 (nucleotide) and SEQ ID NOs: 123, 150, 159, and 168 (amino acid)), and a splice junction with 60 base pairs of flanking sequence derived from matching IgHJ variable regions (e.g., SEQ ID NOs: 124 and 151).

Mouse: Antibody constructs included the J5558H10 heavy chain promoter (SEQ ID NO: 128, V. A Love et. al Molecular Immunology 2000), full length codon optimized antibody light chain (e.g., SEQ ID NO: 130 (nucleotide) and SEQ ID NO: 135 (amino acid)), a 57 amino acid glycine-serine linker containing three tandem copies of the streptag II sequence (SEQ ID NO: 116 (nucleotide) and SEQ ID NO: 122 (amino acid)), codon optimized variable region of the heavy antibody chain (e.g., SEQ ID NO: 133 (nucleotide) and SEQ ID NO: 138 (amino acid)), and a splice junction with 60 base pairs of flanking sequence derived from the mouse IGHJ3 gene segment (e.g., SEQ ID NO: 139).

Full sequences of exemplary antibody constructs are available in FIG. 25B-25I.

Production of recombinant AAV vectors. AAV vectors were generated by triple transfection of AAV vector, serotype 6 capsid, and adenoviral helper plasmids (pHelper) into HEK293T cells using PEI. At 24 hours post-transfection, media was changed to serum-free DMEM, and after 72 hours cells were collected, lysed by freeze-thaw, benzonase treated, purified over iodixanol gradient followed by concentration into PBS using an Amicon Ultra-15 column (EMD Millipore) (Choi, et al., (2007). Curr Protoc Mol Biol Chapter 16: Unit 16 25). Titers of the viral stock were determined by qPCR of AAV genomes, and ranged from $5 \times 10^{10}$ to $1 \times 10^{12}$ per microliter (Aurnhammer, et al., (2012). Hum Gene Ther Methods 23(1): 18-28).

Production of Murine dsDNA emAb Templates.

αRSV-emAb templates were amplified and short homology regions added by modified DNA oligos as follows:

```
Forward primer:
(contains a 5' phosphate,
mouse genomic homology
region in bold)                          (SEQ ID NO: 278)
/5Phos/ACCACCTCTGTGACAGCATTTATACAGTATCCGATGGACAAGT
GAGTGTCTCAGGTTAGGATTCT Reverse primer (contains
phosphorothioate stabilized
DNA bonds (*) mouse genomic
homology region in bold)                 (SEQ ID NO: 279)
T*A*A*AGAAAGTGCCCCACTCCACTCTTTGTCCCTATGCTTGACCACAA
TGAATACTCCCACC
``` dsDNA template was amplified by PCR, purified and concentrated using minElute PCR cleanup columns (Qiagen).

Cell lines. 3T3-msCD40L were obtained from Dr. Mark Connors at the NIH AIDS Reagent Program, Division of AIDS, NIAID, NIH: Cat #12535. 3T3 cells were cultured in DMEM medium with 10% fetal calf serum (Gibco), 100 U/ml penicillin plus 100 µg/mL streptomycin (Gibco), and G418 (350 µg/mL).

RAMOS cells were obtained from ATCC (CRL-1596™). RAMOS cells were cultured in RPMI medium with 10% Fetal calf serum (Gibco) and 100 U/ml penicillin plus 100 µg/mL streptomycin (Gibco).

Mouse B cell culture and electroporation. Base B cell medium included RPMI medium with 10% Fetal calf serum (Gemini Biosciences), 10 mM HEPES (Gibco), 1 mM sodium pyruvate, (Gibco), 55 µM Beta-mercaptoethanol (Sigma), and 100 U/ml penicillin plus 100 µg/mL streptomycin (Gibco) except in antibiotic free steps as noted.

B cells were isolated from spleen and lymph nodes via negative selection with magnetic beads (Miltenyi) and cultured for 24 hours at $2 \times 10^6$/ml in B cell medium supplemented with 100 ng/ml recombinant carrier free HA-tagged mouse CD40L (R&D systems), 100 ng/ml anti-HA antibody (clone 543851, R&D systems), and 4 ng/ml mouse IL-4 (R&D systems). Next, the B cells were electroporated using the Neon transfection system as follows. Cas9 protein (Invitrogen) and synthetic sgRNA (Synthego) were mixed at a ratio of 1 µg Cas9 to 300 ng sgRNA and incubated at room temperature for at least 10 minutes. B cells were washed with PBS and suspended in Neon Buffer T at a final density of $2.5 \times 10^7$ cells/ml with 12 µg of Cas9 RNP/$10^6$ cells. For dsDNA conditions, 7.5 µg dsDNA template/$10^6$ cells was also included in the electroporation. Cells were electroporated (1675 V, 10 milliseconds, 3 pulses) and immediately dispensed into pre-warmed antibiotic free medium. For AAV conditions, concentrated AAV in PBS was added up to 15% of final culture volume. After electroporation, B cells were expanded for an additional 48 hours with B cell medium supplemented with 100 ng/ml recombinant carrier free HA-tagged mouse CD40L (R&D systems), 100 ng/ml anti-HA antibody (clone 543851, R&D systems), 4 ng/ml mouse IL-4 (R&D systems), and 20 ng/ml mouse IL-21. (Biolegend). For secondary expansion, B cells were co-cultured with irradiated (80 gy) NIH 3T3-CD40L feeder cells in the presence of 20 ng/ml mouse IL-21. (Biolegend).

Human B cell culture and electroporation. Basal media for human B cell culture (hBCM) was in IMDM media, with 10% FBS (Gemini Biosciences), 100 U/ml penicillin and 100 µg/mL streptomycin (Gibco), except in antibiotic free steps as noted.

Human PBMCs were obtained through the Fred Hutchinson Cancer Research Center. Cells were thawed, and isolated using negative selection using the Militenyi B Cell Isolation Kit II (Human), according to the manufacturer's protocol. Isolated cells were resuspended at $0.5-1.0*10^6$ cells/mL in hBCM supplemented with 100 ng/mL MEGACD40L (Enzo Life Sciences), 50 ng/mL recombinant IL-2 (Biolegend), 50 ng/mL IL-10 (Shenendoah Biotech), 10 ng/mL IL-15 (Shenendoah Biotech), 1 µg/mL CpG ODN 2006 (IDT).

After 48 hours of stimulation, cells were electroporated using the Neon Transfection System. Cas9 protein (Invitrogen) and H7 sgRNA (Synthego) were precomplexed at a 2:1 ratio in Buffer T for 20 minutes at room temperature. Cells were washed with PBS (Gibco) and resuspended in Buffer T at a final concentration of $2.5*10^7$ cells/ml in Buffer T containing pre-complexed Cas9 RNP. The Cell-RNP mixture was loaded into a 10 uL Neon Transfection Tip, and electroporated according to the manufacturer's protocol with the settings of 1750V, 20 ms, and 1 pulse. Immediately after electroporation, cells were plated into stimulation media as described above, without antibiotics. After 30 minutes, AAV was added to a final concentration of 10-15% culture volume and mixed thoroughly. After 2-4 hours, cells were transferred to a larger culture dish to allow for further expansion.

Two days after electroporation, cells were stained with fluorochrome labeled antigen or streptactin and genetically-modified cells were selected. For secondary expansion, B cells were co-cultured with irradiated (80 gy) NIH 3T3-CD40L feeder cells in hBCM containing 5 µg/mL Human recombinant Insulin (Sigma), 50 µg/mL Transferrin (Sigma), 50 ng/mL recombinant IL-2 (Biolegend), 20 ng/mL IL-21 (Biolegend), and 10 ng/mL IL-15 (Shenandoah Biotech).

In order to promote differentiation to plasma cells, cells were transferred from expansion conditions into fresh feeder-free culture conditions containing hBCM supplemented with 5 µg/mL Human recombinant Insulin (Sigma), 50 µg/mL Transferrin (Sigma), 500 U/mL Universal Type I IFN Protein (R&D Systems), 50 ng/mL IL-6 (Shenendoah Biotech), 10 ng/mL IL-15 (Shenendoah Biotech).

Assessment of sGRNA activity by TIDE. Total genomic DNA was isolated from mock and cas9/sgRNA treated cells at 3-5 days post electroporation. The 500-600 base pair region flanking the sgRNA target site was amplified by PCR using the following oligos:

```
Mouse:
For-                        (SEQ ID NO: 274)
ward:
GGCTCCACCAGACCTCTCTA
Reverse:                    (SEQ ID NO: 275)
AACCTCAGTCACCGTCTCCT
Human:
For-                        (SEQ ID NO: 276)
ward:
ACAGTAAGCATGCCTCCTAAG
Reverse:                    (SEQ ID NO: 277)
GCCACTCTAGGGCCTTTGTT
```

Purified PCR product was Sanger sequenced, and the frequency of indels in Cas9/sgRNA electroporated cells relative to mock electroporated cells was determined using the ICE algorithm (Hsiau, et al., (2018). "Inference of CRISPR Edits from Sanger Trace Data." bioRxiv).

Protein antigens. Pre-fusion RSV-F protein, EBV gh/gl complex, and modified HIV env antigen (426c TM4 d1-3) were produced as described (McLellan, et al., (2013). Science 342(6158): 592-598; McGuire, et al., (2016). Nat Commun 7: 10618; Snijder, et al., (2018). Immunity 48(4): 799-811 e799). Stabilized influenza HA-stem was produced from VRC clone 3925, derived from strain H1 1999 NC as described (Yassine, et al., (2015). Nat Med 21(9): 1065-1070). Monomeric prefusion RSV-F protein was labeled with Alexa-488 (Thermo Fisher). All other proteins were conjugated to biotin using a molar ratio of biotin:protein between 0.8 to 2, followed by tetramerization with streptavidin-PE or -APC (prozyme)

Flow Cytometry. Flow cytometric analysis was done on an FACSymphony machine (BD bioscience), cells were sorted on Aria II (BD bioscience), and data analyzed using FlowJo software (Tree Star).

EmAb therapeutic studies in mice. Animal studies were approved and conducted in accordance with the Fred Hutchinson Cancer Center Institutional Animal Care and Use Committee.

For RSV challenge, EmAb or control B cells were administered as a single intraperitoneal (IP) dose of $1.5 \times 10^7$ cells.

For passive transfer of palivizumab, mice received a single dose of 15 mg/kg i.p. GFP-expressing RSV (here-in referred to as RSV for simplicity) was generously provided (Munir, et al., (2008). J Virol 82(17): 8780-8796). Age matched BALB/cByJ mice (Jackson Labs) were inoculated intranasally with $10^6$ pfu of sucrose purified RSV in 40 μL PBS. Lungs were harvested on day 5 post-infection and the titer was determined as previously described by plaque assay (Murphy, et al., (1990). Vaccine 8(5): 497-502). In brief, lungs were homogenized in 2 mls media in a GentleMACS dissociator, clarified by centrifugation at 400×g for 10 minutes, then flash frozen and stored at −80° C. The supernatant was diluted 1:10 and 1:20 in DMEM media in duplicate. 100 μL of each dilution was added to confluent Vero cells in 24 well plates for 2 hours at 37° C. An overlay of 0.8% methylcellulose was then added, and plates incubated for 5 days prior to imaging on a Typhoon imager with filter settings for GFP. The titer in pfu/lung was calculated by counting the number of plaques in the highest positive dilution and correcting for the dilution factor.

For engraftment of human cells, human emAb B cells were administered as a single IP dose of $5\times10^6$ cells/emAb specificity ($1\times10^7$ total) to NOD-scid IL2Rgamma$^{null}$ (NSG) mice (produced by FHCRC breeding facility). 7 days post transfer, blood was drawn, and human emAb titers to RSV-F and HA-stem in serum determined by ELISA.

Statistical Analysis. Statistical analysis were performed using GraphPad Prism 7. Pairwise comparisons were performed using unpaired t-test with Welch's correction.

Nucleic acid sequences described herein are shown using standard letter abbreviations for nucleotide bases, as defined in 37 C.F.R. § 1.822. In some instances, only one strand of each nucleic acid sequence is shown, but the complementary strand is understood as included in embodiments where it would be appropriate. By way of example, sequences complementary to target sites including SEQ ID NOs: 5-84 provide gRNA targeting sequences to target these sites.

Any nucleic acid that encodes a selected antibody construct as described herein may be utilized. Variants of nucleic acid sequences disclosed herein include various sequence polymorphisms, mutations, and alterations wherein the differences in the sequence do not substantially affect the function of the encoded protein. The term nucleic acid or "gene" may include not only coding sequences but also regulatory regions such as promoters, enhancers, and termination regions. The term further can include all introns and other DNA sequences spliced from the mRNA transcript, along with variants resulting from alternative splice sites. Encoding nucleic acid can be DNA or RNA that directs the expression of the one or more selected antibody constructs. These nucleic acid sequences may be a DNA strand sequence that is transcribed into RNA or an RNA sequence that is translated into protein. The nucleic acid sequences include both the full-length nucleic acid sequences as well as non-full-length sequences derived from the full-length protein. The sequences can also include degenerate codons of the native sequence or sequences that may be introduced to provide codon preference in a specific cell type. Nucleic acid sequences encoding selected antibody constructs can be readily prepared from the relevant amino acid sequence of a selected antibody construct.

"Variants" of protein sequences include those having one or more amino acid additions, deletions, stop positions, or substitutions, as compared to a protein sequence disclosed elsewhere herein.

An amino acid substitution can be a conservative or a non-conservative substitution. Variants of protein sequence disclosed herein can include those having one or more conservative amino acid substitutions. A "conservative substitution" or "conservative amino acid substitution" involves a substitution found in one of the following conservative substitutions groups: Group 1: A, G, S, T; Group 2: D, E; Group 3: N, Q; Group 4: R, K, H; Group 5: I, L, M, V; and Group 6: F, Y, W.

Additionally, amino acids can be grouped into conservative substitution groups by similar function, chemical structure, or composition (e.g., acidic, basic, aliphatic, aromatic, or sulfur-containing). For example, an aliphatic grouping may include, for purposes of substitution, G, A, V, L, and I. Other groups including amino acids that are considered conservative substitutions for one another include: sulfur-containing: M and C; acidic: D, E, N, and Q; small aliphatic, nonpolar or slightly polar residues: A, S, T, P, and G; polar, negatively charged residues and their amides: D, N, E, and Q; polar, positively charged residues: H, R, and K; large aliphatic, nonpolar residues: M, L, I, V, and C; and large aromatic residues: F, Y, and W.

Non-conservative substitutions include those that significantly affect: the structure of the peptide backbone in the area of the alteration (e.g., the alpha-helical or beta-sheet structure); the charge or hydrophobicity of the molecule at the target site; or the bulk of the side chain. Non-conservative substitutions which in general are expected to produce the greatest changes in the protein's properties are those in which (i) a hydrophilic residue (e.g. S or T) can be substituted for (or by) a hydrophobic residue (e.g. L, I, F, V, or A); (ii) a C or P can be substituted for (or by) any other residue; (iii) a residue having an electropositive side chain (e.g. K, R, or H) can be substituted for (or by) an electronegative residue (e.g. Q or D); or (iv) a residue having a bulky side chain (e.g. F), can be substituted for (or by) one not having a bulky side chain, (e.g. G). Additional information is found in Creighton (1984) Proteins, W.H. Freeman and Company.

Variants of nucleic acid and protein sequences disclosed herein also include sequences with at least 70% sequence identity, at least 80% sequence identity, at least 85% sequence identity, at least 90% sequence identity, at least 95% sequence identity, at least 96% sequence identity, at least 97% sequence identity, at least 98% sequence identity, or at least 99% sequence identity to a reference sequence disclosed herein.

"Percent (%) sequence identity" with respect to the sequences identified herein is defined as the percentage of nucleic acid or amino acid residues in a candidate sequence that are identical with the nucleic acid or amino acid residues in a reference sequence after aligning the sequences and introducing gaps, if necessary, to achieve the maximum percent sequence identity. Alignment for purposes of determining percent nucleic acid or amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For example, % sequence identity values generated using the WU-BLAST-2 computer program (Altschul et al., *Methods in Enzymology,* 266:460-480 (1996)) uses several search parameters, most of which are set to the default values. Those that are not set to default values (i.e., the adjustable parameters) are set with the following values: overlap span=1, overlap fraction=0.125, word threshold (T)=11 and scoring matrix BLOSUM62.

Variants will typically exhibit the same qualitative biological activity and elicit a substantially similar biological response as a reference nucleic acid or peptide sequence, although variants can be selected to modify the characteristics of a reference nucleic acid or peptide as needed. Screening of variants can be performed using experimental protocols described herein.

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. A material effect would cause a statistically significant reduction in B cell expression of a selected antibody.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; 19% of the stated value; 18% of the stated value; 17% of the stated value; 16% of the stated value; 15% of the stated value; 14% of the stated value; ±13% of the stated value; ±12% of the stated value; 11% of the stated value; 10% of the stated value; ±9% of the stated value; 8% of the stated value; 7% of the stated value; 6% of the stated value; 5% of the stated value; 4% of the stated value; 3% of the stated value; 2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

SEQUENCE LISTING

<160> NUMBER OF SEQ ID NOS: 366

<210> SEQ ID NO 1
<211> LENGTH: 722
<212> TYPE: DNA
<213> ORGANISM: Homo sapiens

<400> SEQUENCE: 1

```
ctacatggac gtctggggca aagggaccac ggtcaccgtc tcctcaggta agaatggcca      60
ctctagggcc tttgttttct gctactgcct gtggggtttc ctgagcattg caggttggtc     120 ctcgggcat gttccgaggg gacctgggcg gactggccag gaggggatgg gcactggggt      180
gccttgagga tctgggagcc tctgtggatt ttccgatgcc tttggaaaat gggactcagg     240
ttgggtgcgt ctgatggagt aactgagcct ggggcttgg ggagccacat ttggacgaga      300
tgcctgaaca aaccaggggt cttagtgatg gctgaggaat gtgtctcagg agcggtgtct     360
gtaggactgc aagatcgctg cacagcagcg aatcgtgaaa tattttcttt agaattatga     420
ggtgcgctgt gtgtcaacct gcatcttaaa ttctttattg gctggaaaga aactgtcgg     480 agtgggtgaa tccagccagg agggacgcgt agccccggtc ttgatgagag cagggttggg     540
ggcaggggta gcccagaaac ggtggctgcc gtcctgacag gggcttaggg aggctccagg     600
acctcagtgc cttgaagctg gtttccatga gaaaaggatt gtttatctta ggaggcatgc     660
ttactgttaa aagacaggat atgtttgaag tggcttctga gaaaaatggt taagaaaatt     720
at                                                                    722
```

<210> SEQ ID NO 2
<211> LENGTH: 1308
<212> TYPE: DNA
<213> ORGANISM: Homo sapiens

<400> SEQUENCE: 2

```
ctcactttag gataagttttt aggtaaaatg tgcatcatta tcctgaatta tttcagttaa     60
gcatgttagt tggtggcata agagaaaact caatcagata gtgctgaaga caggactgtg    120
gagacacctt agaaggacag attctgttcc gaatcaccga tgcggcgtca gcaggactgg    180
cctagcggag gctctgggag ggtggctgcc aggcccggcc tgggctttgg gtctccccgg    240
actacccaga gctgggatgc gtggcttctg ctgccgggcc gactggctgc tcaggcccca    300
gcccttgtta atggacttgg aggaatgatt ccatgccaaa gctttgcaag gctcgcagtg    360
accaggcgcc cgacatggta agagacaggc agccgccgct gctgcatttg cttctcttaa    420
aactttgtat ttgacgtctt atttccacta gaaggggaac tggtcttaat tgcttgatga    480
agagcaggag actcatttat gtgagtcttt tgagtgacca ttgtctgggt cactcccatt    540
taactttccc taaagcccat ttgaaggaga ggtcgcacga gctgctccac aacctctgaa    600
tggggatggc atgggtaatg atgcttgaga acataccaag ccccactggc atcgcccttg    660
tctaagtcat tgactgtagg tcatcatcgc acccttgaaa gtagcccatg ccttccaaag    720
cgatttatgg taaatggcag aatttttaagt ggcaaattca gataaaatgc atttcttggt    780
tgtttccaat gatgactgtt atctagaggg aatttaaagg caggggttta ctgcagactc    840
agaagggagg ggatgctccg ggaaggtgga ggctctgagc atctcaatac cctcctcttg    900
gtgcagaaga tatgctgcca cttctagagc aaggggacct gctcatttt atcacagcac     960 aggctcctaa attcttggtc tcattctcaa gatgttttaa tgactttaaa gcagcaaaga   1020
aatattccac ccaggtagtg gagggtggta atgattggta atgctttgga accaaaaccc   1080
```

| | | |
|---|---|---|
| aggtggcgct ggggcaggac tgcagggaac tggggtatca agtagaggga gacaaaagat | 1140 | |
| ggaagccagc ctggctgtgc aggaacccgg caatgagatg gctttagctg agacaagcag | 1200 | |
| gtctggtggg ctgaccattt ctggccatga caactccatc cagctttcag aaatggactc | 1260 | |
| agatgggcaa aactgaccta agctgaccta gactaaacaa ggctgaac | 1308 | |

<210> SEQ ID NO 3
<211> LENGTH: 582
<212> TYPE: DNA
<213> ORGANISM: Mus musculus

<400> SEQUENCE: 3

| | |
|---|---|
| ggactactgg ggtcaaggaa cctcagtcac cgtctcctca ggtaagaatg gcctctccag | 60 |
| gtctttattt ttaacctttg ttatggagtt ttctgagcat tgcagactaa tcttggatat | 120 |
| ttgtccctga gggagccggc tgagagaagt tgggaaataa actgtctagg gatctcagag | 180 |
| cctttaggac agattatctc cacatctttg aaaaactaag aatctgtgtg atggtgttgg | 240 |
| tggagtccct ggatgatggg atagggactt ggaggctca tttgaagaag atgctaaaac | 300 |
| aatcctatgg ctggagggat agttgggggct gtagttggag attttcagtt tttagaataa | 360 |
| aagtattagt tgtggaatat acttcaggac cacctctgtg acagcattta tacagtatcc | 420 |
| gatgcatagg gacaaagagt ggagtggggc acttctttta gatttgtgag gaatgttccg | 480 |
| cactagattg tttaaaactt catttgttgg aaggagagct gtcttagtga ttgagtcaag | 540 |
| ggagaaaggc atctagcctc ggtctcaaaa gggtagttgc tg | 582 |

<210> SEQ ID NO 4
<211> LENGTH: 1528
<212> TYPE: DNA
<213> ORGANISM: Mus musculus

<400> SEQUENCE: 4

| | |
|---|---|
| ttatttcagt tgaacatgct ggttggtggt tgagaggaca ctcagtcagt cagtgacgtg | 60 |
| aagggcttct aagccagtcc acatgctctg tgtgaactcc ctctggccct gcttattgtt | 120 |
| gaatgggcca aaggtctgag accaggctgc tgctgggtag gcctggactt tgggtctccc | 180 |
| acccagacct gggaatgtat ggttgtggct tctgccaccc atccacctgg ctgctcatgg | 240 |
| accagccagc ctcggtggct ttgaaggaac aattccacac aaagactctg gacctctccg | 300 |
| aaaccaggca ccgcaaatgg taagccagag gcagccacag ctgtggctgc tgctcttaaa | 360 |
| gcttgtaaac tgtttctgct taagagggac tgagtcttca gtcattgctt tagggggaga | 420 |
| aagagacatt tgtgtgtctt ttgagtaccg ttgtctgggt cactcacatt taactttcct | 480 |
| tgaaaaacta gtaaagaaa aatgttgcct gttaaccaat aatcatagag ctcatggtac | 540 |
| tttgaggaaa tcttagaaag cgtgtataca attgtctgga attatttcag ttaagtgtat | 600 |
| tagttgaggt actgatgctg tctctacttc agttatacat gtgggtttga attttgaatc | 660 |
| tattctggct cttcttaagc agaaaattta gataaaatgg atacctcagt ggttttttaat | 720 |
| ggtgggttta atatagaagg aatttaaatt ggaagctaat ttagaatcag taaggaggga | 780 |
| cccaggctaa gaaggcaatc ctgggattct ggaagaaaag atgttttttag ttttttataga | 840 |
| aaacactact acattcttga tctacaactc aatgtggttt aatgaatttg aagttgccag | 900 |
| taaatgtact tcctggttgt taagaatgg tatcaaagga cagtgcttag atccgaggtg | 960 |
| agtgtgagag gacaggggct ggggtatgga tacgcagaag gaaggccaca gctgtacaga | 1020 |

```
attgagaaag aatagagacc tgcagttgag gccagcaggt cggctggact aactctccag    1080
ccacagtaat gacccagaca gagaaagcca gactcataaa gcttgctgag caaaattaag    1140
ggaacaaggt tgagagccct agtaagcgag gctctaaaaa gcacagctga gctgagatgg    1200
gtgggcttct ctgagtgctt ctaaaatgcg ctaaactgag gtgattactc tgaggtaagc    1260
aaagctgggc ttgagccaaa atgaagtaga ctgtaatgaa ctggaatgag ctgggccgct    1320
aagctaaact aggctggctt aaccgagatg agccaaactg gaatgaactt cattaatcta    1380
ggttgaatag agctaaactc tactgcctac actggactgt tctgagctga gatgagctgg    1440
ggtgagctca gctatgctac gctgtgttgg ggtgagctga tctgaaatga gatactctgg    1500
agtagctgag atggggtgag atggggtg                                       1528

<210> SEQ ID NO 5
<211> LENGTH: 23
<212> TYPE: DNA
<213> ORGANISM: Homo sapiens

<400> SEQUENCE: 5
ggtcctcggg gcatgttccg agg                                             23

<210> SEQ ID NO 6
<211> LENGTH: 23
<212> TYPE: DNA
<213> ORGANISM: Homo sapiens

<400> SEQUENCE: 6
gggcatgttc cgaggggacc tgg                                             23

<210> SEQ ID NO 7
<211> LENGTH: 23
<212> TYPE: DNA
<213> ORGANISM: Homo sapiens

<400> SEQUENCE: 7
gcattgcagg ttggtcctcg ggg                                             23

<210> SEQ ID NO 8
<211> LENGTH: 23
<212> TYPE: DNA
<213> ORGANISM: Homo sapiens

<400> SEQUENCE: 8
tcctcggggc atgttccgag ggg                                             23

<210> SEQ ID NO 9
<211> LENGTH: 23
<212> TYPE: DNA
<213> ORGANISM: Homo sapiens

<400> SEQUENCE: 9
ggcatgttcc gagggggacct ggg                                            23

<210> SEQ ID NO 10
<211> LENGTH: 23
<212> TYPE: DNA
<213> ORGANISM: Homo sapiens

<400> SEQUENCE: 10
gtctcaggag cggtgtctgt agg                                             23
```

```
<210> SEQ ID NO 11
<211> LENGTH: 23
<212> TYPE: DNA
<213> ORGANISM: Homo sapiens

<400> SEQUENCE: 11
agcattgcag gttggtcctc ggg                                            23

<210> SEQ ID NO 12
<211> LENGTH: 23
<212> TYPE: DNA
<213> ORGANISM: Homo sapiens

<400> SEQUENCE: 12
cctgggcgga ctggccagga ggg                                            23

<210> SEQ ID NO 13
<211> LENGTH: 23
<212> TYPE: DNA
<213> ORGANISM: Homo sapiens

<400> SEQUENCE: 13
actggggtgc cttgaggatc tgg                                            23

<210> SEQ ID NO 14
<211> LENGTH: 23
<212> TYPE: DNA
<213> ORGANISM: Homo sapiens

<400> SEQUENCE: 14
ccccagtgcc catcccctcc tgg                                            23

<210> SEQ ID NO 15
<211> LENGTH: 23
<212> TYPE: DNA
<213> ORGANISM: Homo sapiens

<400> SEQUENCE: 15
ctaagacccc tggtttgttc agg                                            23

<210> SEQ ID NO 16
<211> LENGTH: 23
<212> TYPE: DNA
<213> ORGANISM: Homo sapiens

<400> SEQUENCE: 16
tgtggatttt ccgatgcctt tgg                                            23

<210> SEQ ID NO 17
<211> LENGTH: 23
<212> TYPE: DNA
<213> ORGANISM: Homo sapiens

<400> SEQUENCE: 17
aggaccaacc tgcaatgctc agg                                            23

<210> SEQ ID NO 18
<211> LENGTH: 23
<212> TYPE: DNA
<213> ORGANISM: Homo sapiens

<400> SEQUENCE: 18
ctcaggttgg gtgcgtctga tgg                                            23
```

```
<210> SEQ ID NO 19
<211> LENGTH: 23
<212> TYPE: DNA
<213> ORGANISM: Homo sapiens

<400> SEQUENCE: 19
ccctcctggc cagtccgccc agg                                               23

<210> SEQ ID NO 20
<211> LENGTH: 23
<212> TYPE: DNA
<213> ORGANISM: Homo sapiens

<400> SEQUENCE: 20
ggccaggagg ggatgggcac tgg                                               23

<210> SEQ ID NO 21
<211> LENGTH: 23
<212> TYPE: DNA
<213> ORGANISM: Homo sapiens

<400> SEQUENCE: 21
gagatgcctg aacaaaccag ggg                                               23

<210> SEQ ID NO 22
<211> LENGTH: 23
<212> TYPE: DNA
<213> ORGANISM: Homo sapiens

<400> SEQUENCE: 22 agggg tctta gtgatggctg agg                                              23

<210> SEQ ID NO 23
<211> LENGTH: 23
<212> TYPE: DNA
<213> ORGANISM: Homo sapiens

<400> SEQUENCE: 23
atgggcactg gggtgccttg agg                                               23

<210> SEQ ID NO 24
<211> LENGTH: 23
<212> TYPE: DNA
<213> ORGANISM: Homo sapiens

<400> SEQUENCE: 24
ttccgatgcc tttggaaaat ggg                                               23

<210> SEQ ID NO 25
<211> LENGTH: 23
<212> TYPE: DNA
<213> ORGANISM: Homo sapiens

<400> SEQUENCE: 25
ctgacgccgc atcggtgatt cgg                                               23

<210> SEQ ID NO 26
<211> LENGTH: 23
<212> TYPE: DNA
<213> ORGANISM: Homo sapiens

<400> SEQUENCE: 26
ttagacaagg gcgatgccag tgg                                               23
```

```
<210> SEQ ID NO 27
<211> LENGTH: 23
<212> TYPE: DNA
<213> ORGANISM: Homo sapiens

<400> SEQUENCE: 27
cgtgcgacct ctccttcaaa tgg                                              23

<210> SEQ ID NO 28
<211> LENGTH: 23
<212> TYPE: DNA
<213> ORGANISM: Homo sapiens

<400> SEQUENCE: 28
agcatatctt ctgcaccaag agg                                              23

<210> SEQ ID NO 29
<211> LENGTH: 23
<212> TYPE: DNA
<213> ORGANISM: Homo sapiens

<400> SEQUENCE: 29
atattccacc caggtagtgg agg                                              23

<210> SEQ ID NO 30
<211> LENGTH: 23
<212> TYPE: DNA
<213> ORGANISM: Homo sapiens

<400> SEQUENCE: 30
gtgcgacctc tccttcaaat ggg                                              23

<210> SEQ ID NO 31
<211> LENGTH: 23
<212> TYPE: DNA
<213> ORGANISM: Homo sapiens

<400> SEQUENCE: 31
aggtcccctt gctctagaag tgg                                              23

<210> SEQ ID NO 32
<211> LENGTH: 23
<212> TYPE: DNA
<213> ORGANISM: Homo sapiens

<400> SEQUENCE: 32
ctctagataa cagtcatcat tgg                                              23

<210> SEQ ID NO 33
<211> LENGTH: 23
<212> TYPE: DNA
<213> ORGANISM: Homo sapiens

<400> SEQUENCE: 33
ttgtctaagt cattgactgt agg                                              23

<210> SEQ ID NO 34
<211> LENGTH: 23
<212> TYPE: DNA
<213> ORGANISM: Homo sapiens

<400> SEQUENCE: 34
```
ccaaagcgat ttatggtaaa tgg                                          23

<210> SEQ ID NO 35
<211> LENGTH: 23
<212> TYPE: DNA
<213> ORGANISM: Homo sapiens

<400> SEQUENCE: 35
tcttttgagt gaccattgtc tgg                                          23

<210> SEQ ID NO 36
<211> LENGTH: 23
<212> TYPE: DNA
<213> ORGANISM: Homo sapiens

<400> SEQUENCE: 36
ccatttacca taaatcgctt tgg                                          23

<210> SEQ ID NO 37
<211> LENGTH: 23
<212> TYPE: DNA
<213> ORGANISM: Homo sapiens

<400> SEQUENCE: 37
agggcgatgc cagtggggct tgg                                          23

<210> SEQ ID NO 38
<211> LENGTH: 23
<212> TYPE: DNA
<213> ORGANISM: Homo sapiens

<400> SEQUENCE: 38
agctaaagcc atctcattgc cgg                                          23

<210> SEQ ID NO 39
<211> LENGTH: 23
<212> TYPE: DNA
<213> ORGANISM: Homo sapiens

<400> SEQUENCE: 39
ccacaacctc tgaatgggga tgg                                          23

<210> SEQ ID NO 40
<211> LENGTH: 23
<212> TYPE: DNA
<213> ORGANISM: Homo sapiens

<400> SEQUENCE: 40
ttaattgctt gatgaagagc agg                                          23

<210> SEQ ID NO 41
<211> LENGTH: 23
<212> TYPE: DNA
<213> ORGANISM: Homo sapiens

<400> SEQUENCE: 41
tagacaaggg cgatgccagt ggg                                          23

<210> SEQ ID NO 42
<211> LENGTH: 23
<212> TYPE: DNA
<213> ORGANISM: Homo sapiens

<400> SEQUENCE: 42
aagctgacct agactaaaca agg												23

<210> SEQ ID NO 43
<211> LENGTH: 23
<212> TYPE: DNA
<213> ORGANISM: Homo sapiens

<400> SEQUENCE: 43
gcaggaaccc ggcaatgaga tgg												23

<210> SEQ ID NO 44
<211> LENGTH: 23
<212> TYPE: DNA
<213> ORGANISM: Homo sapiens

<400> SEQUENCE: 44
tctgttccga atcaccgatg cgg												23

<210> SEQ ID NO 45
<211> LENGTH: 23
<212> TYPE: DNA
<213> ORGANISM: Mus musculus

<400> SEQUENCE: 45
caactaccct tttgagaccg agg												23

<210> SEQ ID NO 46
<211> LENGTH: 23
<212> TYPE: DNA
<213> ORGANISM: Mus musculus

<400> SEQUENCE: 46
ttatacagta tccgatgcat agg												23

<210> SEQ ID NO 47
<211> LENGTH: 23
<212> TYPE: DNA
<213> ORGANISM: Mus musculus

<400> SEQUENCE: 47
tatacagtat ccgatgcata ggg												23

<210> SEQ ID NO 48
<211> LENGTH: 23
<212> TYPE: DNA
<213> ORGANISM: Mus musculus

<400> SEQUENCE: 48
catctagcct cggtctcaaa agg												23

<210> SEQ ID NO 49
<211> LENGTH: 23
<212> TYPE: DNA
<213> ORGANISM: Mus musculus

<400> SEQUENCE: 49
cactctttgt ccctatgcat cgg												23

<210> SEQ ID NO 50
<211> LENGTH: 23
<212> TYPE: DNA
<213> ORGANISM: Mus musculus

```
<400> SEQUENCE: 50
atctagcctc ggtctcaaaa ggg                                              23

<210> SEQ ID NO 51
<211> LENGTH: 23
<212> TYPE: DNA
<213> ORGANISM: Mus musculus

<400> SEQUENCE: 51
aagttttaaa caatctagtg cgg                                              23

<210> SEQ ID NO 52
<211> LENGTH: 23
<212> TYPE: DNA
<213> ORGANISM: Mus musculus

<400> SEQUENCE: 52
aagatgctaa acaatccta tgg                                               23

<210> SEQ ID NO 53
<211> LENGTH: 23
<212> TYPE: DNA
<213> ORGANISM: Mus musculus

<400> SEQUENCE: 53
tgctaaaaca atcctatggc tgg                                              23

<210> SEQ ID NO 54
<211> LENGTH: 23
<212> TYPE: DNA
<213> ORGANISM: Mus musculus

<400> SEQUENCE: 54
aagtccctat cccatcatcc agg                                              23

<210> SEQ ID NO 55
<211> LENGTH: 23
<212> TYPE: DNA
<213> ORGANISM: Mus musculus

<400> SEQUENCE: 55
gggagaaagg catctagcct cgg                                              23

<210> SEQ ID NO 56
<211> LENGTH: 23
<212> TYPE: DNA
<213> ORGANISM: Mus musculus

<400> SEQUENCE: 56
tgagcattgc agactaatct tgg                                              23

<210> SEQ ID NO 57
<211> LENGTH: 23
<212> TYPE: DNA
<213> ORGANISM: Mus musculus

<400> SEQUENCE: 57
ttagttgtgg aatatacttc agg                                              23

<210> SEQ ID NO 58
<211> LENGTH: 23
<212> TYPE: DNA
<213> ORGANISM: Mus musculus
```

```
<400> SEQUENCE: 58
tggtggagtc cctggatgat ggg                                             23

<210> SEQ ID NO 59
<211> LENGTH: 23
<212> TYPE: DNA
<213> ORGANISM: Mus musculus

<400> SEQUENCE: 59
gtggagataa tctgtcctaa agg                                             23

<210> SEQ ID NO 60
<211> LENGTH: 23
<212> TYPE: DNA
<213> ORGANISM: Mus musculus

<400> SEQUENCE: 60
agtccctatc ccatcatcca ggg                                             23

<210> SEQ ID NO 61
<211> LENGTH: 23
<212> TYPE: DNA
<213> ORGANISM: Mus musculus

<400> SEQUENCE: 61
atcttggata tttgtccctg agg                                             23

<210> SEQ ID NO 62
<211> LENGTH: 23
<212> TYPE: DNA
<213> ORGANISM: Mus musculus

<400> SEQUENCE: 62
gggatagttg gggctgtagt tgg                                             23

<210> SEQ ID NO 63
<211> LENGTH: 23
<212> TYPE: DNA
<213> ORGANISM: Mus musculus

<400> SEQUENCE: 63
caggtaagaa tggcctctcc agg                                             23

<210> SEQ ID NO 64
<211> LENGTH: 23
<212> TYPE: DNA
<213> ORGANISM: Mus musculus

<400> SEQUENCE: 64
tctctcagcc ggctccctca ggg                                             23

<210> SEQ ID NO 65
<211> LENGTH: 23
<212> TYPE: DNA
<213> ORGANISM: Mus musculus

<400> SEQUENCE: 65
ccgaaaccag gcaccgcaaa tgg                                             23

<210> SEQ ID NO 66
<211> LENGTH: 23
<212> TYPE: DNA
```

```
<213> ORGANISM: Mus musculus

<400> SEQUENCE: 66
caccgcaaat ggtaagccag agg                                             23

<210> SEQ ID NO 67
<211> LENGTH: 23
<212> TYPE: DNA
<213> ORGANISM: Mus musculus

<400> SEQUENCE: 67
ggcttaccat ttgcggtgcc tgg                                             23

<210> SEQ ID NO 68
<211> LENGTH: 23
<212> TYPE: DNA
<213> ORGANISM: Mus musculus

<400> SEQUENCE: 68
tgcggtgcct ggtttcggag agg                                             23

<210> SEQ ID NO 69
<211> LENGTH: 23
<212> TYPE: DNA
<213> ORGANISM: Mus musculus

<400> SEQUENCE: 69
cagctatgct acgctgtgtt ggg                                             23

<210> SEQ ID NO 70
<211> LENGTH: 23
<212> TYPE: DNA
<213> ORGANISM: Mus musculus

<400> SEQUENCE: 70
aaggacagtg cttagatccg agg                                             23

<210> SEQ ID NO 71
<211> LENGTH: 23
<212> TYPE: DNA
<213> ORGANISM: Mus musculus

<400> SEQUENCE: 71
tcagtcagtc agtgacgtga agg                                             23

<210> SEQ ID NO 72
<211> LENGTH: 23
<212> TYPE: DNA
<213> ORGANISM: Mus musculus

<400> SEQUENCE: 72
catgctggtt ggtggttgag agg                                             23

<210> SEQ ID NO 73
<211> LENGTH: 23
<212> TYPE: DNA
<213> ORGANISM: Mus musculus

<400> SEQUENCE: 73
tcttttgagt accgttgtct ggg                                             23

<210> SEQ ID NO 74
<211> LENGTH: 23
```

<212> TYPE: DNA
<213> ORGANISM: Mus musculus

<400> SEQUENCE: 74
tggcccattc aacaataagc agg                                              23

<210> SEQ ID NO 75
<211> LENGTH: 23
<212> TYPE: DNA
<213> ORGANISM: Mus musculus

<400> SEQUENCE: 75
ctgggccgct aagctaaact agg                                              23

<210> SEQ ID NO 76
<211> LENGTH: 23
<212> TYPE: DNA
<213> ORGANISM: Mus musculus

<400> SEQUENCE: 76
gccagcctag tttagcttag cgg                                              23

<210> SEQ ID NO 77
<211> LENGTH: 23
<212> TYPE: DNA
<213> ORGANISM: Mus musculus

<400> SEQUENCE: 77
tgaagtagac tgtaatgaac tgg                                              23

<210> SEQ ID NO 78
<211> LENGTH: 23
<212> TYPE: DNA
<213> ORGANISM: Mus musculus

<400> SEQUENCE: 78
gacctgggaa tgtatggttg tgg                                              23

<210> SEQ ID NO 79
<211> LENGTH: 23
<212> TYPE: DNA
<213> ORGANISM: Mus musculus

<400> SEQUENCE: 79
ggtatggata cgcagaagga agg                                              23

<210> SEQ ID NO 80
<211> LENGTH: 23
<212> TYPE: DNA
<213> ORGANISM: Mus musculus

<400> SEQUENCE: 80
gttgagagcc ctagtaagcg agg                                              23

<210> SEQ ID NO 81
<211> LENGTH: 23
<212> TYPE: DNA
<213> ORGANISM: Mus musculus

<400> SEQUENCE: 81
gccgctaagc taaactaggc tgg                                              23

<210> SEQ ID NO 82

-continued

```
<211> LENGTH: 23
<212> TYPE: DNA
<213> ORGANISM: Mus musculus

<400> SEQUENCE: 82
tcagctatgc tacgctgtgt tgg                                              23

<210> SEQ ID NO 83
<211> LENGTH: 23
<212> TYPE: DNA
<213> ORGANISM: Mus musculus

<400> SEQUENCE: 83
ttttagagcc tcgcttacta ggg                                              23

<210> SEQ ID NO 84
<211> LENGTH: 23
<212> TYPE: DNA
<213> ORGANISM: Mus musculus

<400> SEQUENCE: 84
ctctatgatt attggttaac agg                                              23

<210> SEQ ID NO 85
<211> LENGTH: 834
<212> TYPE: DNA
<213> ORGANISM: Homo sapiens

<400> SEQUENCE: 85
gtagttgaaa agtggtcttg aaaaatacta aaatgaaggc cactctatca gaatatcaaa      60
gtgtttctcc ttaatcacaa agagaaaacg agttaaccta aaaagattgt gaacacagtc     120
attatgaaaa taatgctctg aggtatcgaa aaagtatttg agattaatta tcacatgaag     180
ggataacaag ctaatttaaa aaacttttg aatacagtca taaactctcc ctaagactgt      240
ttaatttctt aaacatctta ctttaaaaat gaatgcagtt tagaagttga tatgctgttt     300
gcacaaacta gcagttgata agctaagatt ggaaatgaaa ttcagatagt taaaaaaagc     360
cttttcagtt tcggtcagcc tcgccttatt ttagaaacgc aaattgtcca ggtgttgttt     420
tgctcagtag agcactttca gatctgggcc tgggcaaaac cacctcttca caaccagaag     480
tgataaattt accaattgtg ttttttttgct tcctaaaata gactctcgcg gtgacctgct    540
tcctgccacc tgctgtgggt gccggagacc cccatgcagc catcttgact ctaattcatc    600
atctgcttcc agcttcgctc aattaattaa aaaaataaac ttgatttatg atggtcaaaa    660
cgcagtcccg catcggggcc gacagcactg tgctagtatt tcttagctga gcttgctttg    720
gcctcaattc cagacacata tcactcatgg gtgttaatca aatgataaga atttcaaata    780
cttggacagt taaaaaaatt aatatacttg aaaatctctc acatttttaa gtca           834

<210> SEQ ID NO 86
<211> LENGTH: 1002
<212> TYPE: DNA
<213> ORGANISM: Mus musculus

<400> SEQUENCE: 86
agtctagata attgcattca tttaaaaaaa aagtctttct cctaaaatga atactcagaa      60
agtggtcttg aaaaagattt gtgaagccgt tttgaccaga atgtcaaagt cttaatagta    120
aggcaaaaca acaactaaa aaagatcatg aacaaagtca ctgtaaatgc ttcgggtatt     180
ggaaaagaat tgaatggaga ccaataatca gagggaagaa taatagagta attttaagaa    240
```

```
gttttctaaa tatattagaa attaaagaca ctaaagtcct tcaatttctt acataaccta       300
attttgaaaa tgaattctaa atacatttta gaagtcgata aacttaagtt tggggaaact       360
agaactactc aagctaaaat taaaaggttg aactcaataa gttaaaagag gacctctcca       420
gtttcggctg aatcctcaac ttattttaga aatgcaaatt acccaggtgg tgttttgctc       480
agcctggact ttcggtttgg tggggctgga cagagtgttt caaaaccact tcttcaaacc       540
acagctacaa gttacctag tggttttatt ttcccttccc caaatagcct tgccacatga        600
cctgcttcct gccagctgct gcaggtgttc tggttctgat cggccatctt gactccaact       660
caacattgct caattcattt aaaaatattt gaaacttaat ttattattgt taaaagtcag       720
ttctgaatag gttatgagag agcctcactc ccattcctcg gttaaacttt aagtaatatc       780
agttctacac aaacaagacc tcaaactgat tgacaagaat tttggacatt taaaaaaatg       840
agtacttgaa aaccctctca cattttaaag tcacagtatt taactatttt tcctaggaac       900
caacttaaga gtaaaagcaa catcttctaa tattccatac acatacttct gtgttccttt       960
gaaagctgga cttttgcagg ctccaccaga cctctctaga ca                         1002

<210> SEQ ID NO 87
<211> LENGTH: 20
<212> TYPE: RNA
<213> ORGANISM: Artificial Sequence
<220> FEATURE:
<223> OTHER INFORMATION: mouse sgRNA-mIgH_3 from FIG. 25A

<400> SEQUENCE: 87
uuauacagua uccgaugcau                                                   20

<210> SEQ ID NO 88
<211> LENGTH: 20
<212> TYPE: RNA
<213> ORGANISM: Artificial Sequence
<220> FEATURE:
<223> OTHER INFORMATION: human sgRNA-hIgH-6 from FIG. 25A

<400> SEQUENCE: 88
gcauugcagg uugguccucg                                                   20

<210> SEQ ID NO 89
<211> LENGTH: 20
<212> TYPE: RNA
<213> ORGANISM: Artificial Sequence
<220> FEATURE:
<223> OTHER INFORMATION: human sgRNA-hIgH-7 from FIG. 25A

<400> SEQUENCE: 89
gucucaggag cggugucugu                                                   20

<210> SEQ ID NO 90
<211> LENGTH: 36
<212> TYPE: DNA
<213> ORGANISM: Mus musculus

<400> SEQUENCE: 90
catcggatac tgtataaatg ctgtcacaga ggtggt                                 36

<210> SEQ ID NO 91
<211> LENGTH: 36
<212> TYPE: DNA
<213> ORGANISM: Mus musculus
```

<400> SEQUENCE: 91
catagggaca aagagtggag tggggcactt tctttta 36

<210> SEQ ID NO 92
<211> LENGTH: 36
<212> TYPE: DNA
<213> ORGANISM: Homo sapiens

<400> SEQUENCE: 92
gacaccgctc ctgagacaca ttcctcagcc atcact 36

<210> SEQ ID NO 93
<211> LENGTH: 36
<212> TYPE: DNA
<213> ORGANISM: Homo sapiens

<400> SEQUENCE: 93
tgtaggactg caagatcgct gcacagcagc gaatcg 36

<210> SEQ ID NO 94
<211> LENGTH: 37
<212> TYPE: DNA
<213> ORGANISM: Homo sapiens

<400> SEQUENCE: 94
gggaccaacc tgcaatgctc aggaaacccc acaggca 37

<210> SEQ ID NO 95
<211> LENGTH: 37
<212> TYPE: DNA
<213> ORGANISM: Homo sapiens

<400> SEQUENCE: 95
ttcggggcat gttccgaggg gacctgggcg gactggc 37

<210> SEQ ID NO 96
<211> LENGTH: 127
<212> TYPE: DNA
<213> ORGANISM: Artificial Sequence
<220> FEATURE:
<223> OTHER INFORMATION: upstream splicing oligonucleotide for mouse sgRNA-mIgH_3

<400> SEQUENCE: 96
cttcgagaca tgtacagacc atttagatgt agtatcaaag cctaatatct caatcttaaa 60
atagaatcct aacctgagac actcacttgt ccatcggata ctgtataaat gctgtcacag 120
aggtggt 127

<210> SEQ ID NO 97
<211> LENGTH: 86
<212> TYPE: DNA
<213> ORGANISM: Artificial Sequence
<220> FEATURE:
<223> OTHER INFORMATION: downstream splicing oligonucleotide for mouse sgRNA-mIgH_3

<400> SEQUENCE: 97
cttctcccat tctaaatgca tgttgggggg attctgggcc ttcaggacca catagggaca 60
aagagtggag tggggcactt tcttta 86

<210> SEQ ID NO 98
<211> LENGTH: 127

<212> TYPE: DNA
<213> ORGANISM: Artificial Sequence
<220> FEATURE:
<223> OTHER INFORMATION: upstream splicing oligonucleotide for human sgRNA-hIgH-7

<400> SEQUENCE: 98

```
gtgcacagcg ctcttcccgc tgcagaacaa accccaaccc caggatgcac tcctcactgt      60
gaacccacat tttattggcc taaagattac ggacaccgct cctgagacac attcctcagc     120
catcact                                                               127
```

<210> SEQ ID NO 99
<211> LENGTH: 86
<212> TYPE: DNA
<213> ORGANISM: Artificial Sequence
<220> FEATURE:
<223> OTHER INFORMATION: downstream splicing oligonucleotide for human sgRNA-hIgH-7

<400> SEQUENCE: 99

```
gtctggggat agcggggagc caggtgtact gggccaggca agggctttgg tgtaggactg      60
caagatcgct gcacagcagc gaatcg                                           86
```

<210> SEQ ID NO 100
<211> LENGTH: 128
<212> TYPE: DNA
<213> ORGANISM: Artificial Sequence
<220> FEATURE:
<223> OTHER INFORMATION: upstream splicing oligonucleotide for human sgRNA-hIgH-6

<400> SEQUENCE: 100

```
gtgcacagcg ctcttcccgc tgcagaacaa accccaaccc caggatgcac tcctcactgt      60
gaacccacat tttattggcc taaagattac ggggaccaac ctgcaatgct caggaaaccc     120
cacaggca                                                              128
```

<210> SEQ ID NO 101
<211> LENGTH: 87
<212> TYPE: DNA
<213> ORGANISM: Artificial Sequence
<220> FEATURE:
<223> OTHER INFORMATION: downstream splicing oligonucleotide for human sgRNA-hIgH-6

<400> SEQUENCE: 101

```
gtctggggat agcggggagc caggtgtact gggccaggca agggctttgg ttcggggcat      60
gttccgaggg gacctgggcg gactggc                                          87
```

<210> SEQ ID NO 102
<211> LENGTH: 2531
<212> TYPE: DNA
<213> ORGANISM: Artificial Sequence
<220> FEATURE:
<223> OTHER INFORMATION: human anti-RSV-emAb AAV

<400> SEQUENCE: 102

```
tgtgacgccc ggagacagaa ggtctctggg tggctgggtt tttgtggggt gaggatggac      60
attctgccat tgtgattact actactacta ctacatggac gtctggggca aagggaccac     120
ggtcaccgtc tcctcaggta agaatggcca ctctagggcc tttgttttct gctactgcct     180
gtggggtttc ctgagcattg caggttggtc ctcggggcat gttccgaggg gacctgggcg     240
```

-continued

```
gactggccag gaggggatgg gcactggggt gccttgagga tctgggagcc tctgtggatt    300
ttccgatgcc tttggaaaat gggactcagg ttgggtgcgt ctgatggagt aactgagcct    360
gggggcttgg ggagccacat ttggacgaga tgcctgaaca aaccagggt cttagtgatg     420
gctgaggaat gtgtctcagg agcggtgtct gatcgtaatc tttaggccaa taaaatgtgg    480
gttcacagtg aggagtgcat cctggggttg gggtttgttc tgcagcggga agagcgctgt    540
gcacagaaag cttagaaatg gggcaagaga tgcttttcct caggcaggat ttagggcttg    600
gtctctcagc atcccacact tgtacagctg atgtggcatc tgtgttttct ttctcatcct    660
agatcaggct ttgagctgtg aaatacccctg cctcatgcat atgcaaataa cctgaggtct   720
tctgagataa atatagatat attggtgccc tgaggtttaa acgccgccac catggctacc    780
ggcagcagaa caagcctgct gctcgctttt ggactgctct gtctcccctg gttgcaagaa    840
ggcagcgccg acatccagat gacacagagc cctagcacac tgtctgccag cgtgggcgac    900
agagtgacca tcacatgcaa gtgccagctg agcgtgggct acatgcactg gtatcagcaa    960
aagcccggca aggcccctaa gctgctgatc tacgatacct ccaagctggc ctctggcgtg   1020
ccctccagat tttctggcag cggcagcgga accgagttca ccctgaccat ctcaagcctg   1080
cagcctgacg acttcgctac gtactactgc ttccaaggca gcggctaccc cttcacatt    1140
ggcggcggaa caaagctgga aatcaagcgg actgtggccg ctcctagcgt gttcatcttt   1200
ccacctagca cgagcagct gaagtctggc actgcctctg tcgtgtgcct gctgaacaac    1260
ttctaccctc gagaggccaa ggtgcagtgg aaagtggaca atgccctgca gagcggcaac   1320
agccaagagt ctgtgaccga gcaggactcc aaggattcca cctacagcct gtctagcacc   1380
ctgactctga gcaaggccga ctacgagaag cacaaggtgt acgcctgcga agtgacacac   1440
cagggactga gcagccctgt gaccaagagc ttcaatcggg gcgagtgcgg aggaagtagt   1500
ggcagcggga gtgggtccaa ttggagtcat cctcaatttg agaaggagg gggagggtcc    1560
aattggtctc atccgcagtt tgagaagggc ggcggcggct ccaattggtc ccatccccag   1620
tttgaaaaag gctctggtgg aggtggtagt gctggtgggc aagtgaccct gagagagtct   1680
ggaccctgctc tggtcaagcc cacacagacc ctgacactga cctgcacctt cagcggcttt   1740
agcctgagca aagcggcat gagcgtcggc tggattagac agcctcctgg caaagccctg   1800
gaatggctgg ccgacatttg gtgggacgac aagaaggact acaacccag cctgaagtcc   1860
cggctgacca tcagcaagga caccagcaag aaccaggtgg tgctgaaagt gaccaacatg   1920
gaccctgccg acaccgccac ctactactgt gccagatcca tgatcaccaa ctggtacttc   1980
gacgtgtggg gagccggcac cacaaccgtc tcttcaggta agtctgctgt ctgggatag    2040
cggggagcca ggtgtactgg gccaggcaag ggctttggat cgtaggactg caagatcgct   2100
gcacagcagc gaatcgtgaa atatttctt tagaattatg aggtgcgctg tgtgtcaacc    2160
tgcatcttaa attctttatt ggctggaaag agaactgtcg gagtgggtga atccagccag   2220
gagggacgcg tagccccggt cttgatgaga gcagggttgg gggcagggt agcccagaaa    2280
cggtggctgc cgtcctgaca ggggcttagg gaggctccag gacctcagtg ccttgaagct   2340
ggtttccatg agaaaggat tgttttatctt aggaggcatg cttactgtta aaagacagga   2400
tatgtttgaa gtggcttctg agaaaaatgg ttaagaaaat tatgacttaa aaatgtgaga   2460
gattttcaag tatattaatt tttttaactg tccaagtatt tgaaattctt atcatttgat   2520
taacacccat g                                                        2531
```

<210> SEQ ID NO 103
<211> LENGTH: 3134
<212> TYPE: DNA
<213> ORGANISM: Artificial Sequence
<220> FEATURE:
<223> OTHER INFORMATION: mouse anti-RSV emAb AAV

<400> SEQUENCE: 103

| | |
|---|---|
| ccaggggtga ttctagtcag actctggggt ttttgtcggg tatagaggaa aaatccacta | 60 |
| ttgtgattac tatgctatgg actactgggg tcaaggaacc tcagtcaccg tctcctcagg | 120 |
| taagaatggc ctctccaggt ctttattttt aacctttgtt atggagtttt ctgagcattg | 180 |
| cagactaatc ttggatattt gtccctgagg agccggctg agagaagttg ggaaataaac | 240 |
| tgtctaggga tctcagagcc tttaggacag attatctcca catctttgaa aaactaagaa | 300 |
| tctgtgtgat ggtgttggtg gagtccctgg atgatgggat agggactttg gaggctcatt | 360 |
| tgagggagat gctaaaacaa tcctatggct ggagggatag ttggggctgt agttggagat | 420 |
| tttcagtttt tagaataaaa gtattagttg tggaatatac ttcaggacca cctctgtgac | 480 |
| agcatttata cagtatccga tggatgacaa gtgagtgtct caggttagga ttctatttta | 540 |
| agattgagat attaggcttt gatactacat ctaaatggtc tgtacatgtc tcgaagaaag | 600 |
| ttcttcagac agagttagga cttggatcca ggagttagga cttggactga ctcaggagga | 660 |
| ctctagtttc ttcttctcca gctggaatgt ccttatgtaa gaaaagcctt gcctcatgag | 720 |
| tatgcaaatc atgtgcgact gtgatgatta atataggat atccacacca aacatcatat | 780 |
| gagccctatc ttctctacag acactgaatc tcaaggtcct tacaatggaa accgacacac | 840 |
| tgctgctgtg ggtgctgctt ctttgggtgc ccggaagcac aggcgacatc cagctgacac | 900 |
| agagccctgc catcatgtct gctagccctg gcgagaaagt gacaatgacc tgttccgcca | 960 |
| gcagctccgt gggctacatg cactggtatc agcagaagtc tagcacaagc cccaagctgt | 1020 |
| ggatctacga cacctccaag ctggcctctg gcgtgccagg cagattttct ggaagcggca | 1080 |
| gcggcaacag ctacagcctg actatcagct ccatccaggc cgaggatgtg gctacctact | 1140 |
| actgcttcag aggcagcggc taccccttca catttggcca gggcaccaag ctggaaatca | 1200 |
| aggccgatgc cgctcctacc gtgtctatct ttccacctag cagcgagcag ctgacatctg | 1260 |
| gcggagcctc tgtcgtgtgc ttcctgaaca cttctaccc taaggacatc aacgtcaagt | 1320 |
| ggaagatcga cggctccgag agacagaacg gcgtgctgaa ctcttggacc gaccaggaca | 1380 |
| gcaaggatag cacctacagc atgagcagca ctctgaccct gacaaaggac gagtacgaga | 1440 |
| ggcacaactc ctacacatgc gaggccacac aaagaccag cacatcccca atcgtgaagt | 1500 |
| ccttcaaccg gaacgagtgc ggaggaagta gtggcagcgg gagtgggtcc aattggagtc | 1560 |
| atcctcaatt tgagaaagga gggggagggt ccaattggtc tcatccgcag tttgagaagg | 1620 |
| gcggcggcgg ctccaattgg tcccatcccc agtttgaaaa aggctctggt ggaggtggta | 1680 |
| gtgctggtgg gcaggtggaa ctgcaagaaa gcggccctgg catcctgcag ccttctcaga | 1740 |
| cactgagcct gacctgtagc ttcagcggct tcagcctgag cacaagcggc atgtctgtcg | 1800 |
| gctggatcag acagccttct ggcgaaggac tggaatggct ggccgacatt tggtgggacg | 1860 |
| acaagaagga ctacaacccc agcctgaagt ccagactgac catcagcaag gacaccagca | 1920 |
| gcaaccaggt gttcctgaag atcaccggcg tggacacagc cgataccgcc acctattact | 1980 |
| gcgccagatc catgatcacc aactggtact tcgacgtgtg gggcgctggc accacagtga | 2040 |
| ccgtctcctc aggtgagtcc taacttctcc cattctaaat gcatgttggg gggattctgg | 2100 |

| | | | |
|---|---|---|---|
| gccttcagga | ccaccatgta | ccaaaagcca | taacgatcgg tgggagtatt cattgtggtc 2160 |
| aagatccata | gggacaaaga | gtggagtggg | gcactttctt tagatttgtg aggaatgttc 2220 |
| cgcactagat | tgtttaaaac | ttcatttgtt | ggaaggagag ctgtcttagt gattgagtca 2280 |
| agggagaaag | gcatctagcc | tcggtctcaa | aagggtagtt gctgtctaga gaggtctggt 2340 |
| ggagcctgca | aaagtccagc | tttcaaagga | acacagaagt atgtgtatgg aatattagaa 2400 |
| gatgttgctt | ttactcttaa | gttggttcct | aggaaaaata gttaaatact gtgactttaa 2460 |
| aatgtgagag | ggttttcaag | tactcatttt | tttaaatgtc caaaatttt gtcaatcagt 2520 |
| ttgaggtctt | gtttgtgtag | aactgatatt | acttaaagtt taaccgagga atgggagtga 2580 |
| ggctctctca | taacctattc | agaactgact | tttaacaata ataaattaag tttaaaatat 2640 |
| ttttaaatga | attgagcaat | gttgagttgg | agtcaagatg gccgatcaga accagaacac 2700 |
| ctgcagcagc | tggcaggaag | caggtcatgt | ggcaaggcta tttggggaag ggaaaataaa 2760 |
| accactaggt | aaacttgtag | ctgtggtttg | aagaagtggt tttgaaacac tctgtccagc 2820 |
| cccaccaaac | cgaaagtcca | ggctgagcaa | acaccacct gggtaatttg catttctaaa 2880 |
| ataagttgag | gattcagccg | aaactggaga | ggtcctcttt taacttattg agttcaacct 2940 |
| tttaattta | gcttgagtag | ttctagtttc | cccaaactta agtttatcga cttctaaaat 3000 |
| gtatttagaa | ttcatttca | aaattaggtt | atgtaagaaa ttgaaggact ttagtgtctt 3060 |
| taatttctaa | tatatttaga | aaacttctta | aaattactct attattcttc cctctgatta 3120 |
| ttggtctcca | ttca | | 3134 |

<210> SEQ ID NO 104
<211> LENGTH: 1736
<212> TYPE: DNA
<213> ORGANISM: Artificial Sequence
<220> FEATURE:
<223> OTHER INFORMATION: ms-emAb-RSV-dsDNA

<400> SEQUENCE: 104

| | | | |
|---|---|---|---|
| accacctctg | tgacagcatt | tatacagtat | ccgatggatg acaagtgagt gtctcaggtt 60 |
| aggattctat | tttaagattg | agatattagg | ctttgatact acatctaaat ggtctgtaca 120 |
| tgtctcgaag | aaagttcttc | agacagagtt | aggacttgga tccaggagtt aggacttgga 180 |
| ctgactcagg | aggactctag | tttcttcttc | tccagctgga atgtccttat gtaagaaaag 240 |
| ccttgcctca | tgagtatgca | atcatgtgc | gactgtgatg attaatatag ggatatccac 300 |
| accaaacatc | atatgagccc | tatcttctct | acagacactg aatctcaagg tccttacaat 360 |
| ggaaaccgac | acactgctgc | tgtgggtgct | gcttctttgg gtgcccggaa gcacaggcga 420 |
| catccagctg | acacagagcc | ctgccatcat | gtctgctagc cctggcgaga aagtgacaat 480 |
| gacctgttcc | gccagcagct | ccgtgggcta | catgcactgg tatcagcaga agtctagcac 540 |
| aagccccaag | ctgtggatct | acgacaccte | caagctggcc tctggcgtgc caggcagatt 600 |
| ttctggaagc | ggcagcggca | acagctacag | cctgactatc agctccatcc aggccgagga 660 |
| tgtggctacc | tactactgct | tcagaggcag | cggctacccc ttcacatttg gccagggcac 720 |
| caagctggaa | atcaaggccg | atgccgctcc | taccgtgtct atctttccac ctagcagcga 780 |
| gcagctgaca | tctggcggag | cctctgtcgt | gtgcttcctg aacaacttct accctaagga 840 |
| catcaacgtc | aagtggaaga | tcgacggctc | cgagagacag aacggcgtgc tgaactcttg 900 |
| gaccgaccag | gacagcaagg | atagcaccta | cagcatgagc agcactctga ccctgacaaa 960 |
| ggacgagtac | gagaggcaca | actcctacac | atgcgaggcc acacacaaga ccagcacatc 1020 |

| | |
|---|---|
| cccaatcgtg aagtccttca accggaacga gtgcggagga agtagtggca gcgggagtgg | 1080 |
| gtccaattgg agtcatcctc aatttgagaa aggaggggga gggtccaatt ggtctcatcc | 1140 |
| gcagtttgag aagggcggcg gcggctccaa ttggtcccat ccccagtttg aaaaaggctc | 1200 |
| tggtggaggt ggtagtgctg gtgggcaggt ggaactgcaa gaaagcggcc ctggcatcct | 1260 |
| gcagccttct cagacactga gcctgacctg tagcttcagc ggcttcagcc tgagcacaag | 1320 |
| cggcatgtct gtcggctgga tcagacagcc ttctggcgaa ggactggaat ggctggccga | 1380 |
| catttggtgg gacgacaaga aggactacaa ccccagcctg aagtccagac tgaccatcag | 1440 |
| caaggacacc agcagcaacc aggtgttcct gaagatcacc ggcgtggaca gccgatac | 1500 |
| cgccacctat tactgcgcca gatccatgat caccaactgg tacttcgacg tgggggcgc | 1560 |
| tggcaccaca gtgaccgtct cctcaggtga gtcctaactt ctcccattct aaatgcatgt | 1620 |
| tgggggatt ctgggccttc aggaccacca tgtaccaaaa gccataacga tcggtgggag | 1680 |
| tattcattgt ggtcaagatc catagggaca aagagtggag tggggcactt tctttta | 1736 |

<210> SEQ ID NO 105
<211> LENGTH: 2551
<212> TYPE: DNA
<213> ORGANISM: Artificial Sequence
<220> FEATURE:
<223> OTHER INFORMATION: hu-emAb-VRC01-AAV

<400> SEQUENCE: 105

| | |
|---|---|
| tgtgacgccc ggagacagaa ggtctctggg tggctgggtt tttgtggggt gaggatggac | 60 |
| attctgccat tgtgattact actactacta ctacatggac gtctggggca aagggaccac | 120 |
| ggtcaccgtc tcctcaggta agaatggcca ctctagggcc tttgttttct gctactgcct | 180 |
| gtggggtttc ctgagcattg caggttggtc ctcggggcat gttccgaggg gacctgggcg | 240 |
| gactggccag gaggggatgg gcactggggt gccttgagga tctggagcc tctgtggatt | 300 |
| ttccgatgcc tttggaaaat gggactcagg ttgggtgcgt ctgatggagt aactgagcct | 360 |
| ggggggcttgg ggagccacat ttggacgaga tgcctgaaca aaccagggt cttagtgatg | 420 |
| gctgaggaat gtgtctcagg agcggtgtct gatcgtaatc tttaggccaa taaaatgtgg | 480 |
| gttcacagtg aggagtgcat cctgggggtt gggtttgttc tgcagcggga agagcgctgt | 540 |
| gcacagaaag cttagaaatg gggcaagaga tgcttttcct caggcaggat ttagggcttg | 600 |
| gtctctcagc atcccacact tgtacagctg atgtggcatc tgtgttttct ttctcatcct | 660 |
| agatcaggct ttgagctgtg aaatacccctg cctcatgcat atgcaaataa cctgaggtct | 720 |
| tctgagataa atatagatat attggtgccc tgagagcatc acgccgccac catggctacc | 780 |
| ggcagcagaa caagcctgct gctcgctttt ggactgctct gtctccctg ttgcaagaa | 840 |
| ggcagcgccg aaattgtgtt gacacagtct ccaggcaccc tgtctttgtc tccaggggaa | 900 |
| acagccatca tctcttgtcg gaccagtcag tatggttcct tagcctggta tcaacagagg | 960 |
| cccggccagg cccccaggct cgtcatctat tcgggctcta ctcggccgc tggcatccca | 1020 |
| gacaggttca gcggcagtcg gtgggggcca gactacaatc tcaccatcag caacctggag | 1080 |
| tcgggagatt ttggtgttta ttattgccag cagtatgaat ttttggcca ggggaccaag | 1140 |
| gtccaggtcg acattaagcg cactgtggcc gctcctagcg tgttcatctt tccacctagc | 1200 |
| gacgagcagc tgaagtctgg cactgcctct gtcgtgtgcc tgctgaacaa cttctaccct | 1260 |
| cgagaggcca aggtgcagtg gaaagtggac aatgccctgc agagcggcaa cagccaagag | 1320 |

```
tctgtgaccg agcaggactc caaggattcc acctacagcc tgtctagcac cctgactctg    1380
agcaaggccg actacgagaa gcacaaggtg tacgcctgcg aagtgacaca ccagggactg    1440
agcagccctg tgaccaagag cttcaatcgg ggcgagtgcg gaggctcaag tggctccggg    1500
agtgggagca attggtcaca cccccagttt gaaaaaggcg gtgggggggag taactggtct   1560
catccgcagt tcgaaaaggg tggaggaggg agcaactgga gtcatccaca atttgagaaa    1620
ggctcaggtg gtggtggtag cgctgggggg caggtgcagc tggtgcagtc tgggggtcag    1680
atgaagaagc tggcgagtc gatgagaatt tcttgtcggg cttctggata tgaatttatt     1740
gattgtacgc taaattggat cgtctggcc cccggaaaaa ggcctgagtg gatgggatgg      1800
ctgaagcctc gaggtggcgc ggtcaactac gcacgtccac ttcagggcag agtgaccatg    1860
actcgagacg tttattccga cacagccttt ttggagctgc gctcgttgac agtagacgac    1920
acggccgtct actttgtac taggggaaaa aactgtgatt acaattggga cttcgaacac      1980
tggggccggg gcaccccggt catcgtctca tcaggtgagt tggctttcct tctgcctcct     2040
ttctctgggc ccagcgtcct ctgacctgga gctgggagat aatgtccggg ggctccttat    2100
cgtaggactg caagatcgct gcacagcagc gaatcgtgaa atattttctt tagaattatg     2160
aggtgcgctg tgtgtcaacc tgcatcttaa attctttatt ggctgaaag agaactgtcg      2220
gagtgggtga atccagccag gagggacgcg tagccccggt cttgatgaga gcagggttgg    2280
gggcagggt agcccagaaa cggtggctgc cgtcctgaca ggggcttagg gaggctccag     2340
gacctcagtg ccttgaagct ggtttccatg agaaaaggat tgtttatctt aggaggcatg    2400
cttactgtta aaagacagga tatgtttgaa gtggcttctg agaaaaatgg ttaagaaaat    2460
tatgacttaa aaatgtgaga gattttcaag tatattaatt tttttaactg tccaagtatt    2520
tgaaattctt atcatttgat taacacccat g                                    2551
```

<210> SEQ ID NO 106
<211> LENGTH: 2544
<212> TYPE: DNA
<213> ORGANISM: Artificial Sequence
<220> FEATURE:
<223> OTHER INFORMATION: hu-emAb-Medi8852-AAV

<400> SEQUENCE: 106

```
tgtgacgccc ggagacagaa ggtctctggg tggctgggtt tttgtggggt gaggatggac     60
attctgccat tgtgattact actactacta ctacatggac gtctggggca aagggaccac    120
ggtcaccgtc tcctcaggta agaatggcca ctctagggcc tttgttttct gctactgcct   180
gtggggtttc ctgagggcat gttccgaggg gacctgggcg gactggccag gagggggatgg 240
gcactggggt gccttgagga tctgggagcc tctgtggatt ttccgatgcc tttggaaaat  300
gggactcagg ttgggtgcgt ctgatggagt aactgagcct gggggcttgg ggagccacat   360
ttggacgaga tgcctgaaca aaccagggggt cttagtgatg gctgaggaat gtgtctcagg  420
agcggtgtct gatcgtaatc tttaggccaa taaaatgtgg gttcacagtg aggagtgcat  480
cctggggttg gggtttgttc tgcagcggga agagcgctgt gcacagaaag cttagaaatg   540
gggcaagaga tgctttttcct caggcaggat ttagggcttg gtctctcagc atcccacact    600
tgtacagctg atgtggcatc tgtgttttct ttctcatcct agatcaggct ttgagctgtg   660
aaatacccctg cctcatgcat atgcaaataa cctgaggtct tctgagataa atatagatat  720
attggtgccc tgaggccgcc accatggcta ccggcagcag aacaagcctg ctgctcgctt    780
ttggactgct ctgtctcccc tggttgcaag aaggcagcgc cgatattcag atgacccaga    840
```

```
gcccttccag cctgtccgct tcagtggggg atcgagtgac cattacctgc cgaaccagcc    900
agagcctgag ctcctacacg cactggtatc agcagaagcc cggcaaagcc cctaagctgc    960
tgatctacgc cgcttctagt cggggtccg gagtgccaag ccggttctcc ggatctggga    1020
gtggaaccga ctttaccctg acaatttcaa gcctgcagcc cgaggatttc gctacatact    1080
actgtcagca gagcagaact ttcgggcagg gcactaaggt ggagatcaaa cggactgtgg    1140
ccgctcctag cgtgttcatc tttccaccta gcgacgagca gctgaagtct ggcactgcct    1200
ctgtcgtgtg cctgctgaac aacttctacc ctcgagaggc caaggtgcag tggaaagtgg    1260
acaatgccct gcagagcggc aacagccaag agtctgtgac cgagcaggac tccaaggatt    1320
ccacctacag cctgtctagc accctgactc tgagcaaggc cgactacgag aagcacaagg    1380
tgtacgcctg cgaagtgaca caccaggggac tgagcagccc tgtgaccaag agcttcaatc    1440
ggggcgagtg cggaggaagt agtggcagcg ggagtgggtc caattggagt catcctcaat    1500
ttgagaaagg aggggagggg tccaattggt ctcatccgca gtttgagaag gcggcggcg    1560
gctccaattg gtcccatccc cagtttgaaa aaggctctgg tggaggtggt agtgctggtg    1620
ggcaggtcca gctgcagcag agcggccccg gactggtcaa gccttcacag acactgagcc    1680
tgacatgcgc cattagcgga gatagcgtga gctcctacaa tgccgtgtgg aactggatca    1740
ggcagtctcc aagtcgagga ctggagtggc tgggacgaac atactataga tccgggtggt    1800
acaatgacta tgctgaatca gtgaaaagcc gaattactat caaccccgat acctccaaga    1860
atcagttctc tctgcagctg aacagtgtga cccctgagga cacagccgtg tactactgcg    1920
ccagaagcgg ccatatcacc gtctttggcg tcaatgtgga tgctttcgat atgtggggc    1980
aggggactat ggtcaccgtc tcttcaggtg agttggcttt ccttctgcct cctttctctg    2040
ggcccagcgt cctctgacct ggagctggga gataatgtcc ggggggctcct tatcgtagga    2100
ctgcaagatc gctgcacagc agcgaatcgt gaaatatttt cttttagaatt atgaggtgcg    2160
ctgtgtgtca acctgcatct taaattcttt attggctgga agagaactg tcggagtggg    2220
tgaatccagc caggagggac gcgtagcccc ggtcttgatg agagcagggt tgggggcagg    2280
ggtagcccag aaacggtggc tgccgtcctg acagggggctt agggaggctc caggacctca    2340
gtgccttgaa gctggtttcc atgagaaaag gattgtttat cttaggaggc atgcttactg    2400
ttaaaagaca ggatatgttt gaagtggctt ctgagaaaaa tggttaagaa aattatgact    2460
taaaaatgtg agagattttc aagtatatta atttttttaa ctgtccaagt atttgaaatt    2520
cttatcattt gattaacacc catg                                           2544
```

<210> SEQ ID NO 107
<211> LENGTH: 2555
<212> TYPE: DNA
<213> ORGANISM: Artificial Sequence
<220> FEATURE:
<223> OTHER INFORMATION: hu-emAb-AMM01-AAV

<400> SEQUENCE: 107

```
tgtgacgccc ggagacagaa ggtctctggg tggctgggtt tttgtggggt gaggatggac     60
attctgccat tgtgattact actactacta ctacatggac gtctggggca aagggaccac    120
ggtcaccgtc tcctcaggta agaatggcca ctctagggcc tttgttttct gctactgcct    180
gtggggtttc ctgagggcat gttccgaggg gacctgggcg gactggccag gaggggatgg    240
gcactggggt gccttgagga tctggagcc tctgtggatt ttccgatgcc tttggaaaat    300
```

```
gggactcagg ttgggtgcgt ctgatggagt aactgagcct gggggcttgg ggagccacat    360
ttggacgaga tgcctgaaca aaccaggggt cttagtgatg gctgaggaat gtgtctcagg    420
agcggtgtct gatcgtaatc tttaggccaa taaaatgtgg gttcacagtg aggagtgcat    480 cctgggggttg gggtttgttc tgcagcggga agagcgctgt gcacagaaag cttagaaatg   540
gggcaagaga tgcttttcct caggcaggat ttagggcttg gtctctcagc atcccacact    600
tgtacagctg atgtggcatc tgtgttttct ttctcatcct agatcaggct ttgagctgtg    660 aaatacctg cctcatgcat atgcaaataa cctgaggtct tctgagataa atatagatat     720
attggtgccc tgagagcatc acgccgccac catggctacc ggcagcagaa caagcctgct    780
gctcgctttt ggactgctct gtctcccctg gttgcaagaa ggcagcgcct cctatgagct    840
gactcagcca ccctcagtgt cagtggcccc ggggcagagg ccacaatta cctgtggggg     900 acacaacatc ggagctaaaa atgtccactg gtaccagcag aagccaggcc aggcccctgt    960
cctggtcatc caatatgata gcgaccggcc ctcagggatc cctgagcgat tctctggctc   1020
caactctggg agcacggcca ccctgaccat cagcagggtc gaagccgggg atgaggccga   1080
ctattactgt caggtgtggg atagtggtcg tgggcatccc ctttatgtct tcggaggtgg   1140
gaccaaggtc accgtcctag gtcagcccaa ggccaacccc actgtcactc tgttcccacc   1200
ctcgagtgag gagcttcaag ccaacaaggc cacactggtg tgtctcataa gtgacttcta   1260
cccgggagcc gtgacagtgg cctggaaggc agatagcagc cccgtcaagg cgggagtgga   1320
gaccaccaca ccctccaaac aaagcaacaa caagtacgcg gccagcagct acctgagcct   1380
gacgcctgag cagtggaagt cccacagaag ctacagctgc caggtcacgc atgaagggag   1440
caccgtggag aagacagtgg cccctacaga atgttcagga ggaagtagtg gcagcgggag   1500
tgggtccaat tggagtcatc ctcaatttga gaaggaggg ggagggtcca attggtctca    1560
tccgcagttt gagaagggcg gcggcggctc caattggtcc catccccagt ttgaaaaagg   1620
ctctggtgga ggtggtagtg ctggtgggca ggttcagctg gtgcagtctg gagctgatgt   1680
gaagaagcct ggggcctcag tgaaggtctc ctgcaaggct tctggttaca ccttttattca  1740 ttttggtatc agttgggtgc ggcaggcccc tggacaaggg cttgagtgga tgggatggat   1800
cgacactaat aatggtaaca caaactatgc acagagtctc cagggcagag tcaccatgac   1860
cacagataca tccacgggca cagcctacat ggagctgagg agcctctcga ctgacgacac   1920
ggccgtgtat ttctgtgcgc gagctctgga aatggggcat agaagtggct cccatttga    1980 ctactgggc cagggagtcc tggtcaccgt ctccccaggt gagttggctt ccttctgcc    2040 tcctttctct gggcccagcg tcctctgacc tggagctggg agataatgtc cggggggctcc  2100 ttatcgtagg actgcaagat cgctgcacag cagcgaatcg tgaaatattt tctttagaat   2160
tatgaggtgc gctgtgtgtc aacctgcatc ttaaattctt tattggctgg aaagagaact   2220 gtcgagtgg gtgaatccag ccaggaggga cgcgtagccc cggtcttgat gagagcaggg    2280 ttggggggcag gggtagccca gaaacggtgg ctgccgtcct gacaggggct tagggaggct   2340
ccaggaccct agtgccttga agctggtttc catgagaaaa ggattgttta tcttaggagg   2400
catgcttact gttaaaagac aggatatgtt tgaagtggct tctgagaaaa atggttaaga   2460
aaattatgac ttaaaaatgt gagagatttt caagtatatt aatttttta actgtccaag    2520 tatttgaaat tcttatcatt tgattaacac ccatg                              2555

<210> SEQ ID NO 108
<211> LENGTH: 2261
```

<212> TYPE: DNA
<213> ORGANISM: Artificial Sequence
<220> FEATURE:
<223> OTHER INFORMATION: Balb/C mRSV-splice integration

<400> SEQUENCE: 108

```
ctactggggt caaggaacct cagtcaccgt ctcctcaggt aagaatggcc tctccaggtc      60
tttatttta  acctttgtta tggagttttc tgagcattgc agactaatct tggatatttg     120
tccctgaggg agccggctga gagaagttgg gaaataaact gtctagggat ctcagagcct     180
ttaggacaga ttatctccac atctttgaaa aactaagaat ctgtgtgatg gtgttggtgg     240
agtccctgga tgatgggata gggactttgg aggctcattt gaagaagatg ctaaaacaat     300
cctatggctg gagggatagt tggggctgta gttggagatt ttcagttttt agaataaaag     360
tattagttgt ggaatatact tcaggaccac ctctgtgaca gcatttatac agtatccgat     420
ggacaagtga gtgtctcagg ttaggattct attttaagat tgagatatta ggctttgata     480
ctacatctaa atggtctgta catgtctcga agaaagttct tcagacagag ttaggacttg     540
gatccaggag ttaggacttg gactgactca ggaggactct agtttcttct tctccagctg     600
gaatgtcctt atgtaagaaa agccttgcct catgagtatg caaatcatgt gcgactgtga     660
tgattaatat agggatatcc acaccaaaca tcatatgagc cctatcttct ctacagacac     720
tgaatctcaa ggtccttaca atggaaaccg acacactgct gctgtgggtg ctgcttcttt     780
gggtgcccgg aagcacaggc gacatccagc tgacacagag ccctgccatc atgtctgcta     840
gccctggcga gaaagtgaca atgacctgtt ccgccagcag ctccgtgggc tacatgcact     900
ggtatcagca gaagtctagc acaagcccca agctgtggat ctacgacacc tccaagctgg     960
cctctgcgt  gccaggcaga ttttctggaa gcggcagcgg caacagctac agcctgacta    1020
tcagctccat ccaggccgag gatgtggcta cctactactg cttcagaggc agcggctacc    1080
ccttcacatt tggccagggc accaagctga aaatcaaggc cgatgccgct cctaccgtgt    1140
ctatctttcc acctagcagc gagcagctga catctggcgg agcctctgtc gtgtgcttcc    1200
tgaacaactt ctaccctaag gacatcaacg tcaagtggaa gatcgacggc tccgagagac    1260
agaacggcgt gctgaactct tggaccgacc aggacagcaa ggatagcacc tacagcatga    1320
gcagcactct gaccctgaca aaggacgagt acgagaggca caactcctac acatgcgagg    1380
ccacacacaa gaccagcaca tccccaatcg tgaagtcctt caaccggaac gagtgcggag    1440
gaagtagtgg cagcgggagt gggtccaatt ggagtcatcc tcaatttgag aaaggagggg    1500
gagggtccaa ttggtctcat ccgcagtttg agaaggggcgg cggcggctcc aattggtccc    1560
atccccagtt tgaaaaaggc tctggtggag gtggtagtgc tggtgggcag gtggaactgc    1620
aagaaagcgg ccctggcatc ctgcagcctt ctcagacact gagcctgacc tgtagcttca    1680
gcggcttcag cctgagcaca agcggcatgt ctgtcggctg gatcagacag ccttctggcg    1740
aaggactgga atggctggcc gacatttggt gggacgacaa gaaggactac aaccccagcc    1800
tgaagtccag actgaccatc agcaaggaca ccagcagcaa ccaggtgttc ctgaagatca    1860
ccggcgtgga cacagccgat accgccacct attactgcgc cagatccatg atcaccaact    1920
ggtacttcga cgtgtggggc gctggcacca cagtgaccgt ctcctcaggt gagtcctaac    1980
ttctcccatt ctaaatgcat gttgggggga ttctgggcct tcaggaccac atagggacaa    2040
agagtggagt ggggcacttt ctttagattt gtgaggaatg ttccgcacta gattgtttaa    2100
aacttcattt gttggaagga gagctgtctt agtgattgag tcaagggaga aaggcatcta    2160
```

```
gcctcggtct caaaagggta gttgctgtct agagaggtct ggtggagcct gcaaaagtcc    2220
agctttcaaa ggaacacaga agtatgtgta tggaatatta g                        2261
```

<210> SEQ ID NO 109
<211> LENGTH: 1707
<212> TYPE: DNA
<213> ORGANISM: Artificial Sequence
<220> FEATURE:
<223> OTHER INFORMATION: TT-hRSV-T7-integrated

<400> SEQUENCE: 109

```
gtcttagtga tggctgagga atgtgtctca ggagcggtgt ccgtaatctt taggccaata      60
aaatgtgggt tcacagtgag gagtgcatcc tggggttggg gtttgttctg cagcgggaag     120
agcgctgtgc acagaaagct tagaaatggg gcaagagatg cttttcctca ggcaggattt     180
agggcttggt ctctcagcat cccacacttg tacagctgat gtggcatctg tgttttcttt     240
ctcatcctag atcaggcttt gagctgtgaa atacccctgcc tcatgcatat gcaataacc     300 tgaggtcttc tgagataaat atagatatat tggtgccctg aggtttaaac gccgccacca     360
tggctaccgg cagcagaaca agcctgctgc tcgcttttgg actgctctgt ctcccctggt     420
tgcaagaagg cagcgccgac atccagatga cacagagccc tagcacactg tctgccagcg     480
tgggcgacag agtgaccatc acatgcaagt ccagctgag cgtgggctac atgcactggt     540
atcagcaaaa gcccggcaag gcccctaagc tgctgatcta cgatacctcc aagctggcct     600
ctggcgtgcc ctccagattt tctggcagcg gcagcggaac cgagttcacc ctgaccatct     660
caagcctgca gcctgacgac ttcgctacgt actactgctt ccaaggcagc ggctacccct     720
tcacatttgg cggcggaaca aagctggaaa tcaagcggac tgtggccgct cctagcgtgt     780
tcatctttcc acctagcgac gagcagctga agtctggcac tgcctctgtc gtgtgcctgc     840
tgaacaactt ctaccctcga gaggccaagg tgcagtggaa agtggacaat gccctgcaga     900
gcggcaacag ccaagagtct gtgaccgagc aggactccaa ggattccacc tacagcctgt     960
ctagcaccct gactctgagc aaggccgact acgagaagca caaggtgtac gcctgcgaag    1020
tgacacacca gggactgagc agccctgtga ccaagagctt caatcggggc gagtgcgag     1080 gaagtagtgg cagcgggagt gggtccaatt ggagtcatcc tcaatttgag aaaggagggg    1140
gagggtccaa ttggtctcat ccgcagtttg agagggcgg cggcggctcc aattggtccc    1200
atccccagtt tgaaaaaggc tctggtggag gtggtagtgc tggtgggcaa gtgaccctga    1260
gagagtctgg acctgctctg gtcaagccca cacagaccct gacactgacc tgcaccttca    1320
gcggctttag cctgagcaca agcggcatga gcgtcggctg gattagacag cctcctggca    1380
aagccctgga atggctggcc gacatttggt gggacgacaa aaggactac aaccccagcc    1440 tgaagtcccg gctgaccatc agcaaggaca ccagcaagaa ccaggtggtg ctgaaagtga    1500
ccaacatgga ccctgccgac accgccacct actactgtgc cagatccatg atcaccaact    1560
ggtacttcga cgtgtgggga gccggcacca caaccgtctc ttcaggtaag tctgctgtct    1620
ggggatagcg gggagccagg tgtactgggc caggcaaggg cttttggtgta ggactgcaag    1680 atcgctgcac agcagcgaat cgtgaaa                                         1707
```

<210> SEQ ID NO 110
<211> LENGTH: 450
<212> TYPE: DNA
<213> ORGANISM: Homo sapiens

<400> SEQUENCE: 110

```
tgtgacgccc ggagacagaa ggtctctggg tggctgggtt tttgtggggt gaggatggac    60
attctgccat tgtgattact actactacta ctacatggac gtctgggaca aagggaccac   120
ggtcaccgtc tcctcaggta agaatggcca ctctagggcc tttgttttct gctactgcct   180
gtggggtttc ctgagcattg caggttggtc ctcggggcat gttccgaggg acctgggcg    240 gactggccag gaggggatgg gcactggggt gccttgagga tctgggagcc tctgtggatt   300
ttccgatgcc tttggaaaat gggactcagg ttgggtgcgt ctgatggagt aactgagcct   360
gggggcttgg ggagccacat ttggacgaga tgcctgaaca aaccaggggt cttagtgatg   420
gctgaggaat gtgtctcagg agcggtgtct                                    450

<210> SEQ ID NO 111
<211> LENGTH: 300
<212> TYPE: DNA
<213> ORGANISM: Homo sapiens

<400> SEQUENCE: 111
gtaatcttta ggccaataaa atgtgggttc acagtgagga gtgcatcctg gggttggggt    60
ttgttctgca gcgggaagag cgctgtgcac agaaagctta gaaatggggc aagagatgct   120
tttcctcagg caggatttag ggcttggtct ctcagcatcc cacacttgta cagctgatgt   180
ggcatctgtg ttttctttct catcctagat caggctttga gctgtgaaat accctgcctc   240
atgcatatgc aaataacctg aggtcttctg agataaatat agatatattg gtgccctgag   300

<210> SEQ ID NO 112
<211> LENGTH: 78
<212> TYPE: DNA
<213> ORGANISM: Artificial Sequence
<220> FEATURE:
<223> OTHER INFORMATION: Signal peptide coding sequence

<400> SEQUENCE: 112
atggctaccg gcagcagaac aagcctgctg ctcgcttttg gactgctctg tctcccctgg    60
ttgcaagaag gcagcgcc                                                  78

<210> SEQ ID NO 113
<211> LENGTH: 717
<212> TYPE: DNA
<213> ORGANISM: Artificial Sequence
<220> FEATURE:
<223> OTHER INFORMATION: hRSV light chain coding sequence

<400> SEQUENCE: 113
atggctaccg gcagcagaac aagcctgctg ctcgcttttg gactgctctg tctcccctgg    60
ttgcaagaag gcagcgccga catccagatg acacagagcc tagcacact gtctgccagc   120 gtgggcgaca gagtgaccat cacatgcaag tgccagctga gcgtgggcta catgcactgg   180
tatcagcaaa agcccggcaa ggcccctaag ctgctgatct acgataccto caagctggcc   240 tctggcgtgc cctccagatt ttctggcagc ggcagcggaa ccgagttcac cctgaccatc   300
tcaagcctgc agcctgacga cttcgctacg tactactgct ccaaggcag cggctacccc   360 ttcacatttg gcgcggaac aaagctggaa atcaagcgga ctgtggccgc tcctagcgtg   420
ttcatctttc cacctagcga cgagcagctg aagtctggca ctgcctctgt cgtgtgcctg   480
ctgaacaact tctaccctcg agaggccaag gtgcagtgga agtgacaa tgccctgcag   540 agcggcaaca gccaagagtc tgtgaccgag caggactcca aggattccac ctacagcctg   600
```

```
tctagcaccc tgactctgag caaggccgac tacgagaagc acaaggtgta cgcctgcgaa      660
gtgacacacc agggactgag cagccctgtg accaagagct caatcgggg cgagtgc         717
```

<210> SEQ ID NO 114
<211> LENGTH: 321
<212> TYPE: DNA
<213> ORGANISM: Artificial Sequence
<220> FEATURE:
<223> OTHER INFORMATION: hRSV variable light chain coding sequence
<400> SEQUENCE: 114

```
gacatccaga tgacacagag ccctagcaca ctgtctgcca gcgtgggcga cagagtgacc       60
atcacatgca agtgccagct gagcgtgggc tacatgcact ggtatcagca aaagcccggc      120
aaggccccta gctgctgat ctacgatacc tccaagctgg cctctggcgt gccctccaga       180
ttttctggca gcggcagcgg aaccgagttc accctgacca tctcaagcct gcagcctgac     240
gacttcgcta cgtactactg cttccaaggc agcggctacc ccttcacatt tggcggcgga     300
acaaagctgg aaatcaagcg g                                                321
```

<210> SEQ ID NO 115
<211> LENGTH: 318
<212> TYPE: DNA
<213> ORGANISM: Artificial Sequence
<220> FEATURE:
<223> OTHER INFORMATION: kappa constant light chain coding sequence
<400> SEQUENCE: 115

```
actgtggccg ctcctagcgt gttcatcttt ccacctagcg acgagcagct gaagtctggc       60
actgcctctg tcgtgtgcct gctgaacaac ttctaccctc gagaggccaa ggtgcagtgg      120
aaagtggaca tgcccctgca gagcggcaac agccaagagt ctgtgaccga gcaggactcc     180
aaggattcca cctacagcct gtctagcacc ctgactctga gcaaggccga ctacgagaag     240
cacaaggtgt acgcctgcga agtgacacac cagggactga gcagccctgt gaccaagagc     300
ttcaatcggg gcgagtgc                                                    318
```

<210> SEQ ID NO 116
<211> LENGTH: 171
<212> TYPE: DNA
<213> ORGANISM: Artificial Sequence
<220> FEATURE:
<223> OTHER INFORMATION: GSSG-streptag linker coding sequence
<400> SEQUENCE: 116

```
ggaggaagta gtggcagcgg gagtgggtcc aattggagtc atcctcaatt tgagaaagga       60
gggggagggt ccaattggtc tcatccgcag tttgagaagg cgcggcggcgg ctccaattgg     120 tcccatcccc agtttgaaaa aggctctggt ggaggtggta gtgctggtgg g               171
```

<210> SEQ ID NO 117
<211> LENGTH: 357
<212> TYPE: DNA
<213> ORGANISM: Artificial Sequence
<220> FEATURE:
<223> OTHER INFORMATION: hRSV variable heavy chain coding sequence
<400> SEQUENCE: 117

```
caagtgaccc tgagagagtc tggacctgct ctggtcaagc ccacacagac cctgacactg       60
acctgcacct tcagcggctt tagcctgagc acaagcggta tgagcgtcgg ctggattaga      120
cagcctcctg gcaaagccct ggaatggctg gccgacattt ggtgggacga caagaaggac     180
```

```
tacaacccca gcctgaagtc ccggctgacc atcagcaagg acaccagcaa gaaccaggtg      240
gtgctgaaag tgaccaacat ggaccctgcc gacaccgcca cctactactg tgccagatcc      300
atgatcacca actggtactt cgacgtgtgg ggagccggca ccacaaccgt ctcttca         357
```

<210> SEQ ID NO 118
<211> LENGTH: 26
<212> TYPE: PRT
<213> ORGANISM: Artificial Sequence
<220> FEATURE:
<223> OTHER INFORMATION: signal peptide amino acid sequence

<400> SEQUENCE: 118

```
Met Ala Thr Gly Ser Arg Thr Ser Leu Leu Leu Ala Phe Gly Leu Leu
1               5                   10                  15

Cys Leu Pro Trp Leu Gln Glu Gly Ser Ala
            20                  25
```

<210> SEQ ID NO 119
<211> LENGTH: 239
<212> TYPE: PRT
<213> ORGANISM: Artificial Sequence
<220> FEATURE:
<223> OTHER INFORMATION: hRSV light chain amino acid sequence

<400> SEQUENCE: 119

```
Met Ala Thr Gly Ser Arg Thr Ser Leu Leu Leu Ala Phe Gly Leu Leu
1               5                   10                  15

Cys Leu Pro Trp Leu Gln Glu Gly Ser Ala Asp Ile Gln Met Thr Gln
            20                  25                  30

Ser Pro Ser Thr Leu Ser Ala Ser Val Gly Asp Arg Val Thr Ile Thr
        35                  40                  45

Cys Lys Cys Gln Leu Ser Val Gly Tyr Met His Trp Tyr Gln Gln Lys
    50                  55                  60

Pro Gly Lys Ala Pro Lys Leu Leu Ile Tyr Asp Thr Ser Lys Leu Ala
65                  70                  75                  80

Ser Gly Val Pro Ser Arg Phe Ser Gly Ser Gly Ser Gly Thr Glu Phe
                85                  90                  95

Thr Leu Thr Ile Ser Ser Leu Gln Pro Asp Asp Phe Ala Thr Tyr Tyr
            100                 105                 110

Cys Phe Gln Gly Ser Gly Tyr Pro Phe Thr Phe Gly Gly Gly Thr Lys
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235
```

```
<210> SEQ ID NO 120
<211> LENGTH: 107
<212> TYPE: PRT
<213> ORGANISM: Artificial Sequence
<220> FEATURE:
<223> OTHER INFORMATION: hRSV variable light chain amino acid sequence

<400> SEQUENCE: 120

Asp Ile Gln Met Thr Gln Ser Pro Ser Thr Leu Ser Ala Ser Val Gly
1               5                   10                  15

Asp Arg Val Thr Ile Thr Cys Lys Cys Gln Leu Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys Arg
            100                 105

<210> SEQ ID NO 121
<211> LENGTH: 106
<212> TYPE: PRT
<213> ORGANISM: Artificial Sequence
<220> FEATURE:
<223> OTHER INFORMATION: kappa constant light chain amino acid sequence

<400> SEQUENCE: 121

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 122
<211> LENGTH: 57
<212> TYPE: PRT
<213> ORGANISM: Artificial Sequence
<220> FEATURE:
<223> OTHER INFORMATION: GSSG-streptag linker amino acid sequence

<400> SEQUENCE: 122

Gly Gly Ser Ser Gly Ser Gly Ser Gly Ser Asn Trp Ser His Pro Gln
1               5                   10                  15

Phe Glu Lys Gly Gly Gly Gly Ser Asn Trp Ser His Pro Gln Phe Glu
            20                  25                  30

Lys Gly Gly Gly Gly Ser Asn Trp Ser His Pro Gln Phe Glu Lys Gly
        35                  40                  45
```

```
Ser Gly Gly Gly Gly Ser Ala Gly Gly
    50              55
```

<210> SEQ ID NO 123
<211> LENGTH: 119
<212> TYPE: PRT
<213> ORGANISM: Artificial Sequence
<220> FEATURE:
<223> OTHER INFORMATION: hRSV variable heavy chain amino acid sequence

<400> SEQUENCE: 123

```
Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Trp Tyr Phe Asp Val Trp Gly Ala
            100                 105                 110

Gly Thr Thr Thr Val Ser Ser
        115
```

<210> SEQ ID NO 124
<211> LENGTH: 67
<212> TYPE: DNA
<213> ORGANISM: Artificial Sequence
<220> FEATURE:
<223> OTHER INFORMATION: splice junction with flanking sequence in
      constructs of disclosure

<400> SEQUENCE: 124

```
caggtaagtc tgctgtctgg ggatagcggg gagccaggtg tactgggcca ggcaagggct    60
ttggatc                                                              67
```

<210> SEQ ID NO 125
<211> LENGTH: 450
<212> TYPE: DNA
<213> ORGANISM: Homo sapiens

<400> SEQUENCE: 125

```
gtaggactgc aagatcgctg cacagcagcg aatcgtgaaa tatttctttt agaattatga    60
ggtgcgctgt gtgtcaacct gcatcttaaa ttctttattg gctggaaaga gaactgtcgg   120
agtgggtgaa tccagccagg agggacgcgt agccccggtc ttgatgagag cagggttggg   180
ggcaggggta gcccagaaac ggtggctgcc gtcctgacag gggcttaggg aggctccagg   240
acctcagtgc cttgaagctg gtttccatga gaaaaggatt gtttatctta ggaggcatgc   300
ttactgttaa aagacaggat atgtttgaag tggcttctga gaaaaatggt taagaaaatt   360
atgacttaaa aatgtgagag attttcaagt atattaattt ttttaactgt ccaagtattt   420
gaaattctta tcatttgatt aacacccatg                                   450
```

<210> SEQ ID NO 126

<211> LENGTH: 415
<212> TYPE: PRT
<213> ORGANISM: Artificial Sequence
<220> FEATURE:
<223> OTHER INFORMATION: signal peptide-light chain-streptag linker-variable heavy chain amino acid sequence in human anti-RSV emAb AAV

<400> SEQUENCE: 126

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Asp Ile Gln Met Thr Gln
            20                  25                  30

Ser Pro Ser Thr Leu Ser Ala Ser Val Gly Asp Arg Val Thr Ile Thr
        35                  40                  45

Cys Lys Cys Gln Leu Ser Val Gly Tyr Met His Trp Tyr Gln Gln Lys
    50                  55                  60

Pro Gly Lys Ala Pro Lys Leu Leu Ile Tyr Asp Thr Ser Lys Leu Ala
65                  70                  75                  80

Ser Gly Val Pro Ser Arg Phe Ser Gly Ser Gly Ser Gly Thr Glu Phe
                85                  90                  95

Thr Leu Thr Ile Ser Ser Leu Gln Pro Asp Asp Phe Ala Thr Tyr Tyr
            100                 105                 110

Cys Phe Gln Gly Ser Gly Tyr Pro Phe Thr Phe Gly Gly Gly Thr Lys
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys Gly
225                 230                 235                 240

Gly Ser Ser Gly Ser Gly Ser Gly Ser Asn Trp Ser His Pro Gln Phe
                245                 250                 255

Glu Lys Gly Gly Gly Ser Asn Trp Ser His Pro Gln Phe Glu Lys
            260                 265                 270

Gly Gly Gly Gly Ser Asn Trp Ser His Pro Gln Phe Glu Lys Gly Ser
        275                 280                 285

Gly Gly Gly Gly Ser Ala Gly Gly Gln Val Thr Leu Arg Glu Ser Gly
    290                 295                 300

Pro Ala Leu Val Lys Pro Thr Gln Thr Leu Thr Leu Thr Cys Thr Phe
305                 310                 315                 320

Ser Gly Phe Ser Leu Ser Thr Ser Gly Met Ser Val Gly Trp Ile Arg
                325                 330                 335

Gln Pro Pro Gly Lys Ala Leu Glu Trp Leu Ala Asp Ile Trp Trp Asp
            340                 345                 350

Asp Lys Lys Asp Tyr Asn Pro Ser Leu Lys Ser Arg Leu Thr Ile Ser
        355                 360                 365

Lys Asp Thr Ser Lys Asn Gln Val Val Leu Lys Val Thr Asn Met Asp
    370                 375                 380

Pro Ala Asp Thr Ala Thr Tyr Tyr Cys Ala Arg Ser Met Ile Thr Asn
385                 390                 395                 400

Trp Tyr Phe Asp Val Trp Gly Ala Gly Thr Thr Thr Val Ser Ser
                405                 410                 415

<210> SEQ ID NO 127
<211> LENGTH: 502
<212> TYPE: DNA
<213> ORGANISM: Mus musculus

<400> SEQUENCE: 127

| | | |
|---|---|---|
| ccagggtga ttctagtcag actctggggt ttttgtcggg tatagaggaa aaatccacta | 60 | |
| ttgtgattac tatgctatgg actactgggg tcaaggaacc tcagtcaccg tctcctcagg | 120 | |
| taagaatggc ctctccaggt ctttattttt aacctttgtt atggagtttt ctgagcattg | 180 | |
| cagactaatc ttggatattt gtccctgagg gagccggctg agagaagttg ggaaataaac | 240 | |
| tgtctaggga tctcagagcc tttaggacag attatctcca catctttgaa aaactaagaa | 300 | |
| tctgtgtgat ggtgttggtg gagtccctgg atgatgggat agggactttg gaggctcatt | 360 | |
| tgagggagat gctaaaacaa tcctatggct ggagggatag ttggggctgt agttggagat | 420 | |
| tttcagtttt tagaataaaa gtattagttg tggaatatac ttcaggacca cctctgtgac | 480 | |
| agcatttata cagtatccga tg | 502 | |

<210> SEQ ID NO 128
<211> LENGTH: 319
<212> TYPE: DNA
<213> ORGANISM: Mus musculus

<400> SEQUENCE: 128

| | |
|---|---|
| gacaagtgag tgtctcaggt taggattcta ttttaagatt gagatattag gctttgatac | 60 |
| tacatctaaa tggtctgtac atgtctcgaa gaaagttctt cagacagagt taggacttgg | 120 |
| atccaggagt taggacttgg actgactcag gaggactcta gtttcttctt ctccagctgg | 180 |
| aatgtcctta tgtaagaaaa gccttgcctc atgagtatgc aaatcatgtg cgactgtgat | 240 |
| gattaatata gggatatcca caccaaacat catatgagcc ctatcttctc tacagacact | 300 |
| gaatctcaag gtccttaca | 319 |

<210> SEQ ID NO 129
<211> LENGTH: 60
<212> TYPE: DNA
<213> ORGANISM: Artificial Sequence
<220> FEATURE:
<223> OTHER INFORMATION: Signal peptide coding sequence

<400> SEQUENCE: 129
atggaaaccg acacactgct gctgtgggtg ctgcttcttt gggtgcccgg aagcacaggc    60

<210> SEQ ID NO 130
<211> LENGTH: 696
<212> TYPE: DNA
<213> ORGANISM: Artificial Sequence
<220> FEATURE:
<223> OTHER INFORMATION: mRSV kappa light chain coding sequence

<400> SEQUENCE: 130
atggaaaccg acacactgct gctgtgggtg ctgcttcttt gggtgcccgg aagcacaggc    60

```
gacatccagc tgacacagag ccctgccatc atgtctgcta gccctggcga gaaagtgaca      120
atgacctgtt ccgccagcag ctccgtgggc tacatgcact ggtatcagca gaagtctagc      180
acaagcccca agctgtggat ctacgacacc tccaagctgg cctctggcgt gccaggcaga      240
ttttctggaa gcggcagcgg caacagctac agcctgacta tcagctccat ccaggccgag      300
gatgtggcta cctactactg cttcagaggc agcggctacc ccttcacatt tggccagggc      360
accaagctgg aaatcaaggc cgatgccgct cctaccgtgt ctatctttcc acctagcagc      420
gagcagctga catctggcgg agcctctgtc gtgtgcttcc tgaacaactt ctaccctaag      480
gacatcaacg tcaagtggaa gatcgacggc tccgagagac agaacggcgt gctgaactct      540
tggaccgacc aggacagcaa ggatagcacc tacagcatga gcagcactct gaccctgaca      600
aaggacgagt acgagaggca caactcctac acatgcgagg ccacacacaa gaccagcaca      660
tccccaatcg tgaagtcctt caaccggaac gagtgc                               696
```

<210> SEQ ID NO 131
<211> LENGTH: 318
<212> TYPE: DNA
<213> ORGANISM: Artificial Sequence
<220> FEATURE:
<223> OTHER INFORMATION: mPalivizumab variable light chain coding
      sequence

<400> SEQUENCE: 131

```
gacatccagc tgacacagag ccctgccatc atgtctgcta gccctggcga gaaagtgaca       60
atgacctgtt ccgccagcag ctccgtgggc tacatgcact ggtatcagca gaagtctagc      120
acaagcccca agctgtggat ctacgacacc tccaagctgg cctctggcgt gccaggcaga      180
ttttctggaa gcggcagcgg caacagctac agcctgacta tcagctccat ccaggccgag      240
gatgtggcta cctactactg cttcagaggc agcggctacc ccttcacatt tggccagggc      300
accaagctgg aaatcaag                                                   318
```

<210> SEQ ID NO 132
<211> LENGTH: 318
<212> TYPE: DNA
<213> ORGANISM: Artificial Sequence
<220> FEATURE:
<223> OTHER INFORMATION: mIgL kappa constant light chain coding sequence

<400> SEQUENCE: 132

```
gccgatgccg ctcctaccgt gtctatcttt ccacctagca gcgagcagct gacatctggc       60
ggagcctctg tcgtgtgctt cctgaacaac ttctacccta aggacatcaa cgtcaagtgg      120
aagatcgacg gctccgagag acagaacggc gtgctgaact cttggaccga ccaggacagc      180
aaggatagca cctacagcat gagcagcact ctgaccctga caaaggacga gtacgagagg      240
cacaactcct acacatgcga ggccacacac aagaccagca tccccaatcg tgaagtcc       300 ttcaaccgga acgagtgc                                                   318
```

<210> SEQ ID NO 133
<211> LENGTH: 360
<212> TYPE: DNA
<213> ORGANISM: Artificial Sequence
<220> FEATURE:
<223> OTHER INFORMATION: mPalivizumab variable heavy chain coding
      sequence

<400> SEQUENCE: 133

```
caggtggaac tgcaagaaag cggccctggc atcctgcagc cttctcagac actgagcctg       60
```

```
acctgtagct tcagcggctt cagcctgagc acaagcggca tgtctgtcgg ctggatcaga    120
cagccttctg gcgaaggact ggaatggctg gccgacattt ggtgggacga caagaaggac    180
tacaacccca gcctgaagtc cagactgacc atcagcaagg acaccagcag caaccaggtg    240
ttcctgaaga tcaccggcgt ggacacagcc gataccgcca cctattactg cgccagatcc    300
atgatcacca actggtactt cgacgtgtgg ggcgctggca ccacagtgac cgtctcctca    360
```

<210> SEQ ID NO 134
<211> LENGTH: 20
<212> TYPE: PRT
<213> ORGANISM: Artificial Sequence
<220> FEATURE:
<223> OTHER INFORMATION: Signal peptide amino acid sequence

<400> SEQUENCE: 134

Met Glu Thr Asp Thr Leu Leu Leu Trp Val Leu Leu Leu Trp Val Pro
1               5                   10                  15

Gly Ser Thr Gly
            20

<210> SEQ ID NO 135
<211> LENGTH: 232
<212> TYPE: PRT
<213> ORGANISM: Artificial Sequence
<220> FEATURE:
<223> OTHER INFORMATION: mRSV kappa light chain amino acid sequence

<400> SEQUENCE: 135

Met Glu Thr Asp Thr Leu Leu Leu Trp Val Leu Leu Leu Trp Val Pro
1               5                   10                  15

Gly Ser Thr Gly Asp Ile Gln Leu Thr Gln Ser Pro Ala Ile Met Ser
            20                  25                  30

Ala Ser Pro Gly Glu Lys Val Thr Met Thr Cys Ser Ala Ser Ser Ser
        35                  40                  45

Val Gly Tyr Met His Trp Tyr Gln Gln Lys Ser Ser Thr Ser Pro Lys
    50                  55                  60

Leu Trp Ile Tyr Asp Thr Ser Lys Leu Ala Ser Gly Val Pro Gly Arg
65                  70                  75                  80

Phe Ser Gly Ser Gly Ser Gly Asn Ser Tyr Ser Leu Thr Ile Ser Ser
                85                  90                  95

Ile Gln Ala Glu Asp Val Ala Thr Tyr Tyr Cys Phe Arg Gly Ser Gly
            100                 105                 110

Tyr Pro Phe Thr Phe Gly Gln Gly Thr Lys Leu Glu Ile Lys Ala Asp
        115                 120                 125

Ala Ala Pro Thr Val Ser Ile Phe Pro Pro Ser Glu Gln Leu Thr
    130                 135                 140

Ser Gly Gly Ala Ser Val Val Cys Phe Leu Asn Asn Phe Tyr Pro Lys
145                 150                 155                 160

Asp Ile Asn Val Lys Trp Lys Ile Asp Gly Ser Glu Arg Gln Asn Gly
                165                 170                 175

Val Leu Asn Ser Trp Thr Asp Gln Asp Ser Lys Asp Ser Thr Tyr Ser
            180                 185                 190

Met Ser Ser Thr Leu Thr Leu Thr Lys Asp Glu Tyr Glu Arg His Asn
        195                 200                 205

Ser Tyr Thr Cys Glu Ala Thr His Lys Thr Ser Thr Ser Pro Ile Val
    210                 215                 220

```
Lys Ser Phe Asn Arg Asn Glu Cys
225                 230

<210> SEQ ID NO 136
<211> LENGTH: 106
<212> TYPE: PRT
<213> ORGANISM: Artificial Sequence
<220> FEATURE:
<223> OTHER INFORMATION: mPalivizumab variable light chain amino acid
      sequence

<400> SEQUENCE: 136

Asp Ile Gln Leu Thr Gln Ser Pro Ala Ile Met Ser Ala Ser Pro Gly
1               5                   10                  15

Glu Lys Val Thr Met Thr Cys Ser Ala Ser Ser Ser Val Gly Tyr Met
            20                  25                  30

His Trp Tyr Gln Gln Lys Ser Ser Thr Ser Pro Lys Leu Trp Ile Tyr
        35                  40                  45

Asp Thr Ser Lys Leu Ala Ser Gly Val Pro Gly Arg Phe Ser Gly Ser
    50                  55                  60

Gly Ser Gly Asn Ser Tyr Ser Leu Thr Ile Ser Ser Ile Gln Ala Glu
65                  70                  75                  80

Asp Val Ala Thr Tyr Tyr Cys Phe Arg Gly Ser Gly Tyr Pro Phe Thr
                85                  90                  95

Phe Gly Gln Gly Thr Lys Leu Glu Ile Lys
            100                 105

<210> SEQ ID NO 137
<211> LENGTH: 106
<212> TYPE: PRT
<213> ORGANISM: Artificial Sequence
<220> FEATURE:
<223> OTHER INFORMATION: mIgL kappa constant light chain amino acid
      sequence

<400> SEQUENCE: 137

Ala Asp Ala Ala Pro Thr Val Ser Ile Phe Pro Pro Ser Ser Glu Gln
1               5                   10                  15

Leu Thr Ser Gly Gly Ala Ser Val Val Cys Phe Leu Asn Asn Phe Tyr
            20                  25                  30

Pro Lys Asp Ile Asn Val Lys Trp Lys Ile Asp Gly Ser Glu Arg Gln
        35                  40                  45

Asn Gly Val Leu Asn Ser Trp Thr Asp Gln Asp Ser Lys Asp Ser Thr
    50                  55                  60

Tyr Ser Met Ser Ser Thr Leu Thr Leu Thr Lys Asp Glu Tyr Glu Arg
65                  70                  75                  80

His Asn Ser Tyr Thr Cys Glu Ala Thr His Lys Thr Ser Thr Ser Pro
                85                  90                  95

Ile Val Lys Ser Phe Asn Arg Asn Glu Cys
            100                 105

<210> SEQ ID NO 138
<211> LENGTH: 120
<212> TYPE: PRT
<213> ORGANISM: Artificial Sequence
<220> FEATURE:
<223> OTHER INFORMATION: mPalivizumab variable heavy chain amino acid
      sequence

<400> SEQUENCE: 138

Gln Val Glu Leu Gln Glu Ser Gly Pro Gly Ile Leu Gln Pro Ser Gln
```

```
              1               5                  10                  15
            Thr Leu Ser Leu Thr Cys Ser Phe Ser Gly Phe Ser Leu Ser Thr Ser
                            20                  25                  30

Gly Met Ser Val Gly Trp Ile Arg Gln Pro Ser Gly Glu Gly Leu Glu
                            35                  40                  45

Trp Leu Ala Asp Ile Trp Trp Asp Asp Lys Lys Asp Tyr Asn Pro Ser
                50                  55                  60

Leu Lys Ser Arg Leu Thr Ile Ser Lys Asp Thr Ser Ser Asn Gln Val
            65                  70                  75                  80

Phe Leu Lys Ile Thr Gly Val Asp Thr Ala Asp Thr Ala Thr Tyr Tyr
                            85                  90                  95

Cys Ala Arg Ser Met Ile Thr Asn Trp Tyr Phe Asp Val Trp Gly Ala
                            100                 105                 110

Gly Thr Thr Val Thr Val Ser Ser
                        115                 120

<210> SEQ ID NO 139
<211> LENGTH: 64
<212> TYPE: DNA
<213> ORGANISM: Artificial Sequence
<220> FEATURE:
<223> OTHER INFORMATION: splice junction with flanking sequence

<400> SEQUENCE: 139
caggtgagtc ctaacttctc ccattctaaa tgcatgttgg ggggattctg ggccttcagg      60
acca                                                                  64

<210> SEQ ID NO 140
<211> LENGTH: 968
<212> TYPE: DNA
<213> ORGANISM: Mus musculus

<400> SEQUENCE: 140
catagggaca aagagtggag tggggcactt tctttagatt tgtgaggaat gttccgcact      60
agattgttta aaacttcatt tgttggaagg agagctgtct tagtgattga gtcaagggag     120
aaaggcatct agcctcggtc tcaaaagggt agttgctgtc tagagaggtc tggtggagcc     180
tgcaaaagtc cagcttttca aggaacacag aagtatgtgt atggaatatt agaagatgtt     240
gcttttactc ttaagttggt tcctaggaaa atagttaaa tactgtgact ttaaaatgtg      300
agagggtttt caagtactca tttttttaaa tgtccaaaat ttttgtcaat cagtttgagg     360
tcttgtttgt gtagaactga tattacttaa agtttaaccg aggaatggga gtgaggctct     420
ctcataacct attcagaact gacttttaac aataataaat taagtttaaa atatttttaa     480
atgaattgag caatgttgag ttggagtcaa gatggccgat cagaaccaga acacctgcag     540
cagctggcag gaagcaggtc atgtggcaag ctatttggg gaagggaaaa taaaaccact      600
aggtaaactt gtagctgtgg tttgaagaag tggttttgaa acactctgtc cagccccacc     660
aaaccgaaag tccaggctga gcaaaacacc acctgggtaa tttgcatttc taaaataagt     720
tgaggattca gccgaaactg gagaggtcct cttttaactt attgagttca accttttaat     780
tttagcttga gtagttctag tttccccaaa cttaagttta tcgacttcta aaatgtattt     840
agaattcatt ttcaaaatta ggttatgtaa gaaattgaag gactttagtg tctttaattt     900
ctaatatatt tagaaaactt cttaaaatta ctctattatt cttccctctg attattggtc     960
tccattca                                                             968
```

<210> SEQ ID NO 141
<211> LENGTH: 409
<212> TYPE: PRT
<213> ORGANISM: Artificial Sequence
<220> FEATURE:
<223> OTHER INFORMATION: signal peptide-light chain-streptag linker-variable heavy chain amino acid sequence in mouse anti-RSV emAb AAV

<400> SEQUENCE: 141

```
Met Glu Thr Asp Thr Leu Leu Leu Trp Val Leu Leu Leu Trp Val Pro
1               5                   10                  15

Gly Ser Thr Gly Asp Ile Gln Leu Thr Gln Ser Pro Ala Ile Met Ser
            20                  25                  30

Ala Ser Pro Gly Glu Lys Val Thr Met Thr Cys Ser Ala Ser Ser Ser
        35                  40                  45

Val Gly Tyr Met His Trp Tyr Gln Gln Lys Ser Ser Thr Ser Pro Lys
    50                  55                  60

Leu Trp Ile Tyr Asp Thr Ser Lys Leu Ala Ser Gly Val Pro Gly Arg
65                  70                  75                  80

Phe Ser Gly Ser Gly Ser Gly Asn Ser Tyr Ser Leu Thr Ile Ser Ser
                85                  90                  95

Ile Gln Ala Glu Asp Val Ala Thr Tyr Tyr Cys Phe Arg Gly Ser Gly
            100                 105                 110

Tyr Pro Phe Thr Phe Gly Gln Gly Thr Lys Leu Glu Ile Lys Ala Asp
        115                 120                 125

Ala Ala Pro Thr Val Ser Ile Phe Pro Pro Ser Ser Glu Gln Leu Thr
    130                 135                 140

Ser Gly Gly Ala Ser Val Val Cys Phe Leu Asn Asn Phe Tyr Pro Lys
145                 150                 155                 160

Asp Ile Asn Val Lys Trp Lys Ile Asp Gly Ser Glu Arg Gln Asn Gly
                165                 170                 175

Val Leu Asn Ser Trp Thr Asp Gln Asp Ser Lys Asp Ser Thr Tyr Ser
            180                 185                 190

Met Ser Ser Thr Leu Thr Leu Thr Lys Asp Glu Tyr Glu Arg His Asn
        195                 200                 205

Ser Tyr Thr Cys Glu Ala Thr His Lys Thr Ser Thr Ser Pro Ile Val
    210                 215                 220

Lys Ser Phe Asn Arg Asn Glu Cys Gly Gly Ser Gly Ser Gly Ser Gly
225                 230                 235                 240

Gly Ser Asn Trp Ser His Pro Gln Phe Glu Lys Gly Gly Gly Gly Ser
                245                 250                 255

Asn Trp Ser His Pro Gln Phe Glu Lys Gly Gly Gly Gly Ser Asn Trp
            260                 265                 270

Ser His Pro Gln Phe Glu Lys Gly Ser Gly Gly Gly Ser Ala Gly
        275                 280                 285

Gly Gln Val Glu Leu Gln Glu Ser Gly Pro Gly Ile Leu Gln Pro Ser
    290                 295                 300

Gln Thr Leu Ser Leu Thr Cys Ser Phe Ser Gly Phe Ser Leu Ser Thr
305                 310                 315                 320

Ser Gly Met Ser Val Gly Trp Ile Arg Gln Pro Ser Gly Glu Gly Leu
                325                 330                 335

Glu Trp Leu Ala Asp Ile Trp Trp Asp Asp Lys Lys Asp Tyr Asn Pro
            340                 345                 350

Ser Leu Lys Ser Arg Leu Thr Ile Ser Lys Asp Thr Ser Ser Asn Gln
```

```
                355                 360                 365
Val Phe Leu Lys Ile Thr Gly Val Asp Thr Ala Asp Thr Ala Thr Tyr
    370                 375                 380

Tyr Cys Ala Arg Ser Met Ile Thr Asn Trp Tyr Phe Asp Val Trp Gly
385                 390                 395                 400

Ala Gly Thr Thr Val Thr Val Ser Ser
                405

<210> SEQ ID NO 142
<211> LENGTH: 39
<212> TYPE: DNA
<213> ORGANISM: Mus musculus

<400> SEQUENCE: 142
accacctctg tgacagcatt tatacagtat ccgatggat                          39

<210> SEQ ID NO 143
<211> LENGTH: 39
<212> TYPE: DNA
<213> ORGANISM: Mus musculus

<400> SEQUENCE: 143
atccataggg acaaagagtg gagtggggca ctttctttta                         39

<210> SEQ ID NO 144
<211> LENGTH: 409
<212> TYPE: PRT
<213> ORGANISM: Artificial Sequence
<220> FEATURE:
<223> OTHER INFORMATION: signal peptide-light chain-streptag linker-
      variable heavy chain amino acid sequence in ms-emAb-RSV-dsDNA

<400> SEQUENCE: 144

Met Glu Thr Asp Thr Leu Leu Leu Trp Val Leu Leu Trp Val Pro
1               5                   10                  15

Gly Ser Thr Gly Asp Ile Gln Leu Thr Gln Ser Pro Ala Ile Met Ser
                20                  25                  30

Ala Ser Pro Gly Glu Lys Val Thr Met Thr Cys Ser Ala Ser Ser Ser
            35                  40                  45

Val Gly Tyr Met His Trp Tyr Gln Gln Lys Ser Ser Thr Ser Pro Lys
    50                  55                  60

Leu Trp Ile Tyr Asp Thr Ser Lys Leu Ala Ser Gly Val Pro Gly Arg
65                  70                  75                  80

Phe Ser Gly Ser Gly Ser Gly Asn Ser Tyr Ser Leu Thr Ile Ser Ser
                85                  90                  95

Ile Gln Ala Glu Asp Val Ala Thr Tyr Tyr Cys Phe Arg Gly Ser Gly
            100                 105                 110

Tyr Pro Phe Thr Phe Gly Gln Gly Thr Lys Leu Glu Ile Lys Ala Asp
    115                 120                 125

Ala Ala Pro Thr Val Ser Ile Phe Pro Pro Ser Ser Glu Gln Leu Thr
        130                 135                 140

Ser Gly Gly Ala Ser Val Val Cys Phe Leu Asn Asn Phe Tyr Pro Lys
145                 150                 155                 160

Asp Ile Asn Val Lys Trp Lys Ile Asp Gly Ser Glu Arg Gln Asn Gly
                165                 170                 175

Val Leu Asn Ser Trp Thr Asp Gln Asp Ser Lys Asp Ser Thr Tyr Ser
            180                 185                 190

Met Ser Ser Thr Leu Thr Leu Thr Lys Asp Glu Tyr Glu Arg His Asn
```

```
                195                 200                 205
Ser Tyr Thr Cys Glu Ala Thr His Lys Thr Ser Thr Ser Pro Ile Val
    210                 215                 220
Lys Ser Phe Asn Arg Asn Glu Cys Gly Gly Ser Ser Gly Ser Gly Ser
225                 230                 235                 240
Gly Ser Asn Trp Ser His Pro Gln Phe Glu Lys Gly Gly Gly Gly Ser
                245                 250                 255
Asn Trp Ser His Pro Gln Phe Glu Lys Gly Gly Gly Gly Ser Asn Trp
            260                 265                 270
Ser His Pro Gln Phe Glu Lys Gly Ser Gly Gly Ser Ala Gly
        275                 280                 285
Gly Gln Val Glu Leu Gln Glu Ser Gly Pro Gly Ile Leu Gln Pro Ser
290                 295                 300
Gln Thr Leu Ser Leu Thr Cys Ser Phe Ser Gly Phe Ser Leu Ser Thr
305                 310                 315                 320
Ser Gly Met Ser Val Gly Trp Ile Arg Gln Pro Ser Gly Glu Gly Leu
                325                 330                 335
Glu Trp Leu Ala Asp Ile Trp Trp Asp Asp Lys Lys Asp Tyr Asn Pro
            340                 345                 350
Ser Leu Lys Ser Arg Leu Thr Ile Ser Lys Asp Thr Ser Ser Asn Gln
        355                 360                 365
Val Phe Leu Lys Ile Thr Gly Val Asp Thr Ala Asp Thr Ala Thr Tyr
    370                 375                 380
Tyr Cys Ala Arg Ser Met Ile Thr Asn Trp Tyr Phe Asp Val Trp Gly
385                 390                 395                 400
Ala Gly Thr Thr Val Thr Val Ser Ser
                405

<210> SEQ ID NO 145
<211> LENGTH: 708
<212> TYPE: DNA
<213> ORGANISM: Artificial Sequence
<220> FEATURE:
<223> OTHER INFORMATION: VRC01 light chain coding sequence

<400> SEQUENCE: 145
atggctaccg gcagcagaac aagcctgctg ctcgcttttg gactgctctg tctccctgg      60 ttgcaagaag gcagcgccga aattgtgttg acacagtctc caggcaccct gtctttgtct     120 ccagggaaa cagccatcat ctcttgtcgg accagtcagt atggttcctt agcctggtat     180
caacagaggc ccggccaggc ccccaggctc gtcatctatt cgggctctac tcgggccgct     240
ggcatcccag acaggttcag cggcagtcgg tgggggccag actacaatct caccatcagc     300
aacctggagt cgggagattt tggtgtttat tattgccagc agtatgaatt ttttggccag     360
gggaccaagg tccaggtcga cattaagcgc actgtggccg ctcctagcgt gttcatcttt     420
ccacctagcg acgagcagct gaagtctggc actgcctctg tcgtgtgcct gctgaacaac     480
ttctaccctc gagaggccaa ggtgcagtgg aaagtggaca atgccctgca gagcggcaac     540
agccaagagt ctgtgaccga gcaggactcc aaggattcca cctacagcct gtctagcacc     600
ctgactctga gcaaggccga ctacgagaag cacaaggtgt acgcctgcga agtgacacac     660
cagggactga gcagccctgt gaccaagagc ttcaatcggg gcgagtgc                   708

<210> SEQ ID NO 146
<211> LENGTH: 312
<212> TYPE: DNA
```

<213> ORGANISM: Artificial Sequence
<220> FEATURE:
<223> OTHER INFORMATION: VRC01 variable light chain coding sequence

<400> SEQUENCE: 146

```
gaaattgtgt tgacacagtc tccaggcacc ctgtctttgt ctccagggga aacagccatc    60
atctcttgtc ggaccagtca gtatggttcc ttagcctggt atcaacagag gcccggccag   120
gcccccaggc tcgtcatcta ttcgggctct actcgggccg ctggcatccc agacaggttc   180
agcggcagtc ggtgggggcc agactacaat ctcaccatca gcaacctgga gtcgggagat   240
tttggtgttt attattgcca gcagtatgaa ttttttggcc aggggaccaa ggtccaggtc   300
gacattaagc gc                                                       312
```

<210> SEQ ID NO 147
<211> LENGTH: 363
<212> TYPE: DNA
<213> ORGANISM: Artificial Sequence
<220> FEATURE:
<223> OTHER INFORMATION: VRC01 variable heavy chain coding sequence

<400> SEQUENCE: 147

```
caggtgcagc tggtgcagtc tgggggtcag atgaagaagc tggcgagtc gatgagaatt    60
tcttgtcggg cttctggata tgaatttatt gattgtacgc taaattggat tcgtctggcc   120
cccgaaaaaa ggcctgagtg gatgggatgg ctgaagcctc gaggtggcgc ggtcaactac   180
gcacgtccac ttcagggcag agtgaccatg actcgagacg tttattccga cacagccttt   240
ttggagctgc gctcgttgac agtagacgac acggccgtct actttgtac taggggaaaa   300
aactgtgatt acaattggga cttcgaacac tggggccggg gcaccccggt catcgtctca   360
tca                                                                 363
```

<210> SEQ ID NO 148
<211> LENGTH: 236
<212> TYPE: PRT
<213> ORGANISM: Artificial Sequence
<220> FEATURE:
<223> OTHER INFORMATION: VRC01 light chain amino acid sequence

<400> SEQUENCE: 148

```
Met Ala Thr Gly Ser Arg Thr Ser Leu Leu Leu Ala Phe Gly Leu Leu
1               5                   10                  15

Cys Leu Pro Trp Leu Gln Glu Gly Ser Ala Glu Ile Val Leu Thr Gln
            20                  25                  30

Ser Pro Gly Thr Leu Ser Leu Ser Pro Gly Glu Thr Ala Ile Ile Ser
        35                  40                  45

Cys Arg Thr Ser Gln Tyr Gly Ser Leu Ala Trp Tyr Gln Gln Arg Pro
    50                  55                  60

Gly Gln Ala Pro Arg Leu Val Ile Tyr Ser Gly Ser Thr Arg Ala Ala
65                  70                  75                  80

Gly Ile Pro Asp Arg Phe Ser Gly Ser Arg Trp Gly Pro Asp Tyr Asn
                85                  90                  95

Leu Thr Ile Ser Asn Leu Glu Ser Gly Asp Phe Gly Val Tyr Tyr Cys
            100                 105                 110

Gln Gln Tyr Glu Phe Phe Gly Gln Gly Thr Lys Val Gln Val Asp Ile
        115                 120                 125

Lys Arg Thr Val Ala Ala Pro Ser Val Phe Ile Phe Pro Pro Ser Asp
    130                 135                 140
```

```
Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 149
<211> LENGTH: 104
<212> TYPE: PRT
<213> ORGANISM: Artificial Sequence
<220> FEATURE:
<223> OTHER INFORMATION: VRC01 variable light chain amino acid sequence

<400> SEQUENCE: 149

```
Glu Ile Val Leu Thr Gln Ser Pro Gly Thr Leu Ser Leu Ser Pro Gly
1               5                   10                  15

Glu Thr Ala Ile Ile Ser Cys Arg Thr Ser Gln Tyr Gly Ser Leu Ala
            20                  25                  30

Trp Tyr Gln Gln Arg Pro Gly Gln Ala Pro Arg Leu Val Ile Tyr Ser
        35                  40                  45

Gly Ser Thr Arg Ala Ala Gly Ile Pro Asp Arg Phe Ser Gly Ser Arg
50                  55                  60

Trp Gly Pro Asp Tyr Asn Leu Thr Ile Ser Asn Leu Glu Ser Gly Asp
65                  70                  75                  80

Phe Gly Val Tyr Tyr Cys Gln Gln Tyr Glu Phe Phe Gly Gln Gly Thr
                85                  90                  95

Lys Val Gln Val Asp Ile Lys Arg
            100
```

<210> SEQ ID NO 150
<211> LENGTH: 121
<212> TYPE: PRT
<213> ORGANISM: Artificial Sequence
<220> FEATURE:
<223> OTHER INFORMATION: VRC01 variable heavy chain amino acid sequence

<400> SEQUENCE: 150

```
Gln Val Gln Leu Val Gln Ser Gly Gly Gln Met Lys Lys Pro Gly Glu
1               5                   10                  15

Ser Met Arg Ile Ser Cys Arg Ala Ser Gly Tyr Glu Phe Ile Asp Cys
            20                  25                  30

Thr Leu Asn Trp Ile Arg Leu Ala Pro Gly Lys Arg Pro Glu Trp Met
        35                  40                  45

Gly Trp Leu Lys Pro Arg Gly Gly Ala Val Asn Tyr Ala Arg Pro Leu
50                  55                  60

Gln Gly Arg Val Thr Met Thr Arg Asp Val Tyr Ser Asp Thr Ala Phe
65                  70                  75                  80

Leu Glu Leu Arg Ser Leu Thr Val Asp Asp Thr Ala Val Tyr Phe Cys
                85                  90                  95

Thr Arg Gly Lys Asn Cys Asp Tyr Asn Trp Asp Phe Glu His Trp Gly
            100                 105                 110
```

Arg Gly Thr Pro Val Ile Val Ser Ser
        115                 120

<210> SEQ ID NO 151
<211> LENGTH: 87
<212> TYPE: DNA
<213> ORGANISM: Artificial Sequence
<220> FEATURE:
<223> OTHER INFORMATION: splice junction with flanking sequence in
      constructs of the disclosure

<400> SEQUENCE: 151
caggtgagtt ggctttcctt ctgcctcctt tctctgggcc cagcgtcctc tgacctggag    60
ctgggagata atgtccgggg gctcctt                                        87

<210> SEQ ID NO 152
<211> LENGTH: 414
<212> TYPE: PRT
<213> ORGANISM: Artificial Sequence
<220> FEATURE:
<223> OTHER INFORMATION: signal peptide-light chain-streptag linker-
      variable heavy chain amino acid sequence in Hu-emAb-VRC01-AAV

<400> SEQUENCE: 152

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Glu Ile Val Leu Thr Gln
            20                  25                  30

Ser Pro Gly Thr Leu Ser Leu Ser Pro Gly Glu Thr Ala Ile Ile Ser
        35                  40                  45

Cys Arg Thr Ser Gln Tyr Gly Ser Leu Ala Trp Tyr Gln Gln Arg Pro
    50                  55                  60

Gly Gln Ala Pro Arg Leu Val Ile Tyr Ser Gly Ser Thr Arg Ala Ala
65                  70                  75                  80

Gly Ile Pro Asp Arg Phe Ser Gly Ser Arg Trp Gly Pro Asp Tyr Asn
                85                  90                  95

Leu Thr Ile Ser Asn Leu Glu Ser Gly Asp Phe Gly Val Tyr Tyr Cys
            100                 105                 110

Gln Gln Tyr Glu Phe Phe Gly Gln Gly Thr Lys Val Gln Val Asp Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys Gly Gly Ser Ser
225                 230                 235                 240

Gly Ser Gly Ser Gly Ser Asn Trp Ser His Pro Gln Phe Glu Lys Gly
                245                 250                 255

Gly Gly Gly Ser Asn Trp Ser His Pro Gln Phe Glu Lys Gly Gly Gly

```
                260                 265                 270
Gly Ser Asn Trp Ser His Pro Gln Phe Glu Lys Gly Ser Gly Gly
            275                 280                 285
Gly Ser Ala Gly Gly Gln Val Gln Leu Val Gln Ser Gly Gly Gln Met
        290                 295                 300
Lys Lys Pro Gly Glu Ser Met Arg Ile Ser Cys Arg Ala Ser Gly Tyr
305                 310                 315                 320
Glu Phe Ile Asp Cys Thr Leu Asn Trp Ile Arg Leu Ala Pro Gly Lys
            325                 330                 335
Arg Pro Glu Trp Met Gly Trp Leu Lys Pro Arg Gly Gly Ala Val Asn
        340                 345                 350
Tyr Ala Arg Pro Leu Gln Gly Arg Val Thr Met Thr Arg Asp Val Tyr
            355                 360                 365
Ser Asp Thr Ala Phe Leu Glu Leu Arg Ser Leu Thr Val Asp Asp Thr
        370                 375                 380
Ala Val Tyr Phe Cys Thr Arg Gly Lys Asn Cys Asp Tyr Asn Trp Asp
385                 390                 395                 400
Phe Glu His Trp Gly Arg Gly Thr Pro Val Ile Val Ser Ser
            405                 410

<210> SEQ ID NO 153
<211> LENGTH: 430
<212> TYPE: DNA
<213> ORGANISM: Homo sapiens

<400> SEQUENCE: 153
tgtgacgccc ggagacagaa ggtctctggg tggctgggtt tttgtggggt gaggatggac      60
attctgccat tgtgattact actactacta ctacatggac gtctggggca aagggaccac     120
ggtcaccgtc tcctcaggta agaatggcca ctctagggcc tttgttttct gctactgcct     180
gtggggtttc ctgagggcat gttccgaggg acctgggcg gactggccag aggggatgg      240 gcactggggt gccttgagga tctgggagcc tctgtggatt ttccgatgcc tttggaaaat     300
gggactcagg ttgggtgcgt ctgatggagt aactgagcct gggggcttgg ggagccacat     360
ttggacgaga tgcctgaaca aaccaggggt cttagtgatg gctgaggaat gtgtctcagg     420
agcggtgtct                                                            430

<210> SEQ ID NO 154
<211> LENGTH: 708
<212> TYPE: DNA
<213> ORGANISM: Artificial Sequence
<220> FEATURE:
<223> OTHER INFORMATION: Medi8852 light chain coding sequence

<400> SEQUENCE: 154
atggctaccg gcagcagaac aagcctgctg ctcgcttttg gactgctctg tctccctgg      60 ttgcaagaag gcagcgccga tattcagatg acccagagcc cttccagcct gtccgcttca     120
gtgggggatc gagtgaccat tacctgccga accagccaga gcctgagctc ctacacgcac     180
tggtatcagc agaagcccgg caaagccct aagctgctga tctacgccgc ttctagtcgg     240
gggtccgagt gccaagccg ttctccggat ctgggagtg aaccgactt accctgaca       300 atttcaagcc tgcagccga ggatttcgct acatactact gtcagcagag cagaactttc      360
gggcagggca ctaaggtgga gatcaaacgg actgtggccg ctcctagcgt gttcatcttt     420
ccacctagcg acgagcagct gaagtctggc actgcctctg tcgtgtgcct gctgaacaac     480
```

```
ttctaccctc gagaggccaa ggtgcagtgg aaagtggaca atgccctgca gagcggcaac      540
agccaagagt ctgtgaccga gcaggactcc aaggattcca cctacagcct gtctagcacc      600
ctgactctga gcaaggccga ctacgagaag cacaaggtgt acgcctgcga agtgacacac      660
cagggactga gcagccctgt gaccaagagc ttcaatcggg gcgagtgc                   708
```

<210> SEQ ID NO 155
<211> LENGTH: 309
<212> TYPE: DNA
<213> ORGANISM: Artificial Sequence
<220> FEATURE:
<223> OTHER INFORMATION: MEDI8852-VK anti-stem HA variable light chain coding sequence

<400> SEQUENCE: 155

```
gatattcaga tgacccagag cccttccagc ctgtccgctt cagtggggga tcgagtgacc       60
attacctgcc gaaccagcca gagcctgagc tcctacacgc actggtatca gcagaagccc      120
ggcaaagccc ctaagctgct gatctacgcc gcttctagtc gggggtccgg agtgccaagc      180
cggttctccg gatctgggag tggaaccgac tttaccctga caatttcaag cctgcagccc      240
gaggatttcg ctacatacta ctgtcagcag agcagaactt cgggcagggg cactaaggtg      300
gagatcaaa                                                              309
```

<210> SEQ ID NO 156
<211> LENGTH: 384
<212> TYPE: DNA
<213> ORGANISM: Artificial Sequence
<220> FEATURE:
<223> OTHER INFORMATION: anti-stem HA variable heavy chain coding sequence

<400> SEQUENCE: 156

```
caggtccagc tgcagcagag cggccccgga ctggtcaagc cttcacagac actgagcctg       60
acatgcgcca ttagcggaga tagcgtgagc tcctacaatg ccgtgtggaa ctggatcagg      120
cagtctccaa gtcgaggact ggagtggctg ggacgaacat actatagatc cgggtggtac      180
aatgactatg ctgaatcagt gaaaagccga attactatca ccccgatac ctccaagaat       240 cagttctctc tgcagctgaa cagtgtgacc cctgaggaca cagccgtgta ctactgcgcc      300
agaagcggcc atatcaccgt ctttggcgtc aatgtggatg ctttcgatat gtgggggcag      360
gggactatgg tcaccgtctc ttca                                             384
```

<210> SEQ ID NO 157
<211> LENGTH: 236
<212> TYPE: PRT
<213> ORGANISM: Artificial Sequence
<220> FEATURE:
<223> OTHER INFORMATION: Medi8852 light chain amino acid sequence

<400> SEQUENCE: 157

```
Met Ala Thr Gly Ser Arg Thr Ser Leu Leu Ala Phe Gly Leu Leu
1               5                   10                  15

Cys Leu Pro Trp Leu Gln Glu Gly Ser Ala Asp Ile Gln Met Thr Gln
            20                  25                  30

Ser Pro Ser Ser Leu Ser Ala Ser Val Gly Asp Arg Val Thr Ile Thr
        35                  40                  45

Cys Arg Thr Ser Gln Ser Leu Ser Ser Tyr Thr His Trp Tyr Gln Gln
    50                  55                  60

Lys Pro Gly Lys Ala Pro Lys Leu Leu Ile Tyr Ala Ala Ser Ser Arg
```

```
                65                  70                  75                  80
Gly Ser Gly Val Pro Ser Arg Phe Ser Gly Ser Gly Thr Asp
                    85                  90                  95

Phe Thr Leu Thr Ile Ser Ser Leu Gln Pro Glu Asp Phe Ala Thr Tyr
                100                 105                 110

Tyr Cys Gln Gln Ser Arg Thr Phe Gly Gln Gly Thr Lys Val Glu Ile
            115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 158
<211> LENGTH: 103
<212> TYPE: PRT
<213> ORGANISM: Artificial Sequence
<220> FEATURE:
<223> OTHER INFORMATION: MEDI8852-VK anti-stem HA variable light chain
      amino acid sequence

<400> SEQUENCE: 158

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Ser Leu Ser Ser Tyr
            20                  25                  30

Thr His Trp Tyr Gln Gln Lys Pro Gly Lys Ala Pro Lys Leu Leu Ile
        35                  40                  45

Tyr Ala Ala Ser Ser Arg Gly Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Arg Thr Phe Gly Gln
                85                  90                  95

Gly Thr Lys Val Glu Ile Lys
            100

<210> SEQ ID NO 159
<211> LENGTH: 128
<212> TYPE: PRT
<213> ORGANISM: Artificial Sequence
<220> FEATURE:
<223> OTHER INFORMATION: anti-stem HA variable heavy chain amino acid
      sequence

<400> SEQUENCE: 159

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Tyr
```

```
                  20                  25                  30
Asn Ala Val Trp Asn Trp Ile Arg Gln Ser Pro Ser Arg Gly Leu Glu
             35                  40                  45

Trp Leu Gly Arg Thr Tyr Tyr Arg Ser Gly Trp Tyr Asn Asp Tyr Ala
         50                  55                  60

Glu Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Arg Ser Gly His Ile Thr Val Phe Gly Val Asn Val
            100                 105                 110

Asp Ala Phe Asp Met Trp Gly Gln Gly Thr Met Val Thr Val Ser Ser
            115                 120                 125

<210> SEQ ID NO 160
<211> LENGTH: 421
<212> TYPE: PRT
<213> ORGANISM: Artificial Sequence
<220> FEATURE:
<223> OTHER INFORMATION: signal peptide-light chain-streptag linker-
      variable heavy chain amino acid sequence in  hu-emAb-Medi8852-AAV

<400> SEQUENCE: 160

Met Ala Thr Gly Ser Arg Thr Ser Leu Leu Leu Ala Phe Gly Leu Leu
 1               5                  10                  15

Cys Leu Pro Trp Leu Gln Glu Gly Ser Ala Asp Ile Gln Met Thr Gln
             20                  25                  30

Ser Pro Ser Ser Leu Ser Ala Ser Val Gly Asp Arg Val Thr Ile Thr
         35                  40                  45

Cys Arg Thr Ser Gln Ser Leu Ser Ser Tyr Thr His Trp Tyr Gln Gln
 50                  55                  60

Lys Pro Gly Lys Ala Pro Lys Leu Leu Ile Tyr Ala Ala Ser Ser Arg
 65                  70                  75                  80

Gly Ser Gly Val Pro Ser Arg Phe Ser Gly Ser Gly Ser Gly Thr Asp
                 85                  90                  95

Phe Thr Leu Thr Ile Ser Ser Leu Gln Pro Glu Asp Phe Ala Thr Tyr
            100                 105                 110

Tyr Cys Gln Gln Ser Arg Thr Phe Gly Gln Gly Thr Lys Val Glu Ile
            115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
        210                 215                 220

Ser Pro Val Thr Lys Ser Phe Asn Arg Gly Glu Cys Gly Gly Ser Ser
225                 230                 235                 240

Gly Ser Gly Ser Gly Ser Asn Trp Ser His Pro Gln Phe Glu Lys Gly
                245                 250                 255
```

Gly Gly Gly Ser Asn Trp Ser His Pro Gln Phe Glu Lys Gly Gly Gly
            260                 265                 270

Gly Ser Asn Trp Ser His Pro Gln Phe Glu Lys Gly Gly Gly Gly
        275                 280                 285

Gly Ser Ala Gly Gly Gln Val Gln Leu Gln Gln Ser Gly Pro Gly Leu
        290                 295                 300

Val Lys Pro Ser Gln Thr Leu Ser Leu Thr Cys Ala Ile Ser Gly Asp
305                 310                 315                 320

Ser Val Ser Ser Tyr Asn Ala Val Trp Asn Trp Ile Arg Gln Ser Pro
                325                 330                 335

Ser Arg Gly Leu Glu Trp Leu Gly Arg Thr Tyr Tyr Arg Ser Gly Trp
            340                 345                 350

Tyr Asn Asp Tyr Ala Glu Ser Val Lys Ser Arg Ile Thr Ile Asn Pro
                355                 360                 365

Asp Thr Ser Lys Asn Gln Phe Ser Leu Gln Leu Asn Ser Val Thr Pro
        370                 375                 380

Glu Asp Thr Ala Val Tyr Tyr Cys Ala Arg Ser Gly His Ile Thr Val
385                 390                 395                 400

Phe Gly Val Asn Val Asp Ala Phe Asp Met Trp Gly Gln Gly Thr Met
                405                 410                 415

Val Thr Val Ser Ser
            420

<210> SEQ ID NO 161
<211> LENGTH: 726
<212> TYPE: DNA
<213> ORGANISM: Artificial Sequence
<220> FEATURE:
<223> OTHER INFORMATION: AMM01 light chain coding sequence

<400> SEQUENCE: 161
atggctaccg gcagcagaac aagcctgctg ctcgcttttg gactgctctg tctccctgg     60 ttgcaagaag gcagcgcctc ctatgagctg actcagccac cctcagtgtc agtggccccg    120
gggcagaggg ccacaattac ctgtggggga cacaacatcg agctaaaaa tgtccactgg    180 taccagcaga agccaggcca ggcccctgtc ctggtcatcc aatatgatag cgaccggccc    240
tcagggatcc ctgagcgatt ctctggctcc aactctggga gcacggccac cctgaccatc    300
agcagggtcg aagccgggga tgaggccgac tattactgtc aggtgtggga tagtggtcgt    360
gggcatcccc tttatgtctt cggaggtggg accaaggtca ccgtcctagg tcagcccaag    420 gccaaccccca ctgtcactct gttcccaccc tcgagtgagg agcttcaagc caacaaggcc    480
acactggtgt gtctcataag tgacttctac ccgggagccg tgacagtggc ctggaaggca    540
gatagcagcc ccgtcaaggc gggagtggag accaccacac cctccaaaca aagcaacaac    600
aagtacgcgg ccagcagcta cctgagcctg acgcctgagc agtggaagtc cacagaagc    660 tacagctgcc aggtcacgca tgaagggagc accgtggaga gacagtggc ccctacagaa    720 tgttca                                                                726

<210> SEQ ID NO 162
<211> LENGTH: 372
<212> TYPE: DNA
<213> ORGANISM: Artificial Sequence
<220> FEATURE:
<223> OTHER INFORMATION: AMM01 lambda variable light chain coding
      sequence

<400> SEQUENCE: 162

```
tcctatgagc tgactcagcc accctcagtg tcagtggccc cggggcagag ggccacaatt      60
acctgtgggg gacacaacat cggagctaaa aatgtccact ggtaccagca gaagccaggc     120
caggcccctg tcctggtcat ccaatatgat agcgaccggc cctcagggat ccctgagcga     180
ttctctggct ccaactctgg gagcacggcc accctgacca tcagcagggt cgaagccggg     240
gatgaggccg actattactg tcaggtgtgg gatagtggtc gtgggcatcc cctttatgtc     300
ttcggaggtg ggaccaaggt caccgtccta ggtcagccca aggccaaccc cactgtcact     360
ctgttcccac cc                                                         372

<210> SEQ ID NO 163
<211> LENGTH: 276
<212> TYPE: DNA
<213> ORGANISM: Artificial Sequence
<220> FEATURE:
<223> OTHER INFORMATION: lambda constant light chain coding sequence

<400> SEQUENCE: 163
tcgagtgagg agcttcaagc caacaaggcc acactggtgt gtctcataag tgacttctac      60
ccgggagccg tgacagtggc ctggaaggca gatagcagcc ccgtcaaggc ggggagtggag    120 accaccacac cctccaaaca aagcaacaac aagtacgcgg ccagcagcta cctgagcctg     180
acgcctgagc agtggaagtc ccacagaagc tacagctgcc aggtcacgca tgaagggagc     240
accgtggaga agacagtggc ccctacagaa tgttca                               276

<210> SEQ ID NO 164
<211> LENGTH: 369
<212> TYPE: DNA
<213> ORGANISM: Artificial Sequence
<220> FEATURE:
<223> OTHER INFORMATION: AMM01 variable heavy chain coding sequence

<400> SEQUENCE: 164
caggttcagc tggtgcagtc tggagctgat gtgaagaagc tggggcctc agtgaaggtc       60 tcctgcaagg cttctggtta cacctttatt catttggta tcagttgggt gcggcaggcc     120
cctggacaag gcttgagtg gatgggatgg atcgacacta taatggtaa cacaaactat      180 gcacagagtc tccagggcag agtcaccatg accacagata catccacggg cacagcctac     240
atggagctga ggagcctctc gactgacgac acggccgtgt atttctgtgc gcgagctctg     300
gaaatggggc atagaagtgg cttcccattt gactactggg gccagggagt cctggtcacc     360
gtctcccca                                                            369

<210> SEQ ID NO 165
<211> LENGTH: 242
<212> TYPE: PRT
<213> ORGANISM: Artificial Sequence
<220> FEATURE:
<223> OTHER INFORMATION: AMM01 light chain amino acid sequence

<400> SEQUENCE: 165

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Ser Tyr Glu Leu Thr Gln
                20                  25                  30

Pro Pro Ser Val Ser Val Ala Pro Gly Gln Arg Ala Thr Ile Thr Cys
            35                  40                  45

Gly Gly His Asn Ile Gly Ala Lys Asn Val His Trp Tyr Gln Gln Lys
```

Pro Gly Gln Ala Pro Val Leu Val Ile Gln Tyr Asp Ser Asp Arg Pro
65                  70                  75                  80

Ser Gly Ile Pro Glu Arg Phe Ser Gly Ser Asn Ser Gly Ser Thr Ala
                85                  90                  95

Thr Leu Thr Ile Ser Arg Val Glu Ala Gly Asp Glu Ala Asp Tyr Tyr
            100                 105                 110

Cys Gln Val Trp Asp Ser Gly Arg Gly His Pro Leu Tyr Val Phe Gly
        115                 120                 125

Gly Gly Thr Lys Val Thr Val Leu Gly Gln Pro Lys Ala Asn Pro Thr
    130                 135                 140

Val Thr Leu Phe Pro Pro Ser Ser Glu Glu Leu Gln Ala Asn Lys Ala
145                 150                 155                 160

Thr Leu Val Cys Leu Ile Ser Asp Phe Tyr Pro Gly Ala Val Thr Val
                165                 170                 175

Ala Trp Lys Ala Asp Ser Ser Pro Val Lys Ala Gly Val Glu Thr Thr
            180                 185                 190

Thr Pro Ser Lys Gln Ser Asn Asn Lys Tyr Ala Ala Ser Ser Tyr Leu
        195                 200                 205

Ser Leu Thr Pro Glu Gln Trp Lys Ser His Arg Ser Tyr Ser Cys Gln
    210                 215                 220

Val Thr His Glu Gly Ser Thr Val Glu Lys Thr Val Ala Pro Thr Glu
225                 230                 235                 240

Cys Ser

<210> SEQ ID NO 166
<211> LENGTH: 124
<212> TYPE: PRT
<213> ORGANISM: Artificial Sequence
<220> FEATURE:
<223> OTHER INFORMATION: AMM01 variable light chain amino acid sequence

<400> SEQUENCE: 166

Ser Tyr Glu Leu Thr Gln Pro Pro Ser Val Ser Val Ala Pro Gly Gln
1               5                   10                  15

Arg Ala Thr Ile Thr Cys Gly Gly His Asn Ile Gly Ala Lys Asn Val
                20                  25                  30

His Trp Tyr Gln Gln Lys Pro Gly Gln Ala Pro Val Leu Val Ile Gln
            35                  40                  45

Tyr Asp Ser Asp Arg Pro Ser Gly Ile Pro Glu Arg Phe Ser Gly Ser
        50                  55                  60

Asn Ser Gly Ser Thr Ala Thr Leu Thr Ile Ser Arg Val Glu Ala Gly
65                  70                  75                  80

Asp Glu Ala Asp Tyr Tyr Cys Gln Val Trp Asp Ser Gly Arg Gly His
                85                  90                  95

Pro Leu Tyr Val Phe Gly Gly Gly Thr Lys Val Thr Val Leu Gly Gln
            100                 105                 110

Pro Lys Ala Asn Pro Thr Val Thr Leu Phe Pro Pro
        115                 120

<210> SEQ ID NO 167
<211> LENGTH: 92
<212> TYPE: PRT
<213> ORGANISM: Artificial Sequence
<220> FEATURE:
<223> OTHER INFORMATION: AMM01 lambda constant light chain amino acid
      sequence -continued

<400> SEQUENCE: 167

Ser Ser Glu Glu Leu Gln Ala Asn Lys Ala Thr Leu Val Cys Leu Ile
1               5                   10                  15

Ser Asp Phe Tyr Pro Gly Ala Val Thr Val Ala Trp Lys Ala Asp Ser
            20                  25                  30

Ser Pro Val Lys Ala Gly Val Glu Thr Thr Thr Pro Ser Lys Gln Ser
        35                  40                  45

Asn Asn Lys Tyr Ala Ala Ser Ser Tyr Leu Ser Leu Thr Pro Glu Gln
    50                  55                  60

Trp Lys Ser His Arg Ser Tyr Ser Cys Gln Val Thr His Glu Gly Ser
65                  70                  75                  80

Thr Val Glu Lys Thr Val Ala Pro Thr Glu Cys Ser
                85                  90

<210> SEQ ID NO 168
<211> LENGTH: 123
<212> TYPE: PRT
<213> ORGANISM: Artificial Sequence
<220> FEATURE:
<223> OTHER INFORMATION: AMM01 variable heavy chain amino acid sequence

<400> SEQUENCE: 168

Gln Val Gln Leu Val Gln Ser Gly Ala Asp Val Lys Lys Pro Gly Ala
1               5                   10                  15

Ser Val Lys Val Ser Cys Lys Ala Ser Gly Tyr Thr Phe Ile His Phe
            20                  25                  30

Gly Ile Ser Trp Val Arg Gln Ala Pro Gly Gln Gly Leu Glu Trp Met
        35                  40                  45

Gly Trp Ile Asp Thr Asn Asn Gly Asn Thr Asn Tyr Ala Gln Ser Leu
    50                  55                  60

Gln Gly Arg Val Thr Met Thr Thr Asp Thr Ser Thr Gly Thr Ala Tyr
65                  70                  75                  80

Met Glu Leu Arg Ser Leu Ser Thr Asp Thr Ala Val Tyr Phe Cys
                85                  90                  95

Ala Arg Ala Leu Glu Met Gly His Arg Ser Gly Phe Pro Phe Asp Tyr
            100                 105                 110

Trp Gly Gln Gly Val Leu Val Thr Val Ser Pro
        115                 120

<210> SEQ ID NO 169
<211> LENGTH: 422
<212> TYPE: PRT
<213> ORGANISM: Artificial Sequence
<220> FEATURE:
<223> OTHER INFORMATION: signal peptide-light chain-streptag linker-
      variable heavy chain amino acid sequence in hu-emAb-AMM01-AAV

<400> SEQUENCE: 169

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Ser Tyr Glu Leu Thr Gln
            20                  25                  30

Pro Pro Ser Val Ser Val Ala Pro Gly Gln Arg Ala Thr Ile Thr Cys
        35                  40                  45

Gly Gly His Asn Ile Gly Ala Lys Asn Val His Trp Tyr Gln Gln Lys
    50                  55                  60

Pro Gly Gln Ala Pro Val Leu Val Ile Gln Tyr Asp Ser Asp Arg Pro

```
              65                  70                  75                  80
         Ser Gly Ile Pro Glu Arg Phe Ser Gly Ser Asn Ser Gly Ser Thr Ala
                         85                  90                  95

Thr Leu Thr Ile Ser Arg Val Glu Ala Gly Asp Glu Ala Asp Tyr Tyr
                        100                 105                 110

Cys Gln Val Trp Asp Ser Gly Arg Gly His Pro Leu Tyr Val Phe Gly
                        115                 120                 125

Gly Gly Thr Lys Val Thr Val Leu Gly Gln Pro Lys Ala Asn Pro Thr
                        130                 135                 140

Val Thr Leu Phe Pro Pro Ser Ser Glu Glu Leu Gln Ala Asn Lys Ala
         145                 150                 155                 160

Thr Leu Val Cys Leu Ile Ser Asp Phe Tyr Pro Gly Ala Val Thr Val
                             165                 170                 175

Ala Trp Lys Ala Asp Ser Ser Pro Val Lys Ala Gly Val Glu Thr Thr
                         180                 185                 190

Thr Pro Ser Lys Gln Ser Asn Asn Lys Tyr Ala Ala Ser Ser Tyr Leu
                         195                 200                 205

Ser Leu Thr Pro Glu Gln Trp Lys Ser His Arg Ser Tyr Ser Cys Gln
                 210                 215                 220

Val Thr His Glu Gly Ser Thr Val Glu Lys Thr Val Ala Pro Thr Glu
         225                 230                 235                 240

Cys Ser Gly Gly Ser Gly Ser Gly Ser Asn Trp Ser His
                         245                 250                 255

Pro Gln Phe Glu Lys Gly Gly Gly Ser Asn Trp Ser His Pro Gln
                         260                 265                 270

Phe Glu Lys Gly Gly Gly Ser Asn Trp Ser His Pro Gln Phe Glu
                     275                 280                 285

Lys Gly Ser Gly Gly Gly Ser Ala Gly Gly Gln Val Gln Leu Val
                     290                 295                 300

Gln Ser Gly Ala Asp Val Lys Lys Pro Gly Ala Ser Val Lys Val Ser
         305                 310                 315                 320

Cys Lys Ala Ser Gly Tyr Thr Phe Ile His Phe Gly Ile Ser Trp Val
                         325                 330                 335

Arg Gln Ala Pro Gly Gln Gly Leu Glu Trp Met Gly Trp Ile Asp Thr
                         340                 345                 350

Asn Asn Gly Asn Thr Asn Tyr Ala Gln Ser Leu Gln Gly Arg Val Thr
                         355                 360                 365

Met Thr Thr Asp Thr Ser Thr Gly Thr Ala Tyr Met Glu Leu Arg Ser
         370                 375                 380

Leu Ser Thr Asp Asp Thr Ala Val Tyr Phe Cys Ala Arg Ala Leu Glu
         385                 390                 395                 400

Met Gly His Arg Ser Gly Phe Pro Phe Asp Tyr Trp Gly Gln Gly Val
                         405                 410                 415

Leu Val Thr Val Ser Pro
                         420

<210> SEQ ID NO 170
<211> LENGTH: 39
<212> TYPE: DNA
<213> ORGANISM: Mus musculus

<400> SEQUENCE: 170
aggaccacct ctgtgacagc atttatacag tatccgatg                          39
```

-continued

<210> SEQ ID NO 171
<211> LENGTH: 41
<212> TYPE: DNA
<213> ORGANISM: Mus musculus

<400> SEQUENCE: 171 cataggggaca aagagtggag tggggcactt tctttagatt t         41

<210> SEQ ID NO 172
<211> LENGTH: 409
<212> TYPE: PRT
<213> ORGANISM: Artificial Sequence
<220> FEATURE:
<223> OTHER INFORMATION: signal peptide-light chain-streptag linker-
      variable heavy chain amino acid sequence in Balb/C mRSV-Splice
      Integration

<400> SEQUENCE: 172

```
Met Glu Thr Asp Thr Leu Leu Leu Trp Val Leu Leu Leu Trp Val Pro
1               5                   10                  15

Gly Ser Thr Gly Asp Ile Gln Leu Thr Gln Ser Pro Ala Ile Met Ser
            20                  25                  30

Ala Ser Pro Gly Glu Lys Val Thr Met Thr Cys Ser Ala Ser Ser Ser
        35                  40                  45

Val Gly Tyr Met His Trp Tyr Gln Gln Lys Ser Ser Thr Ser Pro Lys
    50                  55                  60

Leu Trp Ile Tyr Asp Thr Ser Lys Leu Ala Ser Gly Val Pro Gly Arg
65                  70                  75                  80

Phe Ser Gly Ser Gly Ser Gly Asn Ser Tyr Ser Leu Thr Ile Ser Ser
                85                  90                  95

Ile Gln Ala Glu Asp Val Ala Thr Tyr Tyr Cys Phe Arg Gly Ser Gly
            100                 105                 110

Tyr Pro Phe Thr Phe Gly Gln Gly Thr Lys Leu Glu Ile Lys Ala Asp
        115                 120                 125

Ala Ala Pro Thr Val Ser Ile Phe Pro Pro Ser Ser Glu Gln Leu Thr
    130                 135                 140

Ser Gly Gly Ala Ser Val Val Cys Phe Leu Asn Asn Phe Tyr Pro Lys
145                 150                 155                 160

Asp Ile Asn Val Lys Trp Lys Ile Asp Gly Ser Glu Arg Gln Asn Gly
                165                 170                 175

Val Leu Asn Ser Trp Thr Asp Gln Asp Ser Lys Asp Ser Thr Tyr Ser
            180                 185                 190

Met Ser Ser Thr Leu Thr Leu Thr Lys Asp Glu Tyr Glu Arg His Asn
        195                 200                 205

Ser Tyr Thr Cys Glu Ala Thr His Lys Thr Ser Thr Ser Pro Ile Val
    210                 215                 220

Lys Ser Phe Asn Arg Asn Glu Cys Gly Gly Ser Gly Ser Gly Ser
225                 230                 235                 240

Gly Ser Asn Trp Ser His Pro Gln Phe Glu Lys Gly Gly Gly Ser
                245                 250                 255

Asn Trp Ser His Pro Gln Phe Glu Lys Gly Gly Gly Ser Asn Trp
            260                 265                 270

Ser His Pro Gln Phe Glu Lys Gly Ser Gly Gly Ser Ala Gly
        275                 280                 285

Gly Gln Val Glu Leu Gln Glu Ser Gly Pro Gly Ile Leu Gln Pro Ser
    290                 295                 300

Gln Thr Leu Ser Leu Thr Cys Ser Phe Ser Gly Phe Ser Leu Ser Thr
```

```
305                 310                 315                 320

Ser Gly Met Ser Val Gly Trp Ile Arg Gln Pro Ser Gly Glu Gly Leu
                325                 330                 335

Glu Trp Leu Ala Asp Ile Trp Trp Asp Asp Lys Lys Asp Tyr Asn Pro
            340                 345                 350

Ser Leu Lys Ser Arg Leu Thr Ile Ser Lys Asp Thr Ser Ser Asn Gln
        355                 360                 365

Val Phe Leu Lys Ile Thr Gly Val Asp Thr Ala Asp Thr Ala Thr Tyr
    370                 375                 380

Tyr Cys Ala Arg Ser Met Ile Thr Asn Trp Tyr Phe Asp Val Trp Gly
385                 390                 395                 400

Ala Gly Thr Thr Val Thr Val Ser Ser
                405
```

<210> SEQ ID NO 173
<211> LENGTH: 41
<212> TYPE: DNA
<213> ORGANISM: Homo sapiens

<400> SEQUENCE: 173

```
gtcttagtga tggctgagga atgtgtctca ggagcggtgt c                          41
```

<210> SEQ ID NO 174
<211> LENGTH: 41
<212> TYPE: DNA
<213> ORGANISM: Homo sapiens

<400> SEQUENCE: 174

```
tgtaggactg caagatcgct gcacagcagc gaatcgtgaa a                          41
```

<210> SEQ ID NO 175
<211> LENGTH: 415
<212> TYPE: PRT
<213> ORGANISM: Artificial Sequence
<220> FEATURE:
<223> OTHER INFORMATION: signal peptide-light chain-streptag linker-
      variable heavy chain amino acid sequence in TT-hRSV-T7-integrated

<400> SEQUENCE: 175

```
Met Ala Thr Gly Ser Arg Thr Ser Leu Leu Leu Ala Phe Gly Leu Leu
1               5                   10                  15

Cys Leu Pro Trp Leu Gln Glu Gly Ser Ala Asp Ile Gln Met Thr Gln
            20                  25                  30

Ser Pro Ser Thr Leu Ser Ala Ser Val Gly Asp Arg Val Thr Ile Thr
        35                  40                  45

Cys Lys Cys Gln Leu Ser Val Gly Tyr Met His Trp Tyr Gln Gln Lys
    50                  55                  60

Pro Gly Lys Ala Pro Lys Leu Leu Ile Tyr Asp Thr Ser Lys Leu Ala
65                  70                  75                  80

Ser Gly Val Pro Ser Arg Phe Ser Gly Ser Gly Ser Gly Thr Glu Phe
                85                  90                  95

Thr Leu Thr Ile Ser Ser Leu Gln Pro Asp Asp Phe Ala Thr Tyr Tyr
            100                 105                 110

Cys Phe Gln Gly Ser Gly Tyr Pro Phe Thr Phe Gly Gly Gly Thr Lys
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu

```
                    145                 150                 155                 160
Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys Gly
225                 230                 235                 240

Gly Ser Ser Gly Ser Gly Ser Gly Ser Asn Trp Ser His Pro Gln Phe
                245                 250                 255

Glu Lys Gly Gly Gly Ser Asn Trp Ser His Pro Gln Phe Glu Lys
            260                 265                 270

Gly Gly Gly Gly Ser Asn Trp Ser His Pro Gln Phe Glu Lys Gly Ser
        275                 280                 285

Gly Gly Gly Gly Ser Ala Gly Gly Gln Val Thr Leu Arg Glu Ser Gly
    290                 295                 300

Pro Ala Leu Val Lys Pro Thr Gln Thr Leu Thr Leu Thr Cys Thr Phe
305                 310                 315                 320

Ser Gly Phe Ser Leu Ser Thr Ser Gly Met Ser Val Gly Trp Ile Arg
                325                 330                 335

Gln Pro Pro Gly Lys Ala Leu Glu Trp Leu Ala Asp Ile Trp Trp Asp
            340                 345                 350

Asp Lys Lys Asp Tyr Asn Pro Ser Leu Lys Ser Arg Leu Thr Ile Ser
        355                 360                 365

Lys Asp Thr Ser Lys Asn Gln Val Val Leu Lys Val Thr Asn Met Asp
    370                 375                 380

Pro Ala Asp Thr Ala Thr Tyr Tyr Cys Ala Arg Ser Met Ile Thr Asn
385                 390                 395                 400

Trp Tyr Phe Asp Val Trp Gly Ala Gly Thr Thr Val Ser Ser
                405                 410                 415

<210> SEQ ID NO 176
<211> LENGTH: 21
<212> TYPE: PRT
<213> ORGANISM: Artificial Sequence
<220> FEATURE:
<223> OTHER INFORMATION: T2A self-cleaving peptide

<400> SEQUENCE: 176

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 177
<211> LENGTH: 22
<212> TYPE: PRT
<213> ORGANISM: Artificial Sequence
<220> FEATURE:
<223> OTHER INFORMATION: P2A self-cleaving peptide

<400> SEQUENCE: 177

Gly Ser Gly Ala Thr Asn Phe Ser Leu Leu Lys Gln Ala Gly Asp Val
1               5                   10                  15
```

Glu Glu Asn Pro Gly Pro
            20

<210> SEQ ID NO 178
<211> LENGTH: 24
<212> TYPE: PRT
<213> ORGANISM: Artificial Sequence
<220> FEATURE:
<223> OTHER INFORMATION: E2A self-cleaving peptide

<400> SEQUENCE: 178

Gly Ser Gly Gln Cys Thr Asn Tyr Ala Leu Leu Lys Leu Ala Gly Asp
1               5                   10                  15

Val Glu Ser Asn Pro Gly Pro Pro
            20

<210> SEQ ID NO 179
<211> LENGTH: 25
<212> TYPE: PRT
<213> ORGANISM: Artificial Sequence
<220> FEATURE:
<223> OTHER INFORMATION: F2A self-cleaving peptide

<400> SEQUENCE: 179

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 180
<211> LENGTH: 3
<212> TYPE: PRT
<213> ORGANISM: Artificial Sequence
<220> FEATURE:
<223> OTHER INFORMATION: Gly-Ser linker
<220> FEATURE:
<221> NAME/KEY: MISC_FEATURE
<223> OTHER INFORMATION: Gly-Ser linker (GGS)n, where n=1 to 100

<400> SEQUENCE: 180

Gly Gly Ser
1

<210> SEQ ID NO 181
<211> LENGTH: 4
<212> TYPE: PRT
<213> ORGANISM: Artificial Sequence
<220> FEATURE:
<223> OTHER INFORMATION: Gly-Ser linker
<220> FEATURE:
<221> NAME/KEY: MISC_FEATURE
<223> OTHER INFORMATION: Gly-Ser linker (GGGS)n, where n=1 to 100

<400> SEQUENCE: 181

Gly Gly Gly Ser
1

<210> SEQ ID NO 182
<211> LENGTH: 5
<212> TYPE: PRT
<213> ORGANISM: Artificial Sequence
<220> FEATURE:
<223> OTHER INFORMATION: Gly-Ser linker
<220> FEATURE:
<221> NAME/KEY: MISC_FEATURE
<223> OTHER INFORMATION: Gly-Ser linker (GGGGS)n, where n=1 to 100

<400> SEQUENCE: 182

Gly Gly Gly Gly Ser
1               5

<210> SEQ ID NO 183
<211> LENGTH: 18
<212> TYPE: PRT
<213> ORGANISM: Artificial Sequence
<220> FEATURE:
<223> OTHER INFORMATION: linker
<220> FEATURE:
<221> NAME/KEY: MISC_FEATURE
<223> OTHER INFORMATION: linker (KESGSVSSEQLAQFRSLD)n, where n=1 to 100

<400> SEQUENCE: 183

Lys Glu Ser Gly Ser Val Ser Ser Glu Gln Leu Ala Gln Phe Arg Ser
1               5                   10                  15

Leu Asp

<210> SEQ ID NO 184
<211> LENGTH: 14
<212> TYPE: PRT
<213> ORGANISM: Artificial Sequence
<220> FEATURE:
<223> OTHER INFORMATION: linker
<220> FEATURE:
<221> NAME/KEY: MISC_FEATURE
<223> OTHER INFORMATION: linker (EGKSSGSGSESKST)n, where n=1 to 100

<400> SEQUENCE: 184

Glu Gly Lys Ser Ser Gly Ser Gly Ser Glu Ser Lys Ser Thr
1               5                   10

<210> SEQ ID NO 185
<211> LENGTH: 19
<212> TYPE: PRT
<213> ORGANISM: Artificial Sequence
<220> FEATURE:
<223> OTHER INFORMATION: exemplary signal peptide derived from human IgH
      heavy chains

<400> SEQUENCE: 185

Met Glu Leu Gly Leu Ser Trp Ile Phe Leu Leu Ala Ile Leu Lys Gly
1               5                   10                  15

Val Gln Cys

<210> SEQ ID NO 186
<211> LENGTH: 19
<212> TYPE: PRT
<213> ORGANISM: Artificial Sequence
<220> FEATURE:
<223> OTHER INFORMATION: exemplary signal peptide derived from human IgH
      heavy chains

<400> SEQUENCE: 186

Met Glu Leu Gly Leu Arg Trp Val Phe Leu Val Ala Ile Leu Glu Gly
1               5                   10                  15

Val Gln Cys

<210> SEQ ID NO 187
<211> LENGTH: 19
<212> TYPE: PRT
<213> ORGANISM: Artificial Sequence
<220> FEATURE:
<223> OTHER INFORMATION: exemplary signal peptide derived from human IgH
      heavy chains

<400> SEQUENCE: 187

Met Lys His Leu Trp Phe Phe Leu Leu Leu Val Ala Ala Pro Arg Trp
1               5                   10                  15

Val Leu Ser

<210> SEQ ID NO 188
<211> LENGTH: 19
<212> TYPE: PRT
<213> ORGANISM: Artificial Sequence
<220> FEATURE:
<223> OTHER INFORMATION: exemplary signal peptide derived from human IgH
      heavy chains

<400> SEQUENCE: 188

Met Asp Trp Thr Trp Arg Ile Leu Phe Leu Val Ala Ala Ala Thr Gly
1               5                   10                  15

Ala His Ser

<210> SEQ ID NO 189
<211> LENGTH: 19
<212> TYPE: PRT
<213> ORGANISM: Artificial Sequence
<220> FEATURE:
<223> OTHER INFORMATION: exemplary signal peptide derived from human IgH
      heavy chains

<400> SEQUENCE: 189

Met Asp Trp Thr Trp Arg Phe Leu Phe Val Val Ala Ala Ala Thr Gly
1               5                   10                  15

Val Gln Ser

<210> SEQ ID NO 190
<211> LENGTH: 19
<212> TYPE: PRT
<213> ORGANISM: Artificial Sequence
<220> FEATURE:
<223> OTHER INFORMATION: exemplary signal peptide derived from human IgH
      heavy chains

<400> SEQUENCE: 190

Met Glu Phe Gly Leu Ser Trp Leu Phe Leu Val Ala Ile Leu Lys Gly
1               5                   10                  15

Val Gln Cys

<210> SEQ ID NO 191
<211> LENGTH: 19
<212> TYPE: PRT
<213> ORGANISM: Artificial Sequence
<220> FEATURE:
<223> OTHER INFORMATION: exemplary signal peptide derived from human IgH
      heavy chains

<400> SEQUENCE: 191

Met Glu Phe Gly Leu Ser Trp Val Phe Leu Val Ala Leu Phe Arg Gly
1               5                   10                  15

Val Gln Cys

<210> SEQ ID NO 192
<211> LENGTH: 26
<212> TYPE: PRT
<213> ORGANISM: Artificial Sequence
<220> FEATURE:
<223> OTHER INFORMATION: exemplary signal peptide derived from human IgH
      heavy chains

<400> SEQUENCE: 192

Met Asp Leu Leu His Lys Asn Met Lys His Leu Trp Phe Phe Leu Leu
1               5                   10                  15

Leu Val Ala Ala Pro Arg Trp Val Leu Ser
            20                  25

<210> SEQ ID NO 193
<211> LENGTH: 22
<212> TYPE: PRT
<213> ORGANISM: Artificial Sequence
<220> FEATURE:
<223> OTHER INFORMATION: exemplary signal peptide derived from human IgL
      light chains

<400> SEQUENCE: 193

Met Asp Met Arg Val Pro Ala Gln Leu Leu Gly Leu Leu Leu Leu Trp
1               5                   10                  15

Leu Ser Gly Ala Arg Cys
            20

<210> SEQ ID NO 194
<211> LENGTH: 22
<212> TYPE: PRT
<213> ORGANISM: Artificial Sequence
<220> FEATURE:
<223> OTHER INFORMATION: exemplary signal peptide derived from human IgL
      light chains

<400> SEQUENCE: 194

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 195
<211> LENGTH: 8
<212> TYPE: PRT
<213> ORGANISM: Artificial Sequence
<220> FEATURE:
<223> OTHER INFORMATION: Strep tag II

<400> SEQUENCE: 195

Trp Ser His Pro Gln Phe Glu Lys
1               5

<210> SEQ ID NO 196
<211> LENGTH: 8
<212> TYPE: PRT
<213> ORGANISM: Artificial Sequence
<220> FEATURE:
<223> OTHER INFORMATION: Flag tag

<400> SEQUENCE: 196

Asp Tyr Lys Asp Asp Asp Asp Lys
1               5

<210> SEQ ID NO 197
<211> LENGTH: 8
<212> TYPE: PRT
<213> ORGANISM: Artificial Sequence
<220> FEATURE:
<223> OTHER INFORMATION: Xpress tag

<400> SEQUENCE: 197

```
Asp Leu Tyr Asp Asp Asp Asp Lys
1               5

<210> SEQ ID NO 198
<211> LENGTH: 15
<212> TYPE: PRT
<213> ORGANISM: Artificial Sequence
<220> FEATURE:
<223> OTHER INFORMATION: Avi tag

<400> SEQUENCE: 198

Gly Leu Asn Asp Ile Phe Glu Ala Gln Lys Ile Glu Trp His Glu
1               5                   10                  15

<210> SEQ ID NO 199
<211> LENGTH: 26
<212> TYPE: PRT
<213> ORGANISM: Artificial Sequence
<220> FEATURE:
<223> OTHER INFORMATION: calmodulin tag

<400> SEQUENCE: 199

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

<210> SEQ ID NO 200
<211> LENGTH: 9
<212> TYPE: PRT
<213> ORGANISM: Artificial Sequence
<220> FEATURE:
<223> OTHER INFORMATION: HA tag

<400> SEQUENCE: 200

Tyr Pro Tyr Asp Val Pro Asp Tyr Ala
1               5

<210> SEQ ID NO 201
<211> LENGTH: 10
<212> TYPE: PRT
<213> ORGANISM: Artificial Sequence
<220> FEATURE:
<223> OTHER INFORMATION: Myc tag

<400> SEQUENCE: 201

Glu Gln Lys Leu Ile Ser Glu Glu Asp Leu
1               5                   10

<210> SEQ ID NO 202
<211> LENGTH: 13
<212> TYPE: PRT
<213> ORGANISM: Artificial Sequence
<220> FEATURE:
<223> OTHER INFORMATION: Softag 1

<400> SEQUENCE: 202

Ser Leu Ala Glu Leu Leu Asn Ala Gly Leu Gly Gly Ser
1               5                   10

<210> SEQ ID NO 203
<211> LENGTH: 8
<212> TYPE: PRT
<213> ORGANISM: Artificial Sequence
<220> FEATURE:
<223> OTHER INFORMATION: Softag 3
```

```
<400> SEQUENCE: 203

Thr Gln Asp Pro Ser Arg Val Gly
1               5

<210> SEQ ID NO 204
<211> LENGTH: 14
<212> TYPE: PRT
<213> ORGANISM: Artificial Sequence
<220> FEATURE:
<223> OTHER INFORMATION: V5 tag

<400> SEQUENCE: 204

Gly Lys Pro Ile Pro Asn Pro Leu Leu Gly Leu Asp Ser Thr
1               5                   10

<210> SEQ ID NO 205
<211> LENGTH: 106
<212> TYPE: PRT
<213> ORGANISM: Artificial Sequence
<220> FEATURE:
<223> OTHER INFORMATION: variable light chain amino acid sequence of
      exemplary mouse palivizumab

<400> SEQUENCE: 205

Asp Ile Gln Leu Thr Gln Ser Pro Ala Ile Met Ser Ala Ser Pro Gly
1               5                   10                  15

Glu Lys Val Thr Met Thr Cys Ser Ala Ser Ser Val Gly Tyr Met
            20                  25                  30

His Trp Tyr Gln Gln Lys Leu Ser Thr Ser Pro Lys Leu Gln Ile Tyr
        35                  40                  45

Asp Thr Ser Lys Leu Ala Ser Gly Val Pro Gly Arg Phe Ser Gly Ser
    50                  55                  60

Gly Ser Gly Asn Ser Tyr Ser Leu Thr Ile Ser Ser Ile Gln Ala Glu
65                  70                  75                  80

Asp Val Ala Thr Tyr Tyr Cys Phe Arg Gly Ser Gly Tyr Pro Phe Thr
                85                  90                  95

Phe Gly Gln Gly Thr Lys Leu Glu Ile Lys
            100                 105

<210> SEQ ID NO 206
<211> LENGTH: 106
<212> TYPE: PRT
<213> ORGANISM: Artificial Sequence
<220> FEATURE:
<223> OTHER INFORMATION: variable light chain amino acid sequence of
      exemplary human anti-RSV antibody

<400> SEQUENCE: 206

Asp Ile Gln Met Thr Gln Ser Pro Ser Thr Leu Ser Ala Ser Val Gly
1               5                   10                  15

Asp Arg Val Thr Ile Thr Cys Lys Cys Gln Leu Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Phe Ala Thr Tyr Tyr Cys Phe Gln Gly Ser Gly Tyr Pro Phe Thr Phe
                85                  90                  95
```

Gly Gly Gly Thr Lys Leu Glu Ile Lys Arg
            100                 105

<210> SEQ ID NO 207
<211> LENGTH: 12
<212> TYPE: PRT
<213> ORGANISM: Artificial Sequence
<220> FEATURE:
<223> OTHER INFORMATION: CDRH1 of exemplary anti-RSV antibody

<400> SEQUENCE: 207

Gly Ala Ser Ile Asn Ser Asp Asn Tyr Tyr Trp Thr
1               5                   10

<210> SEQ ID NO 208
<211> LENGTH: 16
<212> TYPE: PRT
<213> ORGANISM: Artificial Sequence
<220> FEATURE:
<223> OTHER INFORMATION: CDRH2 of exemplary anti-RSV antibody

<400> SEQUENCE: 208

His Ile Ser Tyr Thr Gly Asn Thr Tyr Tyr Thr Pro Ser Leu Lys Ser
1               5                   10                  15

<210> SEQ ID NO 209
<211> LENGTH: 15
<212> TYPE: PRT
<213> ORGANISM: Artificial Sequence
<220> FEATURE:
<223> OTHER INFORMATION: CDRH3 of exemplary anti-RSV antibody

<400> SEQUENCE: 209

Cys Gly Ala Tyr Val Leu Ile Ser Asn Cys Gly Trp Phe Asp Ser
1               5                   10                  15

<210> SEQ ID NO 210
<211> LENGTH: 11
<212> TYPE: PRT
<213> ORGANISM: Artificial Sequence
<220> FEATURE:
<223> OTHER INFORMATION: CDRL1 of exemplary anti-RSV antibody

<400> SEQUENCE: 210

Gln Ala Ser Gln Asp Ile Ser Thr Tyr Leu Asn
1               5                   10

<210> SEQ ID NO 211
<211> LENGTH: 7
<212> TYPE: PRT
<213> ORGANISM: Artificial Sequence
<220> FEATURE:
<223> OTHER INFORMATION: CDRL2 of exemplary anti-RSV antibody

<400> SEQUENCE: 211

Gly Ala Ser Asn Leu Glu Thr
1               5

<210> SEQ ID NO 212
<211> LENGTH: 9
<212> TYPE: PRT
<213> ORGANISM: Artificial Sequence
<220> FEATURE:
<223> OTHER INFORMATION: CDRL3 of exemplary anti-RSV antibody

<400> SEQUENCE: 212

Gln Gln Tyr Gln Tyr Leu Pro Tyr Thr

```
1               5
```

<210> SEQ ID NO 213
<211> LENGTH: 8
<212> TYPE: PRT
<213> ORGANISM: Artificial Sequence
<220> FEATURE:
<223> OTHER INFORMATION: CDRH1 of exemplary 10E8 anti-HIV antibody

<400> SEQUENCE: 213

```
Gly Phe Asp Phe Asp Asn Ala Trp
1               5
```

<210> SEQ ID NO 214
<211> LENGTH: 10
<212> TYPE: PRT
<213> ORGANISM: Artificial Sequence
<220> FEATURE:
<223> OTHER INFORMATION: CDRH2 of exemplary 10E8 anti-HIV antibody

<400> SEQUENCE: 214

```
Ile Thr Gly Pro Gly Glu Gly Trp Ser Val
1               5                   10
```

<210> SEQ ID NO 215
<211> LENGTH: 20
<212> TYPE: PRT
<213> ORGANISM: Artificial Sequence
<220> FEATURE:
<223> OTHER INFORMATION: CDRH3 of exemplary 10E8 anti-HIV antibody

<400> SEQUENCE: 215

```
Thr Gly Lys Tyr Tyr Asp Phe Trp Ser Gly Tyr Pro Pro Gly Glu Glu
1               5                   10                  15

Tyr Phe Gln Asp
            20
```

<210> SEQ ID NO 216
<211> LENGTH: 11
<212> TYPE: PRT
<213> ORGANISM: Artificial Sequence
<220> FEATURE:
<223> OTHER INFORMATION: CDRL1 of exemplary 10E8 anti-HIV antibody

<400> SEQUENCE: 216

```
Thr Gly Asp Ser Leu Arg Ser His Tyr Ala Ser
1               5                   10
```

<210> SEQ ID NO 217
<211> LENGTH: 7
<212> TYPE: PRT
<213> ORGANISM: Artificial Sequence
<220> FEATURE:
<223> OTHER INFORMATION: CDRL2 of exemplary 10E8 anti-HIV antibody

<400> SEQUENCE: 217

```
Gly Lys Asn Asn Arg Pro Ser
1               5
```

<210> SEQ ID NO 218
<211> LENGTH: 12
<212> TYPE: PRT
<213> ORGANISM: Artificial Sequence
<220> FEATURE:
<223> OTHER INFORMATION: CDRL3 of exemplary 10E8 anti-HIV antibody

<400> SEQUENCE: 218

Ser Ser Arg Asp Lys Ser Gly Ser Arg Leu Ser Val
1               5                   10

<210> SEQ ID NO 219
<211> LENGTH: 8
<212> TYPE: PRT
<213> ORGANISM: Artificial Sequence
<220> FEATURE:
<223> OTHER INFORMATION: CDRH1 of exemplary VRC01 anti-HIV antibody

<400> SEQUENCE: 219

Gly Tyr Glu Phe Ile Asp Cys Thr
1               5

<210> SEQ ID NO 220
<211> LENGTH: 8
<212> TYPE: PRT
<213> ORGANISM: Artificial Sequence
<220> FEATURE:
<223> OTHER INFORMATION: CDRH2 of exemplary VRC01 anti-HIV antibody

<400> SEQUENCE: 220

Lys Pro Arg Gly Gly Ala Val Asn
1               5

<210> SEQ ID NO 221
<211> LENGTH: 14
<212> TYPE: PRT
<213> ORGANISM: Artificial Sequence
<220> FEATURE:
<223> OTHER INFORMATION: CDRH3 of exemplary VRC01 anti-HIV antibody

<400> SEQUENCE: 221

Arg Gly Lys Asn Cys Asp Tyr Asn Trp Asp Phe Glu His Trp
1               5                   10

<210> SEQ ID NO 222
<211> LENGTH: 5
<212> TYPE: PRT
<213> ORGANISM: Artificial Sequence
<220> FEATURE:
<223> OTHER INFORMATION: CDRL3 of exemplary VRC01 anti-HIV antibody

<400> SEQUENCE: 222

Gln Gln Tyr Glu Phe
1               5

<210> SEQ ID NO 223
<211> LENGTH: 30
<212> TYPE: PRT
<213> ORGANISM: Artificial Sequence
<220> FEATURE:
<223> OTHER INFORMATION: CDRH1 of exemplary  anti-Dengue virus antibody

<400> SEQUENCE: 223

Glu Val Gln Leu His Gln Ser Gly Ala Glu Leu Val Lys Pro Gly Ala
1               5                   10                  15

Ser Val Lys Leu Ser Cys Thr Val Ser Gly Phe Asn Ile Lys
            20                  25                  30

<210> SEQ ID NO 224
<211> LENGTH: 13
<212> TYPE: PRT
<213> ORGANISM: Artificial Sequence
<220> FEATURE:
<223> OTHER INFORMATION: CDRH2 of exemplary  anti-Dengue virus antibody

<400> SEQUENCE: 224

Trp Val Lys Gln Arg Pro Glu Gln Gly Leu Glu Trp Ile
1               5                   10

<210> SEQ ID NO 225
<211> LENGTH: 31
<212> TYPE: PRT
<213> ORGANISM: Artificial Sequence
<220> FEATURE:
<223> OTHER INFORMATION: CDRH3 of exemplary anti-Dengue virus antibody

<400> SEQUENCE: 225

Ala Thr Ile Lys Ala Asp Thr Ser Ser Asn Thr Ala Tyr Leu Gln Leu
1               5                   10                  15

Ile Ser Leu Thr Ser Glu Asp Thr Ala Val Tyr Tyr Cys Ala Phe
            20                  25                  30

<210> SEQ ID NO 226
<211> LENGTH: 23
<212> TYPE: PRT
<213> ORGANISM: Artificial Sequence
<220> FEATURE:
<223> OTHER INFORMATION: CDRL1 of exemplary anti-Dengue virus antibody

<400> SEQUENCE: 226

Asp Ile Gln Met Thr Gln Ser Pro Ala Ser Leu Ser Val Ser Val Gly
1               5                   10                  15

Glu Thr Val Thr Ile Thr Cys
            20

<210> SEQ ID NO 227
<211> LENGTH: 15
<212> TYPE: PRT
<213> ORGANISM: Artificial Sequence
<220> FEATURE:
<223> OTHER INFORMATION: CDRL2 of exemplary anti-Dengue virus antibody

<400> SEQUENCE: 227

Trp Tyr Gln Gln Lys Gln Gly Lys Ser Pro Gln Leu Leu Val Tyr
1               5                   10                  15

<210> SEQ ID NO 228
<211> LENGTH: 32
<212> TYPE: PRT
<213> ORGANISM: Artificial Sequence
<220> FEATURE:
<223> OTHER INFORMATION: CDRL3 of exemplary anti-Dengue virus antibody

<400> SEQUENCE: 228

Gly Val Pro Ser Arg Phe Ser Gly Ser Gly Ser Gly Thr Gln Tyr Ser
1               5                   10                  15

Leu Lys Ile Asn Ser Leu Gln Ser Glu Asp Phe Gly Thr Tyr Tyr Cys
            20                  25                  30

<210> SEQ ID NO 229
<211> LENGTH: 9
<212> TYPE: PRT
<213> ORGANISM: Artificial Sequence
<220> FEATURE:
<223> OTHER INFORMATION: CDRH1 of exemplary anti-Dengue virus antibody

<400> SEQUENCE: 229

Tyr Thr Phe Thr Asp Tyr Ala Ile Thr
1               5

<210> SEQ ID NO 230
<211> LENGTH: 18
<212> TYPE: PRT
<213> ORGANISM: Artificial Sequence
<220> FEATURE:
<223> OTHER INFORMATION: CDRH2 of exemplary anti-Dengue virus antibody

<400> SEQUENCE: 230

Gly Leu Ile Ser Thr Tyr Tyr Gly Asp Ser Phe Tyr Asn Gln Lys Phe
1               5                   10                  15
Lys Gly

<210> SEQ ID NO 231
<211> LENGTH: 10
<212> TYPE: PRT
<213> ORGANISM: Artificial Sequence
<220> FEATURE:
<223> OTHER INFORMATION: CDRH3 of exemplary anti-Dengue virus antibody

<400> SEQUENCE: 231

Thr Ile Arg Asp Gly Lys Ala Met Asp Tyr
1               5                   10

<210> SEQ ID NO 232
<211> LENGTH: 16
<212> TYPE: PRT
<213> ORGANISM: Artificial Sequence
<220> FEATURE:
<223> OTHER INFORMATION: CDRL1 of exemplary anti-Dengue virus antibody

<400> SEQUENCE: 232

Arg Ser Ser Gln Ser Leu Val His Ser Asn Gly Asn Thr Tyr Leu His
1               5                   10                  15

<210> SEQ ID NO 233
<211> LENGTH: 7
<212> TYPE: PRT
<213> ORGANISM: Artificial Sequence
<220> FEATURE:
<223> OTHER INFORMATION: CDRL2 of exemplary anti-Dengue virus antibody

<400> SEQUENCE: 233

Lys Val Ser Asn Arg Phe Ser
1               5

<210> SEQ ID NO 234
<211> LENGTH: 9
<212> TYPE: PRT
<213> ORGANISM: Artificial Sequence
<220> FEATURE:
<223> OTHER INFORMATION: CDRL3 of exemplary anti-Dengue virus antibody

<400> SEQUENCE: 234

Ser Gln Ser Thr His Val Pro Tyr Thr
1               5

<210> SEQ ID NO 235
<211> LENGTH: 118
<212> TYPE: PRT
<213> ORGANISM: Artificial Sequence
<220> FEATURE:
<223> OTHER INFORMATION: variable heavy chain of exemplary pertussis
      antibody

<400> SEQUENCE: 235

Gln Val Gln Leu Gln Gln Pro Gly Ser Glu Leu Val Arg Pro Gly Ala
1               5                   10                  15

Ser Val Lys Leu Ser Cys Lys Ala Ser Gly Tyr Lys Phe Thr Ser Tyr
            20                  25                  30

Trp Met His Trp Val Lys Gln Arg Pro Gly Gln Gly Leu Glu Trp Ile
            35                  40                  45

Gly Asn Ile Phe Pro Gly Ser Gly Ser Thr Asn Tyr Asp Glu Lys Phe
        50                  55                  60

Asn Ser Lys Ala Thr Leu Thr Val Asp Thr Ser Asn Thr Ala Tyr
65                  70                  75                  80

Met Gln Leu Ser Ser Leu Thr Ser Glu Asp Ser Ala Val Tyr Tyr Cys
                85                  90                  95

Thr Arg Trp Leu Ser Gly Ala Tyr Phe Asp Tyr Trp Gly Gln Gly Thr
            100                 105                 110

Thr Val Thr Val Ser Ser
        115

<210> SEQ ID NO 236
<211> LENGTH: 106
<212> TYPE: PRT
<213> ORGANISM: Artificial Sequence
<220> FEATURE:
<223> OTHER INFORMATION: variable light chain of exemplary pertussis
      antibody

<400> SEQUENCE: 236

Gln Ile Val Leu Thr Gln Ser Pro Ala Leu Met Ser Ala Ser Pro Gly
1               5                   10                  15

Glu Lys Val Thr Met Thr Cys Ser Ala Ser Ser Ser Val Ser Phe Met
            20                  25                  30

Tyr Trp Tyr Gln Gln Lys Pro Arg Ser Ser Pro Lys Pro Trp Ile Tyr
            35                  40                  45

Leu Thr Ser Asn Leu Pro Ser Gly Val Pro Ala Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser His Pro Pro Thr
                85                  90                  95

Phe Gly Ser Gly Thr Lys Leu Glu Ile Lys
            100                 105

<210> SEQ ID NO 237
<211> LENGTH: 6
<212> TYPE: PRT
<213> ORGANISM: Artificial Sequence
<220> FEATURE:
<223> OTHER INFORMATION: CDRH1 of exemplary anti-hepatitis C antibody

<400> SEQUENCE: 237

Ser Tyr Gly Met His Trp
1               5

<210> SEQ ID NO 238
<211> LENGTH: 18
<212> TYPE: PRT
<213> ORGANISM: Artificial Sequence
<220> FEATURE:
<223> OTHER INFORMATION: CDRH2 of exemplary anti-hepatitis C antibody

<400> SEQUENCE: 238

```
Val Ile Trp Leu Asp Gly Ser Asn Thr Tyr Tyr Ala Asp Ser Val Lys
1               5                   10                  15

Gly Arg

<210> SEQ ID NO 239
<211> LENGTH: 17
<212> TYPE: PRT
<213> ORGANISM: Artificial Sequence
<220> FEATURE:
<223> OTHER INFORMATION: CDRH3 of exemplary anti-hepatitis C antibody

<400> SEQUENCE: 239

Ala Arg Asp Ile Phe Thr Val Ala Arg Gly Val Ile Ile Tyr Phe Asp
1               5                   10                  15

Tyr

<210> SEQ ID NO 240
<211> LENGTH: 11
<212> TYPE: PRT
<213> ORGANISM: Artificial Sequence
<220> FEATURE:
<223> OTHER INFORMATION: CDRL1 of exemplary anti-hepatitis C antibody

<400> SEQUENCE: 240

Arg Ala Ser Gln Ser Val Ser Ser Tyr Leu Ala
1               5                   10

<210> SEQ ID NO 241
<211> LENGTH: 7
<212> TYPE: PRT
<213> ORGANISM: Artificial Sequence
<220> FEATURE:
<223> OTHER INFORMATION: CDRL2 of exemplary anti-hepatitis C antibody

<400> SEQUENCE: 241

Asp Ala Ser Asn Arg Ala Thr
1               5

<210> SEQ ID NO 242
<211> LENGTH: 8
<212> TYPE: PRT
<213> ORGANISM: Artificial Sequence
<220> FEATURE:
<223> OTHER INFORMATION: CDRL3 of exemplary anti-hepatitis C antibody

<400> SEQUENCE: 242

Gln Gln Arg Ser Asn Trp Val Thr
1               5

<210> SEQ ID NO 243
<211> LENGTH: 8
<212> TYPE: PRT
<213> ORGANISM: Artificial Sequence
<220> FEATURE:
<223> OTHER INFORMATION: CDRH1 of exemplary anti-influenza virus
      antibody

<400> SEQUENCE: 243

Gly Met Thr Ser Asn Ser Leu Ala
1               5

<210> SEQ ID NO 244
<211> LENGTH: 8
<212> TYPE: PRT
<213> ORGANISM: Artificial Sequence
<220> FEATURE:
```

```
<223> OTHER INFORMATION: CDRH2 of exemplary anti-influenza virus
      antibody

<400> SEQUENCE: 244

Ile Ile Pro Val Phe Glu Thr Pro
1               5

<210> SEQ ID NO 245
<211> LENGTH: 16
<212> TYPE: PRT
<213> ORGANISM: Artificial Sequence
<220> FEATURE:
<223> OTHER INFORMATION: CDRH3 of exemplary anti-influenza virus
      antibody

<400> SEQUENCE: 245

Ala Thr Ser Ala Gly Gly Ile Val Asn Tyr Tyr Leu Ser Phe Asn Ile
1               5                   10                  15

<210> SEQ ID NO 246
<211> LENGTH: 6
<212> TYPE: PRT
<213> ORGANISM: Artificial Sequence
<220> FEATURE:
<223> OTHER INFORMATION: CDRL1 of exemplary anti-influenza virus
      antibody

<400> SEQUENCE: 246

Gln Thr Ile Thr Thr Trp
1               5

<210> SEQ ID NO 247
<211> LENGTH: 9
<212> TYPE: PRT
<213> ORGANISM: Artificial Sequence
<220> FEATURE:
<223> OTHER INFORMATION: CDRL3 of exemplary anti-influenza virus
      antibody

<400> SEQUENCE: 247

Gln Gln Tyr Ser Thr Tyr Ser Gly Thr
1               5

<210> SEQ ID NO 248
<211> LENGTH: 10
<212> TYPE: PRT
<213> ORGANISM: Artificial Sequence
<220> FEATURE:
<223> OTHER INFORMATION: CDRH1 of exemplary anti-EBV AMM01 antibody

<400> SEQUENCE: 248

Tyr Thr Phe Ile His Phe Gly Ile Ser Trp
1               5                   10

<210> SEQ ID NO 249
<211> LENGTH: 16
<212> TYPE: PRT
<213> ORGANISM: Artificial Sequence
<220> FEATURE:
<223> OTHER INFORMATION: CDRH2 of exemplary anti-EBV AMM01 antibody

<400> SEQUENCE: 249

Ile Asp Thr Asn Asn Gly Asn Thr Asn Tyr Ala Gln Ser Leu Gln Gly
1               5                   10                  15

<210> SEQ ID NO 250
<211> LENGTH: 15
```

```
<212> TYPE: PRT
<213> ORGANISM: Artificial Sequence
<220> FEATURE:
<223> OTHER INFORMATION: CDRH3 of exemplary anti-EBV AMM01 antibody

<400> SEQUENCE: 250

Arg Ala Leu Glu Met Gly His Arg Ser Gly Phe Pro Phe Asp Tyr
1               5                   10                  15

<210> SEQ ID NO 251
<211> LENGTH: 11
<212> TYPE: PRT
<213> ORGANISM: Artificial Sequence
<220> FEATURE:
<223> OTHER INFORMATION: CDRL1 of exemplary anti-EBV AMM01 antibody

<400> SEQUENCE: 251

Gly Gly His Asn Ile Gly Ala Lys Asn Val His
1               5                   10

<210> SEQ ID NO 252
<211> LENGTH: 7
<212> TYPE: PRT
<213> ORGANISM: Artificial Sequence
<220> FEATURE:
<223> OTHER INFORMATION: CDRL2 of exemplary anti-EBV AMM01 antibody

<400> SEQUENCE: 252

Tyr Asp Ser Asp Arg Pro Ser
1               5

<210> SEQ ID NO 253
<211> LENGTH: 14
<212> TYPE: PRT
<213> ORGANISM: Artificial Sequence
<220> FEATURE:
<223> OTHER INFORMATION: CDRL3 of exemplary anti-EBV AMM01 antibody

<400> SEQUENCE: 253

Cys Gln Val Trp Asp Ser Gly Arg Gly His Pro Leu Tyr Val
1               5                   10

<210> SEQ ID NO 254
<211> LENGTH: 19
<212> TYPE: PRT
<213> ORGANISM: Artificial Sequence
<220> FEATURE:
<223> OTHER INFORMATION: beginning of heavy chain of infliximab

<400> SEQUENCE: 254

Glu Val Lys Leu Glu Glu Ser Gly Gly Gly Leu Val Gln Pro Gly Gly
1               5                   10                  15

Ser Met Lys

<210> SEQ ID NO 255
<211> LENGTH: 18
<212> TYPE: PRT
<213> ORGANISM: Artificial Sequence
<220> FEATURE:
<223> OTHER INFORMATION: beginning of light chain of infliximab

<400> SEQUENCE: 255

Asp Ile Leu Leu Thr Gln Ser Pro Ala Ile Leu Ser Val Ser Pro Gly
1               5                   10                  15

Glu Arg
```

```
<210> SEQ ID NO 256
<211> LENGTH: 6
<212> TYPE: PRT
<213> ORGANISM: Artificial Sequence
<220> FEATURE:
<223> OTHER INFORMATION: CDRH1 of exemplary infliximab

<400> SEQUENCE: 256

Ile Phe Ser Asn His Trp
1               5

<210> SEQ ID NO 257
<211> LENGTH: 10
<212> TYPE: PRT
<213> ORGANISM: Artificial Sequence
<220> FEATURE:
<223> OTHER INFORMATION: CDRH2 of exemplary infliximab

<400> SEQUENCE: 257

Arg Ser Lys Ser Ile Asn Ser Ala Thr His
1               5                   10

<210> SEQ ID NO 258
<211> LENGTH: 7
<212> TYPE: PRT
<213> ORGANISM: Artificial Sequence
<220> FEATURE:
<223> OTHER INFORMATION: CDRH3 of exemplary infliximab

<400> SEQUENCE: 258

Asn Tyr Tyr Gly Ser Thr Tyr
1               5

<210> SEQ ID NO 259
<211> LENGTH: 7
<212> TYPE: PRT
<213> ORGANISM: Artificial Sequence
<220> FEATURE:
<223> OTHER INFORMATION: CDRL1 of exemplary infliximab

<400> SEQUENCE: 259

Phe Val Gly Ser Ser Ile His
1               5

<210> SEQ ID NO 260
<211> LENGTH: 7
<212> TYPE: PRT
<213> ORGANISM: Artificial Sequence
<220> FEATURE:
<223> OTHER INFORMATION: CDRL2 of exemplary infliximab

<400> SEQUENCE: 260

Lys Tyr Ala Ser Glu Ser Met
1               5

<210> SEQ ID NO 261
<211> LENGTH: 5
<212> TYPE: PRT
<213> ORGANISM: Artificial Sequence
<220> FEATURE:
<223> OTHER INFORMATION: CDRL3 of exemplary infliximab

<400> SEQUENCE: 261

Gln Ser His Ser Trp
1               5
```

```
<210> SEQ ID NO 262
<211> LENGTH: 6
<212> TYPE: PRT
<213> ORGANISM: Artificial Sequence
<220> FEATURE:
<223> OTHER INFORMATION: CDRH1 of exemplary adalimumab

<400> SEQUENCE: 262

Thr Phe Asp Asp Tyr Ala
1               5

<210> SEQ ID NO 263
<211> LENGTH: 8
<212> TYPE: PRT
<213> ORGANISM: Artificial Sequence
<220> FEATURE:
<223> OTHER INFORMATION: CDRH2 of exemplary adalimumab

<400> SEQUENCE: 263

Thr Trp Asn Ser Gly His Ile Asp
1               5

<210> SEQ ID NO 264
<211> LENGTH: 10
<212> TYPE: PRT
<213> ORGANISM: Artificial Sequence
<220> FEATURE:
<223> OTHER INFORMATION: CDRH3 of exemplary adalimumab

<400> SEQUENCE: 264

Val Ser Tyr Leu Ser Thr Ala Ser Ser Leu
1               5                   10

<210> SEQ ID NO 265
<211> LENGTH: 7
<212> TYPE: PRT
<213> ORGANISM: Artificial Sequence
<220> FEATURE:
<223> OTHER INFORMATION: CDRL1 of exemplary adalimumab

<400> SEQUENCE: 265

Gly Ile Arg Asn Tyr Leu Ala
1               5

<210> SEQ ID NO 266
<211> LENGTH: 7
<212> TYPE: PRT
<213> ORGANISM: Artificial Sequence
<220> FEATURE:
<223> OTHER INFORMATION: CDRL2 of exemplary adalimumab

<400> SEQUENCE: 266

Tyr Ala Ala Ser Thr Leu Gln
1               5

<210> SEQ ID NO 267
<211> LENGTH: 5
<212> TYPE: PRT
<213> ORGANISM: Artificial Sequence
<220> FEATURE:
<223> OTHER INFORMATION: CDRL3 of exemplary adalimumab

<400> SEQUENCE: 267

Arg Tyr Asn Arg Ala
1               5

<210> SEQ ID NO 268
```

```
<211> LENGTH: 6
<212> TYPE: PRT
<213> ORGANISM: Artificial Sequence
<220> FEATURE:
<223> OTHER INFORMATION: CDRH1 of exemplary certolizumab

<400> SEQUENCE: 268

Val Phe Thr Asp Tyr Gly
1               5

<210> SEQ ID NO 269
<211> LENGTH: 8
<212> TYPE: PRT
<213> ORGANISM: Artificial Sequence
<220> FEATURE:
<223> OTHER INFORMATION: CDRH2 of exemplary certolizumab

<400> SEQUENCE: 269

Asn Thr Tyr Ile Gly Glu Pro Ile
1               5

<210> SEQ ID NO 270
<211> LENGTH: 7
<212> TYPE: PRT
<213> ORGANISM: Artificial Sequence
<220> FEATURE:
<223> OTHER INFORMATION: CDRH3 of exemplary certolizumab

<400> SEQUENCE: 270

Gly Tyr Arg Ser Tyr Ala Met
1               5

<210> SEQ ID NO 271
<211> LENGTH: 7
<212> TYPE: PRT
<213> ORGANISM: Artificial Sequence
<220> FEATURE:
<223> OTHER INFORMATION: CDRL1 of exemplary certolizumab

<400> SEQUENCE: 271

Asn Val Gly Thr Asn Val Ala
1               5

<210> SEQ ID NO 272
<211> LENGTH: 7
<212> TYPE: PRT
<213> ORGANISM: Artificial Sequence
<220> FEATURE:
<223> OTHER INFORMATION: CDRL2 of exemplary certolizumab

<400> SEQUENCE: 272

Tyr Ser Ala Ser Phe Leu Tyr
1               5

<210> SEQ ID NO 273
<211> LENGTH: 5
<212> TYPE: PRT
<213> ORGANISM: Artificial Sequence
<220> FEATURE:
<223> OTHER INFORMATION: CDRL3 of exemplary certolizumab

<400> SEQUENCE: 273

Gln Tyr Asn Ile Tyr
1               5

<210> SEQ ID NO 274
<211> LENGTH: 20
```

```
<212> TYPE: DNA
<213> ORGANISM: Artificial Sequence
<220> FEATURE:
<223> OTHER INFORMATION: mouse forward oligo for amplification of region
      flanking cut site

<400> SEQUENCE: 274
ggctccacca gacctctcta                                                     20

<210> SEQ ID NO 275
<211> LENGTH: 20
<212> TYPE: DNA
<213> ORGANISM: Artificial Sequence
<220> FEATURE:
<223> OTHER INFORMATION: mouse reverse oligo for amplification of region
      flanking cut site

<400> SEQUENCE: 275
aacctcagtc accgtctcct                                                     20

<210> SEQ ID NO 276
<211> LENGTH: 21
<212> TYPE: DNA
<213> ORGANISM: Artificial Sequence
<220> FEATURE:
<223> OTHER INFORMATION: human forward oligo for amplification of region
      flanking cut site

<400> SEQUENCE: 276
acagtaagca tgcctcctaa g                                                   21

<210> SEQ ID NO 277
<211> LENGTH: 20
<212> TYPE: DNA
<213> ORGANISM: Artificial Sequence
<220> FEATURE:
<223> OTHER INFORMATION: human reverse oligo for amplification of region
      flanking cut site

<400> SEQUENCE: 277
gccactctag ggcctttgtt                                                     20

<210> SEQ ID NO 278
<211> LENGTH: 65
<212> TYPE: DNA
<213> ORGANISM: Artificial Sequence
<220> FEATURE:
<223> OTHER INFORMATION: mouse forward primer to amplify anti-RSV-emAb
      template

<400> SEQUENCE: 278
accacctctg tgacagcatt tatacagtat ccgatggaca agtgagtgtc tcaggttagg         60
attct                                                                     65

<210> SEQ ID NO 279
<211> LENGTH: 61
<212> TYPE: DNA
<213> ORGANISM: Artificial Sequence
<220> FEATURE:
<223> OTHER INFORMATION: mouse reverse primer to amplify anti-RSV-emAb
      template

<400> SEQUENCE: 279
taaagaaagt gccccactcc actctttgtc cctatgcttg accacaatga atactcccac         60
c                                                                         61
```

<210> SEQ ID NO 280
<211> LENGTH: 639
<212> TYPE: DNA
<213> ORGANISM: Artificial Sequence
<220> FEATURE:
<223> OTHER INFORMATION: hRSV light chain coding sequence without signal
      sequence in human anti-RSV emAb AAV

<400> SEQUENCE: 280

```
gacatccaga tgacacagag ccctagcaca ctgtctgcca gcgtgggcga cagagtgacc      60
atcacatgca agtgccagct gagcgtgggc tacatgcact ggtatcagca aaagcccggc     120
aaggccccta agctgctgat ctacgatacc tccaagctgg cctctggcgt gccctccaga     180
ttttctggca gcggcagcgg aaccgagttc accctgacca tctcaagcct gcagcctgac     240
gacttcgcta cgtactactg cttccaaggc agcggctacc ccttcacatt tggcggcgga     300
acaaagctgg aaatcaagcg gactgtggcc gctcctagcg tgttcatctt ccacctagc     360
gacgagcagc tgaagtctgg cactgcctct gtcgtgtgcc tgctgaacaa cttctaccct     420
cgagaggcca aggtgcagtg gaaagtggac aatgccctgc agagcggcaa cagccaagag     480
tctgtgaccg agcaggactc caaggattcc acctacagcc tgtctagcac cctgactctg     540
agcaaggccg actacgagaa gcacaaggtg tacgcctgcg aagtgacaca ccagggactg     600
agcagccctg tgaccaagag cttcaatcgg ggcgagtgc                            639
```

<210> SEQ ID NO 281
<211> LENGTH: 636
<212> TYPE: DNA
<213> ORGANISM: Artificial Sequence
<220> FEATURE:
<223> OTHER INFORMATION: mRSV kappa light chain coding sequence without
      signal sequence in mouse anti-RSV emAb AAV

<400> SEQUENCE: 281

```
gacatccagc tgacacagag ccctgccatc atgtctgcta gccctggcga gaaagtgaca      60
atgacctgtt ccgccagcag ctccgtgggc tacatgcact ggtatcagca gaagtctagc     120
acaagcccca gctgtggat ctacgacacc tccaagctgg cctctggcgt gccaggcaga     180
ttttctggaa gcggcagcgg caacagctac agcctgacta tcagctccat ccaggccgag     240
gatgtggcta cctactactg cttcagaggc agcggctacc ccttcacatt tggccagggc     300
accaagctgg aaatcaaggc cgatgccgct cctaccgtgt ctatctttcc acctagcagc     360
gagcagctga catctggcgg agcctctgtc gtgtgcttcc tgaacaactt ctaccctaag     420
gacatcaacg tcaagtggaa gatcgacggc tccgagagac agaacggcgt gctgaactct     480
tggaccgacc aggacagcaa ggatagcacc tacagcatga gcagcactct gaccctgaca     540
aaggacgagt acgagaggca caactcctac acatgcgagg ccacacacaa gaccagcaca     600
tccccaatcg tgaagtcctt caaccggaac gagtgc                              636
```

<210> SEQ ID NO 282
<211> LENGTH: 630
<212> TYPE: DNA
<213> ORGANISM: Artificial Sequence
<220> FEATURE:
<223> OTHER INFORMATION: VRC01 light chain coding sequence without
      signal sequence in Hu-emAb-VRC01-AAV

<400> SEQUENCE: 282

```
gaaattgtgt tgacacagtc tccaggcacc ctgtctttgt ctccagggga aacagccatc      60
```

```
atctcttgtc ggaccagtca gtatggttcc ttagcctggt atcaacagag gcccggccag    120
gcccccaggc tcgtcatcta ttcgggctct actcgggccg ctggcatccc agacaggttc    180
agcggcagtc ggtgggggcc agactacaat ctcaccatca gcaacctgga gtcgggagat    240
tttggtgttt attattgcca gcagtatgaa ttttttggcc aggggaccaa ggtccaggtc    300
gacattaagc gcactgtggc cgctcctagc gtgttcatct ttccacctag cgacgagcag    360
ctgaagtctg gcactgcctc tgtcgtgtgc ctgctgaaca acttctaccc tcgagaggcc    420
aaggtgcagt ggaaagtgga caatgccctg cagagcggca cagccaaga gtctgtgacc     480 gagcaggact ccaaggattc cacctacagc ctgtctagca ccctgactct gagcaaggcc    540
gactacgaga agcacaaggt gtacgcctgc gaagtgacac caggggact gagcagccct     600 gtgaccaaga gcttcaatcg gggcgagtgc                                     630
```

<210> SEQ ID NO 283
<211> LENGTH: 630
<212> TYPE: DNA
<213> ORGANISM: Artificial Sequence
<220> FEATURE:
<223> OTHER INFORMATION: Medi8852 light chain coding sequence without
      signal sequence in hu-emAb-Medi8852-AAV

<400> SEQUENCE: 283

```
gatattcaga tgacccagag cccttccagc ctgtccgctt cagtggggga tcgagtgacc    60
attacctgcc gaaccagcca gagcctgagc tcctacacgc actggtatca gcagaagccc    120
ggcaaagccc ctaagctgct gatctacgcc gcttctagtc gggggtccgg agtgccaagc    180
cggttctccg gatctgggag tggaaccgac tttaccctga caatttcaag cctgcagccc    240
gaggatttcg ctacatacta ctgtcagcag agcagaactt tcgggcaggg cactaaggtg    300
gagatcaaac ggactgtggc cgctcctagc gtgttcatct ttccacctag cgacgagcag    360
ctgaagtctg gcactgcctc tgtcgtgtgc ctgctgaaca acttctaccc tcgagaggcc    420
aaggtgcagt ggaaagtgga caatgccctg cagagcggca cagccaaga gtctgtgacc     480 gagcaggact ccaaggattc cacctacagc ctgtctagca ccctgactct gagcaaggcc    540
gactacgaga agcacaaggt gtacgcctgc gaagtgacac caggggact gagcagccct     600 gtgaccaaga gcttcaatcg gggcgagtgc                                     630
```

<210> SEQ ID NO 284
<211> LENGTH: 648
<212> TYPE: DNA
<213> ORGANISM: Artificial Sequence
<220> FEATURE:
<223> OTHER INFORMATION: AMM01 light chain coding sequence without
      signal sequence in hu-emAb-AMM01-AAV

<400> SEQUENCE: 284

```
tcctatgagc tgactcagcc accctcagtg tcagtggccc cggggcagag ggccacaatt    60
acctgtgggg gacacaacat cggagctaaa aatgtccact ggtaccagca gaagccaggc    120
caggcccctg tcctggtcat ccaatatgat agcgaccggc cctcagggat ccctgagcga    180
ttctctggct ccaactctgg gagcacggcc accctgacca tcagcagggt cgaagccggg    240
gatgaggccg actattactg tcaggtgtgg gatagtggtc gtgggcatcc cctttatgtc    300
ttcggaggtg ggaccaaggt caccgtccta ggtcagccca ggccaacccc actgtcact    360 ctgttcccac cctcgagtga ggagcttcaa gccaacaagg ccacactggt gtgtctcata    420
agtgacttct acccgggagc cgtgacagtg gcctggaagg cagatagcag cccgtcaag    480
```

```
gcgggagtgg agaccaccac accctccaaa caaagcaaca acaagtacgc ggccagcagc      540
tacctgagcc tgacgcctga gcagtggaag tcccacagaa gctacagctg ccaggtcacg      600
catgaaggga gcaccgtgga agacagtg gcccctacag aatgttca                    648
```

<210> SEQ ID NO 285
<211> LENGTH: 213
<212> TYPE: PRT
<213> ORGANISM: Artificial Sequence
<220> FEATURE:
<223> OTHER INFORMATION: hRSV light chain amino acid sequence without
      signal peptide in human anti-RSV emAb AAV

<400> SEQUENCE: 285

```
Asp Ile Gln Met Thr Gln Ser Pro Ser Thr Leu Ser Ala Ser Val Gly
1               5                   10                  15

Asp Arg Val Thr Ile Thr Cys Lys Cys Gln Leu Ser Val Gly Tyr Met
                20                  25                  30

His Trp Tyr Gln Gln Lys Pro Gly Lys Ala Pro Lys Leu Leu Ile Tyr
            35                  40                  45

Asp Thr Ser Lys Leu Ala Ser Gly Val Pro Ser Arg Phe Ser Gly Ser
        50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 286
<211> LENGTH: 212
<212> TYPE: PRT
<213> ORGANISM: Artificial Sequence
<220> FEATURE:
<223> OTHER INFORMATION: mRSV kappa light chain amino acid sequence
      without signal peptide in mouse anti-RSV emAb AAV

<400> SEQUENCE: 286

```
Asp Ile Gln Leu Thr Gln Ser Pro Ala Ile Met Ser Ala Ser Pro Gly
1               5                   10                  15

Glu Lys Val Thr Met Thr Cys Ser Ala Ser Ser Ser Val Gly Tyr Met
                20                  25                  30

His Trp Tyr Gln Gln Lys Ser Ser Thr Ser Pro Lys Leu Trp Ile Tyr
            35                  40                  45
```

Asp Thr Ser Lys Leu Ala Ser Gly Val Pro Gly Arg Phe Ser Gly Ser
            50                  55                  60

Gly Ser Gly Asn Ser Tyr Ser Leu Thr Ile Ser Ile Gln Ala Glu
65                  70                  75                  80

Asp Val Ala Thr Tyr Tyr Cys Phe Arg Gly Ser Gly Tyr Pro Phe Thr
                85                  90                  95

Phe Gly Gln Gly Thr Lys Leu Glu Ile Lys Ala Asp Ala Ala Pro Thr
            100                 105                 110

Val Ser Ile Phe Pro Pro Ser Glu Gln Leu Thr Ser Gly Gly Ala
            115                 120                 125

Ser Val Val Cys Phe Leu Asn Asn Phe Tyr Pro Lys Asp Ile Asn Val
130                 135                 140

Lys Trp Lys Ile Asp Gly Ser Glu Arg Gln Asn Gly Val Leu Asn Ser
145                 150                 155                 160

Trp Thr Asp Gln Asp Ser Lys Asp Ser Thr Tyr Ser Met Ser Ser Thr
            165                 170                 175

Leu Thr Leu Thr Lys Asp Glu Tyr Glu Arg His Asn Ser Tyr Thr Cys
            180                 185                 190

Glu Ala Thr His Lys Thr Ser Thr Ser Pro Ile Val Lys Ser Phe Asn
            195                 200                 205

Arg Asn Glu Cys
    210

<210> SEQ ID NO 287
<211> LENGTH: 210
<212> TYPE: PRT
<213> ORGANISM: Artificial Sequence
<220> FEATURE:
<223> OTHER INFORMATION: VRC01 light chain amino acid sequence without
      signal peptide in Hu-emAb-VRC01-AAV

<400> SEQUENCE: 287

Glu Ile Val Leu Thr Gln Ser Pro Gly Thr Leu Ser Leu Ser Pro Gly
1               5                   10                  15

Glu Thr Ala Ile Ile Ser Cys Arg Thr Ser Gln Tyr Gly Ser Leu Ala
            20                  25                  30

Trp Tyr Gln Gln Arg Pro Gly Gln Ala Pro Arg Leu Val Ile Tyr Ser
            35                  40                  45

Gly Ser Thr Arg Ala Ala Gly Ile Pro Asp Arg Phe Ser Gly Ser Arg
            50                  55                  60

Trp Gly Pro Asp Tyr Asn Leu Thr Ile Ser Asn Leu Glu Ser Gly Asp
65                  70                  75                  80

Phe Gly Val Tyr Tyr Cys Gln Gln Tyr Glu Phe Phe Gly Gln Gly Thr
                85                  90                  95

Lys Val Gln Val Asp Ile Lys Arg Thr Val Ala Ala Pro Ser Val Phe
            100                 105                 110

Ile Phe Pro Pro Ser Asp Glu Gln Leu Lys Ser Gly Thr Ala Ser Val
            115                 120                 125

Val Cys Leu Leu Asn Asn Phe Tyr Pro Arg Glu Ala Lys Val Gln Trp
130                 135                 140

Lys Val Asp Asn Ala Leu Gln Ser Gly Asn Ser Gln Glu Ser Val Thr
145                 150                 155                 160

Glu Gln Asp Ser Lys Asp Ser Thr Tyr Ser Leu Ser Ser Thr Leu Thr
            165                 170                 175

Leu Ser Lys Ala Asp Tyr Glu Lys His Lys Val Tyr Ala Cys Glu Val 180                 185                 190

Thr His Gln Gly Leu Ser Ser Pro Val Thr Lys Ser Phe Asn Arg Gly
        195                 200                 205

Glu Cys
    210

<210> SEQ ID NO 288
<211> LENGTH: 210
<212> TYPE: PRT
<213> ORGANISM: Artificial Sequence
<220> FEATURE:
<223> OTHER INFORMATION: Medi8852 light chain amino acid sequence
      without signal peptide in hu-emAb-Medi8852-AAV

<400> SEQUENCE: 288

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Ser Leu Ser Ser Tyr
            20                  25                  30

Thr His Trp Tyr Gln Gln Lys Pro Gly Lys Ala Pro Lys Leu Leu Ile
        35                  40                  45

Tyr Ala Ala Ser Ser Arg Gly Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Arg Thr Phe Gly Gln
                85                  90                  95

Gly Thr Lys Val Glu Ile Lys Arg Thr Val Ala Ala Pro Ser Val Phe
            100                 105                 110

Ile Phe Pro Pro Ser Asp Glu Gln Leu Lys Ser Gly Thr Ala Ser Val
        115                 120                 125

Val Cys Leu Leu Asn Asn Phe Tyr Pro Arg Glu Ala Lys Val Gln Trp
130                 135                 140

Lys Val Asp Asn Ala Leu Gln Ser Gly Asn Ser Gln Glu Ser Val Thr
145                 150                 155                 160

Glu Gln Asp Ser Lys Asp Ser Thr Tyr Ser Leu Ser Ser Thr Leu Thr
                165                 170                 175

Leu Ser Lys Ala Asp Tyr Glu Lys His Lys Val Tyr Ala Cys Glu Val
            180                 185                 190

Thr His Gln Gly Leu Ser Ser Pro Val Thr Lys Ser Phe Asn Arg Gly
        195                 200                 205

Glu Cys
    210

<210> SEQ ID NO 289
<211> LENGTH: 216
<212> TYPE: PRT
<213> ORGANISM: Artificial Sequence
<220> FEATURE:
<223> OTHER INFORMATION: AMM01 light chain amino acid sequence without
      signal peptide in hu-emAb-AMM01-AAV

<400> SEQUENCE: 289

Ser Tyr Glu Leu Thr Gln Pro Pro Ser Val Ser Val Ala Pro Gly Gln
1               5                   10                  15

Arg Ala Thr Ile Thr Cys Gly Gly His Asn Ile Gly Ala Lys Asn Val
            20                  25                  30

His Trp Tyr Gln Gln Lys Pro Gly Gln Ala Pro Val Leu Val Ile Gln

```
                    35                  40                  45
Tyr Asp Ser Asp Arg Pro Ser Gly Ile Pro Glu Arg Phe Ser Gly Ser
 50                  55                  60

Asn Ser Gly Ser Thr Ala Thr Leu Thr Ile Ser Arg Val Glu Ala Gly
 65                  70                  75                  80

Asp Glu Ala Asp Tyr Tyr Cys Gln Val Trp Asp Ser Gly Arg Gly His
                 85                  90                  95

Pro Leu Tyr Val Phe Gly Gly Gly Thr Lys Val Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 290
<211> LENGTH: 20
<212> TYPE: RNA
<213> ORGANISM: Artificial Sequence
<220> FEATURE:
<223> OTHER INFORMATION: Human _1_gRNA_1 from FIG. 11B

<400> SEQUENCE: 290
gguccucggg gcauguuccg                                                   20

<210> SEQ ID NO 291
<211> LENGTH: 20
<212> TYPE: RNA
<213> ORGANISM: Artificial Sequence
<220> FEATURE:
<223> OTHER INFORMATION: Human _1_gRNA_2 from FIG. 11B

<400> SEQUENCE: 291
gggcauguuc cgaggggacc                                                   20

<210> SEQ ID NO 292
<211> LENGTH: 20
<212> TYPE: RNA
<213> ORGANISM: Artificial Sequence
<220> FEATURE:
<223> OTHER INFORMATION: Human _1_gRNA_4 from FIG. 11B

<400> SEQUENCE: 292
uccucggggc auguuccgag                                                   20

<210> SEQ ID NO 293
<211> LENGTH: 20
<212> TYPE: RNA
<213> ORGANISM: Artificial Sequence
<220> FEATURE:
<223> OTHER INFORMATION: Human _1_gRNA_5 from FIG. 11B
```

<400> SEQUENCE: 293
ggcauguucc gagggggaccu								20

<210> SEQ ID NO 294
<211> LENGTH: 20
<212> TYPE: RNA
<213> ORGANISM: Artificial Sequence
<220> FEATURE:
<223> OTHER INFORMATION: Human _1_gRNA_7 from FIG. 11B

<400> SEQUENCE: 294
agcauugcag guugguccuc								20

<210> SEQ ID NO 295
<211> LENGTH: 20
<212> TYPE: RNA
<213> ORGANISM: Artificial Sequence
<220> FEATURE:
<223> OTHER INFORMATION: Human _1_gRNA_8 from FIG. 11B

<400> SEQUENCE: 295
ccugggcgga cuggccagga								20

<210> SEQ ID NO 296
<211> LENGTH: 20
<212> TYPE: RNA
<213> ORGANISM: Artificial Sequence
<220> FEATURE:
<223> OTHER INFORMATION: Human _1_gRNA_9 from FIG. 11B

<400> SEQUENCE: 296 acugggugc cuugaggauc								20

<210> SEQ ID NO 297
<211> LENGTH: 20
<212> TYPE: RNA
<213> ORGANISM: Artificial Sequence
<220> FEATURE:
<223> OTHER INFORMATION: Human _1_gRNA_10 from FIG. 11B

<400> SEQUENCE: 297
ccccagugcc cauccccucc								20

<210> SEQ ID NO 298
<211> LENGTH: 20
<212> TYPE: RNA
<213> ORGANISM: Artificial Sequence
<220> FEATURE:
<223> OTHER INFORMATION: Human _1_gRNA_11 from FIG. 11B

<400> SEQUENCE: 298
cuaagacccc ugguuuguuc								20

<210> SEQ ID NO 299
<211> LENGTH: 20
<212> TYPE: RNA
<213> ORGANISM: Artificial Sequence
<220> FEATURE:
<223> OTHER INFORMATION: Human _1_gRNA_12 from FIG. 11B

<400> SEQUENCE: 299
uguggauuuu ccgaugccuu								20

<210> SEQ ID NO 300
<211> LENGTH: 20

```
<212> TYPE: RNA
<213> ORGANISM: Artificial Sequence
<220> FEATURE:
<223> OTHER INFORMATION: Human _1_gRNA_13 from FIG. 11B

<400> SEQUENCE: 300
aggaccaacc ugcaaugcuc                                               20

<210> SEQ ID NO 301
<211> LENGTH: 20
<212> TYPE: RNA
<213> ORGANISM: Artificial Sequence
<220> FEATURE:
<223> OTHER INFORMATION: Human _1_gRNA_14 from FIG. 11B

<400> SEQUENCE: 301
cucagguugg gugcgucuga                                               20

<210> SEQ ID NO 302
<211> LENGTH: 20
<212> TYPE: RNA
<213> ORGANISM: Artificial Sequence
<220> FEATURE:
<223> OTHER INFORMATION: Human _1_gRNA_15

<400> SEQUENCE: 302
cccuccuggc caguccgccc                                               20

<210> SEQ ID NO 303
<211> LENGTH: 20
<212> TYPE: RNA
<213> ORGANISM: Artificial Sequence
<220> FEATURE:
<223> OTHER INFORMATION: Human _1_gRNA_16 from FIG. 11B

<400> SEQUENCE: 303
ggccaggagg ggaugggcac                                               20

<210> SEQ ID NO 304
<211> LENGTH: 20
<212> TYPE: RNA
<213> ORGANISM: Artificial Sequence
<220> FEATURE:
<223> OTHER INFORMATION: Human _1_gRNA_17

<400> SEQUENCE: 304
gagaugccug aacaaaccag                                               20

<210> SEQ ID NO 305
<211> LENGTH: 20
<212> TYPE: RNA
<213> ORGANISM: Artificial Sequence
<220> FEATURE:
<223> OTHER INFORMATION: Human _1_gRNA_18 from FIG. 11B

<400> SEQUENCE: 305
aggggucuua gugauggcug                                               20

<210> SEQ ID NO 306
<211> LENGTH: 20
<212> TYPE: RNA
<213> ORGANISM: Artificial Sequence
<220> FEATURE:
<223> OTHER INFORMATION: Human _1_gRNA_19 from FIG. 11B

<400> SEQUENCE: 306
```

```
augggcacug ggugccuug                                                 20

<210> SEQ ID NO 307
<211> LENGTH: 20
<212> TYPE: RNA
<213> ORGANISM: Artificial Sequence
<220> FEATURE:
<223> OTHER INFORMATION: Human_1_gRNA_20 from FIG. 11B

<400> SEQUENCE: 307
uuccgaugcc uuuggaaaau                                                20

<210> SEQ ID NO 308
<211> LENGTH: 20
<212> TYPE: RNA
<213> ORGANISM: Artificial Sequence
<220> FEATURE:
<223> OTHER INFORMATION: Human_2_gRNA_1 from FIG. 12B

<400> SEQUENCE: 308
cugacgccgc aucggugauu                                                20

<210> SEQ ID NO 309
<211> LENGTH: 20
<212> TYPE: RNA
<213> ORGANISM: Artificial Sequence
<220> FEATURE:
<223> OTHER INFORMATION: Human_2_gRNA_2 from FIG. 12B

<400> SEQUENCE: 309
uuagacaagg gcgaugccag                                                20

<210> SEQ ID NO 310
<211> LENGTH: 20
<212> TYPE: RNA
<213> ORGANISM: Artificial Sequence
<220> FEATURE:
<223> OTHER INFORMATION: Human_2_gRNA_3 from FIG. 12B

<400> SEQUENCE: 310
cgugcgaccu cuccuucaaa                                                20

<210> SEQ ID NO 311
<211> LENGTH: 20
<212> TYPE: RNA
<213> ORGANISM: Artificial Sequence
<220> FEATURE:
<223> OTHER INFORMATION: Human_2_gRNA_4 from FIG. 12B

<400> SEQUENCE: 311
agcauaucuu cugcaccaag                                                20

<210> SEQ ID NO 312
<211> LENGTH: 20
<212> TYPE: RNA
<213> ORGANISM: Artificial Sequence
<220> FEATURE:
<223> OTHER INFORMATION: Human_2_gRNA_5 from FIG. 12B

<400> SEQUENCE: 312
auauuccacc cagguagugg                                                20

<210> SEQ ID NO 313
<211> LENGTH: 20
<212> TYPE: RNA
<213> ORGANISM: Artificial Sequence
```

-continued

<220> FEATURE:
<223> OTHER INFORMATION: Human_2_gRNA_6 from FIG. 12B

<400> SEQUENCE: 313
gugcgaccuc uccuucaaau                                               20

<210> SEQ ID NO 314
<211> LENGTH: 20
<212> TYPE: RNA
<213> ORGANISM: Artificial Sequence
<220> FEATURE:
<223> OTHER INFORMATION: Human_2_gRNA_7 from FIG. 12B

<400> SEQUENCE: 314 aggucccuu gcucagaag                                                 20

<210> SEQ ID NO 315
<211> LENGTH: 20
<212> TYPE: RNA
<213> ORGANISM: Artificial Sequence
<220> FEATURE:
<223> OTHER INFORMATION: Human_2_gRNA_8 from FIG. 12B

<400> SEQUENCE: 315
cucuagauaa cagucaucau                                               20

<210> SEQ ID NO 316
<211> LENGTH: 20
<212> TYPE: RNA
<213> ORGANISM: Artificial Sequence
<220> FEATURE:
<223> OTHER INFORMATION: Human_2_gRNA_9 from FIG. 12B

<400> SEQUENCE: 316
uugucuaagu cauugacugu                                               20

<210> SEQ ID NO 317
<211> LENGTH: 20
<212> TYPE: RNA
<213> ORGANISM: Artificial Sequence
<220> FEATURE:
<223> OTHER INFORMATION: Human_2_gRNA_10 from FIG. 12B

<400> SEQUENCE: 317
ccaaagcgau uuaugguaaa                                               20

<210> SEQ ID NO 318
<211> LENGTH: 20
<212> TYPE: RNA
<213> ORGANISM: Artificial Sequence
<220> FEATURE:
<223> OTHER INFORMATION: Human_2_gRNA_11 from FIG. 12B

<400> SEQUENCE: 318
ucuuuugagu gaccauuguc                                               20

<210> SEQ ID NO 319
<211> LENGTH: 20
<212> TYPE: RNA
<213> ORGANISM: Artificial Sequence
<220> FEATURE:
<223> OTHER INFORMATION: Human_2_gRNA_12 from FIG. 12B

<400> SEQUENCE: 319
ccauuuacca uaaaucgcuu                                               20

```
<210> SEQ ID NO 320
<211> LENGTH: 20
<212> TYPE: RNA
<213> ORGANISM: Artificial Sequence
<220> FEATURE:
<223> OTHER INFORMATION: Human_2_gRNA_13 from FIG. 12B

<400> SEQUENCE: 320
agggcgaugc caguggggcu                                                   20

<210> SEQ ID NO 321
<211> LENGTH: 20
<212> TYPE: RNA
<213> ORGANISM: Artificial Sequence
<220> FEATURE:
<223> OTHER INFORMATION: Human_2_gRNA_14 from FIG. 12B

<400> SEQUENCE: 321
agcuaaagcc aucucauugc                                                   20

<210> SEQ ID NO 322
<211> LENGTH: 20
<212> TYPE: RNA
<213> ORGANISM: Artificial Sequence
<220> FEATURE:
<223> OTHER INFORMATION: Human_2_gRNA_15 from FIG. 12B

<400> SEQUENCE: 322
ccacaaccuc ugaaugggga                                                   20

<210> SEQ ID NO 323
<211> LENGTH: 20
<212> TYPE: RNA
<213> ORGANISM: Artificial Sequence
<220> FEATURE:
<223> OTHER INFORMATION: Human_2_gRNA_16 from FIG. 12B

<400> SEQUENCE: 323
uuaauugcuu gaugaagagc                                                   20

<210> SEQ ID NO 324
<211> LENGTH: 20
<212> TYPE: RNA
<213> ORGANISM: Artificial Sequence
<220> FEATURE:
<223> OTHER INFORMATION: Human_2_gRNA_17 from FIG. 12B

<400> SEQUENCE: 324
uagacaaggg cgaugccagu                                                   20

<210> SEQ ID NO 325
<211> LENGTH: 20
<212> TYPE: RNA
<213> ORGANISM: Artificial Sequence
<220> FEATURE:
<223> OTHER INFORMATION: Human_2_gRNA_18 from FIG. 12B

<400> SEQUENCE: 325
aagcugaccu agacuaaaca                                                   20

<210> SEQ ID NO 326
<211> LENGTH: 20
<212> TYPE: RNA
<213> ORGANISM: Artificial Sequence
<220> FEATURE:
<223> OTHER INFORMATION: Human_2_gRNA_19 from FIG. 12B
```

-continued

<400> SEQUENCE: 326
gcaggaaccc ggcaaugaga                                               20

<210> SEQ ID NO 327
<211> LENGTH: 20
<212> TYPE: RNA
<213> ORGANISM: Artificial Sequence
<220> FEATURE:
<223> OTHER INFORMATION: Human_2_gRNA_20 from FIG. 12B

<400> SEQUENCE: 327
ucuguuccga aucaccgaug                                               20

<210> SEQ ID NO 328
<211> LENGTH: 20
<212> TYPE: RNA
<213> ORGANISM: Artificial Sequence
<220> FEATURE:
<223> OTHER INFORMATION: Mouse_1_gRNA_1 from FIG. 13B

<400> SEQUENCE: 328 caacuaccccu uuugagaccg                                              20

<210> SEQ ID NO 329
<211> LENGTH: 20
<212> TYPE: RNA
<213> ORGANISM: Artificial Sequence
<220> FEATURE:
<223> OTHER INFORMATION: Mouse_1_gRNA_3 from FIG. 13B

<400> SEQUENCE: 329
uauacaguau ccgaugcaua                                               20

<210> SEQ ID NO 330
<211> LENGTH: 20
<212> TYPE: RNA
<213> ORGANISM: Artificial Sequence
<220> FEATURE:
<223> OTHER INFORMATION: Mouse_1_gRNA_4 from FIG. 13B

<400> SEQUENCE: 330
caucuagccu cggucucaaa                                               20

<210> SEQ ID NO 331
<211> LENGTH: 20
<212> TYPE: RNA
<213> ORGANISM: Artificial Sequence
<220> FEATURE:
<223> OTHER INFORMATION: Mouse_1_gRNA_5 from FIG. 13B

<400> SEQUENCE: 331
cacucuuugu cccuaugcau                                               20

<210> SEQ ID NO 332
<211> LENGTH: 20
<212> TYPE: RNA
<213> ORGANISM: Artificial Sequence
<220> FEATURE:
<223> OTHER INFORMATION: Mouse_1_gRNA_6 from FIG. 13B

<400> SEQUENCE: 332
aucuagccuc ggucucaaaa                                               20

<210> SEQ ID NO 333

```
<211> LENGTH: 20
<212> TYPE: RNA
<213> ORGANISM: Artificial Sequence
<220> FEATURE:
<223> OTHER INFORMATION: Mouse_1_gRNA_7 from FIG. 13B

<400> SEQUENCE: 333
aaguuuuaaa caaucuagug                                              20

<210> SEQ ID NO 334
<211> LENGTH: 20
<212> TYPE: RNA
<213> ORGANISM: Artificial Sequence
<220> FEATURE:
<223> OTHER INFORMATION: Mouse_1_gRNA_8 from FIG. 13B

<400> SEQUENCE: 334
aagaugcuaa aacaauccua                                              20

<210> SEQ ID NO 335
<211> LENGTH: 20
<212> TYPE: RNA
<213> ORGANISM: Artificial Sequence
<220> FEATURE:
<223> OTHER INFORMATION: Mouse_1_gRNA_9 from FIG. 13B

<400> SEQUENCE: 335
ugcuaaaaca auccuauggc                                              20

<210> SEQ ID NO 336
<211> LENGTH: 20
<212> TYPE: RNA
<213> ORGANISM: Artificial Sequence
<220> FEATURE:
<223> OTHER INFORMATION: Mouse_1_gRNA_10 from FIG. 13B

<400> SEQUENCE: 336 aagcccuau cccaucaucc                                               20

<210> SEQ ID NO 337
<211> LENGTH: 20
<212> TYPE: RNA
<213> ORGANISM: Artificial Sequence
<220> FEATURE:
<223> OTHER INFORMATION: Mouse_1_gRNA_11 from FIG. 13B

<400> SEQUENCE: 337
gggagaaagg caucuagccu                                              20

<210> SEQ ID NO 338
<211> LENGTH: 20
<212> TYPE: RNA
<213> ORGANISM: Artificial Sequence
<220> FEATURE:
<223> OTHER INFORMATION: Mouse_1_gRNA_12 from FIG. 13B

<400> SEQUENCE: 338
ugagcauugc agacuaaucu                                              20

<210> SEQ ID NO 339
<211> LENGTH: 20
<212> TYPE: RNA
<213> ORGANISM: Artificial Sequence
<220> FEATURE:
<223> OTHER INFORMATION: Mouse_1_gRNA_13 from FIG. 13B

<400> SEQUENCE: 339
```

-continued uuaguugugg aauauacuuc                                          20

<210> SEQ ID NO 340
<211> LENGTH: 20
<212> TYPE: RNA
<213> ORGANISM: Artificial Sequence
<220> FEATURE:
<223> OTHER INFORMATION: Mouse_1_gRNA_14 from FIG. 13B

<400> SEQUENCE: 340
ugguggaguc ccuggaugau                                          20

<210> SEQ ID NO 341
<211> LENGTH: 20
<212> TYPE: RNA
<213> ORGANISM: Artificial Sequence
<220> FEATURE:
<223> OTHER INFORMATION: Mouse_1_gRNA_15 from FIG. 13B

<400> SEQUENCE: 341
guggagauaa ucuguccuaa                                          20

<210> SEQ ID NO 342
<211> LENGTH: 20
<212> TYPE: RNA
<213> ORGANISM: Artificial Sequence
<220> FEATURE:
<223> OTHER INFORMATION: Mouse_1_gRNA_16 from FIG. 13B

<400> SEQUENCE: 342
agucccuauc ccaucaucca                                          20

<210> SEQ ID NO 343
<211> LENGTH: 20
<212> TYPE: RNA
<213> ORGANISM: Artificial Sequence
<220> FEATURE:
<223> OTHER INFORMATION: Mouse_1_gRNA_17 from FIG. 13B

<400> SEQUENCE: 343
aucuuggaua uuugucccug                                          20

<210> SEQ ID NO 344
<211> LENGTH: 20
<212> TYPE: RNA
<213> ORGANISM: Artificial Sequence
<220> FEATURE:
<223> OTHER INFORMATION: Mouse_1_gRNA_18 from FIG. 13B

<400> SEQUENCE: 344
gggauaguug gggcuguagu                                          20

<210> SEQ ID NO 345
<211> LENGTH: 20
<212> TYPE: RNA
<213> ORGANISM: Artificial Sequence
<220> FEATURE:
<223> OTHER INFORMATION: Mouse_1_gRNA_19 from FIG. 13B

<400> SEQUENCE: 345
cagguaagaa uggccucucc                                          20

<210> SEQ ID NO 346
<211> LENGTH: 20
<212> TYPE: RNA

```
<213> ORGANISM: Artificial Sequence
<220> FEATURE:
<223> OTHER INFORMATION: Mouse_1_gRNA_20 from FIG. 13B

<400> SEQUENCE: 346
ucucucagcc ggcucccuca                                               20

<210> SEQ ID NO 347
<211> LENGTH: 20
<212> TYPE: RNA
<213> ORGANISM: Artificial Sequence
<220> FEATURE:
<223> OTHER INFORMATION: MOUSE_2_gRNA_1 from FIG. 14B

<400> SEQUENCE: 347
ccgaaaccag gcaccgcaaa                                               20

<210> SEQ ID NO 348
<211> LENGTH: 20
<212> TYPE: RNA
<213> ORGANISM: Artificial Sequence
<220> FEATURE:
<223> OTHER INFORMATION: MOUSE_2_gRNA_2 from FIG. 14B

<400> SEQUENCE: 348
caccgcaaau gguaagccag                                               20

<210> SEQ ID NO 349
<211> LENGTH: 20
<212> TYPE: RNA
<213> ORGANISM: Artificial Sequence
<220> FEATURE:
<223> OTHER INFORMATION: MOUSE_2_gRNA_3 from FIG. 14B

<400> SEQUENCE: 349
ggcuuaccau uugcggugcc                                               20

<210> SEQ ID NO 350
<211> LENGTH: 20
<212> TYPE: RNA
<213> ORGANISM: Artificial Sequence
<220> FEATURE:
<223> OTHER INFORMATION: MOUSE_2_gRNA_4 from FIG. 14B

<400> SEQUENCE: 350
ugcggugccu gguuucggag                                               20

<210> SEQ ID NO 351
<211> LENGTH: 20
<212> TYPE: RNA
<213> ORGANISM: Artificial Sequence
<220> FEATURE:
<223> OTHER INFORMATION: MOUSE_2_gRNA_5 from FIG. 14B

<400> SEQUENCE: 351
cagcuaugcu acgcuguguu                                               20

<210> SEQ ID NO 352
<211> LENGTH: 20
<212> TYPE: RNA
<213> ORGANISM: Artificial Sequence
<220> FEATURE:
<223> OTHER INFORMATION: MOUSE_2_gRNA_6 from FIG. 14B

<400> SEQUENCE: 352
aaggacagug cuuagauccg                                               20
```

```
<210> SEQ ID NO 353
<211> LENGTH: 20
<212> TYPE: RNA
<213> ORGANISM: Artificial Sequence
<220> FEATURE:
<223> OTHER INFORMATION: MOUSE_2_gRNA_7 from FIG. 14B

<400> SEQUENCE: 353
ucagucaguc agugacguga                                                      20

<210> SEQ ID NO 354
<211> LENGTH: 20
<212> TYPE: RNA
<213> ORGANISM: Artificial Sequence
<220> FEATURE:
<223> OTHER INFORMATION: MOUSE_2_gRNA_8 from FIG. 14B

<400> SEQUENCE: 354
caugcugguu ggugguugag                                                      20

<210> SEQ ID NO 355
<211> LENGTH: 20
<212> TYPE: RNA
<213> ORGANISM: Artificial Sequence
<220> FEATURE:
<223> OTHER INFORMATION: MOUSE_2_gRNA_9 from FIG. 14B

<400> SEQUENCE: 355
ucuuuugagu accguugucu                                                      20

<210> SEQ ID NO 356
<211> LENGTH: 20
<212> TYPE: RNA
<213> ORGANISM: Artificial Sequence
<220> FEATURE:
<223> OTHER INFORMATION: MOUSE_2_gRNA_10 from FIG. 14B

<400> SEQUENCE: 356
uggcccauuc aacaauaagc                                                      20

<210> SEQ ID NO 357
<211> LENGTH: 20
<212> TYPE: RNA
<213> ORGANISM: Artificial Sequence
<220> FEATURE:
<223> OTHER INFORMATION: MOUSE_2_gRNA_11 from FIG. 14B

<400> SEQUENCE: 357
cugggccgcu aagcuaaacu                                                      20

<210> SEQ ID NO 358
<211> LENGTH: 20
<212> TYPE: RNA
<213> ORGANISM: Artificial Sequence
<220> FEATURE:
<223> OTHER INFORMATION: MOUSE_2_gRNA_12 from FIG. 14B

<400> SEQUENCE: 358
gccagccuag uuuagcuuag                                                      20

<210> SEQ ID NO 359
<211> LENGTH: 20
<212> TYPE: RNA
<213> ORGANISM: Artificial Sequence
<220> FEATURE:
```

<223> OTHER INFORMATION: MOUSE_2_gRNA_13 from FIG. 14B

<400> SEQUENCE: 359
ugaaguagac uguaaugaac                                               20

<210> SEQ ID NO 360
<211> LENGTH: 20
<212> TYPE: RNA
<213> ORGANISM: Artificial Sequence
<220> FEATURE:
<223> OTHER INFORMATION: MOUSE_2_gRNA_14 from FIG. 14B

<400> SEQUENCE: 360
gaccugggaa uguaugguug                                               20

<210> SEQ ID NO 361
<211> LENGTH: 20
<212> TYPE: RNA
<213> ORGANISM: Artificial Sequence
<220> FEATURE:
<223> OTHER INFORMATION: MOUSE_2_gRNA_15 from FIG. 14B

<400> SEQUENCE: 361
gguauggaua cgcagaagga                                               20

<210> SEQ ID NO 362
<211> LENGTH: 20
<212> TYPE: RNA
<213> ORGANISM: Artificial Sequence
<220> FEATURE:
<223> OTHER INFORMATION: MOUSE_2_gRNA_16 from FIG. 14B

<400> SEQUENCE: 362
guugagagcc cuaguaagcg                                               20

<210> SEQ ID NO 363
<211> LENGTH: 20
<212> TYPE: RNA
<213> ORGANISM: Artificial Sequence
<220> FEATURE:
<223> OTHER INFORMATION: MOUSE_2_gRNA_17 from FIG. 14B

<400> SEQUENCE: 363
gccgcuaagc uaaacuaggc                                               20

<210> SEQ ID NO 364
<211> LENGTH: 20
<212> TYPE: RNA
<213> ORGANISM: Artificial Sequence
<220> FEATURE:
<223> OTHER INFORMATION: MOUSE_2_gRNA_18 from FIG. 14B

<400> SEQUENCE: 364
ucagcuaugc uacgcugugu                                               20

<210> SEQ ID NO 365
<211> LENGTH: 20
<212> TYPE: RNA
<213> ORGANISM: Artificial Sequence
<220> FEATURE:
<223> OTHER INFORMATION: MOUSE_2_gRNA_19 from FIG. 14B

<400> SEQUENCE: 365
uuuuagagcc ucgcuuacua                                               20

-continued

```
<210> SEQ ID NO 366
<211> LENGTH: 20
<212> TYPE: RNA
<213> ORGANISM: Artificial Sequence
<220> FEATURE:
<223> OTHER INFORMATION: MOUSE_2_gRNA_20 from FIG. 14B

<400> SEQUENCE: 366
cucuaugauu auugguuaac                                                  20
```

What is claimed is:

1. A method of genetically engineering B cells to express a selected antibody, the method comprising
delivering into B cells:
a gene editing agent that cuts a targeted genomic region in the B cells; and
a genetic construct comprising from 5' to 3':
(i) a nucleotide sequence of a heavy chain promoter;
(ii) a nucleotide sequence encoding a signal peptide;
(iii) a nucleotide sequence encoding the light chain of the selected antibody;
(iv) a nucleotide sequence encoding a flexible linker or a self-cleaving peptide or a nucleotide sequence of a skipping element;
(v) a nucleotide sequence encoding the variable region of the heavy chain of the selected antibody; and
(vi) a nucleotide sequence comprising a splice junction,
wherein the genomic region comprises a sequence as set forth in:
(A) SEQ ID NO: 1;
(B) SEQ ID NO: 2;
(C) SEQ ID NO: 3; or
(D) SEQ ID NO: 4,
and wherein the genetic construct is inserted at the genomic region of (A), (B), (C), or (D) after the cutting by the gene editing agent, thereby genetically engineering the B cells to express the selected antibody.

2. The method of claim 1, wherein the B cells' endogenous variable heavy chain encoding genome is not excised.

3. The method of claim 1, wherein the gene editing agent comprises a nuclease associated with a guide RNA (gRNA) having a sequence as set forth in:
SEQ ID NO: 88, 89, 290, 291, 292, 293, 294, 295, 296, 297, 298, 299, 300, 301, 302, 303, 304, 305, 306, or 307 when the genomic region is (A);
SEQ ID NO: 308, 309, 310, 311, 312, 313, 314, 315, 316, 317, 318, 319, 320, 321, 322, 323, 324, 325, 326, or 327 when the genomic region is (B);
SEQ ID NO: 87, 328, 329, 330, 331, 332, 333, 334, 335, 336, 337, 338, 339, 340, 341, 342, 343, 344, 345, or 346 when the genomic region is (C); or
SEQ ID NO: 347, 348, 349, 350, 351, 352, 353, 354, 355, 356, 357, 358, 359, 360, 361, 362, 363, 364, 365, or 366 when the genomic region is (D).

4. The method of claim 1, wherein the delivering is through electroporation, a nanoparticle, or viral-mediated delivery.

5. The method of claim 3, wherein the gRNA and nuclease are delivered through electroporation and the genetic construct is delivered as part of an adeno-associated viral vector.

6. The method of claim 3, wherein the nuclease is Cas9 or Cpf1.

7. The method of claim 1, wherein the heavy chain promoter has a sequence as set forth in SEQ ID NO: 111 when the genomic region is (A) or (B); or has a sequence as set forth in SEQ ID NO: 128 when the genomic region is (C) or (D).

8. The method of claim 1, wherein the signal peptide
has an amino acid sequence as set forth in SEQ ID NO: 185, 186, 187, 188, 189, 190, 191, or 192;
has an amino acid sequence as set forth in SEQ ID NO: 193 or 194;
has an amino acid sequence as set forth in SEQ ID NO: 118 when the genomic region is (A) or (B); or
has an amino acid sequence as set forth in SEQ ID NO: 134 when the genomic region is (C) or (D).

9. The method of claim 1, wherein the flexible linker
is encoded by a nucleotide sequence as set forth in SEQ ID NO: 116;
has an amino acid sequence as set forth in SEQ ID NOs: 122, 180, 181, 182, 183, or 184; and/or
is a Gly-Ser linker comprising 50-80 amino acids.

10. The method of claim 1, wherein the self-cleaving peptide has a sequence as set forth in SEQ ID NO: 176, 177, 178, or 179 or wherein the skipping element is an internal ribosome entry site (IRES).

11. The method of claim 1, wherein the nucleotide sequence comprising the splice junction is as set forth in SEQ ID NO: 124 or 151 when the genomic region is (A) or (B); or is as set forth in SEQ ID NO: 139 when the genomic region is (C) or (D).

12. The method of claim 1, wherein the genetic construct further encodes a tag having a sequence as set forth in SEQ ID NO: 195, 196, 197, 198, 199, 200, 201, 202, 203, or 204.

13. The method of claim 1, wherein the selected antibody comprises an anti-Respiratory Syncytial Virus (RSV) antibody comprising
(a) a variable heavy chain having the amino acid sequence as set forth in SEQ ID NO: 138 and a variable light chain having the amino acid sequence as set forth in SEQ ID NO: 136;
(b) a variable heavy chain having the amino acid sequence as set forth in SEQ ID NO: 138 and a variable light chain having the amino acid sequence as set forth in SEQ ID NO: 205;
(c) a variable heavy chain having the amino acid sequence as set forth in SEQ ID NO: 123 and a variable light chain having the amino acid sequence as set forth in SEQ ID NO: 120; or
(d) a variable heavy chain having the amino acid sequence as set forth in SEQ ID NO: 123 and a variable light chain having the amino acid sequence as set forth in SEQ ID NO: 206;
an anti-human immunodeficiency virus (HIV) antibody comprising a variable heavy chain having the amino acid sequence as set forth in SEQ ID NO: 150 and a variable light chain having the amino acid sequence as set forth in SEQ ID NO: 149;

an anti-pertussis antibody comprising a variable heavy chain having the amino acid sequence as set forth in SEQ ID NO: 235 and a variable light chain having the amino acid sequence as set forth in SEQ ID NO: 236;

an anti-influenza antibody comprising a variable heavy chain having the amino acid sequence as set forth in SEQ ID NO: 159 and a variable light chain having the amino acid sequence as set forth in SEQ ID NO: 158;

an anti-Epstein Barr virus (EBV) antibody comprising variable heavy chain having the amino acid sequence as set forth in SEQ ID NO: 168 and a variable light chain having the amino acid sequence as set forth in SEQ ID NO: 166; or an anti-tumor necrosis factor (TNF) antibody comprising a variable heavy chain having the amino acid sequence as set forth in SEQ ID NO: 254 and a variable light chain having the amino acid sequence as set forth in SEQ ID NO: 255.

14. The method of claim 1, wherein the selected antibody comprises a CDRH1 sequence as set forth in SEQ ID NO: 207, a CDRH2 sequence as set forth in SEQ ID NO: 208, a CDRH3 sequence as set forth in SEQ ID NO: 209; a CDRL1 sequence as set forth in SEQ ID NO: 210, a CDRL2 sequence as set forth in SEQ ID NO: 211, and a CDRL3 sequence as set forth in SEQ ID NO: 212;
 a CDRH1 sequence as set forth in SEQ ID NO: 213, a CDRH2 sequence as set forth in SEQ ID NO: 214, a CDRH3 sequence as set forth in SEQ ID NO: 215, a CDRL1 sequence as set forth in SEQ ID NO: 216, a CDRL2 sequence as set forth in SEQ ID NO: 217, and a CDRL3 sequence as set forth in SEQ ID NO: 218;
 a CDRH1 sequence as set forth in SEQ ID NO: 219, a CDRH2 sequence as set forth in SEQ ID NO: 220, a CDRH3 sequence as set forth in SEQ ID NO: 221, a CDRL1 of QYGS, a CDRL2 sequence as set forth in SGS, and a CDRL3 sequence as set forth in SEQ ID NO: 222;
 a CDRH1 sequence as set forth in SEQ ID NO: 223, a CDRH2 sequence as set forth in SEQ ID NO: 224, a CDRH3 sequence as set forth in SEQ ID NO: 225; a CDRL1 sequence as set forth in SEQ ID NO: 226, a CDRL2 sequence as set forth in SEQ ID NO: 227, and a CDRKL3 as set forth in SEQ ID NO: 228;
 a CDRH1 sequence as set forth in SEQ ID NO: 229, a CDRH2 sequence as set forth in SEQ ID NO: 230, a CDRH3 sequence as set forth in SEQ ID NO: 231, a CDRL1 sequence as set forth in SEQ ID NO: 232, a CDRL2 sequence as set forth in SEQ ID NO: 233, and a CDRL3 sequence as set forth in SEQ ID NO: 234;
 a CDRH1 sequence as set forth in SEQ ID NO: 237, a CDRH2 sequence as set forth in SEQ ID NO: 238, a CDRH3 sequence as set forth in SEQ ID NO: 239, a CDRL1 sequence as set forth in SEQ ID NO: 240, a CDRL2 sequence as set forth in SEQ ID NO: 241, and a CDRL3 sequence as set forth in SEQ ID NO: 242;
 a CDRH1 sequence as set forth in SEQ ID NO: 243, a CDRH2 sequence as set forth in SEQ ID NO: 244, a CDRH3 sequence as set forth in SEQ ID NO: 245, a CDRL1 sequence as set forth in SEQ ID NO: 246, a CDRL2 of KTS, and a CDRL3 sequence as set forth in SEQ ID NO: 247;
 a CDRH1 sequence as set forth in SEQ ID NO: 248, a CDRH2 sequence as set forth in SEQ ID NO: 249, a CDRH3 sequence as set forth in SEQ ID NO: 250, a CDRL1 sequence as set forth in SEQ ID NO: 251, a CDRL2 sequence as set forth in SEQ ID NO: 252, and a CDRL3 sequence as set forth in SEQ ID NO: 253;
 a CDRH1 sequence as set forth in SEQ ID NO: 256, a CDRH2 sequence as set forth in SEQ ID NO: 257, and a CDRH3 sequence as set forth in SEQ ID NO: 258; a CDRL1 sequence as set forth in SEQ ID NO: 259, a CDRL2 sequence as set forth in SEQ ID NO: 260, and a CDRL3 sequence as set forth in SEQ ID NO: 261;
 a CDRH1 sequence as set forth in SEQ ID NO: 262, a CDRH2 sequence as set forth in SEQ ID NO: 263, and a CDRH3 sequence as set forth in SEQ ID NO: 264; a CDRL1 sequence as set forth in SEQ ID NO: 265, a CDRL2 sequence as set forth in SEQ ID NO: 266, and a CDRL3 sequence as set forth in SEQ ID NO: 267; or
 a CDRH1 sequence as set forth in SEQ ID NO: 268, a CDRH2 sequence as set forth in SEQ ID NO: 269, and a CDRH3 sequence as set forth in SEQ ID NO: 270; or a CDRL1 sequence as set forth in SEQ ID NO: 271, a CDRL2 sequence as set forth in SEQ ID NO: 272, and a CDRL3 sequence as set forth in SEQ ID NO: 273,
 each according to Kabat numbering.

15. The method of claim 1, wherein the selected antibody is an anti-Respiratory Syncytial Virus (RSV) antibody, an anti-human immunodeficiency virus (HIV) antibody, an anti-Dengue virus antibody, an anti-*Bordatella pertussis* antibody, an anti-hepatitis C antibody, an anti-influenza virus antibody, an anti-parainfluenza virus antibody, an anti-metapneumovirus (MPV) antibody, an anti-cytomegalovirus antibody, an anti-Epstein Barr virus antibody; an anti-herpes simplex virus antibody, an anti-*Clostridium difficile* bacterial toxin antibody, or an anti-tumor necrosis factor (TNF) antibody.

16. The method of claim 1, wherein the genetic construct comprises a homology arm 5' of the heavy chain promoter and a homology arm 3' of the splice junction.

17. The method of claim 16, wherein the genetic construct comprises a nucleotide sequence as set forth in SEQ ID NO: 102 comprising a coding sequence encoding an anti-RSV antibody having the amino acid sequence as set forth in SEQ ID NO: 126;
 a nucleotide sequence as set forth in SEQ ID NO: 103 comprising a coding sequence encoding an anti-RSV antibody having the amino acid sequence as set forth in SEQ ID NO: 141;
 a nucleotide sequence as set forth in SEQ ID NO: 104 comprising a coding sequence encoding an anti-RSV antibody having the amino acid sequence as set forth in SEQ ID NO: 141;
 a nucleotide sequence as set forth in SEQ ID NO: 105 comprising a coding sequence encoding an anti-HIV antibody having the amino acid sequence as set forth in SEQ ID NO: 152;
 a nucleotide sequence as set forth in SEQ ID NO: 106 comprising a coding sequence encoding an anti-influenza antibody having the amino acid sequence as set forth in SEQ ID NO: 160; or
 a nucleotide sequence as set forth in SEQ ID NO: 107 comprising a coding sequence encoding an anti-EBV antibody having the amino acid sequence as set forth in SEQ ID NO: 169.

18. The method of claim 16, wherein
when the genomic region is (A),
 the 5' homology arm is as set forth in SEQ ID NO: 110 or 153, and the 3' homology arm is as set forth in SEQ ID NO: 125;

the 5' homology arm is as set forth in SEQ ID NO: 92, and the 3' homology arm is as set forth in SEQ ID NO: 93; or the 5' homology arm is as set forth in SEQ ID NO: 94, and the 3' homology arm is as set forth in SEQ ID NO: 95 or when the genomic region is (C), the 5' homology arm is as set forth in SEQ ID NO: 127 and the 3' homology arm is as set forth in SEQ ID NO: 140;

the 5' homology arm is as set forth in SEQ ID NO: 90 and the 3' homology arm is as set forth in SEQ ID NO: 91; or the 5' homology arm is as set forth in SEQ ID NO: 142 and the 3' homology arm is as set forth in SEQ ID NO: 143.

19. The method of claim 16, wherein when the genomic region comprises (A), the genetic construct comprises:
(i) the 5' homology arm sequence as set forth in SEQ ID NO: 110;
(ii) the heavy chain promoter having the sequence as set forth in SEQ ID NO: 111;
(iii) a coding sequence encoding the signal peptide having the amino acid sequence as set forth in SEQ ID NO: 118;
(iv) a coding sequence encoding the light chain of the selected antibody having the amino acid sequence as set forth in SEQ ID NO: 285;
(v) a coding sequence encoding the flexible linker having an amino acid sequence as set forth in SEQ ID NO: 122;
(vi) a coding sequence encoding the variable region of the heavy chain of the selected antibody having the amino acid sequence as set forth in SEQ ID NO: 123;
(vii) the splice junction having a sequence as set forth in SEQ ID NO: 124; and
(viii) the 3' homology arm sequence as set forth in SEQ ID NO: 125; or when the genomic region comprises (A), the genetic construct comprises:
(i) the 5' homology arm sequence as set forth in SEQ ID NO: 110;
(ii) the heavy chain promoter having a sequence as set forth in SEQ ID NO: 111;
(iii) a coding sequence encoding the signal peptide having an amino acid sequence as set forth in SEQ ID NO: 118;
(iv) a coding sequence encoding the light chain of the selected antibody having an amino acid sequence as set forth in SEQ ID NO: 287;
(v) a coding sequence encoding the flexible linker having an amino acid sequence as set forth in SEQ ID NO: 122;
(vi) a coding sequence encoding the variable region of the heavy chain of the selected antibody having an amino acid sequence as set forth in SEQ ID NO: 150;
(vii) the splice junction having a sequence as set forth in SEQ ID NO: 151; and
(viii) the 3' homology arm sequence as set forth in SEQ ID NO: 125; or when the genomic region comprises (A), the genetic construct comprises:
(i) the 5' homology arm sequence as set forth in SEQ ID NO: 153;
(ii) the heavy chain promoter having a sequence as set forth in SEQ ID NO: 111;
(iii) a coding sequence encoding the signal peptide having an amino acid sequence as set forth in SEQ ID NO: 118;
(iv) a coding sequence encoding the light chain of the selected antibody having an amino acid sequence as set forth in SEQ ID NO: 288;
(v) a coding sequence encoding the flexible linker having an amino acid sequence as set forth in SEQ ID NO: 122;
(vi) a coding sequence encoding the variable region of the heavy chain of the selected antibody having an amino acid sequence as set forth in SEQ ID NO: 159;
(vii) the splice junction having a sequence as set forth in SEQ ID NO: 151; and
(viii) the 3' homology arm sequence as set forth in SEQ ID NO: 125; or when the genomic region comprises (A), the genetic construct comprises:
(i) the 5' homology arm sequence as set forth in SEQ ID NO: 153;
(ii) the heavy chain promoter having a sequence as set forth in SEQ ID NO: 111;
(iii) a coding sequence encoding the signal peptide having an amino acid sequence as set forth in SEQ ID NO: 118;
(iv) a coding sequence encoding the light chain of the selected antibody having an amino acid sequence as set forth in SEQ ID NO: 289;
(v) a coding sequence encoding the flexible linker having an amino acid sequence as set forth in SEQ ID NO: 122;
(vi) a coding sequence encoding the variable region of the heavy chain of the selected antibody having an amino acid sequence as set forth in SEQ ID NO: 168;
(vii) the splice junction having a sequence as set forth in SEQ ID NO: 151; and
(viii) the 3' homology arm sequence as set forth in SEQ ID NO: 125; or when the genomic region comprises (C), the genetic construct comprises:
(i) the 5' homology arm sequence as set forth in SEQ ID NO: 127;
(ii) the heavy chain promoter having a sequence as set forth in SEQ ID NO: 128;
(iii) a coding sequence encoding the signal peptide having an amino acid sequence as set forth in SEQ ID NO: 134;
(iv) a coding sequence encoding the light chain of the selected antibody having an amino acid sequence as set forth in SEQ ID NO: 286;
(v) a coding sequence encoding the flexible linker having an amino acid sequence as set forth in SEQ ID NO: 122;
(vi) a coding sequence encoding the variable region of the heavy chain of the selected antibody having an amino acid sequence as set forth in SEQ ID NO: 138;
(vii) the splice junction having a sequence as set forth in SEQ ID NO: 139; and
(viii) the 3' homology arm sequence as set forth in SEQ ID NO: 140; or when the genomic region comprises (C), the genetic construct comprises:
(i) the 5' homology arm sequence as set forth in SEQ ID NO: 142;

(ii) the heavy chain promoter having a sequence as set forth in SEQ ID NO: 128;
(iii) a coding sequence encoding the signal peptide having an amino acid sequence as set forth in SEQ ID NO: 134;
(iv) a coding sequence encoding the light chain of the selected antibody having an amino acid sequence as set forth in SEQ ID NO: 286;
(v) a coding sequence encoding the flexible linker having an amino acid sequence as set forth in SEQ ID NO: 122;
(vi) a coding sequence encoding the variable region of the heavy chain of the selected antibody having an amino acid sequence as set forth in SEQ ID NO: 138;
(vii) the splice junction having a sequence as set forth in SEQ ID NO: 139; and
(viii) the 3' homology arm sequence as set forth in SEQ ID NO: 143.

20. The method of claim 1, wherein the B cell is an antibody-producing B cell, a memory B cell, a naïve B cell, a B1 B cell or a marginal zone B cell.

21. A B cell modified according to a method of claim 1.

22. The B cell of claim 21, wherein the B cell is an antibody-secreting B cell, a memory B cell, a naïve B cell, a B1 B cell or a marginal zone B cell.

23. A method of providing an antibody in a subject in need thereof comprising administering a therapeutically effective amount of the B cells of claim 21 to the subject, thereby providing an antibody to the subject.

* * * * *